US007331951B2

(12) United States Patent
Eshel et al.

(10) Patent No.: US 7,331,951 B2
(45) Date of Patent: **\*Feb. 19, 2008**

(54) DEVICES AND METHODOLOGIES USEFUL IN BODY AESTHETICS

(75) Inventors: Yoram Eshel, Tel Aviv (IL); Leonid Kushculey, Rehovot (IL); Ariel Sverdlik, Tel Aviv (IL); Ilia Vitsnudel, Even Yehuda (IL)

(73) Assignee: Ultrashape Inc., Yoqneam Illite (IL)

( * ) Notice: Subject to any disclaimer, the term of this patent is extended or adjusted under 35 U.S.C. 154(b) by 173 days.

This patent is subject to a terminal disclaimer.

(21) Appl. No.: 10/520,054

(22) PCT Filed: Jun. 25, 2002

(86) PCT No.: PCT/IL02/00510

§ 371 (c)(1),
(2), (4) Date: Apr. 25, 2005

(87) PCT Pub. No.: WO04/000116

PCT Pub. Date: Dec. 31, 2003

(65) Prior Publication Data

US 2005/0261584 A1    Nov. 24, 2005

(51) Int. Cl.
*A61N 5/06* (2006.01)
*A61B 17/22* (2006.01)

(52) U.S. Cl. .............................. 606/2.5; 606/2; 606/27; 606/32; 606/53; 601/2; 128/897; 128/898

(58) Field of Classification Search ................ 601/2–4; 600/139, 439; 607/100; 606/2.5, 27, 32, 606/53; 128/897, 898

See application file for complete search history.

(56) References Cited

U.S. PATENT DOCUMENTS

| 4,605,009 A | 8/1986 | Pourcelot et al. |
| 4,938,216 A | 7/1990 | Lele |
| 4,986,275 A | 1/1991 | Ishida et al. |
| 5,005,579 A | 4/1991 | Wurster et al. |
| 5,079,952 A | 1/1992 | Nakaso et al. |
| 5,080,102 A | 1/1992 | Dory |

(Continued)

FOREIGN PATENT DOCUMENTS

EP          1 060 728        12/2000

(Continued)

OTHER PUBLICATIONS

U.S. Appl. No. 10/021,238, "Non-invasive ultrasonic body contouring", Oct. 25, 2001.

(Continued)

*Primary Examiner*—Eric F. Winakur
*Assistant Examiner*—Joel Lamprecht
(74) *Attorney, Agent, or Firm*—EMPK & Shiloh, LLP

(57) ABSTRACT

A methodology and system for lysis or induction of apoptosis in cellulite and fat including directing ultrasonic energy at a multiplicity of target volumes within the region, which target volumes contain cellulite and fat, thereby to selectively lyse or induce apoptosis in the cellulite and fat in the target volumes and generally not lyse or not induce apoptosis in non-cellulite and non-fat tissue in the target volumes and computerized tracking of the multiplicity of target volumes notwithstanding movement of the body.

20 Claims, 18 Drawing Sheets

U.S. PATENT DOCUMENTS

| | | |
|---|---|---|
| 5,111,822 A | 5/1992 | Dory |
| 5,143,063 A | 9/1992 | Fellner |
| 5,143,073 A | 9/1992 | Dory |
| 5,209,221 A | 5/1993 | Reidlinger |
| 5,219,401 A | 6/1993 | Cathignol et al. |
| 5,301,660 A | 4/1994 | Rattner |
| 5,419,761 A | 5/1995 | Narayanan et al. |
| 5,431,621 A | 7/1995 | Dory |
| 5,507,790 A | 4/1996 | Weiss |
| 5,526,815 A | 6/1996 | Grantz et al. |
| 5,618,275 A | 4/1997 | Bock |
| 5,640,371 A | 6/1997 | Schmidt et al. |
| 5,827,204 A | 10/1998 | Grandia |
| 5,884,631 A | 3/1999 | Silberg |
| 5,938,608 A | 8/1999 | Bieger et al. |
| 6,039,048 A | 3/2000 | Silberg |
| 6,071,239 A * | 6/2000 | Cribbs et al. ............... 600/439 |
| 6,086,535 A | 7/2000 | Ishibashi et al. |
| 6,113,558 A | 9/2000 | Rosenschein et al. |
| 6,206,873 B1 | 3/2001 | Paolini et al. |
| 6,384,516 B1 | 5/2002 | Fraser |
| 6,607,498 B2 | 8/2003 | Eshel |
| 6,645,162 B2 * | 11/2003 | Friedman et al. ............... 601/2 |

FOREIGN PATENT DOCUMENTS

| | | |
|---|---|---|
| GB | 2 303 552 A1 | 2/1997 |
| WO | WO-02/24076 A1 | 3/2002 |

OTHER PUBLICATIONS

Rod. J. Rodrich, et al., "Comparative Lipoplasty Analysis of in Vivo-Treated Adipose Tissue", Plastic and Reconstruction Journal, 2000, vol. 105, pp. 2152-2158, no date.

Abstract. Japanese Application No. JP-11-187493-A2, "Spherical Langevin Transducer", Jul. 9, 1999.

Abstract. Japanese Application No. JP-10-277483-A2, "Bolted Langevin Type Vibrator", Daishinku Co., Oct. 20, 1998.

Abstract. Japanese Application No. JP-08-089893-A2, "Bolted Langevin Transducer", Tokin Corp., Apr. 9, 1996.

Abstract. Japanese Application No. JP-58-181399-A2, "Manufacture of Multi-Element Arranging Type Langevin Oscillator", Oki Electric Ind. Co. Ltd., Oct. 24, 1983.

\* cited by examiner

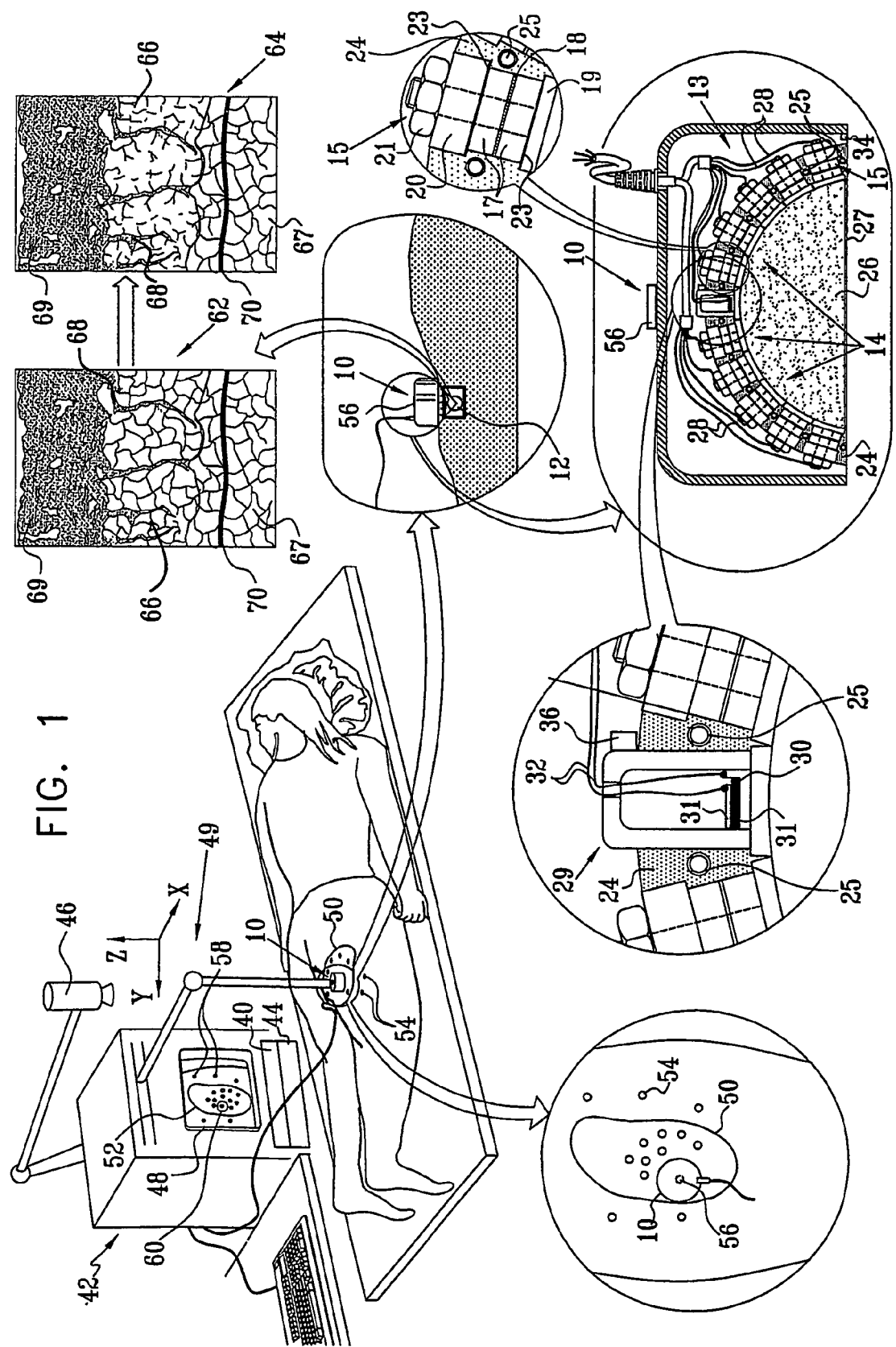

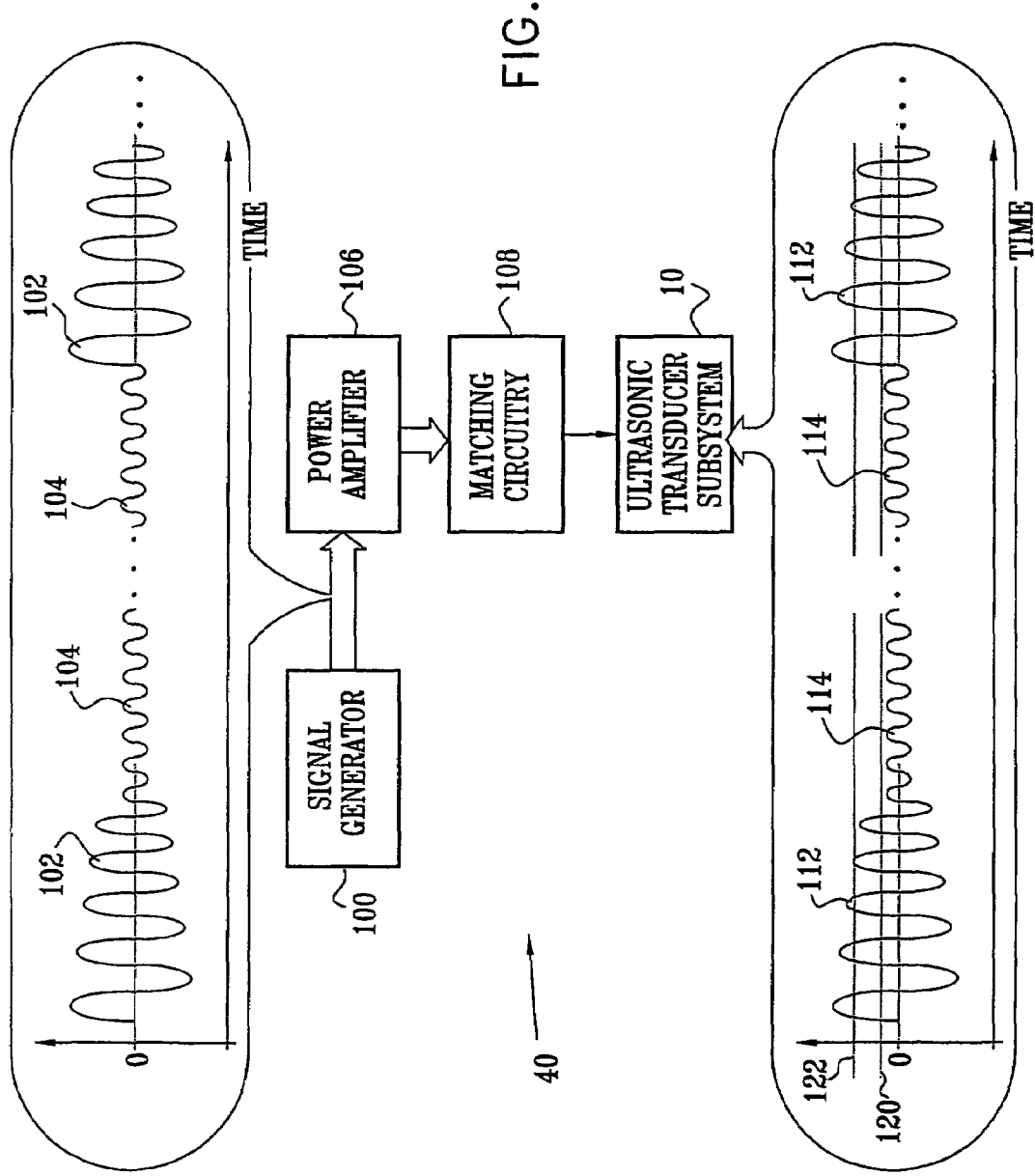

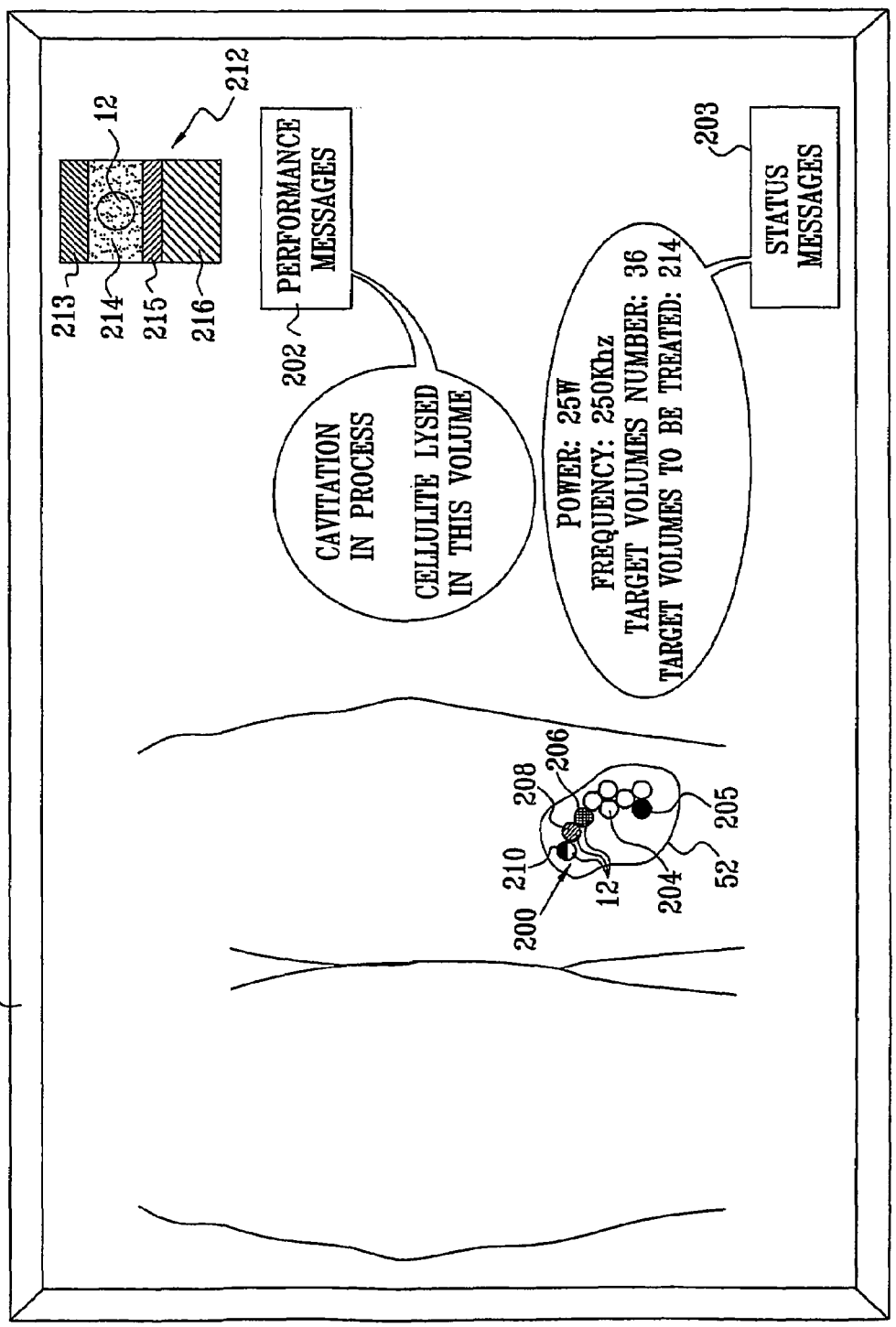

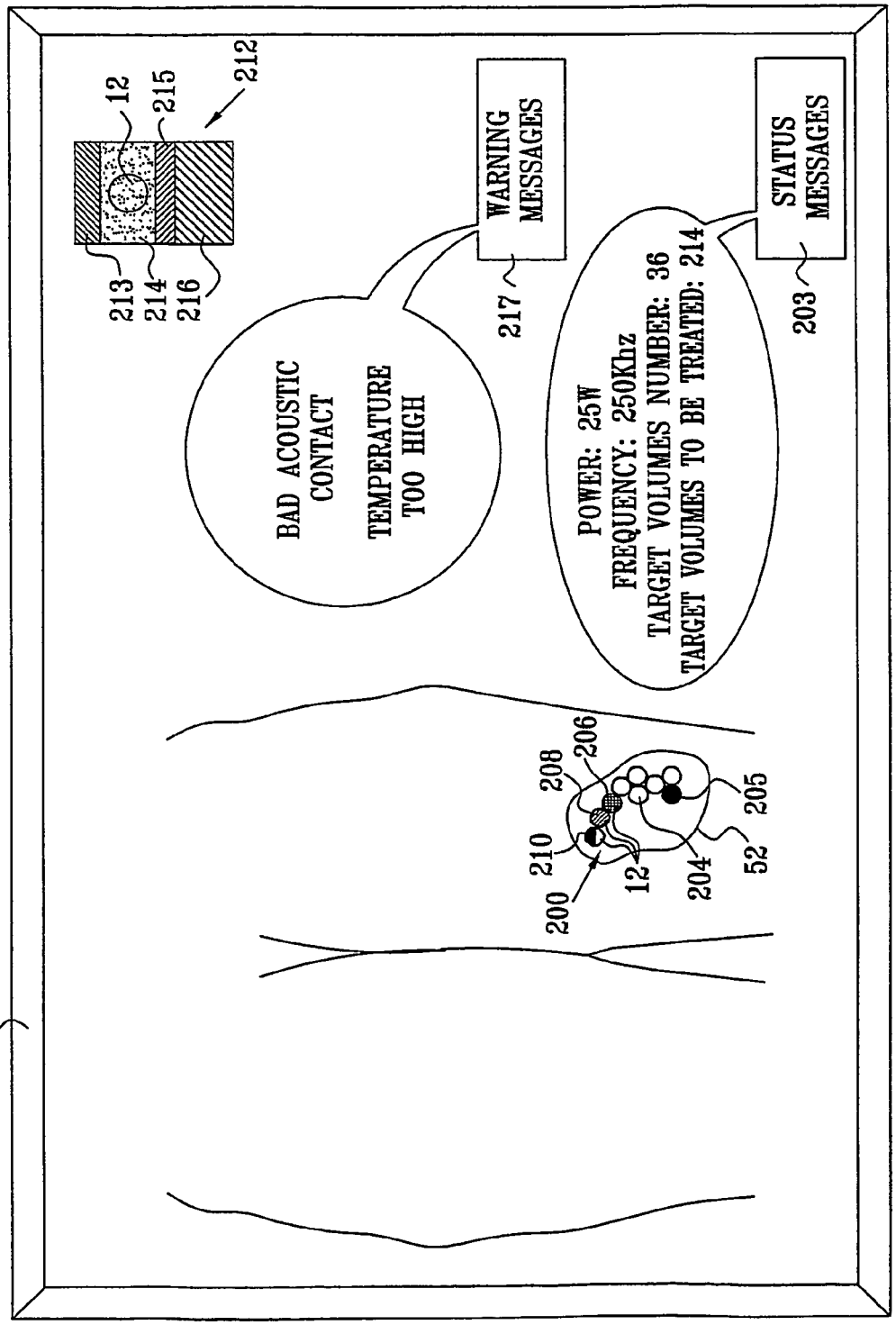

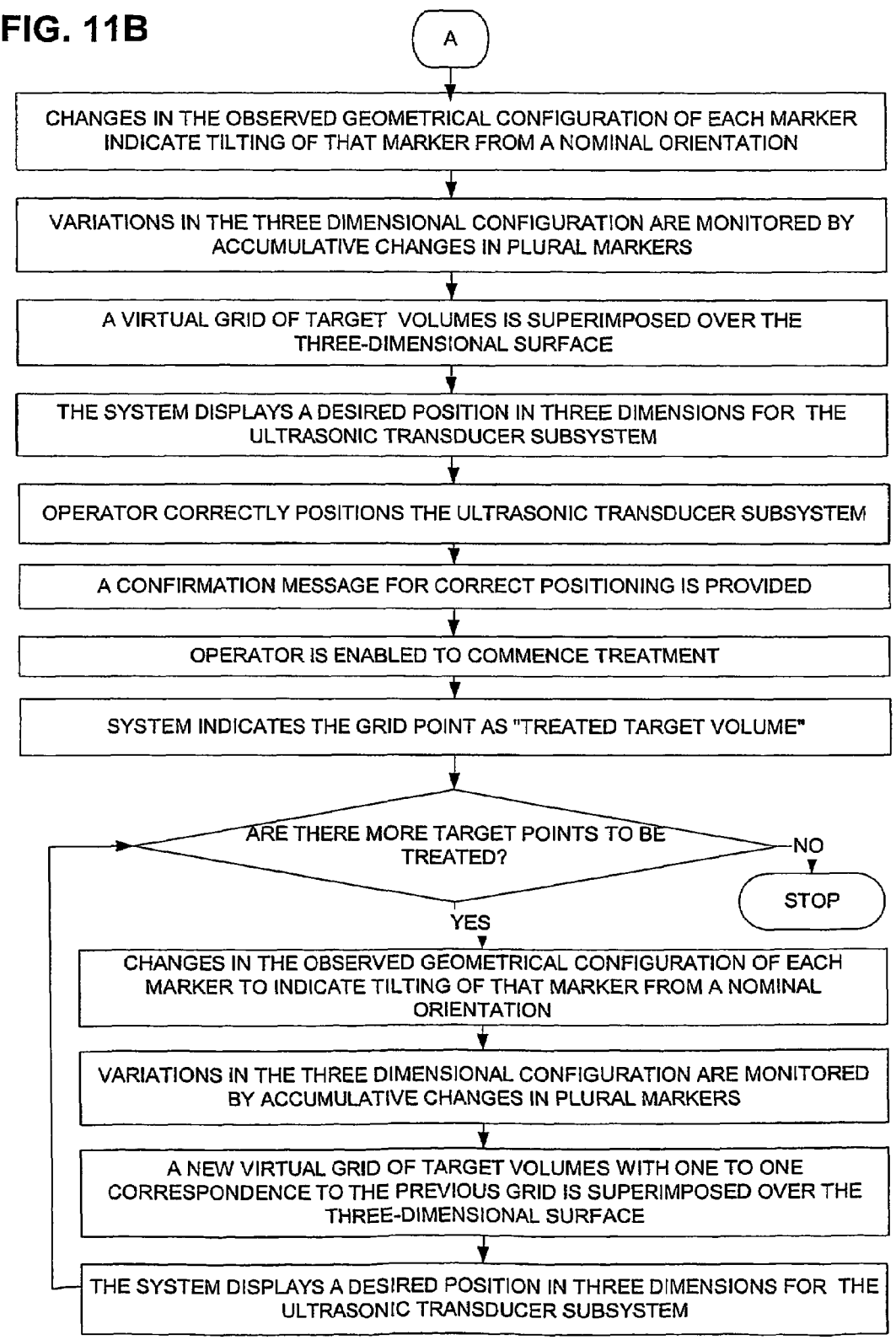

DEVICES AND METHODOLOGIES USEFUL IN BODY AESTHETICS

REFERENCE TO CO-PENDING APPLICATIONS

Reference is hereby made to applicant's copending PCT Application Serial No. PCT/IL01/01220 filed Dec. 31, 2001 and U.S. patent application Ser. No. 09/752,530, filed Jan. 3, 2001 and Ser. No. 10/021,238, filed Oct. 29, 2001, the disclosures of which are hereby incorporated by reference.

FIELD OF THE INVENTION

The present invention relates to body aesthetics generally and also to cellulite treatment and to devices and methodologies finding application therein.

BACKGROUND OF THE INVENTION

The following Patents and published patent applications are believed to represent the current state of the art:

| | | | | |
|---|---|---|---|---|
| U.S. Pat. No. 4,986,275; | U.S. Pat. No. 5,143,063; | U.S. Pat. No. 5,143,073; | U.S. Pat. No. 5,209,221; | U.S. Pat. No. 5,301,660; |
| U.S. Pat. No. 5,431,621; | U.S. Pat. No. 5,507,790; | U.S. Pat. No. 5,526,815; | U.S. Pat. No. 5,884,631; | U.S. Pat. No. 6,039,048; |
| U.S. Pat. No. 6,071,239; | U.S. Pat. No. 6,113,558; | U.S. Pat. No. 6,206,873; | GB2303552; | WO02/24076 |
| JP58181399; | JP11187493; | JP10277483; | JP8089893; | |

SUMMARY OF THE INVENTION

The present invention seeks to provide improved apparatus and methodology for ultrasonic cellulite treatment.

There is thus provided in accordance with a preferred embodiment of the present invention a method for lysing cellulite including the steps of:

directing focused ultrasonic energy at a target volume in a region of a body containing cellulite; and modulating the focused ultrasonic energy so as to selectively lyse the cellulite in the target volume and generally not lyse non-cellulite tissue in the target volume.

Additionally in accordance with a preferred embodiment of the present invention, there is provided a method for lysing cellulite including the steps of:

generating, at a source outside a body, ultrasonic energy which selectively generally lyses cellulite and generally does not lyse non-cellulite tissue; and directing the ultrasonic energy, from the source outside the body, at a target volume of a body containing cellulite.

Further in accordance with a preferred embodiment of the present invention there is provided a method for lysing cellulite including the steps of:

defining a region in a body at least partially by detecting spatial indications on the body; and directing ultrasonic energy at a multiplicity of target volumes within the region, which target volumes contain cellulite, thereby to selectively lyse the cellulite in the target volumes and generally not lyse non-cellulite tissue in the target volumes.

Further in accordance with a preferred embodiment of the present invention there is provided a method for lysing cellulite including the steps of:

sending a low power ultrasonic signal to the body, receiving the echo signal and analyzing it to identify the dermis, cellulite and fascia and computing the overlap of the target volume and cellulite area.

Additionally in accordance with a preferred embodiment of the present invention, there is provided a method for lysing cellulite including the steps of:

directing ultrasonic energy at a multiplicity of target volumes within the region which target volumes contain cellulite, thereby to selectively lyse the cellulite in the target volumes and generally not lyse non-cellulite tissue in the target volumes; and computerized tracking of the multiplicity of target volumes notwithstanding movement of the body.

There is additionally provided in accordance with a preferred embodiment of the present invention apparatus for lysing cellulite including:

a focused ultrasonic energy director, directing focused ultrasonic energy at a target volume in a region of a body containing cellulite; and a modulator, cooperating with the energy director to produce a focused ultrasonic energy so as to selectively lyse the cellulite in the target volume and generally not lyse non-cellulite tissue in the target volume.

There is further provided in accordance with a preferred embodiment of the present invention apparatus for lysing cellulite including:

a source outside a body generating ultrasonic energy;

an ultrasonic energy director, which employs the ultrasonic energy to selectively generally lyse cellulite and generally not lyse non-cellulite tissue in a target volume of a body containing cellulite.

There is additionally provided in accordance with a preferred embodiment of the present invention apparatus for lysing cellulite including the steps of:

a region definer, defining a region in a body at least partially by detecting spatial indications on the body; and a director, directing ultrasonic energy at a multiplicity of target volumes within the region, which target volumes contain cellulite thereby to selectively lyse the cellulite in the target volumes and generally not lyse non-cellulite tissue in the target volumes.

There is still further provided in accordance with a preferred embodiment of the present invention apparatus for lysing cellulite including:

a director, directing ultrasonic energy at a multiplicity of target volumes within the region which target volumes contain cellulite, thereby to selectively lyse the cellulite in the target volumes and generally not lyse non-cellulite tissue in the target volumes; and computerized tracking functionality providing computerized tracking of the multiplicity or target volumes notwithstanding movement of the body.

Preferably, directing focused ultrasonic energy generally prevents lysis of tissue outside of the target volume.

In accordance with a preferred embodiment of the present invention, the method also includes ultrasonic imaging of the region at least partially concurrently with directing the focused ultrasonic energy at the target volume.

Preferably, directing includes positioning at least one ultrasonic transducer relative to the body in order to direct the focused ultrasonic energy at the target volume.

The directing may also include varying the focus of at least one ultrasonic transducer in order to direct the focused ultrasonic energy at the target volume. Varying the focus may change the volume of the target volume, and/or the distance of the target volume from the at least one ultrasonic transducer.

The directing may also include positioning at least one ultrasonic transducer relative to the body in order to direct the focused ultrasonic energy at the target volume.

The method preferably also includes sensing ultrasonic energy coupling to an external surface of the body adjacent the target volume.

The method preferably additionally includes sensing of cavitation at the target volume.

Preferably, directing takes place from an ultrasonic transducer located outside of the body.

In accordance with a preferred embodiment of the present invention, the ultrasonic energy target volume is distal to the dermis and proximal to the fascia.

In accordance with a preferred embodiment of the present invention, the ultrasonic energy has a frequency in a range of 50 KHz-1000 KHz, more preferably in a range of 100 KHz-500 KHz, and most preferably in a range of 150 KHz-300 KHz.

Preferably, the modulating provides a duty cycle between 1:2 and 1:50, more preferably between 1:5 and 1:30 and most preferably between 1:10 and 1:20.

In accordance with a preferred embodiment of the present invention, the modulating provides between 2 and 1000 sequential cycles at an amplitude above a cavitation threshold, more preferably between 25 and 500 sequential cycles at an amplitude above a cavitation threshold and most preferably between 100 and 300 sequential cycles at an amplitude above a cavitation threshold.

Preferably, the modulating includes modulating the amplitude of the ultrasonic energy over time.

Preferably, directing includes directing focused ultrasonic energy at a multiplicity of target volumes in a time sequence.

In accordance with a preferred embodiment of the present invention, directing includes directing focused ultrasonic energy at plural ones of the multiplicity of target volumes at times, which at least partially overlap.

Preferably, at least some of the multiplicity of target volumes at least partially overlap in space.

In accordance with a preferred embodiment of the present invention, the method includes defining the region by marking at least one surface of the body. The method may also include defining the region by selecting at least one depth in the body and/or by detecting cellulite in the body and/or by detecting non-lysed cellulite.

Preferably directing also includes defining the target volumes as unit volumes of non-lysed cellulite within the region.

In accordance with a preferred embodiment of the present invention, modulating the ultrasonic energy so as to selectively lyse the cellulite in the multiplicity of target volumes proceeds sequentially in time wherein selective lysis of cellulite in each target volume takes place only following detection of non-lysed cellulite therein.

Preferably, the method also includes computerized tracking of the multiplicity of target volumes notwithstanding movement of the body.

Preferably, the computerized tracking includes sensing changes in the position of markings on the body and employing sensed changes for tracking the positions of the target volumes in the body.

Preferably, the modulation provides decreasing amplitude over time, which exceeds a cavitation threshold.

In accordance with a preferred embodiment of the present invention, the destruction of the cells can be done, instead of by direct lysis of the cells membrane, by induction of apoptosis of the cells by ultrasonic energy from a source outside the body.

There is still further provided in accordance with a preferred embodiment of the present invention apparatus for ultrasonic therapy comprising an ultrasonic energy director assembly comprising a plurality of Langevin ultrasonic transducers coupled together to provide focused ultrasonic energy on a target volume.

Preferably, the Langevin ultrasonic transducers each comprises a pair of piezoelectric elements separated by a positive contact electrode, and negative contact electrodes located on both sides of the pair of piezoelectric elements and held tightly against the pair of piezoelectric elements by a bolt and nut.

Preferably, the plurality of Langevin ultrasonic transducers are embedded in a vibration damping material to avoid mechanical cross talk therebetween. Preferably the apparatus for ultrasonic therapy includes a cooling system.

BRIEF DESCRIPTION OF THE DRAWINGS AND APPENDIX

The present invention will be understood and appreciated more fully from the following detailed description, taken in conjunction with the drawings and appendix in which:

FIG. 1 is a simplified pictorial illustration of the general structure and operation of ultrasonic cellulite treatment apparatus constructed and operative in accordance with a preferred embodiment of the present invention;

FIG. 2 is a simplified block diagram illustration of a preferred power source and modulator showing a pattern of variation of ultrasonic pressure over time in accordance with a preferred embodiment of the present invention;

FIGS. 3A and 3B are simplified pictorial illustrations of the appearance of an operator interface display during normal operation and faulty operation respectively;

Figure 11A:
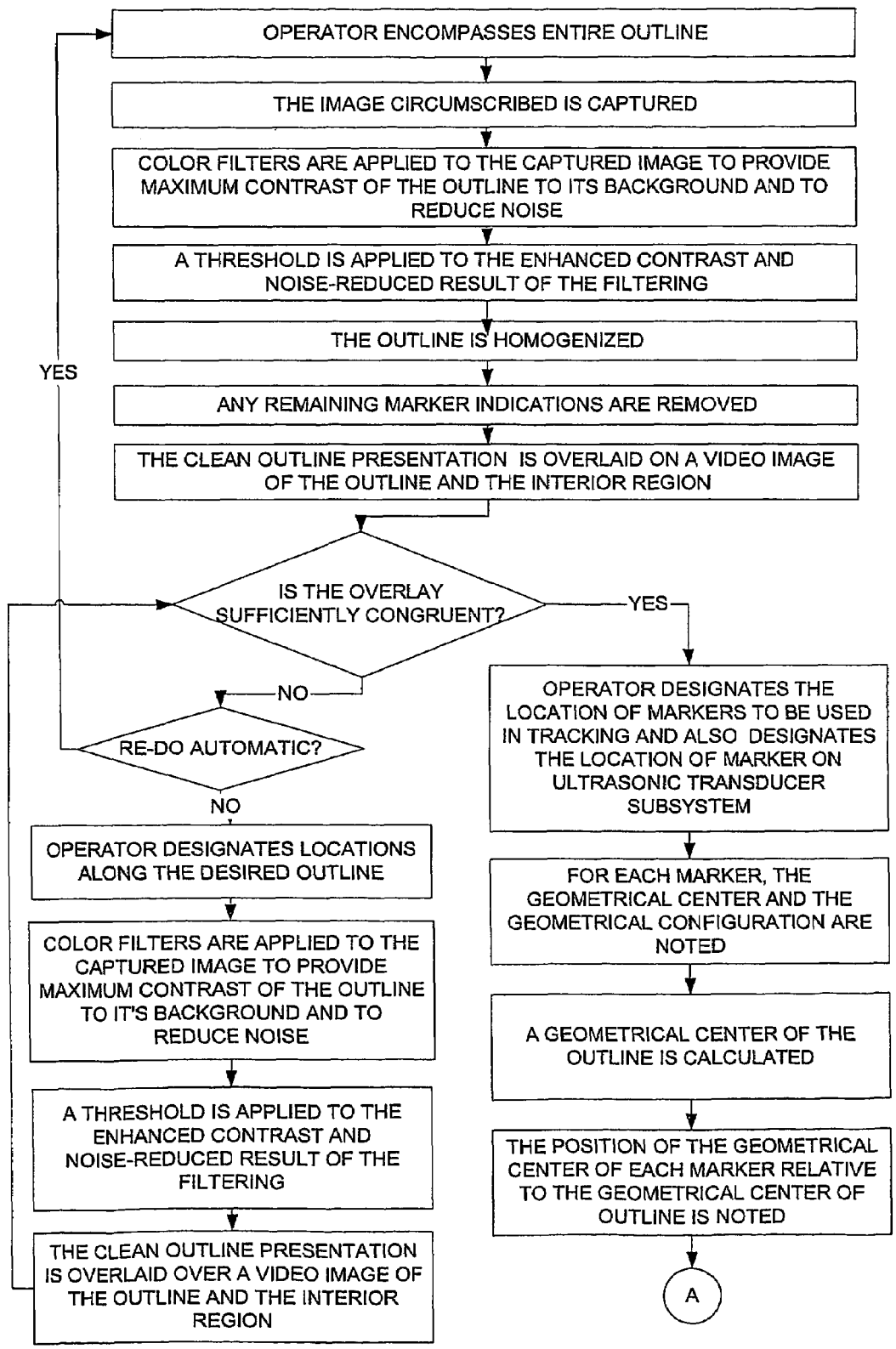

FIGS. 11A, and 11B which are together a simplified flowchart illustrating steps in carrying out unit by unit tracking within a time variable three dimensional outline in accordance with a preferred embodiment of the present invention;

BRIEF DESCRIPTION OF THE APPENDIX

The Appendix includes computer listings which, taken together, form a computational tracking functionality in accordance with a preferred software embodiment of the present invention.

DETAILED DESCRIPTION OF PREFERRED EMBODIMENTS

Cellulite is the appearance of an unattractive dimpled skin or "dimpled fat" on the outer thighs, buttocks and other body areas where large areas of fat are found in close proximity to the skin. "Cellulite" is not a medical term but commonly refers to a "disease" that affects only women. Most women over the age of 18 have some degree of cellulite. The gender specificity is an expression of the difference in the inner structural connection between the skin and subcutaneous tissues. Vertical fibrous tissue strands connect the skin to deeper tissue layers and create separate compartments that contain fat cells. When fat cells increase in size, these compartments bulge and produce a waffled appearance of the skin since the vertical connective septa are inelastic compared to the fat tissue. The fat in the cellulite is the same like the fat tissue elsewhere. A person does not have to be overweight to develop this dimpled skin called cellulite. Cellulite is not always reduced by weight loss. Destruction of the fat content of cellulite is known to improve the skin appearance. The destruction can be achieved in accordance with the present invention by breaking cell membranes through the application of cavitational mechanical forces on the cells membranes or by induction of apoptosis, e.g. programmed cell death.

Reference is now made to FIG. 1, which is a simplified pictorial illustration of the general structure and operation of ultrasonic cellulite treatment apparatus constructed and operative in accordance with a preferred embodiment of the present invention. As seen in FIG. 1, an ultrasonic energy generator and director, such as an ultrasonic transducer subsystem 10, disposed outside a body, generates ultrasonic energy which, by suitable placement of the transducer subsystem 10 relative to the body is directed to a target volume 12 inside the body and is operative to selectively generally lyse cellulite and generally not lyse non-cellulite tissue in the target volume.

A preferred embodiment of ultrasonic energy generator and director useful in the present invention comprises an ultrasonic therapeutic transducer assembly 13 including a curved phased array 14 of transducers 15, typically defining a portion of a sphere or of a cylinder. The transducers 15 may be of any suitable configuration, shape and distribution. Preferably, transducer 15 is preferably a piezoelectric transducer or a Langevin type transducer. A preferred Langevin type transducer is shown and includes a pair of piezoelectric elements 17 separated by positive contact electrode 18. A metal bolt 19 cooperates with a metal disk 20 and a nut 21. Negative contact electrodes 23 are located on both sides of the pair of piezoelectric elements 17 and held together tightly against the pair of piezoelectric elements 17 and the disk 20 by the bolt 19 and the nut 21. Pair of piezoelectric elements 17 can be multiplied to any even number of elements.

Preferably, transducers 15 are embedded in a vibration damping material 24 to avoid mechanical cross talk between transducers 15. An inner cooling system 25 may be associated with the transducers 15. An intermediate element 26, formed of a material such as polyurethane, which has acoustic impedance similar to that of soft mammalian tissue, generally fills the curvature defined by phased array 14 and defines a contact surface 27 for engagement with the body, typically via a suitable coupling gel (not shown). Contact surface 27 may be planar, but need not be.

Suitably modulated AC electrical power is supplied by conductors 28 to negative contact electrodes 23 to cause the transducers 15 to provide a desired focused acoustic energy output.

In accordance with a preferred embodiment of the present invention, a cellulite imaging ultrasonic transducer subassembly 29 is incorporated within transducer assembly 13 and typically comprises a piezoelectric transducer 30 having conductive surfaces 31 associated with opposite surfaces thereof Suitably modulated AC electrical power is supplied by conductors 32 to conductive surfaces 31 in order to cause the piezoelectric transducer 30 to provide an acoustic energy output. Conductors 32, coupled to conductive surfaces 31, also provide an imaging output from imaging ultrasonic transducer subassembly 29.

It is appreciated that high frequency commercially available ultrasonic transducers may be employed for imaging or alternatively high frequency A-mode transducers may be used for this purpose. As a further alternative, cellulite imaging ultrasonic transducer subassembly 29 may be eliminated.

It is further appreciated that various types of ultrasonic transducer assemblies 13 may be employed. For example, such transducer assemblies may include multiple piezoelectric elements, multi-layered piezoelectric elements and piezoelectric elements of various shapes and sizes arranged in a phase array, multiple Langevin type elements multi-layered Langevin type elements and Langevin type elements of various shapes and sizes arranged in a phase array.

In a preferred embodiment of the present invention shown in FIG. 1, the ultrasonic energy generator and director are combined in transducer assembly 13. Alternatively, the functions of generating ultrasonic energy and focusing such energy may be provided by distinct devices.

In accordance with a preferred embodiment of the present invention, a skin temperature sensor 34, such as an infrared sensor, may be mounted in proximity to the contact surface 27 as shown in FIG. 1 Further in accordance with a preferred embodiment of the present invention a transducer temperature sensor 36, such as a thermocouple may also be mounted alongside imaging ultrasonic transducer subassembly 29.

Ultrasonic transducer subsystem 10 preferably receives suitably modulated electrical power from a power source and modulator assembly 40, forming part of a control subsystem 42. Control subsystem 42 also typically includes a cellulite treatment control computer 44, having associated therewith a camera 46, such as a video camera, and a display 48. A preferred embodiment of power source and modulator assembly 40 is illustrated in FIG. 2 and described hereinbelow. Ultrasonic transducer subsystem 10 is preferably positioned automatically or semi-automatically as by an X-Y-Z positioning assembly 49. Alternatively, ultrasonic transducer subsystem 10 may be positioned at desired positions by an operator.

In accordance with a preferred embodiment of the present invention, camera 46 is operative for imaging a portion of the body on which cellulite treatment is to be performed. A picture of the portion of the patients body viewed by the camera is preferably displayed in real time on display 48.

An operator may designate the outline of a region containing cellulite. In accordance with one embodiment of the present invention, designation of this region is effected by an operator marking the skin of a patient with an outline 50, which outline is imaged by camera 46 and displayed on display 48 and is also employed by the cellulite treatment control computer 44 for controlling the application of ultrasonic energy to locations within the region. A computer calculated representation of the outline may also be displaced on display 48 as designated by reference numeral 52. Alternatively, the operator may make a virtual marking on the skin, such as by using a digitizer (not shown), which also may provide computer calculated outline representation 52 on display 48.

In addition to the outline representation 52, the functionality of the system of the present invention preferably also employs a plurality of markers 54 which are typically located outside the region containing cellulite, but may be located inside the region designated by outline 50. Markers 54 are visually sensible markers, which are clearly seen by camera 46, captured by camera 46 and displayed on display 48. Markers 54 may be natural anatomic markers, such as distinct portions of the body or alternatively artificial markers such as colored stickers. These markers are preferably employed to assist the system in dealing with deformation of the region nominally defined by outline 50 due to movement and reorientation of the body. Preferably, the transducer subsystem 10 also bears a visible marker 56 which is also captured by camera 46 and displayed on display 48.

Markers 54 and 56 are typically processed by computer 44 and may be displayed on display 48 as respective computed marker representations 58 and 60 on display 48.

FIG. 1 illustrates the transducer subsystem 10 being positioned on the body over a location within the region containing cellulite. Blocks designated by reference numerals 62 and 64 show typical portions of a region containing cellulite, respectively before and after cellulite treatment in accordance with a preferred embodiment of the invention. It is seen from a comparison of blocks 62 and 64 that, in accordance with a preferred embodiment of the present invention, within the region containing cellulite, the cellulite, designated by reference numeral 66, is lysed, while non-cellulite tissue, such as connective tissue, designated by reference numeral 68, dermis designed by reference 69, fascia designated by reference 70 and deep fat designated by reference 67 are not lysed.

Reference is now FIG. 2, which is a simplified block diagram illustration of a preferred power source and modulator assembly 40 (FIG. 1), showing a pattern of variation of ultrasonic pressure over time in accordance with a preferred embodiment of the present invention. As seen in FIG. 2, the power source and modulator assembly 40 preferably comprises a signal generator 100 which provides a time varying signal which is modulated so as to have a series of relatively high amplitude portions 102 separated in time by a series of typically relatively low amplitude portions 104. Each relatively high amplitude portion 102 preferably corresponds to a cavitation period and preferably has decreasing amplitude over time.

Preferably the relationship between the time durations of portions 102 and portions 104 is such as to provide a duty cycle between 1:2 and 1:50, more preferably between 1:5 and 1:30 and most preferably between 1:10 and 1:20.

Preferably, the output of signal generator 100 has a frequency in a range of 50 KHz-1000 KHz, more preferably between 100 KHz-500 KHz and most preferably between 150 KHz-300 KHz.

The output of signal generator 100 is preferably provided to a suitable power amplifier 106, which outputs via impedance matching circuitry 108 to an input of ultrasonic transducer subsystem 10 (FIG. 1), which converts the electrical signal received thereby to a corresponding ultrasonic energy output. As seen in FIG. 2, the ultrasonic energy output comprises a time varying signal which is modulated correspondingly to the output of signal generator 100 so as to having a series of relatively high amplitude portions 112, corresponding to portions 102, separated in time by a series of typically relatively low amplitude portions 114, corresponding to portions 104.

Each relatively high amplitude portion 102 preferably corresponds to a cavitation period and has amplitude at a target volume 12 (FIG. 1) in the body, which exceeds a cavitation-maintaining threshold 120 and preferably has decreasing amplitude over time. At least an initial pulse of each relatively high amplitude portion 112 has amplitude at the target volume 12, which also exceeds a cavitation initiation threshold 122.

Relatively low amplitude portions 114 have amplitude that lies below both thresholds 120 and 122.

Preferably the relationship between the time durations of portions 112 and portions 114 is such as to provide a duty cycle between 1:2 and 1:50, more preferably between 1:5 and 1:30 and most preferably between 1:10 and 1:20.

Preferably, the ultrasonic energy output of ultrasonic transducer 10 has a frequency in a range of 50 KHz-1000 KHz, more preferably between 100-500 KHz and most preferably between 150 KHz-300 KHz.

Preferably, each high amplitude portion 112 is comprised of between 2 and 1000 sequential cycles at an amplitude above the cavitation maintaining threshold 120, more preferably between 25 and 500 sequential cycles at an amplitude above the cavitation maintaining threshold 120 and most preferably between 100 and 300 sequential cycles at an amplitude above the cavitation maintaining threshold 120.

Reference is now made to FIGS. 3A and 3B, which are simplified pictorial illustrations of the appearance of an operator interface display during normal operation and faulty operation respectively. As seen in FIG. 3A, during normal operation, display 48 typically shows a plurality of target volumes 12 (FIG. 1) within a calculated target region 200, typically delimited by outline representation 52 (FIG. 1). Additionally, display 48 preferably provides one or more pre-programmed performance messages 202 and status messages 203.

It is seen the various target volumes 12 are shown with different shading in order to indicate their treatment status. For example, unshaded target volumes, here designated by reference numerals 204, have already experienced cellulite treatment A blackened target volume 12, designated by reference numeral 206 is the target volume next in line for cellulite treatment. A partially shaded target volume 206 typically represents a target volume, which has been insufficiently treated to achieve complete cellulite treatment, typically due to insufficient treatment duration.

Other types of target volumes, such as those not to be treated due to insufficient presence of cellulite therein or for other reasons, may be designated by suitable colors or other designations, and are here indicated by reference numerals 208 and 210.

Typical performance messages 202 may include "CAVITATION IN PROCESS" and "CELLULITE LYSED IN THIS VOLUME". Typical status messages 203 may include an indication of the power level, the operating frequency, the number of target volumes 12 within the calculated target region 200 and the number of target volumes 12 which remain to undergo cellulite treatment.

Display 48 also preferably includes a graphical cross sectional presentation 212 derived from an ultrasonic image preferably provided by imaging ultrasonic transducer subassembly 29 (FIG. 1). Presentation 212 preferably indicates various tissues in the body in cross section and shows the target volumes 12 in relation thereto. In accordance with a preferred embodiment of the present invention, presentation 212 may also provide a visually sensible indication of cavitation within the target volume 12. In accordance with a preferred embodiment of the present invention, presentation 212 may also provide schematic representations 213, 214, 215 and 216 of dermis 69, cellulite 66, fascia 70 and deep fat 67, respectively.

Turning to FIG. 3B, it is seen that during abnormal operation, display 48 provides pre-programmed warning messages 217. Typical warning messages may include "BAD ACOUSTIC CONTACT", "TEMPERATURE TOO HIGH". The "TEMPERATURE TOO HIGH" message typically relates to the skin tissue, although it may alternatively or additionally relate to other tissue inside or outside of the target volume of the transducer subsystem 10 (FIG. 1).

Additionally, display 48 may also provided a visual indication of both lysed cellulite and non-lysed cellulite following treatment.

Figure 4:
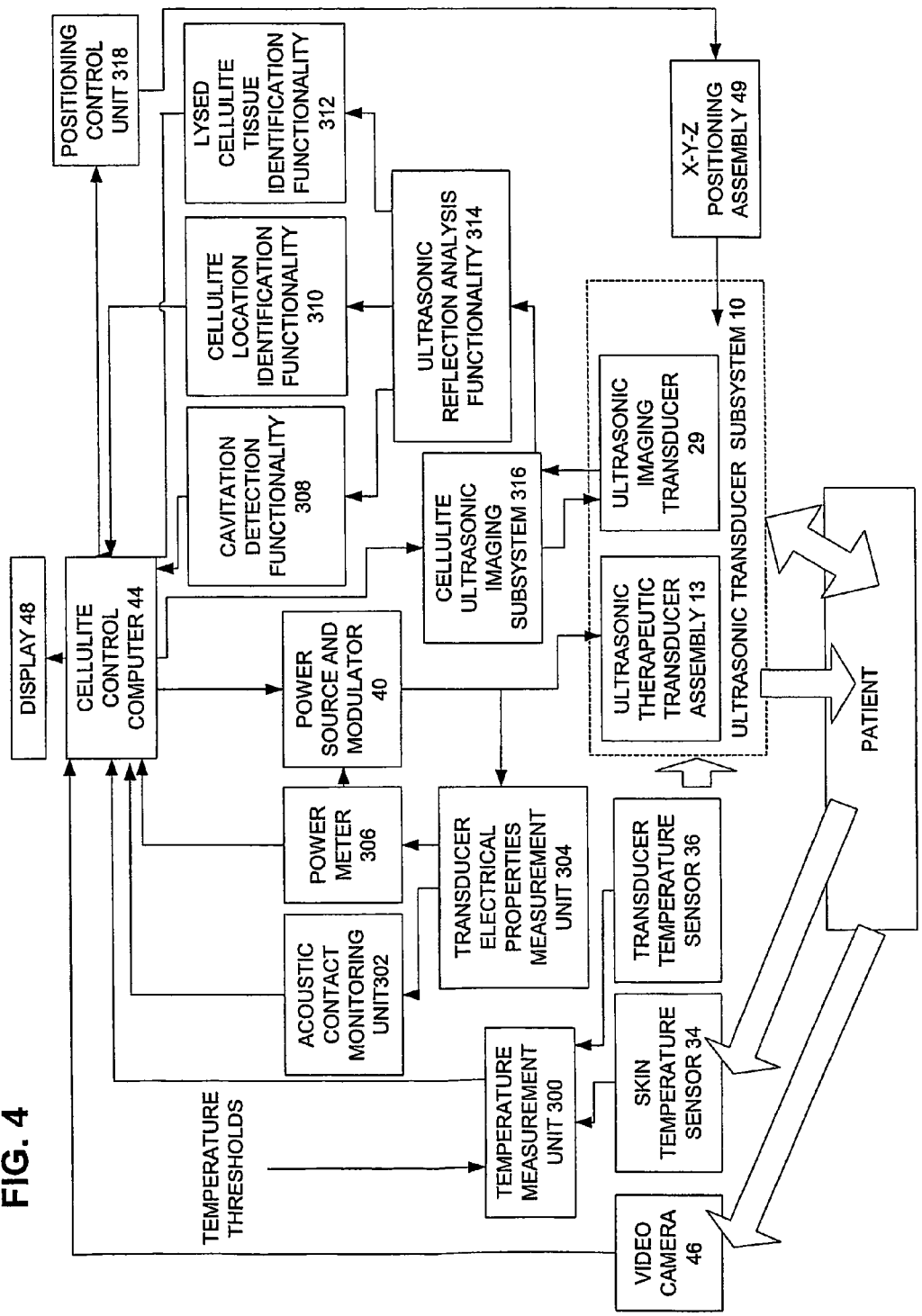
FIG. 4 is a simplified block diagram illustration of an ultrasonic cellulite treatment system constructed and operative in accordance with a preferred embodiment of the present invention.

Reference is now made to FIG. 4, which illustrates an ultrasonic cellulite treatment system constructed and operative in accordance with a preferred embodiment of the present invention. As described hereinabove with reference to FIG. 1 and as seen in FIG. 4, the ultrasonic cellulite treatment system comprises a cellulite treatment control computer 44, which outputs to a display 48. Cellulite treatment control computer 44 preferably receives inputs from video camera 46 (FIG. 1) and from a temperature measurement unit 300, which receives temperature threshold settings as well as inputs from skin temperature sensor 34 (FIG. 1) and transducer temperature sensor 36 (FIG. 1). Temperature measurement unit 300 preferably compares the outputs of both sensors 34 and 36 with appropriate threshold settings and provides an indication to cellulite treatment control computer 44 of temperature exceeding either temperature threshold.

Cellulite treatment control computer 44 also preferably receives an input from an acoustic contact-monitoring unit 302, which in turn preferably receives an input from a transducer electrical properties measurement unit 304. Transducer electrical properties measurement unit 304 preferably monitors the output of power source and modulator assembly 40 (FIG. 1) applies to ultrasonic therapeutic transducer assembly 13.

An output of transducer electrical properties measurement unit 304 is preferably also supplied to a power meter 306, which provides an output to the cellulite treatment control computer 44 and a feedback output to power source and modulator assembly 40.

Cellulite treatment control computer 44 also preferably receives inputs from cavitation detection functionality 308, cellulite location identification functionality 310 and lysed cellulite identification functionality 312, all of which receive inputs from ultrasonic reflection analysis functionality 314. Ultrasonic reflection analysis functionality 314 receives ultrasonic imaging inputs from an ultrasonic imaging subsystem 316, which operates ultrasonic imaging transducer 29 (FIG. 1).

Cellulite treatment control computer 44 provides outputs to power source and modulator assembly 40, for operating ultrasonic therapeutic transducer assembly 13 and to ultrasonic imaging subsystem 316, for operating ultrasonic imaging transducer 29. A positioning control unit 318 also receives an output from cellulite treatment control computer 44 for driving X-Y-Z positioning assembly 49 (FIG. 1) in order to correctly position transducer subsystem 10, which includes ultrasonic therapeutic transducer assembly 13 and ultrasonic imaging transducer 29.

Figure 5A:
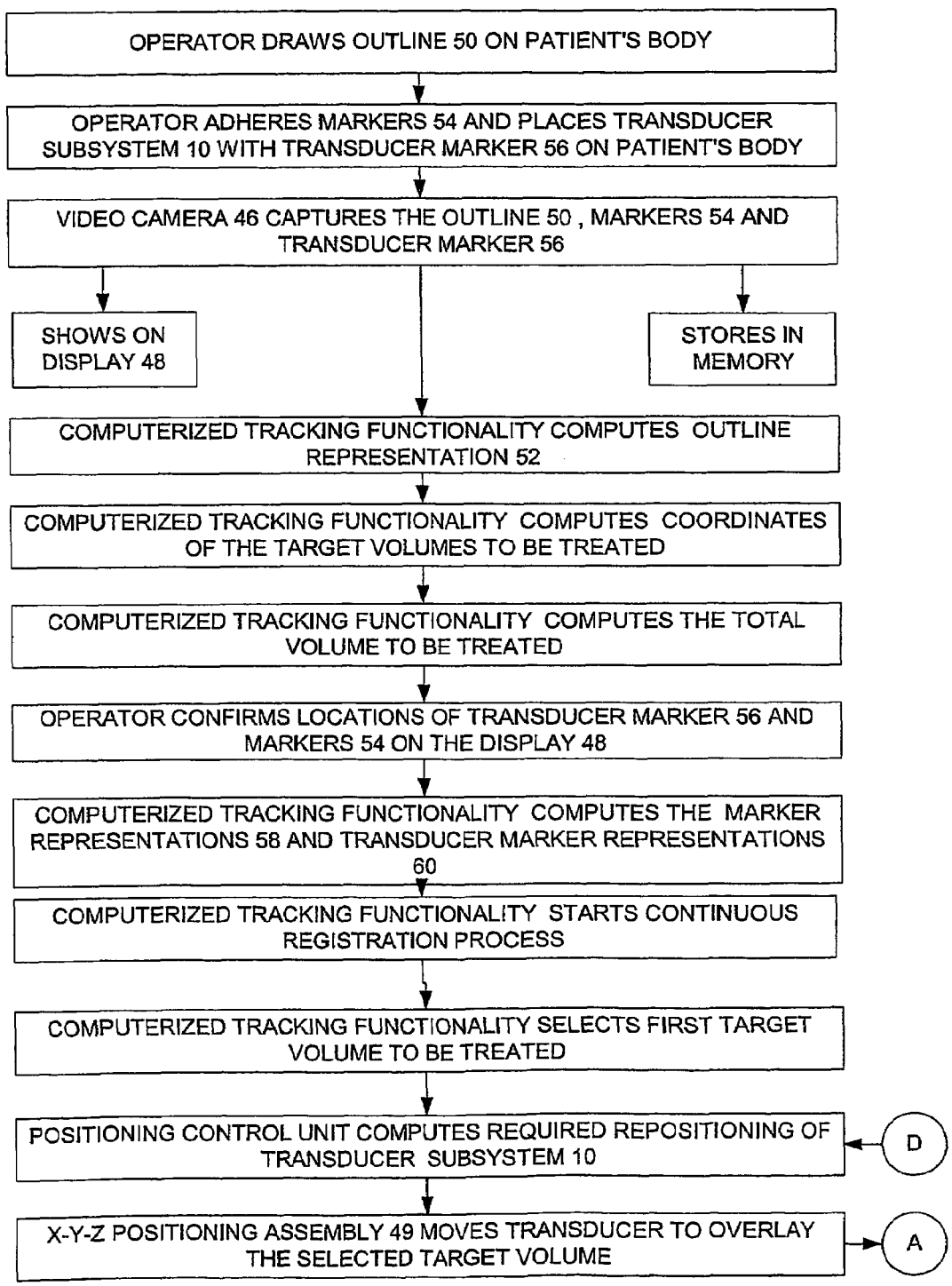
FIGS. 5A, 5B and 5C are together a simplified flowchart illustrating operator steps in carrying out cellulite treatment in accordance with a preferred embodiment of the present invention.
Figure 5B:
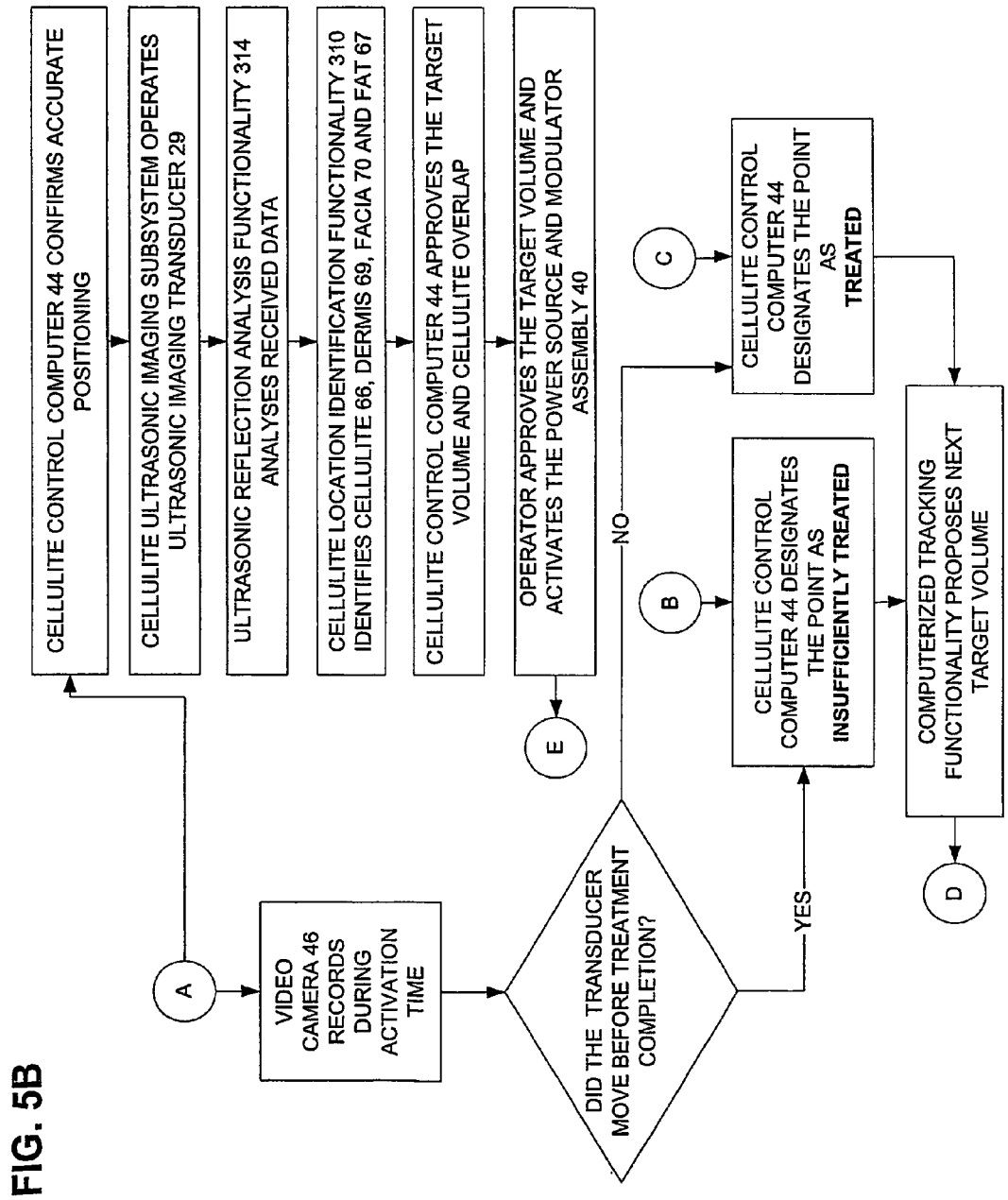
Figure 5C:
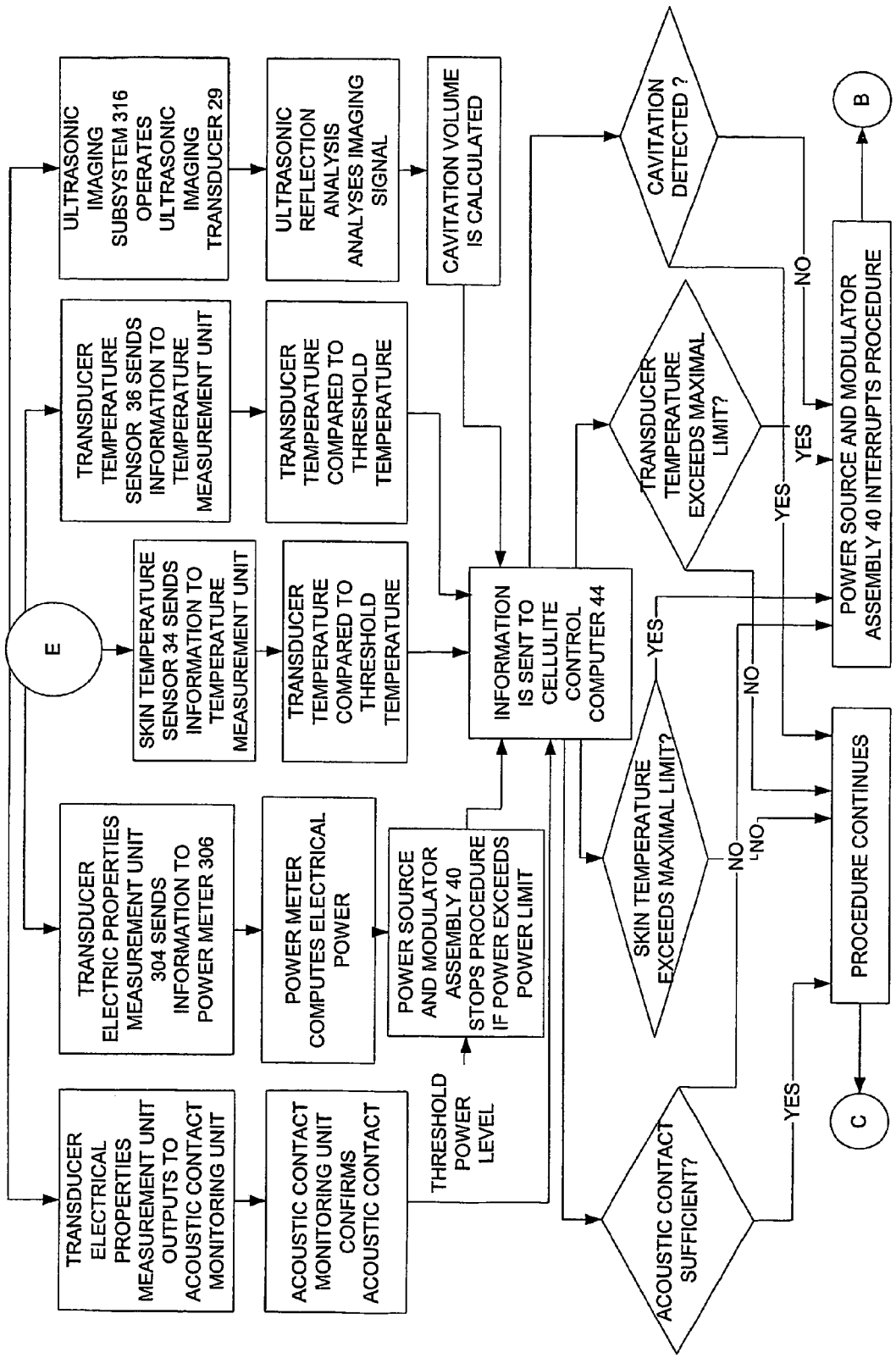

Reference is now made to FIGS. 5A, 5B and 5C, which are together a simplified flowchart illustrating operator steps in carrying out cellulite treatment in accordance with a preferred embodiment of the present invention. As seen in FIG. 5A, initially an operator preferably draws an outline 50 (FIG. 1) on a patients body. Preferably, the operator also adheres stereotactic markers 54 (FIG. 1) to the patients body and places transducer subsystem 10, bearing transducer marker 56, at a desired location within outline 50.

Camera 46 (FIG. 1) captures outline 50 and markers 54 and 56. Preferably, outline 50 and markers 54 and 56 are displayed on display 48 in real time. The output of camera 46 is also preferably supplied to a memory associated with cellulite treatment control computer 44 (FIG. 1).

A computerized tracking functionality preferably embodied in cellulite treatment control computer 44 preferably employs the output of camera 46 for computing outline representation 52, which may be displayed for the operator on display 48. The computerized tracking functionality also preferably computes coordinates of target volumes for cellulite treatment, as well as adding up the total volume of tissue sought to undergo cellulite treatment.

Preferably the operator confirms the locations of markers 54 and 56 on display 48 and the computerized tracking functionality calculates corresponding marker representations 58 and 60.

In accordance with a preferred embodiment of the present invention the computerized tracking functionality employs markers 54 and marker representations 58 for continuously maintaining registration of outline 50 with respect to outline representation 52, and thus of target volumes 12 with respect to the patient's body, notwithstanding movements of the patients body during treatment, such as due to breathing or any other movements, such as the patient leaving and returning to the treatment location.

The computerized tracking functionality selects an initial target volume to be treated and positioning control unit 318 (FIG. 4), computes the required repositioning of transducer subsystem 10. X-Y-Z positioning assembly 49 repositions transducer subsystem 10 to overlie the selected target volume.

Referring additionally to FIG. 5B, it is seen that following repositioning of transducer subsystem 10, the cellulite treatment control computer 44 confirms accurate positioning of transducer subsystem 10 with respect to the selected target volume. The ultrasonic imaging subsystem 316 (FIG. 4) operates ultrasonic imaging transducer 29, causing it to provide an output to ultrasonic reflection analysis functionality 314 for analysis.

Cellulite location identification functionality 310 (FIG. 4) is operative to identify dermis 69, cellulite 66, fascia 70 and deep fat 67. Upon the cellulite computer 44 receiving and approving of an indication of cellulite location, an operator may approve the selected target volume and activate the power source and modulator assembly 40 (FIG. 1).

Turning additionally to FIG. 5C, it is seen that the following functionalities take place:

Transducer electrical properties measurement unit 304 provides an output to acoustic contact monitoring unit 302, which determines whether sufficient acoustic contact with the patient is present preferably by analyzing the current and voltage at therapeutic transducer assembly 13.

Transducer electrical properties measurement unit 304 provides an output to power meter 306, which computes the average electrical power received by the therapeutic transducer assembly 13. If the average electrical power received by the therapeutic transducer assembly 13 exceeds a predetermined threshold, operation of the power source and modulator assembly 40 may be automatically terminated.

Skin temperature sensor 34 measures the current temperature of the skin at transducer subsystem 10 and supplies it to temperature measurement unit 300, which compares the skin temperature to the threshold temperature. Similarly, transducer temperature sensor 36 measures the current temperature at transducer subsystem 10 and supplies it to temperature measurement unit 300, which compares the transducer subsystem temperature to the threshold temperature. The outputs of temperature measurement unit 300 are supplied to cellulite treatment control computer 44.

The ultrasonic imaging subsystem 316 operates ultrasonic imaging transducer 29 and supplies an imaging output, which is analyzed by ultrasonic reflection analysis functionality 314. The result of this analysis is employed for cavitation detection and a cavitation detection output is supplied to cellulite treatment control computer 44.

Should any of the following four conditions occur, the power source and modulator assembly 40 automatically terminates operation of therapeutic transducer assembly 13. Should none of the following conditions occur, the automatic operation of power source and modulator assembly 40 continues:
1. Acoustic contact is insufficient.
2. Skin temperature exceeds skin threshold temperature level.
3. Transducer assembly 13 temperature exceeds transducer threshold temperature level.
4. Cavitation is not detected.

Returning to FIG. 5B, it is noted that during automatic operation of power source and modulator assembly 40, video camera 46 preferably records the target region and notes whether the transducer subsystem 10 remained stationary during the entire treatment duration of the selected target volume 12. If so, and if none of the aforesaid four conditions took place cellulite treatment control computer 44 confirms that the selected target volume was treated. The computerized tracking functionality of cellulite treatment control computer 44 then proposes a further target volume 12 to be treated.

If, however, the transducer subsystem 10 did not remain stationary for a sufficient duration, the selected target volume is designated by cellulite treatment control computer 44 as having been insufficiently treated.

It is appreciated that by using multiple transducers multiplicity of target volumes can be treated at various time patterns such as sequential time patterns or partially overlapping time patterns.

It is also appreciated that the multiplicity of target volumes may also overlap in space or partially overlap in space.

Figure 6:
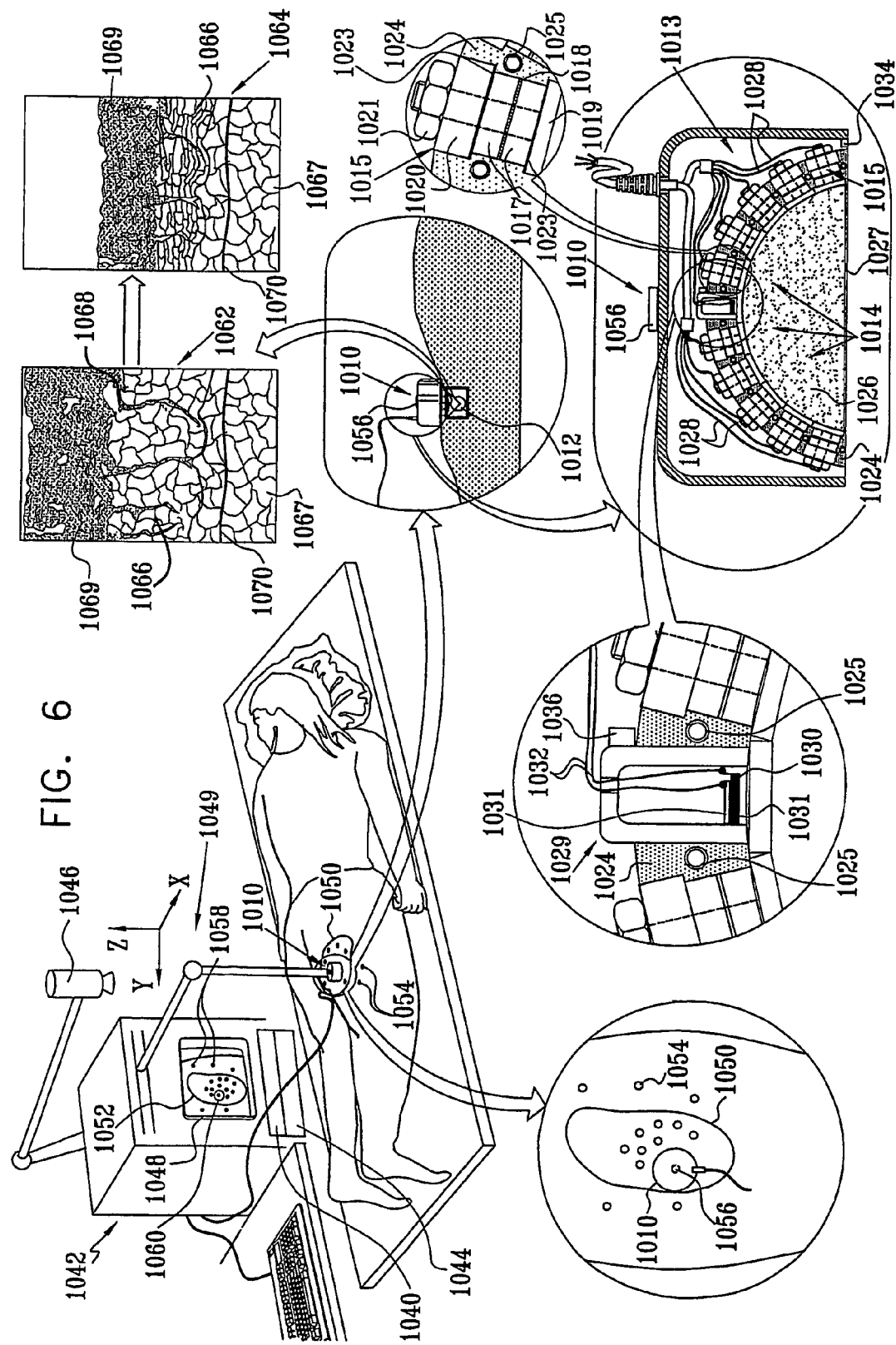
FIG. 6 is a simplified pictorial illustration of the general structure and operation of ultrasonic apoptosis induction apparatus constructed and operative in accordance with a preferred embodiment of the present invention.

Reference is now made to FIG. 6, which is a simplified pictorial illustration of the general structure and operation of ultrasonic apoptosis induction apparatus constructed and operative in accordance with a preferred embodiment of the present invention and particularly useful for inducing apoptosis of cellulite and fat. As seen in FIG. 6 an ultrasonic energy generator and director, such as an ultrasonic transducer subsystem 1010 disposed outside a body generates ultrasonic energy which, by suitable placement of the transducer subsystem 1010 relative to the body, is directed to a target volume 1012 inside the body and is operative to selectively generally induce apoptosis in cellulite and fat and generally not induce apoptosis in non-cellulite and non-fat tissue in the target volume.

A preferred embodiment of ultrasonic energy generator and director useful in the present invention comprises an ultrasonic therapeutic transducer assembly 1013 including a curved phased array 1014 of transducers 1015, typically defining a portion of a sphere or of a cylinder. The transducers 1015 may be of any suitable configuration, shape and distribution. Preferably, transducer 1015 is preferably a piezoelectric transducer or a Langevin type transducer. A preferred Langevin type transducer is shown and includes a pair of piezoelectric elements 1017 separated by a positive contact electrode 1018. A metal bolt 1019 cooperates with a metal disk 1020 and a nut 1021. Negative contact electrodes 1023 are located on both sides of the pair of piezoelectric elements 1017 and are electrically insulated from the bolt 1019 and the disk 1020.

Preferably transducers 1015 are embedded in a vibration damping material 1024 to avoid mechanical cross talk between transducers 1015. An internal cooling system 1025 may be associated with the transducers 1015. An intermediate element 1026 formed of a material such as polyurethane, which has acoustic impedance similar to that of soft mammalian tissue, generally fills the curvature defined by phased array 1014 and defines a contact surface 1027 for engagement with the body, typically via a suitable coupling gel (not shown). Contact surface 1027 may be planar, but need not be.

Suitably modulated AC electrical power is supplied by conductors 1028 to electrodes 1018 and 1023 of transducers 1015 to cause the array 1014 of transducers 1015 to provide a desired focused acoustic energy output.

In accordance with a preferred embodiment of the present invention, a cellulite imaging ultrasonic transducer subassembly 1029 is incorporated within transducer assembly 1013 and typically comprises a piezoelectric transducer 1030 having conductive surfaces 1031 associated with opposite surfaces thereof. Suitably modulated AC electrical power is supplied by conductors 1032 to conductive surfaces 1031 in order to cause the piezoelectric transducer 1030 to provide an acoustic energy output. Conductors 1032, coupled to conductive surfaces 1031, also provide an imaging output from imaging ultrasonic transducer subassembly 1029.

It is appreciated that high frequency commercially available ultrasonic transducers may be employed for imaging or alternatively high frequency A-mode transducers may be used for this purpose. As a further alternative, imaging ultrasonic transducer subassembly 1029 may be eliminated.

It is further appreciated that various types of ultrasonic transducer assemblies 1013 may be employed. For example, such transducer assemblies may include multiple piezoelectric elements, multi-layered piezoelectric elements and piezoelectric elements of various shapes and sizes arranged in a phase array, multiple Langevin type elements, multi-layered Langevin type elements and Langevin type elements of various shapes and sizes arranged in a phase array.

In a preferred embodiment of the present invention shown in FIG. 6, the ultrasonic energy generator and director are combined in transducer assembly 1013. Alternatively, the functions of generating ultrasonic energy and focusing such energy may be provided by distinct devices.

In accordance with a preferred embodiment of the present invention, a skin temperature sensor 1034, such as an infrared sensor, may be mounted in proximity to the contact surface 1027, as shown in FIG. 6. Further in accordance with a preferred embodiment of the present invention a transducer temperature sensor 1036, such as a thermocouple, may also be mounted alongside imaging ultrasonic transducer subassembly 1029.

Figure 7:
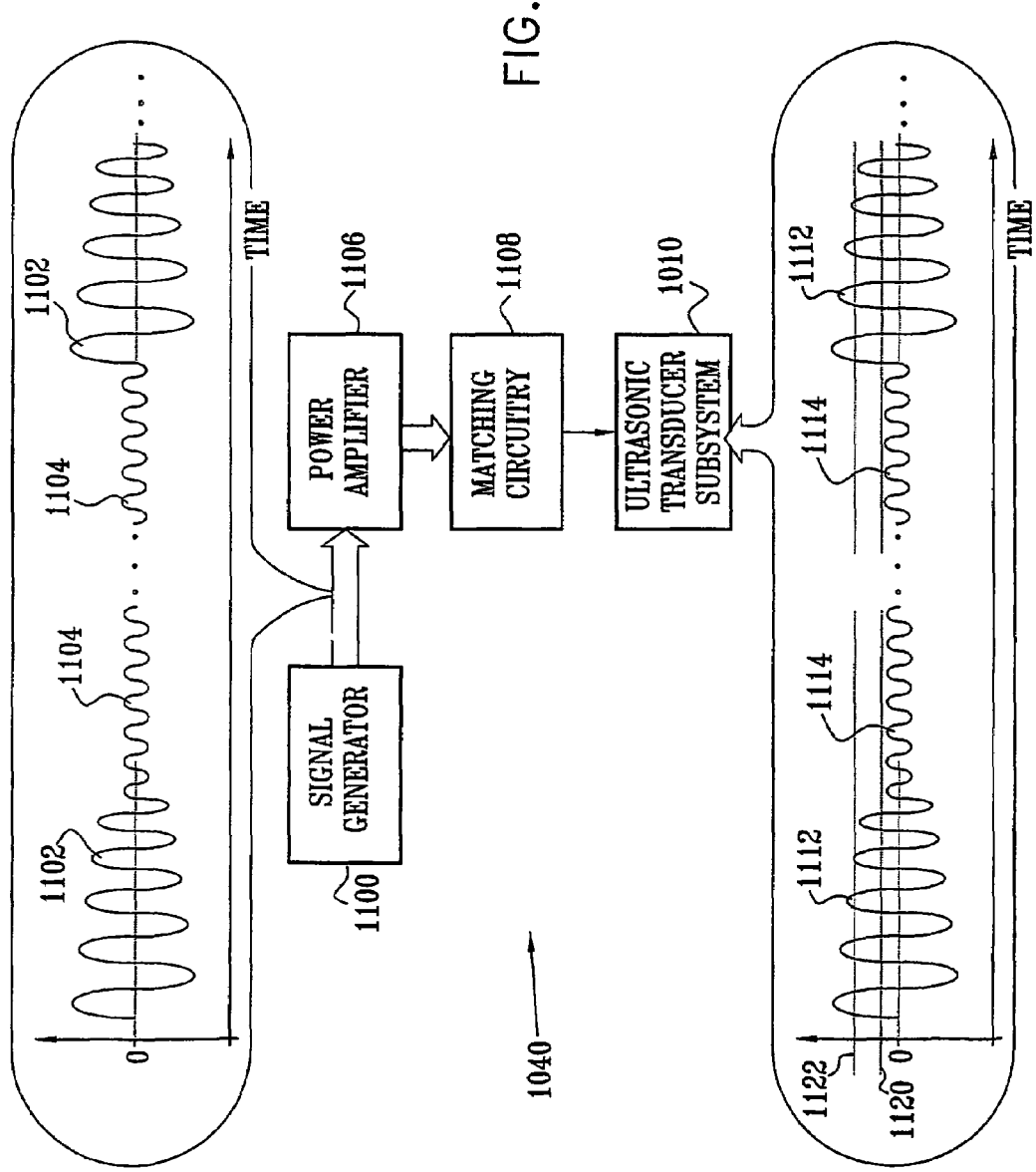
FIG. 7 is a simplified block diagram illustration of a preferred power source and modulator showing a pattern of variation of ultrasonic pressure over time in accordance with a preferred embodiment of the present invention.

Ultrasonic transducer subsystem 1010 preferably receives suitably modulated electrical power from a power source and modulator assembly 1040, forming part of a control subsystem 1042. Control subsystem 1042 also typically includes a apoptosis induction control computer 1044, having associated therewith a camera 1046, such as a video camera, and a display 1048. A preferred embodiment of power source and modulator assembly 1040 is illustrated in FIG. 7 and described hereinbelow. Ultrasonic transducer subsystem 1010 is preferably positioned automatically or semi-automatically as by an X-Y-Z positioning assembly 1049. Alternatively, ultrasonic transducer subsystem 1010 may be positioned at desired positions by an operator.

In accordance with a preferred embodiment of the present invention, camera 1046 is operative for imaging a portion of the body on which apoptotic cellulite and fat treatment is to be performed. A picture of the portion of the patients body viewed by the camera is preferably displayed in real time on display 1048.

An operator may designate the outline of a region containing cellulite or fat. In accordance with one embodiment of the present invention, designation of this region is effected by an operator marking the skin of a patient with an outline 1050, which outline is imaged by camera 1046 and displayed on display 1048 and is also employed by the apoptosis induction control computer 1044 for controlling the application of ultrasonic energy to locations within the region. A computer calculated representation of the outline may also be displayed on display 1048, as designated by reference numeral 1052. Alternatively, the operator may make a virtual marking on the skin such as by using a digitizer (not shown), which also may provide computer calculated outline representation 1052 on display 1048.

In addition to the outline representation 1052, the functionality of the system of the present invention preferably also employs a plurality of markers 1054 which are typically located outside the region containing cellulite and fat, but may be located inside the region designated by outline 1050. Markers 1054 are visually sensible markers, which are clearly seen by camera 1046, captured by camera 1046 and displayed on display 1048. Markers 1054 may be natural anatomic markers, such as distinct portions of the body or alternatively artificial markers such as colored stickers. These markers are preferably employed to assist the system in dealing with deformation of the region nominally defined by outline 1050 due to movement and reorientation of the body. Preferably, the transducer subsystem 1010 also bears a visible marker 1056 which is also captured by camera 1046 and displayed on display 1048.

Markers 1054 and 1056 are typically processed by computer 1044 and may be displayed on display 1048 as respective computed marker representations 1058 and 1060 on display 1048.

FIG. 6 illustrates the transducer subsystem 1010 being positioned on the body over a location within a region containing cellulite and fat. Blocks designated by reference numerals 1062 and 1064 show typical portions of a region containing cellulite and fat respectively before and after apoptotic cellulite and fat treatment in accordance with a preferred embodiment of the invention. It is seen from a comparison of blocks 1062 and 1064 that in accordance with a preferred embodiment of the present invention, within the region containing cellulite and fat, the cellulite, designated by reference numeral 1066, and the fat designated by reference numeral 1067 is removed, while non-cellulite tissue, such as connective tissue, designated by reference numeral 1068, dermis designated by reference numeral 1069 and fascia designated by reference 1070 are generally not removed.

Reference is now made to FIG. 7, which is a simplified block diagram illustration of a preferred power source and modulator assembly 1040 (FIG. 6), showing a pattern of variation of ultrasonic pressure over time in accordance with a preferred embodiment of the present invention. As seen in FIG. 7, the power source and modulator assembly 1040 preferably comprises a signal generator 1100 which provides a time varying signal which is modulated so as to have a series of relatively high amplitude portions 1102 separated in time by a series of typically relatively low amplitude portions 1104. Each relatively high amplitude portion 1102 preferably corresponds to an apoptosis inducing period and preferably has decreasing amplitude over time.

Preferably the relationship between the time durations of portions 1102 and portions 1104 is such as to provide a duty cycle between 1:2 and 1:50, more preferably between 1:5 and 1:30 and most preferably between 1:10 and 1:20.

Preferably, the output of signal generator 1100 has a frequency in a range of 50 KHz-1000 KHz, more preferably between 100 KHz-500 KHz and most preferably between 150 KHz-300 KHz.

The output of signal generator 1100 is preferably provided to a suitable power amplifier 1106, which outputs via impedance matching circuitry 1108 to an input of ultrasonic transducer subsystem 1010 (FIG. 6), which converts the electrical signal received thereby to a corresponding ultrasonic energy output As seen in FIG. 7, the ultrasonic energy output comprises a time varying signal which is modulated correspondingly to the output of signal generator 1100 so as to have a series of relatively high amplitude portions 1112, corresponding to portions 1102, separated in time by a series of typically relatively low amplitude portions 1114, corresponding to portions 1104.

Each relatively high amplitude portion 1112 preferably corresponds to an apoptosis period and has amplitude at a target volume 1012 (FIG. 6) in the body, which exceeds an apoptosis threshold 1120 and preferably has decreasing amplitude over time. At least an initial pulse of each relatively high amplitude portion 1112 has amplitude at the target volume 1012, which also exceeds an apoptosis initiation threshold 1122.

Relatively low amplitude portions 1114 have amplitudes that lie below both thresholds 1120 and 1122.

Preferably the relationship between the time durations of portions 1112 and portions 1114 is such as to provide a duty cycle between 1:2 and 1:50, more preferably between 1:5 and 1:30 and most preferably between 1:10 and 1:20.

Preferably, the ultrasonic energy output of ultrasonic transducer 1010 has a frequency in a range of 50 KHz-1000 KHz, more preferably between 100 KHz-500 KHz and most preferably between 150 KHz-300 KHz.

Preferably, each high amplitude portion 1112 is comprised of between 2 and 1000 sequential cycles at an amplitude above the apoptosis maintaining threshold 1120, more preferably between 25 and 500 sequential cycles at an amplitude above the apoptosis threshold 1120 and most preferably between 100 and 300 sequential cycles at an amplitude above the apoptosis threshold 1120.

Figure 8A:
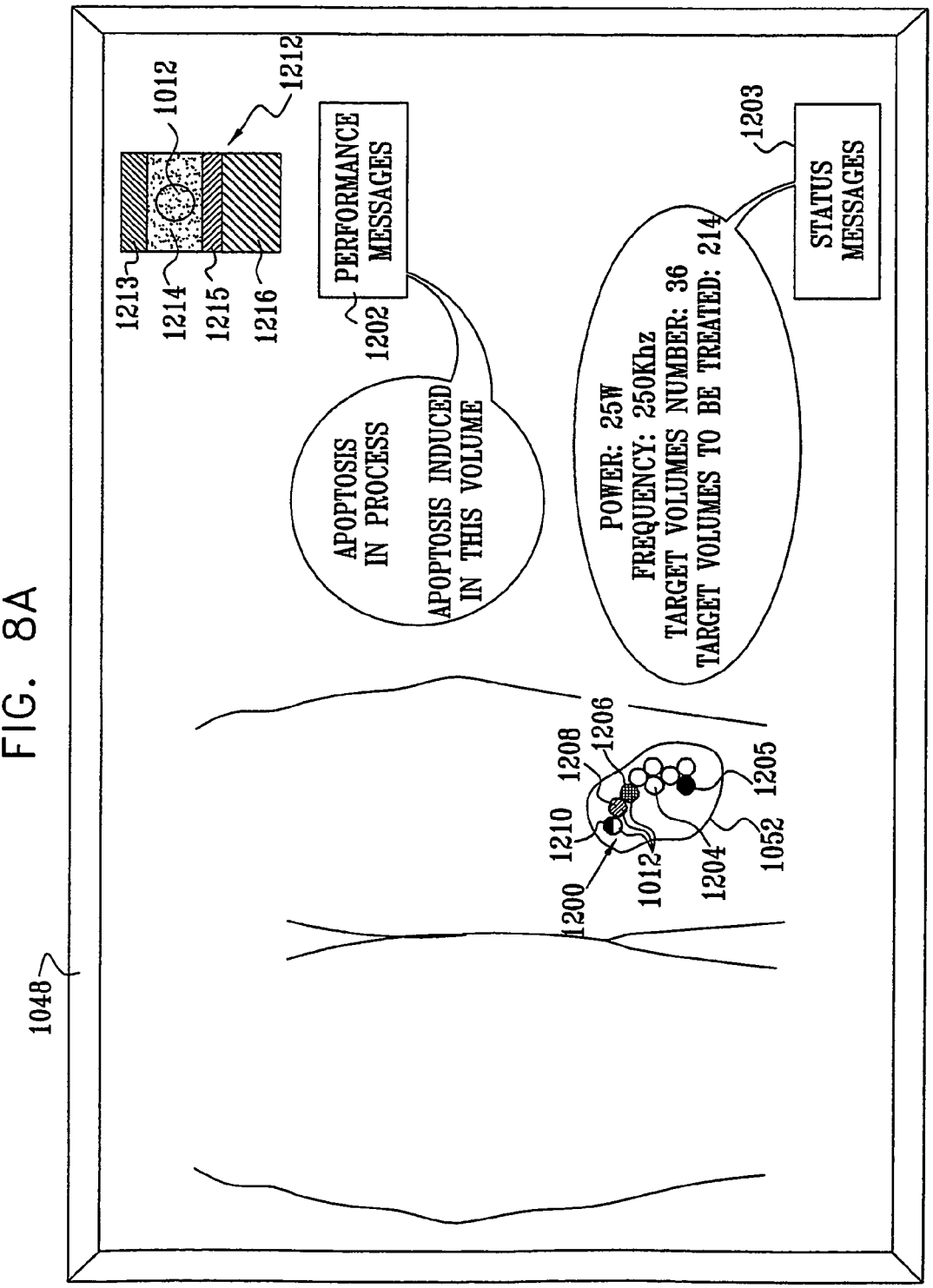
FIGS. 8A and 8B are simplified pictorial illustrations of the appearance of an operator interface display during normal operation and faulty operation respectively.
Figure 8B:
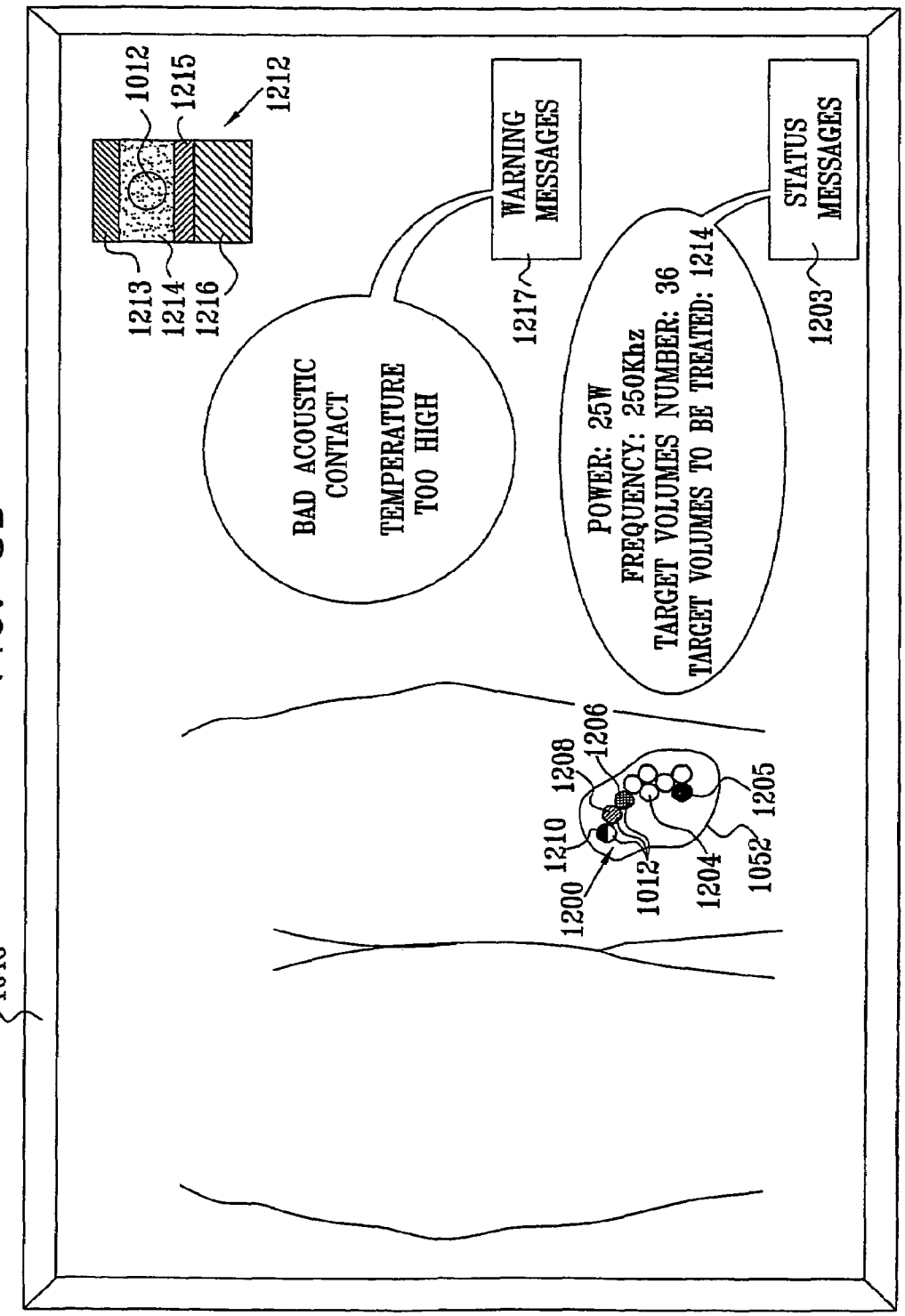

Reference is now made to FIGS. 8A and 8B, which are simplified pictorial illustrations of the appearance of an operator interface display during normal operation and faulty operation respectively. As seen in FIG. 8A, during normal operation display 1048 typically shows a plurality of target volumes 1012 (FIG. 6) within a calculated target region 1200, typically delimited by outline representation 1052 (FIG. 6). Additionally, display 1048 preferably provides one or more pre-programmed performance messages 1202 and status messages 1203.

It is seen the various target volumes 1012 are shown with different shading in order to indicate their treatment status. For example, unshaded target volumes, here designated by reference numerals 1204, have already experienced apoptosis cellulite and fat treatment A blackened target volume 1012, designated by reference numeral 1205 is the target volume next in line for apoptosis cellulite and fat treatment. A partially shaded target volume 1206 typically represents a target volume, which has been insufficiently treated to achieve complete apoptosis cellulite and fat treatment, typically due to insufficient treatment duration.

Other types of target volumes, such as those not to be treated due to insufficient presence of cellulite or fat therein or for other reasons, may be designated by suitable colors or other designations, and are here indicated by reference numerals 1208 and 1210.

Typical performance messages 1202 may include "APOPTOSIS IN PROCESS" and "APOPTOSIS INDUCED IN THIS VOLUME". Typical status messages 1203 may include an indication of the power level, the operating frequency, the number of target volumes 1012 within the calculated target region 1200 and the number of target volumes 1012 which remain to undergo apoptotic cellulite and fat treatment.

Display 1048 also preferably includes a graphical cross sectional presentation 1212 derived from an ultrasonic image preferably provided by imaging ultrasonic transducer subassembly 1029 (FIG. 6). Presentation 1212 preferably indicates various tissues in the body in cross section and shows the target volumes 1012 in relation thereto. In accordance with a preferred embodiment of the present invention, presentation 1212 may also provide a visually sensible indication of apoptosis inducement within the target volume 1012. In accordance with a preferred embodiment of the present invention, presentation 1212 may also provide schematic representations 1213, 1214, 1215 and 1216 of dermis 1069, cellulite 1066, fascia 1070 and fat 1067, respectively.

Turning to FIG. 8B, it is seen that during abnormal operation, display 1048 provides pre-programmed warning messages 1217. Typical warning messages may include "BAD ACOUSTIC CONTACT", "TEMPERATURE TOO HIGH". The "TEMPERATURE TOO HIGH" message typically relates to the skin tissue, although it may alternatively or additionally relate to other tissue inside or outside of the target volume of the transducer subsystem 1010 (FIG. 6).

Figure 9:
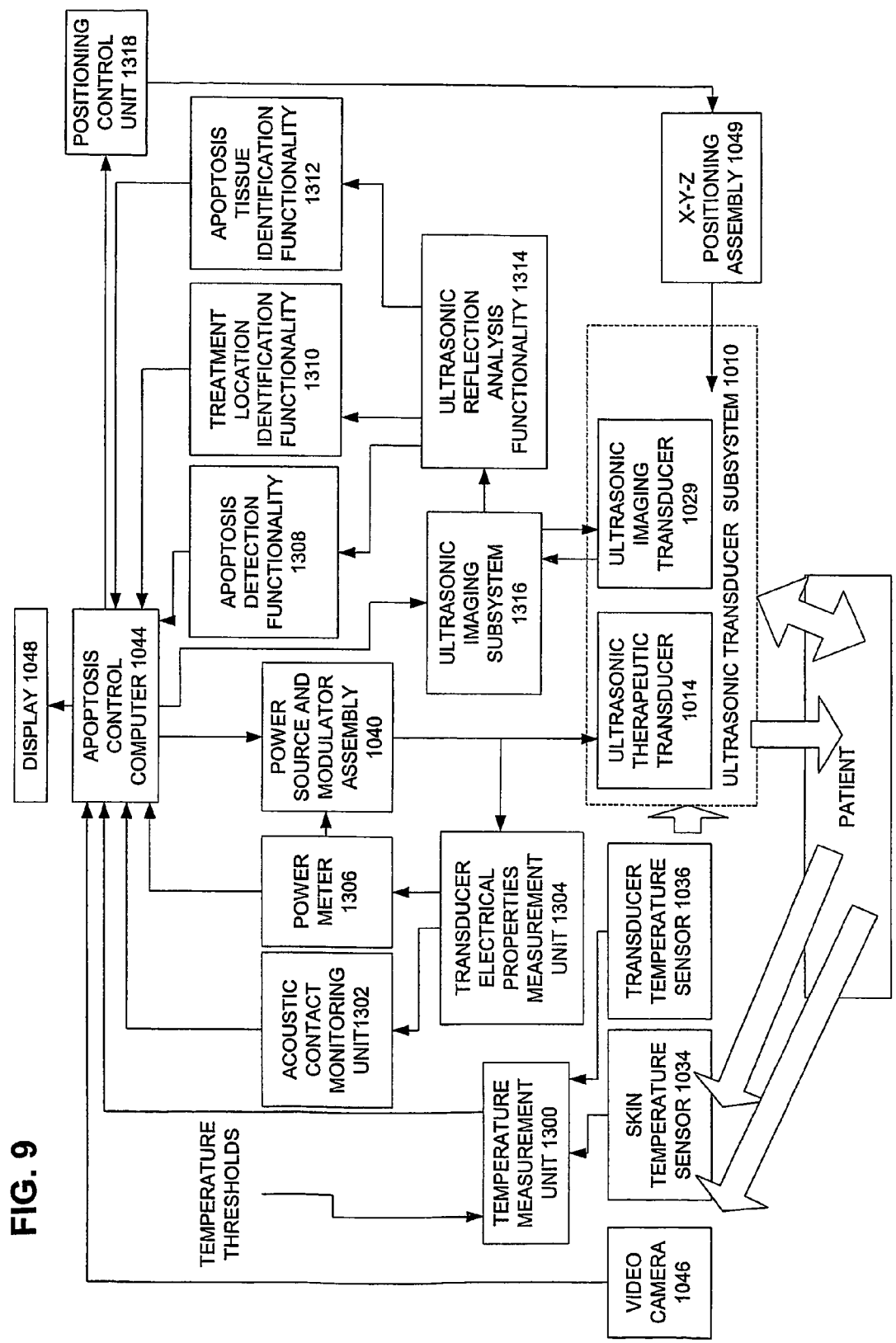
FIG. 9 is a simplified block diagram illustration of ultrasonic apoptosis induction apparatus constructed and operative in accordance with a preferred embodiment of the present invention.

Reference is now made to FIG. 9, which illustrates an ultrasonic apoptosis induction apparatus constructed and operative in accordance with a preferred embodiment of the present invention. As described hereinabove with reference to FIG. 6 and as seen in FIG. 9, the ultrasonic apoptosis induction apparatus comprises an apoptosis control computer 1044, which outputs to a display 1048. Apoptosis control computer 1044 preferably receives inputs from video camera 1046 (FIG. 6) and from a temperature measurement unit 1300, which receives temperature threshold settings as well as inputs from skin temperature sensor 1034 (FIG. 6) and transducer temperature sensor 1036 (FIG. 6). Temperature measurement unit 1300 preferably compares the outputs of both sensors 1034 and 1036 with appropriate threshold settings and provides an indication to apoptosis control computer 1044 of temperature exceeding either temperature thresholds.

Apoptosis control computer 1044 also preferably receives an input from an acoustic contact-monitoring unit 1302, which in turn preferably receives an input from a transducer electrical properties measurement unit 1304. Transducer electrical properties measurement unit 1304 preferably monitors the output of power source and modulator assembly 1040 (FIG. 6) applies to ultrasonic therapeutic transducer assembly 1013.

An output of transducer electrical properties measurement unit 1304 is preferably also supplied to a power meter 1306, which provides an output to the apoptosis control computer 1044 and a feedback output to power source and modulator assembly 1040.

Apoptosis control computer 1044 also preferably receives inputs from apoptosis detection functionality 1308, treatment location identification functionality 1310 and apoptosis tissue identification functionality 1312, all of which receive inputs from ultrasonic reflection analysis functionality 1314. Ultrasonic reflection analysis functionality 1314 receives ultrasonic imaging inputs from an ultrasonic imaging subsystem 1316 which operates ultrasonic imaging transducer subassembly 1029 (FIG. 6).

Apoptosis control computer 1044 provides outputs to power source and modulator assembly 1040, for operating ultrasonic therapeutic transducer assembly 1013 and to ultrasonic imaging subsystem 1316, for operating ultrasonic imaging transducer subassembly 1029. A positioning control unit 1318 also receives an output from apoptosis control computer 1044 for driving X-Y-Z positioning assembly 1049 (FIG. 6) in order to correctly position transducer subsystem 1010, which includes ultrasonic therapeutic transducer assembly 1014 and ultrasonic imaging transducer subassembly 1029.

Figure 10A:
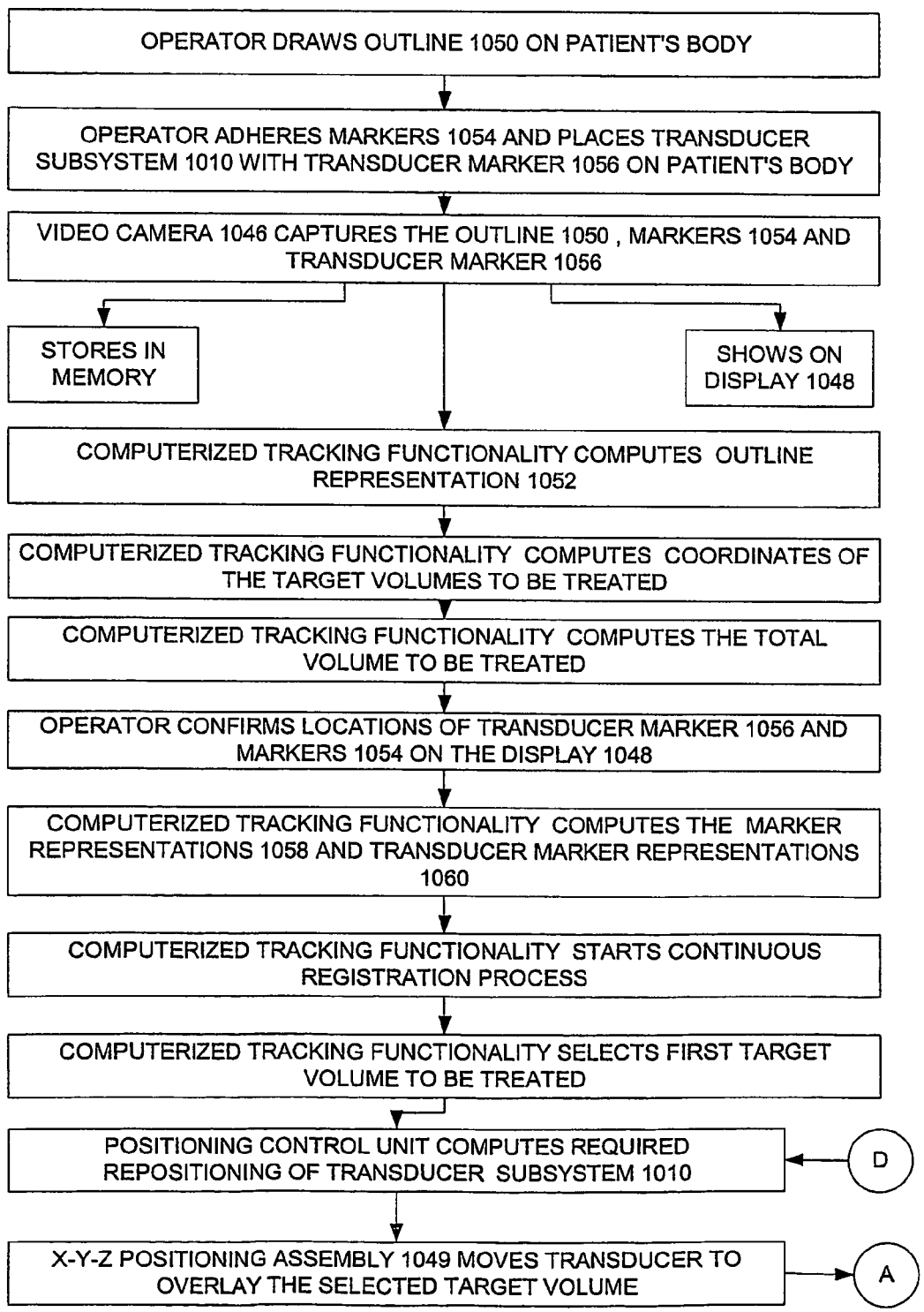
FIGS. 10A, 10B and 10C are together a simplified flowchart illustrating operator steps in carrying out apoptosis induction treatment in accordance with a preferred embodiment of the present invention.
Figure 10B:
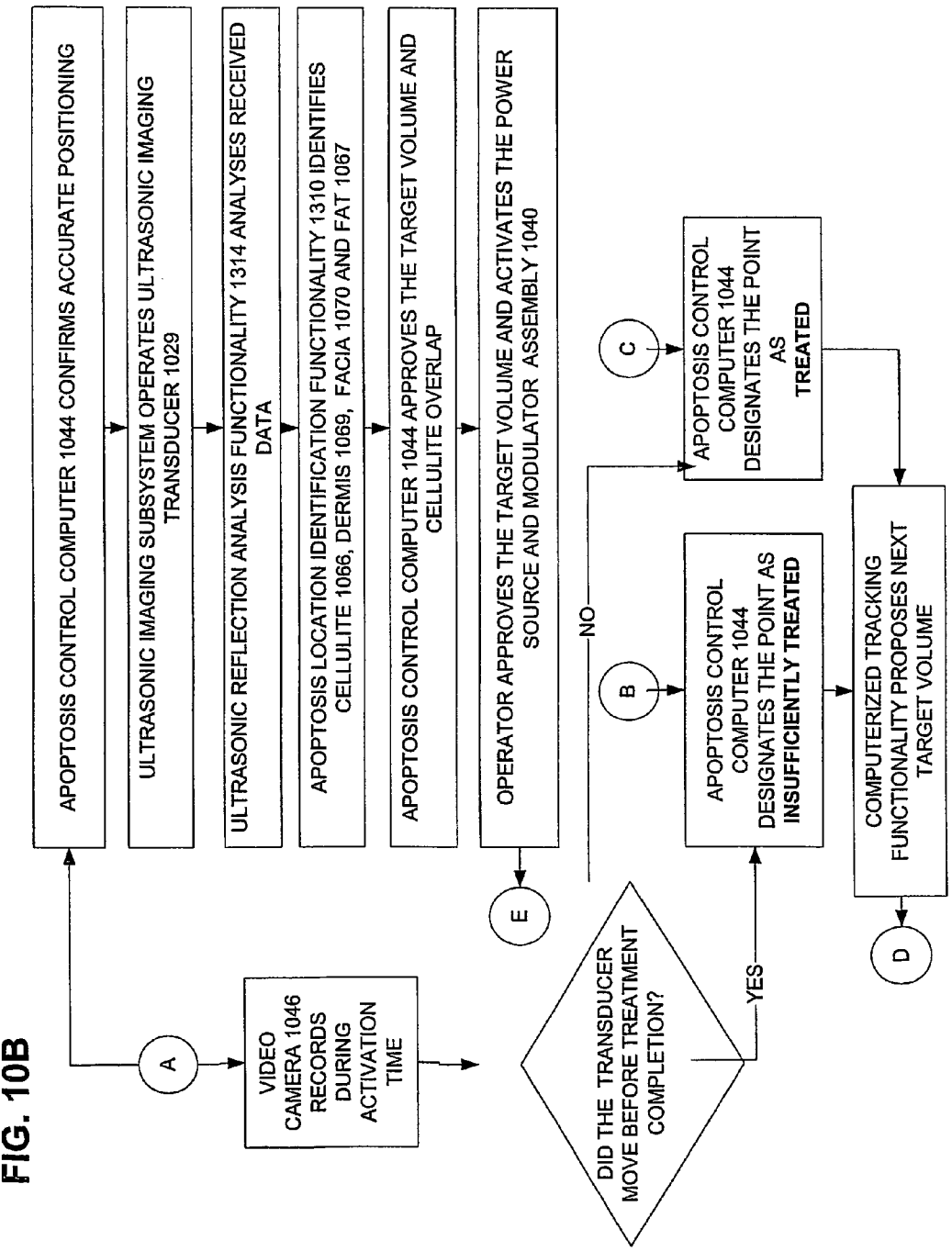
Figure 10C:
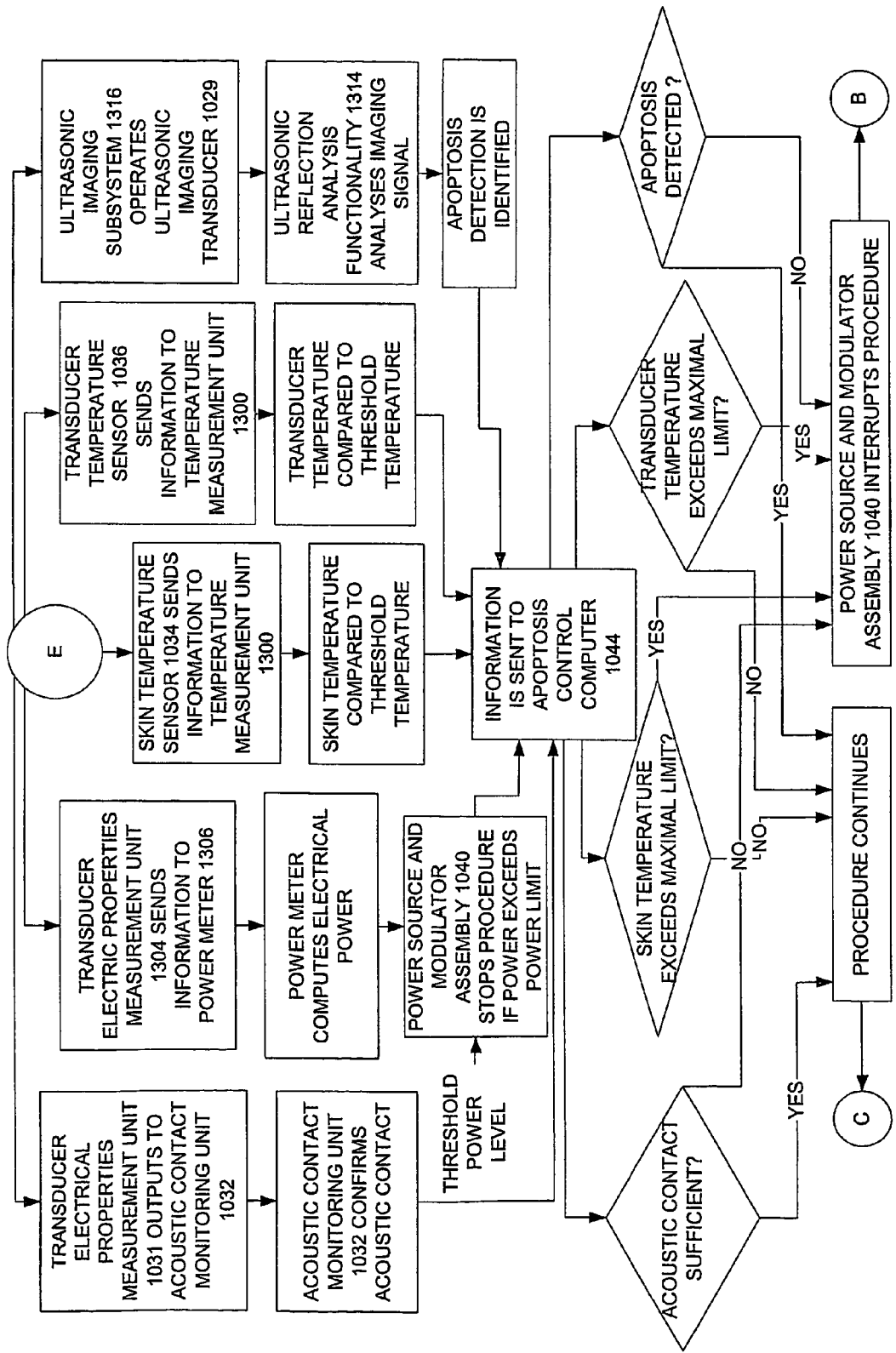

Reference is now made to FIGS. 10A, 10B and 10C, which are together a simplified flowchart illustrating operator steps in carrying out apoptotic cellulite and fat treatment in accordance with a preferred embodiment of the present invention. As seen in FIG. 10A initially an operator preferably draws an outline 1050 (FIG. 6) on a patient's body. Preferably the operator also adheres stereotactic markers 1054 (FIG. 6) to the patient's body and places transducer subsystem 1010, bearing transducer marker 1056, at a desired location within outline 1050.

Camera 1046 (FIG. 6) captures outline 1050 and markers 1054 and 1056. Preferably, outline 1050 and markers 1054 and 1056 are displayed on display 1048 in real time. The output of camera 1046 is also preferably supplied to a memory associated with apoptosis control computer 1044 (FIG. 6).

A computerized tracking functionality preferably embodied in apoptosis control computer 1044 preferably employs the output of camera 1046 for computing outline representation 1052 which may be displayed for the operator on display 1048. The computerized tracking functionality also preferably computes coordinates of target volumes for apoptotic cellulite and fat treatment, as well as summing the total volume of tissue sought to undergo apoptotic cellulite and fat treatment.

Preferably, the operator confirms the locations of markers 1054 and 1056 on display 1048 and the computerized tracking functionality calculates corresponding marker representations 1058 and 1060.

In accordance with a preferred embodiment of the present invention the computerized tracking functionality employs markers 1054 and marker representations 1058 for continuously maintaining registration of outline 1050 with respect to outline representation 1052 and thus of target volumes 1012 with respect to the patient's body, notwithstanding movements of the patients body during treatment such as due to breathing or any other movements, such as the patient leaving and returning to the treatment location.

The computerized tracking functionality selects an initial target volume to be treated and positioning control unit 1318 (FIG. 9), computes the required repositioning of transducer subsystem 1010. X-Y-Z positioning assembly 1049 repositions transducer subsystem 1010 to overlie the selected target volume.

Referring additionally to FIG. 10B, it is seen that following repositioning of transducer subsystem 1010, the apoptosis control computer 1044 confirms accurate positioning of transducer subsystem 1010 with respect to the selected target volume. The ultrasonic imaging subsystem 1316 (FIG. 9) operates ultrasonic imaging transducer subassembly 1029, causing it to provide an output to ultrasonic reflection analysis functionality 1314 for analysis.

Treatment location identification functionality 1310 (FIG. 9) is operative to identify dermis 1069, cellulite 1066, fascia 1070 and fat 1067. Upon the apoptosis computer 1044 receiving and approving an indication of treatment location, an operator may approve the selected target volume and activate the power source and modulator assembly 1040 (FIG. 6).

Turning additionally to FIG. 10C, it is seen that the following functionalities take place:

Transducer electrical properties measurement unit 1304 provides an output to acoustic contact monitoring unit 1302, which determines whether sufficient acoustic contact with the patient is present, preferably by analyzing the current and voltage at therapeutic transducer assembly 1013.

Transducer electrical properties measurement unit 1304 provides an output to power meter 1306, which computes the average electrical power received by the therapeutic transducer assembly 1013. If the average electrical power received by the therapeutic transducer assembly 1013 exceeds a predetermined threshold, operation of the power source and modulator assembly 1040 may be automatically terminated.

Skin temperature sensor 1034 measures the current temperature of the skin at transducer subsystem 1010 and supplies it to temperature measurement unit 1300 which compares the skin temperature to the threshold temperature. Similarly, transducer temperature sensor 1036 measures the current temperature at transducer subsystem 1010 and supplies it to temperature measurement unit 1300, which compares the transducer subsystem temperature to the threshold temperature. The outputs of temperature measurement unit 1300 are supplied to apoptosis control computer 1044.

The ultrasonic imaging subsystem 1316 operates ultrasonic imaging transducer subassembly 1029 and receives an imaging output, which is analyzed by ultrasonic reflection analysis functionality 1314. The result of this analysis is employed for apoptosis detection and an apoptosis detection output is supplied to apoptosis control computer 1044.

Should any of the following four conditions occur, the power source and modulator assembly 1040 automatically terminates operation of therapeutic transducer assembly 1013. Should none of the following conditions occur, the automatic operation of power source and modulator assembly 1040 continues:

1. Acoustic contact is insufficient.
2. Skin temperature exceeds skin threshold temperature level.
3. Transducer assembly 1013 temperature exceeds transducer threshold temperature level.
4. Apoptosis is not detected.

Returning to FIG. 10B, it is noted that during automatic operation of power source and modulator assembly 1040, video camera 1046 preferably records the target region and notes whether the transducer subsystem 1010 remained stationary during the entire treatment duration of the selected target volume 1012. If so, and if none of the aforesaid four conditions took place, apoptosis control computer 1044 confirms that the selected target volume was treated. The computerized tracking functionality of apoptosis control computer 1044 then proposes a further target volume 1012 to be treated.

If, however, the transducer subsystem 1010 did not remain stationary for a sufficient duration, the selected target volume is designated by apoptosis control computer 1044 as having been insufficiently treated.

It is appreciated that by using multiple transducers multiplicity of target volumes can be treated at various time patterns such as sequential time patterns or partially overlapping time patterns.

It is also appreciated that the multiplicity of target volumes may also overlap in space or partially overlap in space.

Reference is now made to FIGS. 11A and 11B which are together a simplified flowchart illustrating steps in carrying out unit by unit tracking within a time variable three dimensional outline in accordance with a preferred embodiment of the present invention.

The functionality described hereinbelow and shown in FIGS. 11A and 11B is particularly useful as part of the functionality described hereinabove with reference to FIGS. 1 and 6 wherein motion of markers 54, 56, 1054 and 1056 is tracked and employed to track the target volumes notwithstanding motion of the body. It is appreciated that this functionality is also applicable for many other types of computerized medical treatment and diagnosis, hereinafter collectively referred to as treatment, employing machine vision and even to non medical applications wherein machine vision is used to track multiple relatively moving elements.

As seen in FIG. 11A, an operator initiates a process of outline detection typically by drawing on a computer screen a line which encompasses the entire outline to be detected. The image so circumscribed is captured. Various color filters are applied to the captured image to provide maximum contrast of the outline with respect to its background and to reduce noise. A threshold is applied to the enhanced contrast and noise-reduced result of the filtering. The outline is then homogenized and any remaining marker indications are removed, thereby producing a clean, unambiguous outline presentation. The clean unambiguous outline presentation is overlaid upon a video image of the outline and the image content interior thereof. If the overlay is not sufficiently congruent with the video image, manual intervention may take place.

Once the overlay is sufficiently congruent with the clean outline presentation, the operator designates the locations of those markers, inside or outside of the outline, which are to be used in tracking. The marker which is attached to the ultrasonic transducer subsystem is specifically designated as such and may contain information as to the geometrical and other operational characteristics thereof, such as those relating to the size and relative position of its characteristic target volume. For each such designated marker the geometrical center and the geometrical configuration of the marker are noted.

A geometrical center of the outline is calculated and the position of the geometrical center of each marker relative to the geometrical center of the outline is noted.

Referring now to FIG. 11B, changes in the observed geometrical configuration of each marker indicate tilting of that marker from a nominal orientation thereof. By collectively observing changes in plural markers distributed over a three-dimensional surface, variations in the three dimensional configuration of that surface may be monitored. A calculation is made to define a virtual grid of target volumes superimposed over the three-dimensional surface, the grid units preferably being the size of the target volumes characteristic of the ultrasonic transducer subsystem. The grid units may or may not be selected to be partially mutually overlapping. Any suitable grid unit shape may be employed.

The system then displays a desired position in three dimensions for the ultrasonic transducer subsystem for treatment of a first target volume. When the operator correctly positions the ultrasonic transducer subsystem, a visual and/or other confirmation of correct positioning is provided to the operator and the operator is enabled to commence treatment of that target volume.

After completion of treatment, the system designates the grid point as "treated target volume" and checks for more target volumes to be treated. The system, again checks for changes in the observed geometrical configuration of each marker indicate tilting of that marker from a nominal orientation thereof. By collectively observing changes in plural markers distributed over a three-dimensional surface, variations in the three dimensional configuration of that surface may be monitored. A calculation is made to define a new virtual grid of target volumes superimposed over the three-dimensional surface, the grid units are in one to one correspondence with the previous grid, and all data on treated grid points is kept.

The system then displays a desired position in three dimensions for a subsequent target volume for further operation in a similar manner. Alternatively, the subsequent target volume is selected by the operator. A further alternative, the operator scans the region within the outline and the system ensures that treatment is not applied to grid units which have already been treated or do not require treatment.

It is appreciated that the functionality described hereinabove is operative notwithstanding motion of the body and resulting reconfiguration of the three dimensional surface thereof, both during and between treatments of various target volumes therein. This is accomplished by continuously monitoring the position and orientation of the various markers and extrapolating the monitored position and orientation to each grid unit in the virtual grid.

The Appendix includes a software object code for the computational tracking functionality and includes the following steps:

1). Provide a PC computer, such as an Intel-based Pentium III 800 MHz computer with Microsoft Windows 2000 operating system, a hard disk with a minimal capacity of 10 GB, 1 available PCI slot and a 17" computer screen.

2). Matrox Orion Frame Grabber Hardware installation/configuration:
  a). Remove/Disable the VGA board present in the PC computer.
  b). Place the Matrox Orion Frame Grabber board available from Matrox (1055 boul. St-Regis, Dorval, Quebec Canada H9P 2T4) into an available PCI slot in the PC computer.
  c). Under Microsoft Windows 2000, on booting the computer, Microsoft Windows Plug-and-Play system detects a new Multimedia Video Device and requests to assign it a driver. At this point, click Cancel.
  d). Install the JAI CV-S3200 DSP Surveillance Color CCD Camera available from JAI America Inc., 23046 Avenida de la Carlota, Suite 450, Laguna Hills, Calif. 92653 United States and connect to the Matrox Orion Framer Grabber.
  e). Set the computer screen impedance switches, red, green, and blue inputs to 75 ohms.
  f). Set the computer screen synchronization inputs to high impedance and external sync mode.
  g). Connect the computer screen to Matrox Orion's 15-pin female VGA output connector (DB-15).

3). Matrox MIL-Lite software (version 6.1) installation:
  a). Run the Matrox MIL-Lite setup.exe program and follow the default prompts.
  b). Run the Matrix Expansion Pack (version 1.0).
  c). Choose "PAL-YC mode of grabbing" when prompted.
  d). Establish the RS-232 serial communication between the PC and the JAI camera by registering and installing the "JAI Camera ActiveX object"

4). Track Software Installation:
  a). Create the following respective directories:
    (1). <Track root>—a root directory for Track project
    (2). <Track root>\Src—contains source code files
    (3). <Track root>\Debug—contains an executable file for Track project
    (4). <Track root>\Images—contains BMP files for debugging the interior region detection process.
    (5). <Track root>\Log—contains log files and BMP image of the scene
    (6). <Track root>\Timing—contains timing data files for debugging
  b). Create the file TRACKOBJ.HEX based on the Appendix and place it into a temporary directory.
  c). Unhex the computer listing TRACKOBJ.HEX using HEX IT V1.8 or greater by John Augustine, 3129 Earl St., Laureldale, Penn. 19605 creating file TRACKOBJ.ZIP
  d). Decompress the file TRACKOBJ.ZIP using WINZIP version 6.2 or greater, extracting all files into a temporary directory essentially extracting the following file objects:

1). CAMERADLG.OBJ
2). DISPLAYFUNCS.OBJ
3). IMAGEPROC.OBJ
4). INTERIORREGION.OBJ
5). MARKERS.OBJ

6). NODES.OBJ
7). PARAMETERSDLG.OBJ
8). STDAFX.OBJ
9). TRACK.OBJ
10). TRACK.RES
11). TRACKDLG.OBJ
12). TRANSDUCER.OBJ
13). UTILS.OBJ
14). VIDEOMATROX.OBJ e). Compile the Object code stored in the temporary directory created in step 4d using Microsoft Visual C++ compiler version 6.0 The resulting application is created: TRACK.EXE f). To run the Track software, execute the program TRACK.EXE and follow the on-line help to operate the program.

It is appreciated that the software components of the present invention may, if desired, be implemented in ROM (read-only memory) form. The software components may, generally, be implemented in hardware, if desired, using conventional techniques.

It is appreciated that the particular embodiment implemented by the Appendix is intended only to provide an extremely detailed disclosure of the present invention and is not intended to be limiting.

It will be appreciated by persons skilled in the art that the present invention is not limited by what has been particularly shown and described hereinabove. Rather the scope of the present invention includes both combinations and sub combinations of the various features described hereinabove as well as variations and modifications which would occur to persons skilled in the art upon reading the specification and which are not in the prior art.

APPENDIX

```
00000000: 4D 5A 90 00 03 00 00 00 04 00 00 00 FF FF 00 00
00000010: B8 00 00 00 00 00 00 00 40 00 00 00 00 00 00 00
00000020: 00 00 00 00 00 00 00 00 00 00 00 00 00 00 00 00
00000030: 00 00 00 00 00 00 00 00 00 00 00 00 E0 00 00 00
00000040: 0E 1F BA 0E 00 B4 09 CD 21 B8 01 4C CD 21 54 68
00000050: 69 73 20 70 72 6F 67 72 61 6D 20 63 61 6E 6E 6F
00000060: 74 20 62 65 20 72 75 6E 20 69 6E 20 44 4F 53 20
00000070: 6D 6F 64 65 2E 0D 0D 0A 24 00 00 00 00 00 00 00
00000080: E6 70 07 AD A2 11 69 FE A2 11 69 FE A2 11 69 FE
00000090: C0 0E 7A FE A4 11 69 FE 21 0D 67 FE A3 11 69 FE
000000A0: 4A 0E 63 FE A9 11 69 FE A2 11 68 FE 1D 11 69 FE
000000B0: 4A 0E 6D FE 86 11 69 FE 4A 0E 62 FE B2 11 69 FE
000000C0: 1A 17 6F FE A3 11 69 FE 52 69 63 68 A2 11 69 FE
000000D0: 00 00 00 00 00 00 00 00 00 00 00 00 00 00 00 00
000000E0: 50 45 00 00 4C 01 04 00 BF 7A D6 3B 00 00 00 00
000000F0: 00 00 00 00 E0 00 0F 01 0B 01 06 00 00 80 00 00
00000100: 00 80 98 00 00 00 00 00 50 83 00 00 00 10 00 00
00000110: 00 90 00 00 00 00 40 00 00 10 00 00 00 10 00 00
00000120: 04 00 00 00 00 00 00 00 04 00 00 00 00 00 00 00
00000130: 00 10 99 00 00 10 00 00 00 00 00 00 02 00 00 00
00000140: 00 00 10 00 00 10 00 00 00 00 10 00 00 10 00 00
00000150: 00 00 00 00 10 00 00 00 00 00 00 00 00 00 00 00
00000160: 88 9E 00 00 A0 00 00 00 00 99 00 70 0D 00 00
00000170: 00 00 00 00 00 00 00 00 00 00 00 00 00 00 00 00
00000180: 00 00 00 00 00 00 00 00 00 00 00 00 00 00 00 00
00000190: 00 00 00 00 00 00 00 00 00 00 00 00 00 00 00 00
000001A0: 00 00 00 00 00 00 00 00 00 00 00 00 00 00 00 00
000001B0: 00 00 00 00 00 00 00 00 00 90 00 00 84 03 00 00
000001C0: 00 00 00 00 00 00 00 00 00 00 00 00 00 00 00 00
000001D0: 00 00 00 00 00 00 00 00 2E 74 65 78 74 00 00 00
000001E0: 45 77 00 00 10 00 00 00 80 00 00 00 10 00 00 00
000001F0: 00 00 00 00 00 00 00 00 00 00 00 00 20 00 00 60
00000200: 2E 72 64 61 74 61 00 00 B2 16 00 00 00 90 00 00
00000210: 00 20 00 00 90 00 00 00 00 00 00 00 00 00 00 00
00000220: 00 00 00 00 40 00 00 40 2E 64 61 74 61 00 00 00
00000230: F8 4C 98 00 00 B0 00 00 00 10 00 00 00 B0 00 00
00000240: 00 00 00 00 00 00 00 00 00 00 00 00 40 00 00 C0
```

APPENDIX-continued

```
00000250: 2E 72 73 72 63 00 00 00 70 0D 00 00 00 00 99 00
00000260: 00 10 00 00 00 C0 00 00 00 00 00 00 00 00 00 00
00000270: 00 00 00 00 40 00 00 40 00 00 00 00 00 00 00 00
00000280: 00 00 00 00 00 00 00 00 00 00 00 00 00 00 00 00
00000290: 00 00 00 00 00 00 00 00 00 00 00 00 00 00 00 00
000002A0: 00 00 00 00 00 00 00 00 00 00 00 00 00 00 00 00
000002B0: 00 00 00 00 00 00 00 00 00 00 00 00 00 00 00 00
000002C0: 00 00 00 00 00 00 00 00 00 00 00 00 00 00 00 00
000002D0: 00 00 00 00 00 00 00 00 00 00 00 00 00 00 00 00
000002E0: 00 00 00 00 00 00 00 00 00 00 00 00 00 00 00 00
000002F0: 00 00 00 00 00 00 00 00 00 00 00 00 00 00 00 00
00000300: 00 00 00 00 00 00 00 00 00 00 00 00 00 00 00 00
00000310: 00 00 00 00 00 00 00 00 00 00 00 00 00 00 00 00
00000320: 00 00 00 00 00 00 00 00 00 00 00 00 00 00 00 00
00000330: 00 00 00 00 00 00 00 00 00 00 00 00 00 00 00 00
00000340: 00 00 00 00 00 00 00 00 00 00 00 00 00 00 00 00
00000350: 00 00 00 00 00 00 00 00 00 00 00 00 00 00 00 00
00000360: 00 00 00 00 00 00 00 00 00 00 00 00 00 00 00 00
00000370: 00 00 00 00 00 00 00 00 00 00 00 00 00 00 00 00
00000380: 00 00 00 00 00 00 00 00 00 00 00 00 00 00 00 00
00000390: 00 00 00 00 00 00 00 00 00 00 00 00 00 00 00 00
000003A0: 00 00 00 00 00 00 00 00 00 00 00 00 00 00 00 00
000003B0: 00 00 00 00 00 00 00 00 00 00 00 00 00 00 00 00
000003C0: 00 00 00 00 00 00 00 00 00 00 00 00 00 00 00 00
000003D0: 00 00 00 00 00 00 00 00 00 00 00 00 00 00 00 00
000003E0: 00 00 00 00 00 00 00 00 00 00 00 00 00 00 00 00
000003F0: 00 00 00 00 00 00 00 00 00 00 00 00 00 00 00 00
00000400: 00 00 00 00 00 00 00 00 00 00 00 00 00 00 00 00
00000410: 00 00 00 00 00 00 00 00 00 00 00 00 00 00 00 00
00000420: 00 00 00 00 00 00 00 00 00 00 00 00 00 00 00 00
00000430: 00 00 00 00 00 00 00 00 00 00 00 00 00 00 00 00
00000440: 00 00 00 00 00 00 00 00 00 00 00 00 00 00 00 00
00000450: 00 00 00 00 00 00 00 00 00 00 00 00 00 00 00 00
00000460: 00 00 00 00 00 00 00 00 00 00 00 00 00 00 00 00
00000470: 00 00 00 00 00 00 00 00 00 00 00 00 00 00 00 00
00000480: 00 00 00 00 00 00 00 00 00 00 00 00 00 00 00 00
00000490: 00 00 00 00 00 00 00 00 00 00 00 00 00 00 00 00
000004A0: 00 00 00 00 00 00 00 00 00 00 00 00 00 00 00 00
000004B0: 00 00 00 00 00 00 00 00 00 00 00 00 00 00 00 00
000004C0: 00 00 00 00 00 00 00 00 00 00 00 00 00 00 00 00
000004D0: 00 00 00 00 00 00 00 00 00 00 00 00 00 00 00 00
000004E0: 00 00 00 00 00 00 00 00 00 00 00 00 00 00 00 00
000004F0: 00 00 00 00 00 00 00 00 00 00 00 00 00 00 00 00
00000500: 00 00 00 00 00 00 00 00 00 00 00 00 00 00 00 00
00000510: 00 00 00 00 00 00 00 00 00 00 00 00 00 00 00 00
00000520: 00 00 00 00 00 00 00 00 00 00 00 00 00 00 00 00
00000530: 00 00 00 00 00 00 00 00 00 00 00 00 00 00 00 00
00000540: 00 00 00 00 00 00 00 00 00 00 00 00 00 00 00 00
00000550: 00 00 00 00 00 00 00 00 00 00 00 00 00 00 00 00
00000560: 00 00 00 00 00 00 00 00 00 00 00 00 00 00 00 00
00000570: 00 00 00 00 00 00 00 00 00 00 00 00 00 00 00 00
00000580: 00 00 00 00 00 00 00 00 00 00 00 00 00 00 00 00
00000590: 00 00 00 00 00 00 00 00 00 00 00 00 00 00 00 00
000005A0: 00 00 00 00 00 00 00 00 00 00 00 00 00 00 00 00
000005B0: 00 00 00 00 00 00 00 00 00 00 00 00 00 00 00 00
000005C0: 00 00 00 00 00 00 00 00 00 00 00 00 00 00 00 00
000005D0: 00 00 00 00 00 00 00 00 00 00 00 00 00 00 00 00
000005E0: 00 00 00 00 00 00 00 00 00 00 00 00 00 00 00 00
000005F0: 00 00 00 00 00 00 00 00 00 00 00 00 00 00 00 00
00000600: 00 00 00 00 00 00 00 00 00 00 00 00 00 00 00 00
00000610: 00 00 00 00 00 00 00 00 00 00 00 00 00 00 00 00
00000620: 00 00 00 00 00 00 00 00 00 00 00 00 00 00 00 00
00000630: 00 00 00 00 00 00 00 00 00 00 00 00 00 00 00 00
00000640: 00 00 00 00 00 00 00 00 00 00 00 00 00 00 00 00
00000650: 00 00 00 00 00 00 00 00 00 00 00 00 00 00 00 00
00000660: 00 00 00 00 00 00 00 00 00 00 00 00 00 00 00 00
00000670: 00 00 00 00 00 00 00 00 00 00 00 00 00 00 00 00
00000680: 00 00 00 00 00 00 00 00 00 00 00 00 00 00 00 00
00000690: 00 00 00 00 00 00 00 00 00 00 00 00 00 00 00 00
000006A0: 00 00 00 00 00 00 00 00 00 00 00 00 00 00 00 00
000006B0: 00 00 00 00 00 00 00 00 00 00 00 00 00 00 00 00
000006C0: 00 00 00 00 00 00 00 00 00 00 00 00 00 00 00 00
000006D0: 00 00 00 00 00 00 00 00 00 00 00 00 00 00 00 00
000006E0: 00 00 00 00 00 00 00 00 00 00 00 00 00 00 00 00
000006F0: 00 00 00 00 00 00 00 00 00 00 00 00 00 00 00 00
00000700: 00 00 00 00 00 00 00 00 00 00 00 00 00 00 00 00
00000710: 00 00 00 00 00 00 00 00 00 00 00 00 00 00 00 00
00000720: 00 00 00 00 00 00 00 00 00 00 00 00 00 00 00 00
00000730: 00 00 00 00 00 00 00 00 00 00 00 00 00 00 00 00
```

APPENDIX-continued

```
00000740: 00 00 00 00 00 00 00 00 00 00 00 00 00 00 00 00
00000750: 00 00 00 00 00 00 00 00 00 00 00 00 00 00 00 00
00000760: 00 00 00 00 00 00 00 00 00 00 00 00 00 00 00 00
00000770: 00 00 00 00 00 00 00 00 00 00 00 00 00 00 00 00
00000780: 00 00 00 00 00 00 00 00 00 00 00 00 00 00 00 00
00000790: 00 00 00 00 00 00 00 00 00 00 00 00 00 00 00 00
000007A0: 00 00 00 00 00 00 00 00 00 00 00 00 00 00 00 00
000007B0: 00 00 00 00 00 00 00 00 00 00 00 00 00 00 00 00
000007C0: 00 00 00 00 00 00 00 00 00 00 00 00 00 00 00 00
000007D0: 00 00 00 00 00 00 00 00 00 00 00 00 00 00 00 00
000007E0: 00 00 00 00 00 00 00 00 00 00 00 00 00 00 00 00
000007F0: 00 00 00 00 00 00 00 00 00 00 00 00 00 00 00 00
00000800: 00 00 00 00 00 00 00 00 00 00 00 00 00 00 00 00
00000810: 00 00 00 00 00 00 00 00 00 00 00 00 00 00 00 00
00000820: 00 00 00 00 00 00 00 00 00 00 00 00 00 00 00 00
00000830: 00 00 00 00 00 00 00 00 00 00 00 00 00 00 00 00
00000840: 00 00 00 00 00 00 00 00 00 00 00 00 00 00 00 00
00000850: 00 00 00 00 00 00 00 00 00 00 00 00 00 00 00 00
00000860: 00 00 00 00 00 00 00 00 00 00 00 00 00 00 00 00
00000870: 00 00 00 00 00 00 00 00 00 00 00 00 00 00 00 00
00000880: 00 00 00 00 00 00 00 00 00 00 00 00 00 00 00 00
00000890: 00 00 00 00 00 00 00 00 00 00 00 00 00 00 00 00
000008A0: 00 00 00 00 00 00 00 00 00 00 00 00 00 00 00 00
000008B0: 00 00 00 00 00 00 00 00 00 00 00 00 00 00 00 00
000008C0: 00 00 00 00 00 00 00 00 00 00 00 00 00 00 00 00
000008D0: 00 00 00 00 00 00 00 00 00 00 00 00 00 00 00 00
000008E0: 00 00 00 00 00 00 00 00 00 00 00 00 00 00 00 00
000008F0: 00 00 00 00 00 00 00 00 00 00 00 00 00 00 00 00
00000900: 00 00 00 00 00 00 00 00 00 00 00 00 00 00 00 00
00000910: 00 00 00 00 00 00 00 00 00 00 00 00 00 00 00 00
00000920: 00 00 00 00 00 00 00 00 00 00 00 00 00 00 00 00
00000930: 00 00 00 00 00 00 00 00 00 00 00 00 00 00 00 00
00000940: 00 00 00 00 00 00 00 00 00 00 00 00 00 00 00 00
00000950: 00 00 00 00 00 00 00 00 00 00 00 00 00 00 00 00
00000960: 00 00 00 00 00 00 00 00 00 00 00 00 00 00 00 00
00000970: 00 00 00 00 00 00 00 00 00 00 00 00 00 00 00 00
00000980: 00 00 00 00 00 00 00 00 00 00 00 00 00 00 00 00
00000990: 00 00 00 00 00 00 00 00 00 00 00 00 00 00 00 00
000009A0: 00 00 00 00 00 00 00 00 00 00 00 00 00 00 00 00
000009B0: 00 00 00 00 00 00 00 00 00 00 00 00 00 00 00 00
000009C0: 00 00 00 00 00 00 00 00 00 00 00 00 00 00 00 00
000009D0: 00 00 00 00 00 00 00 00 00 00 00 00 00 00 00 00
000009E0: 00 00 00 00 00 00 00 00 00 00 00 00 00 00 00 00
000009F0: 00 00 00 00 00 00 00 00 00 00 00 00 00 00 00 00
00000A00: 00 00 00 00 00 00 00 00 00 00 00 00 00 00 00 00
00000A10: 00 00 00 00 00 00 00 00 00 00 00 00 00 00 00 00
00000A20: 00 00 00 00 00 00 00 00 00 00 00 00 00 00 00 00
00000A30: 00 00 00 00 00 00 00 00 00 00 00 00 00 00 00 00
00000A40: 00 00 00 00 00 00 00 00 00 00 00 00 00 00 00 00
00000A50: 00 00 00 00 00 00 00 00 00 00 00 00 00 00 00 00
00000A60: 00 00 00 00 00 00 00 00 00 00 00 00 00 00 00 00
00000A70: 00 00 00 00 00 00 00 00 00 00 00 00 00 00 00 00
00000A80: 00 00 00 00 00 00 00 00 00 00 00 00 00 00 00 00
00000A90: 00 00 00 00 00 00 00 00 00 00 00 00 00 00 00 00
00000AA0: 00 00 00 00 00 00 00 00 00 00 00 00 00 00 00 00
00000AB0: 00 00 00 00 00 00 00 00 00 00 00 00 00 00 00 00
00000AC0: 00 00 00 00 00 00 00 00 00 00 00 00 00 00 00 00
00000AD0: 00 00 00 00 00 00 00 00 00 00 00 00 00 00 00 00
00000AE0: 00 00 00 00 00 00 00 00 00 00 00 00 00 00 00 00
00000AF0: 00 00 00 00 00 00 00 00 00 00 00 00 00 00 00 00
00000B00: 00 00 00 00 00 00 00 00 00 00 00 00 00 00 00 00
00000B10: 00 00 00 00 00 00 00 00 00 00 00 00 00 00 00 00
00000B20: 00 00 00 00 00 00 00 00 00 00 00 00 00 00 00 00
00000B30: 00 00 00 00 00 00 00 00 00 00 00 00 00 00 00 00
00000B40: 00 00 00 00 00 00 00 00 00 00 00 00 00 00 00 00
00000B50: 00 00 00 00 00 00 00 00 00 00 00 00 00 00 00 00
00000B60: 00 00 00 00 00 00 00 00 00 00 00 00 00 00 00 00
00000B70: 00 00 00 00 00 00 00 00 00 00 00 00 00 00 00 00
00000B80: 00 00 00 00 00 00 00 00 00 00 00 00 00 00 00 00
00000B90: 00 00 00 00 00 00 00 00 00 00 00 00 00 00 00 00
00000BA0: 00 00 00 00 00 00 00 00 00 00 00 00 00 00 00 00
00000BB0: 00 00 00 00 00 00 00 00 00 00 00 00 00 00 00 00
00000BC0: 00 00 00 00 00 00 00 00 00 00 00 00 00 00 00 00
00000BD0: 00 00 00 00 00 00 00 00 00 00 00 00 00 00 00 00
00000BE0: 00 00 00 00 00 00 00 00 00 00 00 00 00 00 00 00
00000BF0: 00 00 00 00 00 00 00 00 00 00 00 00 00 00 00 00
00000C00: 00 00 00 00 00 00 00 00 00 00 00 00 00 00 00 00
00000C10: 00 00 00 00 00 00 00 00 00 00 00 00 00 00 00 00
00000C20: 00 00 00 00 00 00 00 00 00 00 00 00 00 00 00 00
00000C30: 00 00 00 00 00 00 00 00 00 00 00 00 00 00 00 00
00000C40: 00 00 00 00 00 00 00 00 00 00 00 00 00 00 00 00
00000C50: 00 00 00 00 00 00 00 00 00 00 00 00 00 00 00 00
00000C60: 00 00 00 00 00 00 00 00 00 00 00 00 00 00 00 00
00000C70: 00 00 00 00 00 00 00 00 00 00 00 00 00 00 00 00
00000C80: 00 00 00 00 00 00 00 00 00 00 00 00 00 00 00 00
00000C90: 00 00 00 00 00 00 00 00 00 00 00 00 00 00 00 00
00000CA0: 00 00 00 00 00 00 00 00 00 00 00 00 00 00 00 00
00000CB0: 00 00 00 00 00 00 00 00 00 00 00 00 00 00 00 00
00000CC0: 00 00 00 00 00 00 00 00 00 00 00 00 00 00 00 00
00000CD0: 00 00 00 00 00 00 00 00 00 00 00 00 00 00 00 00
00000CE0: 00 00 00 00 00 00 00 00 00 00 00 00 00 00 00 00
00000CF0: 00 00 00 00 00 00 00 00 00 00 00 00 00 00 00 00
00000D00: 00 00 00 00 00 00 00 00 00 00 00 00 00 00 00 00
00000D10: 00 00 00 00 00 00 00 00 00 00 00 00 00 00 00 00
00000D20: 00 00 00 00 00 00 00 00 00 00 00 00 00 00 00 00
00000D30: 00 00 00 00 00 00 00 00 00 00 00 00 00 00 00 00
00000D40: 00 00 00 00 00 00 00 00 00 00 00 00 00 00 00 00
00000D50: 00 00 00 00 00 00 00 00 00 00 00 00 00 00 00 00
00000D60: 00 00 00 00 00 00 00 00 00 00 00 00 00 00 00 00
00000D70: 00 00 00 00 00 00 00 00 00 00 00 00 00 00 00 00
00000D80: 00 00 00 00 00 00 00 00 00 00 00 00 00 00 00 00
00000D90: 00 00 00 00 00 00 00 00 00 00 00 00 00 00 00 00
00000DA0: 00 00 00 00 00 00 00 00 00 00 00 00 00 00 00 00
00000DB0: 00 00 00 00 00 00 00 00 00 00 00 00 00 00 00 00
00000DC0: 00 00 00 00 00 00 00 00 00 00 00 00 00 00 00 00
00000DD0: 00 00 00 00 00 00 00 00 00 00 00 00 00 00 00 00
00000DE0: 00 00 00 00 00 00 00 00 00 00 00 00 00 00 00 00
00000DF0: 00 00 00 00 00 00 00 00 00 00 00 00 00 00 00 00
00000E00: 00 00 00 00 00 00 00 00 00 00 00 00 00 00 00 00
00000E10: 00 00 00 00 00 00 00 00 00 00 00 00 00 00 00 00
00000E20: 00 00 00 00 00 00 00 00 00 00 00 00 00 00 00 00
00000E30: 00 00 00 00 00 00 00 00 00 00 00 00 00 00 00 00
00000E40: 00 00 00 00 00 00 00 00 00 00 00 00 00 00 00 00
00000E50: 00 00 00 00 00 00 00 00 00 00 00 00 00 00 00 00
00000E60: 00 00 00 00 00 00 00 00 00 00 00 00 00 00 00 00
00000E70: 00 00 00 00 00 00 00 00 00 00 00 00 00 00 00 00
00000E80: 00 00 00 00 00 00 00 00 00 00 00 00 00 00 00 00
00000E90: 00 00 00 00 00 00 00 00 00 00 00 00 00 00 00 00
00000EA0: 00 00 00 00 00 00 00 00 00 00 00 00 00 00 00 00
00000EB0: 00 00 00 00 00 00 00 00 00 00 00 00 00 00 00 00
00000EC0: 00 00 00 00 00 00 00 00 00 00 00 00 00 00 00 00
00000ED0: 00 00 00 00 00 00 00 00 00 00 00 00 00 00 00 00
00000EE0: 00 00 00 00 00 00 00 00 00 00 00 00 00 00 00 00
00000EF0: 00 00 00 00 00 00 00 00 00 00 00 00 00 00 00 00
00000F00: 00 00 00 00 00 00 00 00 00 00 00 00 00 00 00 00
00000F10: 00 00 00 00 00 00 00 00 00 00 00 00 00 00 00 00
00000F20: 00 00 00 00 00 00 00 00 00 00 00 00 00 00 00 00
00000F30: 00 00 00 00 00 00 00 00 00 00 00 00 00 00 00 00
00000F40: 00 00 00 00 00 00 00 00 00 00 00 00 00 00 00 00
00000F50: 00 00 00 00 00 00 00 00 00 00 00 00 00 00 00 00
00000F60: 00 00 00 00 00 00 00 00 00 00 00 00 00 00 00 00
00000F70: 00 00 00 00 00 00 00 00 00 00 00 00 00 00 00 00
00000F80: 00 00 00 00 00 00 00 00 00 00 00 00 00 00 00 00
00000F90: 00 00 00 00 00 00 00 00 00 00 00 00 00 00 00 00
00000FA0: 00 00 00 00 00 00 00 00 00 00 00 00 00 00 00 00
00000FB0: 00 00 00 00 00 00 00 00 00 00 00 00 00 00 00 00
00000FC0: 00 00 00 00 00 00 00 00 00 00 00 00 00 00 00 00
00000FD0: 00 00 00 00 00 00 00 00 00 00 00 00 00 00 00 00
00000FE0: 00 00 00 00 00 00 00 00 00 00 00 00 00 00 00 00
00000FF0: 00 00 00 00 00 00 00 00 00 00 00 00 00 00 00 00
00001000: 8B 44 24 04 56 50 8B F1 68 81 00 00 00 E8 34 71
00001010: 00 00 C7 06 A8 93 40 00 8B C6 5E C2 04 00 90 90
00001020: E9 2D 71 00 00 90 90 90 90 90 90 90 90 90 90 90
00001030: A1 34 91 40 00 C3 90 90 90 90 90 90 90 90 90 90
00001040: B8 88 93 40 00 C3 90 90 90 90 90 90 90 90 90 90
00001050: C3 90 90 90 90 90 90 90 90 90 90 90 90 90 90 90
00001060: C2 04 00 90 90 90 90 90 90 90 90 90 90 90 90 90
00001070: 8B 41 20 6A 00 50 FF 15 7C 93 40 00 C3 90 90 90
00001080: 8B 41 20 6A 01 50 FF 15 7C 93 40 00 C3 90 90 90
00001090: 56 68 86 7F 00 00 6A 00 FF 15 6C 93 40 00 8B 0D
000010A0: 10 BC 40 00 8B F0 25 FF FF 00 00 50 6A F4 51 FF
000010B0: 15 70 93 40 00 56 FF 15 74 93 40 00 5E C3 90 90
000010C0: 56 68 00 7F 00 00 6A 00 FF 15 6C 93 40 00 8B 0D
000010D0: 10 BC 40 00 8B F0 25 FF FF 00 00 50 6A F4 51 FF
000010E0: 15 70 93 40 00 56 FF 15 74 93 40 00 5E C3 90 90
000010F0: A1 10 BC 40 00 56 50 FF 15 68 93 40 00 8B 35 18
00001100: 90 40 00 68 FF 00 00 40 A3 04 BC 40 00 FF D6 68
00001110: 00 FF 00 40 A3 00 BC 40 00 FF D6 68 00 00 FF 40
```

APPENDIX-continued

```
00001120: A3 FC BB 40 00 FF D6 6A 00 A3 F8 BB 40 00 FF D6
00001130: 8B 35 1C 90 40 00 68 FF 00 00 40 6A 03 A3 F0 BB
00001140: 40 00 FF D6 68 00 FF 00 40 6A 03 A3 EC BB 40 00
00001150: FF D6 68 00 00 FF 40 6A 03 A3 E8 BB 40 00 FF D6
00001160: 6A 00 6A 03 A3 E4 BB 40 00 FF D6 8B 35 0C 90 40
00001170: 00 68 FF 00 00 40 6A 01 6A 00 A3 DC BB 40 00 FF
00001180: D6 68 00 FF 00 40 6A 01 6A 00 A3 D8 BB 40 00 FF
00001190: D6 68 00 00 FF 40 6A 01 6A 00 A3 D4 BB 40 00 FF
000011A0: D6 6A 00 6A 01 6A 00 A3 D0 BB 40 00 FF D6 A3 C8
000011B0: BB 40 00 5E C3 90 90 90 90 90 90 90 90 90 90 90
000011C0: A1 F0 BB 40 00 56 8B 35 14 90 40 00 50 FF D6 8B
000011D0: 0D F8 BB 40 00 51 FF D6 8B 15 FC BB 40 00 52 FF
000011E0: D6 A1 00 BC 40 00 50 FF D6 8B 0D 04 BC 40 00 8B
000011F0: 15 10 BC 40 00 51 52 FF 15 64 93 40 00 5E C3 90
00001200: 83 EC 10 8B 0D B0 FC D8 00 8B 15 F0 BB 40 00 33
00001210: C0 89 4C 24 0C 8B 0D 04 BC 40 00 89 44 24 00 89
00001220: 44 24 04 A1 AC FC D8 00 89 44 24 08 8D 44 24 00
00001230: 52 50 51 FF 15 60 93 40 00 83 C4 10 C3 90 90 90
00001240: A1 30 B0 40 00 83 EC 10 83 F8 02 56 57 75 1E 8B
00001250: 7C 24 1C 8B 35 B0 00 D8 00 8B 0D B4 00 D8 00 2B
00001260: FE 8B 74 24 20 2B F1 D1 E7 D1 E6 EB 08 8B 74 24
00001270: 20 8B 7C 24 1C 83 FF 03 0F 8C B5 00 00 00 83 FE
00001280: 03 0F 8C AC 00 00 00 A1 AC FC D8 00 83 C0 FD 3B
00001290: F8 0F 8D 9C 00 00 00 8B 0D B0 FC D8 00 83 C1 FD
000012A0: 3B F1 0F 8D 8B 00 00 00 8B 15 10 BC 40 00 53 52
000012B0: FF 15 68 93 40 00 8B D8 8D 47 FD 89 44 24 0C 8B
000012C0: 44 24 28 8D 4E FD 83 C7 03 83 C6 03 3D 00 FF 00
000012D0: 40 89 4C 24 10 89 7C 24 14 89 74 24 18 7F 1D 74
000012E0: 13 85 C0 74 1E 3D FF 00 00 40 75 17 8B 15 00 BC
000012F0: 40 00 EB 1D 8B 15 FC BB 40 00 EB 15 3D 00 00 FF
00001300: 40 74 08 8B 15 F0 BB 40 00 EB 06 8B 15 F8 BB 40
00001310: 00 8B 0D 04 BC 40 00 8D 44 24 0C 52 50 51 FF 15
00001320: 60 93 40 00 8B 15 10 BC 40 00 52 FF D6 A1 18 93
00001330: 40 00 5B 5F 5E 83 C4 10 C3 90 90 90 90 90 90 90
00001340: A1 30 B0 40 00 83 EC 10 83 F8 02 53 55 8B 6C 24
00001350: 1C 56 75 1E 8B 35 B0 00 D8 00 8B 5C 24 24 8B 0D
00001360: B4 00 D8 00 2B EE 2B D9 D1 E5 D1 E3 89 5C 24 24
00001370: EB 04 8B 5C 24 24 83 FD 03 0F 8C 09 01 00 00 83
00001380: FB 03 0F 8C 00 01 00 00 A1 AC FC D8 00 83 C0 FD
00001390: 3B E8 0F 8D F0 00 00 00 8B 0D B0 FC D8 00 83 C1
000013A0: FD 3B D9 0F 8D DF 00 00 00 8B 15 10 BC 40 00 57
000013B0: 52 FF 15 68 93 40 00 8B F0 6A 00 56 FF 15 08 90
000013C0: 40 00 DB 05 30 B0 40 00 DC 0D 58 B3 40 00 DC 0D
000013D0: 88 94 40 00 DC 05 80 94 40 00 E8 21 6F 00 00 8B
000013E0: 4C 24 28 8B FD 2B F8 2B D8 03 68 03 C1 89 44 24
000013F0: 1C 8B 44 24 2C 3D 00 FF 00 40 7F 37 74 20 85 C0
00001400: 74 38 3D FF 00 00 40 75 31 8B 15 D8 BB 40 00 52
00001410: 56 FF 15 00 90 40 00 A1 EC BB 40 00 EB 44 8B 15
00001420: D4 BB 40 00 52 56 FF 15 00 90 40 00 A1 E8 BB 40
00001430: 00 EB 2F 3D 00 00 00 FF 40 74 15 8B 15 C8 BB 40 00
00001440: 52 56 FF 15 00 90 40 00 A1 DC BB 40 00 EB 13 8B
00001450: 15 D0 BB 40 00 52 56 FF 15 00 90 40 00 A1 E4 BB
00001460: 40 00 50 56 FF 15 00 90 40 00 8B 4C 24 1C 51 55
00001470: 53 57 56 FF 15 10 90 40 00 8B 15 10 BC 40 00 56
00001480: 52 FF 15 64 93 40 00 5F 5E 5D 5B 83 C4 10 C3 90
00001490: A1 20 FF D7 00 56 33 F6 85 C0 7E 24 8B 04 B5 1C
000014A0: BF D7 00 8B 0C B5 1C CF D7 00 6A 00 50 51 E8 8D
000014B0: FE FF FF A1 20 FF D7 00 83 C4 0C 46 3B F0 7C DC
000014C0: 3B 35 EF D7 00 7D 1C 8B 14 B5 1C BF D7 00 8B
000014D0: 04 B5 1C CF D7 00 6A 00 6A 09 52 50 E8 0F 02 00
000014E0: 00 83 C4 10 5E C3 90 90 90 90 90 90 90 90 90 90
000014F0: A1 20 FF D7 00 56 33 F6 85 C0 7E 2B 8B 04 B5 1C
00001500: DF D7 00 8B 0C B5 1C EF D7 00 68 FF 00 00 40 50
00001510: 51 E8 2A FE FF FF A1 20 FF D7 00 83 C4 0C 46 3B
00001520: F0 7C D9 3B 35 28 FF D7 00 7D 1F 8B 14 B5 1C DF
00001530: D7 00 8B 04 B5 1C EF D7 00 68 00 FF 00 40 6A 09
00001540: 52 50 E8 A9 01 00 00 83 C4 10 5E C3 90 90 90 90
00001550: A1 54 99 D7 00 57 33 FF 85 C0 7E 2C 56 BE 70 99
00001560: D7 00 8B 46 04 8B 0E 6A 00 50 51 E8 D0 FC FF FF
00001570: A1 54 99 D7 00 83 C4 0C 47 3B C6 5C 3B F8 7C E2
00001580: 5E B8 01 00 00 00 5F C3 B8 01 00 00 00 5F C3 90
00001590: A1 54 99 D7 00 57 33 FF 85 C0 7E 35 56 BE 6C 99
000015A0: D7 00 83 7E 44 01 75 14 8B 06 8B 4E FC 68 00 00
000015B0: FF 40 50 51 E8 87 FC FF FF 83 C4 0C A1 54 99 D7
000015C0: 00 47 83 C6 5C 3B F8 7C D9 5E 8B 01 00 00 00 5F
000015D0: C3 B8 01 00 00 00 5F C3 90 90 90 90 90 90 90 90
000015E0: 83 3D 20 FB D8 00 01 75 1A A1 DC FA D8 00 8B 0D
000015F0: D8 FA D8 00 68 FF 00 00 40 50 51 E8 40 FC FF FF
00001600: 83 C4 0C B8 01 00 00 00 C3 90 90 90 90 90 90 90
00001610: A1 10 BC 40 00 83 EC 10 56 57 50 FF 15 68 93 40
00001620: 00 8B F8 6A 10 57 FF 15 04 90 40 00 A1 D8 B1 40
00001630: 00 33 F6 85 C0 0F 8E 91 00 00 00 53 8B 1D 60 93
00001640: 40 00 8B 15 30 B0 40 00 8B 04 B5 48 FA C0 00 8B
00001650: 0C B5 A8 F4 C0 00 83 FA 02 75 14 8B 15 B0 00 D8
00001660: 00 2B C2 8B 15 B4 00 D8 00 2B CA D1 E0 D1 E1 83
00001670: F8 02 7C 49 83 F9 02 7C 44 8B 15 AC FC D5 00 83
00001680: C2 FE 3B C2 7D 37 8B 15 B0 FC D8 00 83 C2 FE 3B
00001690: CA 7D 2A 8D 50 FE 83 C0 02 89 54 24 0C 8D 51 FE
000016A0: 83 C1 02 89 44 24 14 A1 FC BB 40 00 89 4C 24 18
000016B0: 8D 4C 24 0C 50 51 57 89 54 24 1C FF D3 A1 D8 B1
000016C0: 40 00 46 3B F0 0F 8C 77 FF FF FF 5B 8B 15 10 BC
000016D0: 40 00 57 52 FF 15 64 93 40 00 5F B8 01 00 00 00
000016E0: 5E 83 C4 10 C3 90 90 90 90 90 90 90 90 90 90 90
000016F0: 8B 44 24 0C 83 EC 10 99 53 2B C2 56 8B F0 A1 30
00001700: B0 40 00 57 D1 FE 83 F8 02 75 1E 8B 5C 24 20 8B
00001710: 3D B0 00 D8 00 8B 0D B4 00 D8 00 2B DF 8B 7C 24
00001720: 24 2B F9 D1 E3 D1 E7 EB 08 8B 7C 24 24 8B 5C 24
00001730: 20 3B DE 0F 8C AE 00 00 00 3B FE 0F 8C A6 00 00
00001740: 00 A1 AC FC D8 00 2B C6 3B D8 0F 8D 97 00 00 00
00001750: 8B 0D B0 FC D8 00 2B CE 3B F9 0F 8D 87 00 00 00
00001760: 8B 15 10 BC 40 00 55 52 FF 15 68 93 40 00 8B E8
00001770: 8B C3 2B C6 8B CF 89 44 24 10 8B 44 24 30 2B CE
00001780: 8D 14 1E 03 F7 3D 00 FF 00 40 89 4C 24 14 89 54
00001790: 24 18 89 74 24 1C 7F 1B 74 12 85 C0 74 1C 3D FF
000017A0: 00 00 40 75 15 A1 00 BC 40 00 EB 1A A1 FC BB 40
000017B0: 00 EB 13 3D 00 00 FF 40 74 07 A1 F0 BB 40 00 EB
000017C0: 05 A1 F8 BB 40 00 8B 15 04 BC 40 00 8D 4C 24 10
000017D0: 50 51 52 FF 15 60 93 40 00 A1 10 BC 40 00 55 50
000017E0: FF 15 64 93 40 00 5D 5F 5E 5B 83 C4 10 C3 90 90
000017F0: A1 18 93 40 00 56 8B 35 EC 92 40 00 83 C0 40 68
00001800: 5C B0 40 00 50 FF D6 8B 4C 24 10 8B 15 18 93 40
00001810: 00 51 83 C2 40 68 58 B0 40 00 52 FF D6 A1 18 93
00001820: 40 00 68 38 B0 40 00 83 C0 40 50 FF D6 83 C4 1C
00001830: 6A 01 FF 15 2C 93 40 00 5E 90 90 90 90 90 90 90
00001840: 56 8B 74 24 08 8B C6 57 8B 7C 24 10 C1 E0 1E 2B
00001850: C6 03 C7 8D 0C 85 08 00 00 00 51 FF 15 20 93 40
00001860: 00 8B F8 83 C4 04 85 FF 75 0D 68 84 B0 40 00 E8
00001870: 7C FF FF FF 83 C4 04 8D 14 B5 00 00 00 00 8B C7
00001880: 2B C2 5F 83 C0 04 5E C3 90 90 90 90 90 90 90 90
00001890: 56 8B 74 24 08 8B C6 57 8B 7C 24 10 C1 E0 1D 2B
000018A0: C6 03 C7 8D 0C C5 10 00 00 00 51 FF 15 20 93 40
000018B0: 00 8B F8 83 C4 04 85 FF 75 0D 68 A4 B0 40 00 E8
000018C0: 2C FF FF FF 83 C4 04 8D 14 F5 00 00 00 00 8B C7
000018D0: 2B C2 5F 83 C0 08 5E C3 90 90 90 90 90 90 90 90
000018E0: 53 8B 5C 24 14 8B 44 24 10 55 8B 6C 24 0C 56 57
000018F0: 8B 7C 24 18 2B FD 2B D8 47 43 8D 04 BD 04 00 00
00001900: 00 50 FF 15 20 93 40 00 8B F0 83 C4 04 85 F6 75
00001910: 0D 68 E8 B0 40 00 E8 D5 FE FF FF 83 C4 04 8B D3
00001920: B9 04 00 00 00 0F AF D7 C1 E5 02 8D 04 D5 08 00
00001930: 00 00 2B CD 50 03 F1 FF 15 20 93 40 00 83 C4 04
00001940: 89 04 2E 85 C0 75 0D 68 C4 B0 40 00 E8 9F FE FF
00001950: FF 83 C4 04 8B 4C 24 1C B8 08 00 00 00 8D 14 CD
00001960: 00 00 00 00 8B 4C 24 14 2B C2 8B 14 2E 03 D0 8B
00001970: 44 24 18 89 14 2E 8D 51 01 3B D0 7F 17 2B C2 8D
00001980: 0C 96 C1 E3 03 40 8B 51 FC 83 C1 04 03 D3 48 89
00001990: 51 FC 75 F2 8B C6 5F 5E 5D 5B C3 90 90 90 90 90
000019A0: 8B 44 24 08 8B 4C 24 04 8D 54 81 FC 52 FF 15 1C
000019B0: 93 40 00 59 C3 90 90 90 90 90 90 90 90 90 90 90
000019C0: 8B 44 24 08 8B 4C 24 04 8D 54 C1 F8 52 FF 15 1C
000019D0: 93 40 00 59 C3 90 90 90 90 90 90 90 90 90 90 90
000019E0: 8B 4C 24 10 53 56 8B 74 24 0C 57 8B 7C 24 14 8B
000019F0: 1D 1C 93 40 00 8B 04 BE 8D 54 C8 F8 52 FF D3 8D
00001A00: 44 BE FC 50 FF D3 83 C4 08 5F 5E 5B C3 90 90 90
00001A10: 55 8B EC 83 E4 F8 83 EC 34 53 8B 5D 0C 56 57 53
00001A20: 6A 01 E8 19 FD FF FF 8B F0 53 6A 01 89 74 24 40
00001A30: E8 0B FE FF FF 53 6A 01 89 44 24 38 E8 FF FD FF
00001A40: FF 83 C4 18 83 FB 01 89 44 24 14 0F 8C 11 03 00
00001A50: 00 8D 78 04 8B CB 33 C0 83 FB 01 F3 AB 0F 8C FF
00001A60: 02 00 00 8D 46 04 89 5C 24 2C 89 44 24 1C 8B 44
00001A70: 24 20 2B C6 8B 74 24 34 89 44 24 10 8B 7D 08 B9
00001A80: 01 00 00 00 C7 44 24 38 00 00 00 00 C7 44 24 3C
00001A90: 00 00 00 00 8D 47 04 89 4C 24 24 8B D0 8B 44 24
00001AA0: 14 2B C7 89 54 24 28 89 44 24 34 83 3C 10 01 74
00001AB0: 6A 8B 44 24 14 BF 01 00 00 00 83 C0 04 89 44 24
00001AC0: 18 8B 44 24 18 8B 00 85 C0 75 1E 8B 02 DD 04 F8
00001AD0: D9 E1 DC 54 24 38 DF E0 F6 C4 01 75 28 DD 5C 24
00001AE0: 38 89 4C 24 0C 8B F7 EB 1E 83 F8 01 7E 19 68 28
00001AF0: B1 40 00 E8 F8 FC FF FF 8B 54 24 2C 8B 4C 24 28
```

APPENDIX-continued

```
00001B00: 83 C4 04 EB 02 DD D8 8B 44 24 18 47 83 C0 04 3B
00001B10: FB 89 44 24 18 7E AA 8B 44 24 34 41 83 C2 04 3B
00001B20: CB 89 4C 24 24 89 54 24 28 7E 80 8B 44 24 14 8B
00001B30: 0C B0 41 89 0C B0 8B 44 24 0C 3B C6 74 69 B9 01
00001B40: 00 00 00 8B 55 08 8B 7C 24 0C 8D 04 CD 00 00 00
00001B50: 00 8B 14 BA 8B 7D 08 8B D8 03 D0 03 1C B7 DD 02
00001B60: DD 03 DD 1A 8B 1C B7 DD 1C 18 03 C3 8B 5D 0C 41
00001B70: 3B CB 7E CF 8B 4D 14 B8 01 00 00 00 3B C8 7C 27
00001B80: 8B 55 10 8B 4C 24 0C 8B 0C 8A 8B 3C B2 DD 04 C1
00001B90: DD 04 C7 8D 0C C1 40 DD 19 8B 14 B2 8B 4D 14 DD
00001BA0: 5C C2 F8 3B C1 7E D9 8B 4C 24 10 8B 44 24 1C 8B
00001BB0: 54 24 0C 8D 3C F5 00 00 00 00 89 14 01 8B 55 08
00001BC0: 89 30 8B C7 03 04 B2 DD 00 DC 1D 90 94 40 00 DF
00001BD0: E0 F6 C4 40 74 10 68 0C B1 40 00 E8 10 FC FF FF
00001BE0: 8B 55 08 83 C4 04 8B 0C B2 DD 05 80 94 40 00 DC
00001BF0: 34 0F 8D 04 0F C7 00 00 00 00 00 C7 40 04 00 00
00001C00: F0 3F B8 01 00 00 00 8B 0C B2 D9 C0 DC 0C C1 8D
00001C10: 0C C1 40 3B C3 DD 19 7E EE 8B 7D 14 B8 01 00 00
00001C20: 00 3B F8 7C 15 8B 4D 10 D9 C0 8B 0C B1 DC 0C C1
00001C30: 8D 0C C1 40 3B C7 DD 19 7E EB 8B 45 10 B9 01 00
00001C40: 00 00 2B C2 89 4C 24 28 DD D8 8D 7A 04 89 44 24
00001C50: 34 3B CE 74 6F 8B 17 B9 01 00 00 00 DD 04 F2 8D
00001C60: 04 F2 C7 00 00 00 00 00 C7 40 04 00 00 00 00 8B
00001C70: 17 8B 5D 08 8D 04 CD 00 00 00 00 03 D0 03 04 B3
00001C80: 8B 5D 0C 41 D9 C0 DC 08 3B CB DC 2A DD 1A 7E DF
00001C90: 8B 4D 14 B8 01 00 00 00 3B C8 0F 8C EF 00 00 00
00001CA0: 8B 54 24 34 8B 5D 10 8B 0C 3A D9 C0 8B 1C B3 8D
00001CB0: 0C C1 DC 0C C3 40 DC 29 DD 19 3B 45 14 7E E5 8B
00001CC0: 5D 0C DD D8 8B 4C 24 28 83 C7 04 41 3B CB 89 4C
00001CD0: 24 28 0F 8E 79 FF FF FF 8B 4C 24 1C 8B 44 24 2C
00001CE0: 83 C1 04 48 89 4C 24 1C 89 44 24 2C 0F 85 8A FD
00001CF0: FF FF 8B 74 24 30 83 FB 01 7C 67 8B 7C 24 20 8D
00001D00: 04 9E 2B FE 89 5C 24 28 89 7C 24 10 8B 14 38 8B
00001D10: 08 3B D1 74 3F 83 FB 01 7C 3A 8B 4D 08 89 5C 24
00001D20: 2C 83 C1 04 8B 11 8B 34 38 8B 38 83 C1 04 DD 04
00001D30: F2 DD 04 FA 8D 34 F2 8B 7C 24 10 DD 1E 8B 10 8B
00001D40: 71 FC DD 1C D6 8B 54 24 2C 4A 89 54 24 2C 75 D4
00001D50: 8B 74 24 30 8B 4C 24 28 83 E8 04 49 89 4C 24 28
00001D60: 75 AA 8B 44 24 14 53 6A 01 50 E8 31 FC FF FF 8B
00001D70: 4C 24 2C 53 6A 01 51 E8 24 FC FF FF 53 6A 01 56
00001D80: E8 1B FC FE FF 83 C4 24 5F 5E 5B 8B E5 5D C3 DD
00001D90: D8 E9 2E FF FF FF 90 90 90 90 90 90 90 90 90 90
00001DA0: 56 57 8B 3D 28 FF D7 00 33 F6 85 FF 0F 8E A1 00
00001DB0: 00 00 DB 04 B5 1C 9F D7 00 DB 04 B5 1C AF D7 00
00001DC0: D9 C0 D8 CA D9 E0 D9 C1 D8 CA D9 E0 DC 0D 48 5A
00001DD0: D3 00 D9 C1 DC 0D 50 5A D3 00 DE C1 D9 C2 DC 0D
00001DE0: 18 5A D3 00 DE C1 D9 C3 DC 0D 20 5A D3 00 DE C1
00001DF0: DC 05 28 5A D3 00 DC 05 88 94 40 00 E8 FF 64 00
00001E00: 00 D9 C2 D8 CB 89 04 B5 1C EF D7 00 D9 E0 DC 0D
00001E10: 50 5A D3 00 D9 C9 DC 0D 48 5A D3 00 DE C1 D9 C9
00001E20: DC 0D 30 5A D3 00 DE C1 D9 C9 DC 0D 38 5A D3 00
00001E30: DE C1 DC 05 40 5A D3 00 DC 05 88 94 40 00 E8 BD
00001E40: 64 00 00 89 04 B5 1C DF D7 00 46 3B F7 0F 8C 5F
00001E50: FF FF FF 5F 5E B8 01 00 00 00 5E C3 90 90 90 90
00001E60: DB 44 24 0C DB 44 24 10 D9 C0 D8 CA D9 E0 D9 C2
00001E70: D8 CB D9 E0 DC 0D 48 5A D3 00 D9 C1 DC 0D 50 5A
00001E80: D3 00 DE C1 D9 C2 DC 0D 20 5A D3 00 DE C1 D9 C3
00001E90: DC 0D 18 5A D3 00 DE C1 DC 05 28 5A D3 00 DC 05
00001EA0: 88 94 40 00 E8 57 64 00 00 8B 4C 24 04 D9 C1 D8
00001EB0: CA 89 01 D9 E0 DC 0D 50 5A D3 00 D9 CA DC 0D 38
00001EC0: 5A D3 00 DE C2 DC 0D 48 5A D3 00 DE C1 D9 C9 DC
00001ED0: 0D 30 5A D3 00 DE C1 DC 05 40 5A D3 00 DC 05 88
00001EE0: 94 40 00 E8 18 64 00 00 8B 54 24 08 89 02 B8 01
00001EF0: 00 00 00 C3 90 90 90 90 90 90 90 90 90 90 90 90
00001F00: 55 8B EC 83 E4 F8 81 EC B8 00 00 00 DB 05 14 50
00001F10: D3 00 B9 01 00 00 00 C7 44 24 10 00 8B 1A C7
00001F20: 44 24 14 00 00 00 F0 3F 8D 44 24 20 DC 6D 10 D9 C0
00001F30: DB 05 18 50 D3 00 DC 6D 08 DD 54 24 00 D9 C0 D8
00001F40: C9 D9 C2 D8 CB DE C1 D9 FA DD 5C 24 08 DD D8 DD
00001F50: 5D DD 44 24 00 D9 C1 D8 89 4C 24 00 D8 44 24 00 41
00001F60: 83 C0 10 83 F9 0A 89 4C 24 00 D8 C9 D9 C0 D9 FE
00001F70: DD 58 E8 D9 FF DD 58 F0 7E E1 DD D8 DD 05 90 94
00001F80: 40 00 33 C0 DD 80 E8 FF C0 00 DC 4C 04 10 83 C0
00001F90: 08 3D A8 00 00 00 DC 17 CE EA DB 45 18 D8 C1 DC
00001FA0: 5C 24 08 DF E0 F6 C4 01 DD D8 75 09 D8 75 08 B8 01 00 00
00001FB0: 00 8B E5 5D C3 33 C0 8B E5 5D C3 90 90 90 90 90
00001FC0: 55 8B EC 83 E4 F8 83 EC 08 53 56 6A 15 6A 01 6A
00001FD0: 15 6A 01 E8 08 F9 FF FF 6A 01 6A 01 6A 15 6A 01
00001FE0: 89 44 24 2C E8 F7 F8 FF FF 8B 55 0C 83 C4 20 83
00001FF0: FA 01 8B F0 7C 1B 8D 46 04 8B CA 8B 18 83 C0 04
00002000: 49 C7 43 08 00 00 00 00 C7 43 0C 00 00 F0 3F 75
00002010: EA 8B 45 08 6A 01 56 52 50 E8 F2 F9 FF FF 8B 4C
00002020: 24 1C 6A 15 6A 01 6A 15 6A 01 51 E8 B0 F9 FF FF
00002030: 6A 01 6A 01 6A 15 6A 01 56 E8 A2 F9 FF FF 83 C4
00002040: 38 B8 01 00 00 00 5E 5B 8B E5 5D C3 90 90 90 90
00002050: 53 8B 5C 24 14 56 8B 74 24 0C 53 56 E8 5F FF FF
00002060: FF 83 C4 08 85 DB 7E 52 8B 44 24 14 55 57 8B 7C
00002070: 24 18 83 C6 04 89 5C 24 20 C7 00 00 00 00 00 C7
00002080: 40 04 00 00 00 00 B9 08 00 00 00 8B D3 8B 2E DD
00002090: 04 39 DC 0C 29 83 C1 08 4A DC 00 DD 18 75 EE 8B
000020A0: 4C 24 20 83 C6 04 83 C0 08 49 89 4C 24 20 75 C9
000020B0: 5F 5D 5E B8 01 00 00 00 5B C3 5E B8 01 00 00 00
000020C0: 5B C3 90 90 90 90 90 90 90 90 90 90 90 90 90 90
000020D0: 57 8B 7C 24 08 85 FF 0F 8E E2 00 00 00 D9 05 98
000020E0: 94 40 00 D9 05 98 94 40 00 D9 05 98 94 40 00 D9
000020F0: 05 98 94 40 00 53 55 8B 6C 24 18 56 8B 74 24 18
00002100: 7E 15 8B CE 8B C5 2B CD 8B D7 DA 04 01 DB 00 83
00002110: C0 04 4A DE C2 75 F3 DB 44 24 14 D9 5C 24 14 D8
00002120: 74 24 14 DC 05 88 94 40 00 E8 D2 61 00 00 D8 74
00002130: 24 14 8B 5C 24 20 89 03 DC 05 88 94 40 00 E8 BD
00002140: 61 00 00 8B 4C 24 24 89 01 8B 4C 24 28 85 C9 74
00002150: 60 8B 4C 24 2C 85 C9 74 58 85 FF 7E 32 8B 1B 8B
00002160: D5 2B F5 8B 0C 32 83 C2 04 2B CB 8B E9 0F AF E9
00002170: 8B 4A FC 89 6C 24 1C 2B C8 8B E9 0F AF E9 DA 44
00002180: 24 1C 89 6C 24 1C 4F DB 44 24 1C DE C2 75 D4 D8
00002190: 74 24 14 8B 54 24 28 8B 44 24 2C 5E 5D 5B 5F D9
000021A0: FA D9 1A D8 74 24 04 D9 FA D9 18 B8 01 00 00 00
000021B0: C3 5E 5D DD D8 5B B8 01 00 00 00 DD D8 5F C3 33
000021C0: C0 5F C3 90 90 90 90 90 90 90 90 90 90 90 90 90
000021D0: 83 EC 08 53 55 33 DB 56 57 89 5C 24 10 BD 60 5A
000021E0: D5 00 33 F6 8B FD 89 74 24 14 85 F6 74 77 81 FD
000021F0: 60 5A D5 00 74 6F DB 44 24 10 DB 44 24 14 D9 C1
00002200: DC 0D A8 94 40 00 D8 F1 D9 E1 DC 15 A0 94 40 00
00002210: DF E0 F6 C4 01 75 09 DD D8 B8 FF FF 00 00 EB 05
00002220: E8 DB 60 00 00 DC 0D A8 94 40 00 66 89 07 DE F1
00002230: D9 E1 DC 15 A0 94 40 00 DF E0 F6 C4 01 75 14 8D
00002240: 0C 33 B8 FF FF 00 00 DD D8 66 89 04 4D 60 5A D3
00002250: 00 EB 24 E8 A8 60 00 00 8D 0C 33 66 89 04 4D 60
00002260: 5A D3 00 EB 12 8D 14 33 66 C7 07 00 00 66 C7 04
00002270: 55 60 5A D3 00 00 00 46 81 C7 00 02 00 00 81 FE
00002280: 00 01 00 00 89 74 24 14 0F 8C 5C FF FF FF 8B 74
00002290: 24 10 83 C5 02 46 81 C3 00 01 00 00 81 FD 60 5C
000022A0: D5 00 89 74 24 10 0F 8C 36 FF FF FF 5F 5E 5D 5B
000022B0: 83 C4 08 C3 90 90 90 90 90 90 90 90 90 90 90 90
000022C0: 83 EC 18 8B 4C 24 38 8B 54 24 30 33 C0 53 89 44
000022D0: 24 04 89 44 24 18 8B 44 24 40 55 56 8B 74 24 40
000022E0: 8B E8 2B F2 2B E9 57 8B DD 8B FE 85 C0 89 4C 24
000022F0: 1C 89 54 24 20 89 7C 24 18 48 0F 8C 34
00002300: 02 00 00 3B 0D B0 FC D8 00 0F 8D 28 02 00 00 8B
00002310: 44 24 44 85 C0 0F 8C 1C 02 00 00 3B 15 AC FC D8
00002320: 00 0F 8D 10 02 00 00 85 C9 7D 52 F7 D9 85 C9 C7
00002330: 44 24 1C 00 00 00 00 89 4C 24 10 7E 40 8B 54 24
00002340: 38 8B 7C 24 3C 8B C1 2B FA 89 44 24 14 33 C9 85
00002350: F6 7E 18 8B 04 17 41 3B CE 66 C7 44 48 FE 40 00
00002360: 8B 02 66 C7 44 48 FE 40 00 7C E8 8B 44 24 14 83
00002370: C2 04 48 89 44 24 14 75 D4 8B 54 24 40 8B 44 24
00002380: 34 8B 4C 24 4C 3B C8 7C 45 2B C1 03 D8 3B DD 89
00002390: 5C 24 18 7D 39 8B 44 24 38 8B 7C 24 3C 2B F8 8D
000023A0: 14 98 8B C5 2B C3 33 C9 85 F6 7E 18 8B 1C 3A 41
000023B0: 3B CE 66 C7 44 4B FE 40 00 8B 1A 66 C7 44 4B FE
000023C0: 40 00 7C E8 83 C2 04 48 75 DC 8B 54 24 40 85 D2
000023D0: 7D 55 8B C2 C7 44 24 20 00 00 00 00 F7 D8 85 ED
000023E0: 89 44 24 24 7E 41 8B C2 8B 7C 24 3C 99 33 C2 89
000023F0: 6C 24 40 2B C2 8B 54 24 38 2B FA 33 C9 85 C0 7E
00002400: 18 8B 1C 3A 41 3B C8 66 C7 44 4B FE 40 00 8B 1A
00002410: 66 C7 44 4B FE 40 00 7C E8 8B 4C 24 40 83 C2 04
00002420: 49 89 4C 24 40 75 D4 8B 5C 24 30 8B 44 24 44 3B
00002430: C3 7C 44 8B 54 24 48 8B CB 2B C8 03 D1 85 ED 89
00002440: 54 24 48 7E 32 8B 4C 24 38 8B 54 24 3C 2B D1 8B
00002450: 44 24 48 8B F8 3B FE 7D 18 8B 3C 11 40 3B C6 66
00002460: C7 44 47 FE 40 00 8B 39 66 C7 44 47 FE 40 00 7C
00002470: E8 83 C1 04 4D 75 D8 8B 44 24 18 8B 54 24 10 3B
00002480: D0 0F 8D E2 00 00 00 46 81 C7 00 00 02 00 8B 74 24 20 8B
00002490: 6C 24 3C 8D 3C 91 8D 0C 9D 00 00 00 00 89 4C 24
000024A0: 44 8B 4C 24 1C 0F AF CB 8B 5C 24 38 03 CE 8B 74
000024B0: 24 2C 2B DD 2B C2 8D 0C 8E 89 44 24 3C 89 4C 24
000024C0: 40 8B 54 24 48 8B C1 8B 4C 24 24 3B CA 7D 3F 66
000024D0: 8B 10 66 8B 70 01 8B 2C 3B 40 81 E2 FF FF 00 00
```

APPENDIX-continued

```
000024E0: 81 E6 FF FF 00 00 83 C0 03 41 66 8B 14 55 60 5A
000024F0: D5 00 66 89 54 4D FE 8B 17 66 8B 34 75 60 5A D3
00002500: 00 66 89 74 4A FE 8B 54 24 48 3B CA 7C C1 8B 4C
00002510: 24 40 8B 74 24 44 8B 44 24 3C 03 CE 83 C7 04 48
00002520: 89 4C 24 40 89 44 24 3C 75 97 5F 5E 5D B8 01 00
00002530: 00 00 5B 83 C4 18 C3 85 DB 7E 2E 8B 4C 24 38 8B
00002540: 54 24 3C 2B D1 33 C0 85 FF 7E 18 8B 34 11 40 3B
00002550: C7 66 C7 44 46 FE 40 00 8B 31 66 C7 44 46 FE 40
00002560: 00 7C E8 83 C1 04 4B 75 DC 5F 5E 5D B8 01 00 00
00002570: 00 5B 83 C4 18 C3 90 90 90 90 90 90 90 90 90 90
00002580: 81 EC 38 04 00 00 53 55 8B AC 24 54 04 00 00 56
00002590: 8B B4 24 5C 04 00 00 8B C5 99 0F AF EE 2B C2 57
000025A0: 8B D8 8B C6 99 2B C2 8B 8C 24 58 04 00 00 8B F8
000025B0: 8B 84 24 64 04 00 00 2B E8 33 C0 89 44 24 40 89
000025C0: 44 24 3C 89 44 24 44 89 44 24 10 8D 46 FF 99 D1
000025D0: FF 2B C2 2B CF D1 FB D1 F8 45 3B C1 89 5C 24 14
000025E0: 89 7C 24 20 89 4C 24 38 0F 8D 12 02 00 00 8B 94
000025F0: 24 4C 04 00 00 2B C8 89 54 24 1C 8B 94 24 50 04
00002600: 00 00 89 4C 24 30 8D 14 82 89 54 24 2C EB 07 8B
00002610: B4 24 60 04 00 00 B9 00 01 00 00 33 C0 8D 7C 24
00002620: 48 F3 AB 8B 44 24 10 03 F0 3B C6 89 74 24 34 7D
00002630: 2D 8B 7C 24 1C 2B F0 8B 9C 24 5C 04 00 00 33 C0
00002640: 85 DB 7E 14 8B 17 33 C9 8A 0C 02 FF 44 8C 48 8D
00002650: 4C 8C 48 40 3B C3 7C EE 83 C7 04 4E 75 D9 33 FF
00002660: 33 F6 85 ED B8 FF 00 00 00 89 7C 24 44 89 74 24
00002670: 40 7E 22 8D 8C 24 44 04 00 00 85 C0 7C 17 03 FE
00002680: 48 89 7C 24 44 8B 31 83 E9 04 89 74 24 40 8D 14
00002690: 37 3B D5 7C E5 8D 48 01 8B 84 24 5C 04 00 00 8B
000026A0: 5C 24 14 48 99 2B C2 8B 94 24 54 04 00 00 2B D3
000026B0: 89 4C 24 3C D1 F8 4A C7 44 24 24 00 00 00 00 3B
000026C0: C2 89 44 24 18 89 54 24 28 0F 8D FA 00 00 00 8B
000026D0: 54 24 2C 8B 12 88 0C 02 8B 44 24 34 8B 54 24 10
000026E0: 3B D0 7D 7F 8B 5C 24 1C 8B CA 2B C1 8B 13 8B 7C
000026F0: 24 24 33 C9 8A 0C 3A 8B 74 8C 48 4E 89 74 8C 48
00002700: 8B 74 24 3C 3B CE 7E 06 FF 4C 24 44 EB 06 75 04
00002710: FF 4C 24 40 8B B4 24 5C 04 00 00 03 D7 33 C9 8A
00002720: 0C 32 8B D1 8B 7C 94 48 47 89 7C 94 48 8B 4C 24
00002730: 3C 3B D1 7E 0B 8B 7C 24 44 47 89 7C 24 44 EB 15
00002740: 75 0F 8B 74 24 40 8B 7C 24 44 46 89 74 24 40 EB
00002750: 08 8B 7C 24 44 8B 74 24 40 83 C3 04 48 75 8D 8B
00002760: 5C 24 14 3B FD 7C 1F 81 F9 00 01 00 00 7D 17 41
00002770: 89 4C 24 3C 8B 74 8C 48 2B FE 89 74 24 40 3B FD
00002780: 89 7C 24 44 7D E1 8D 14 37 3B D5 7D 1E 85 C9 7C
00002790: 1A 49 8B FA 89 4C 24 3C 89 7C 24 44 8B 74 8C 48
000027A0: 89 74 24 40 8D 14 37 3B D5 7C E2 8B 44 24 15 8B
000027B0: 54 24 40 42 89 54 24 28 8B 54 24 28 3B C2 89
000027C0: 44 24 18 0F 8C 06 FF FF FF 8B 54 24 2C 8B 7C 24
000027D0: 10 47 8B 32 83 C2 04 89 7C 24 10 89 54 24 2C 88
000027E0: 0C 06 8B 74 24 1C 8B 44 24 30 83 C6 04 48 FE 24
000027F0: 24 1C 89 44 24 30 0F 85 13 FE FF FF 8B 7C 24 20
00002800: 8B AC 24 54 04 00 00 8B C3 8B CD 2B CB 3B D9 89
00002810: 4C 24 28 7D 67 85 FF 7E 5E 8B 94 24 50 04 00 00
00002820: 8B B4 24 58 04 00 00 8B 7C 24 20 8B CA 8D 74 B2
00002830: FC EB 07 8B 94 24 50 04 00 00 8B 5C 24 20 83 C1
00002840: 04 83 EE 04 4F 8B 14 9A 8B 59 FC 8A 14 02 88 14
00002850: 18 8B 94 24 50 04 00 00 8B 5C 24 38 8B 54 9A FC
00002860: 8B 5E 04 8A 14 02 88 14 03 75 C8 8B 5C 24 14 8B
00002870: 4C 24 2C 88 8B 7C 24 20 40 3B C1 7C 99 8B BC 24 58
00002880: 04 00 00 85 FF 7E 31 8B B4 24 50 04 00 00 33 C9
00002890: 85 DB 7C 1E 8B 06 8A 54 18 01 88 14 08 8B 06 8B
000028A0: D0 2B C1 2B D3 41 3B CB 8A 54 2A FE 88 54 28 FF
000028B0: 7E E2 83 C6 04 4F 75 D6 5F 5E 5D 5B 81 C4 38 04
000028C0: 00 00 C3 90 90 90 90 90 90 90 90 90 90 90 90 90
000028D0: 53 56 8B 74 24 18 BA 01 00 00 00 57 8B 7C 24 14
000028E0: 8D 46 FF 3B C2 7E 77 8B 44 24 18 8B 5C 24 10 55
000028F0: 8D 68 FF B8 01 00 00 00 8B 7E 59 8B 4C 93 FC
00002900: 03 C8 80 79 FF 00 74 41 80 39 00 74 3C 80 79 01
00002910: 00 74 36 8B 0C 93 03 C8 80 79 FF 00 74 2B 80 39
00002920: 00 74 26 80 79 01 00 74 20 8B 4C 93 04 03 C8 80
00002930: 79 FF 00 74 14 80 39 00 74 0F 80 79 01 00 74 09
00002940: 8B 0C 97 C6 04 01 FF EB 07 8B 0C 97 C6 04 01 00
00002950: 40 3B C5 7C A7 42 8D 46 FF 3B D0 7C 96 5D 8B 4C
00002960: 24 18 33 C0 85 C9 7E 1E 8B 57 04 8B 1F 8A 14 02
00002970: 88 14 03 8B B7 F8 8B 5C 24 14 02 88 14
00002980: 03 40 3B C1 7C E2 85 F6 7E 1E 8B C7 8B 08 83 C0
00002990: 04 8A 51 01 88 11 8B 48 FC 8B 54 24 18 03 CA 4E
000029A0: 8A 51 FE 88 51 FF 75 E4 5F 5E 5B C3 90 90 90 90
000029B0: 83 EC 38 8B 44 24 4C 53 99 8B 5C 24 48 55 2B C2
000029C0: 56 8B F0 8B 44 24 54 D1 FE 57 8D 3C 70 8D 2C 73
000029D0: 57 55 89 7C 24 24 E8 85 3C 00 00 57 55 89 44 24
000029E0: 20 E8 7A 3C 00 00 55 89 44 24 40 E8 F0 3C 00 00
000029F0: 83 C4 14 89 44 24 14 85 FF 7E 34 8B 54 24 10 89
00002A00: 7C 24 34 33 C9 85 F6 7E 18 8B 2A 8D 04 73 2B C1
00002A10: 41 3B CE C6 44 28 FF 00 8B 02 C6 44 01 FF 00 7C
00002A20: E8 8B 44 24 34 83 C2 04 48 89 44 24 34 75 D4 8D
00002A30: 04 73 33 ED 85 C0 7E 33 8D 56 01 85 D2 7E 24 8B
00002A40: 44 24 10 8B C8 8D 44 B8 FC 8B 38 83 E8 04 83 C1
00002A50: 04 4A C6 04 2F 00 8B 79 FC C6 04 2F 00 75 EA 8B
00002A60: 7C 24 1C 45 8D 04 73 3B E8 7C CD 8B 44 24 58 85
00002A70: C0 7E 4D 8B 4C 24 10 8B 6C 24 4C 89 44 24 34 8D
00002A80: 14 B1 89 54 24 4C 33 C9 85 DB 7E 1B 8B 45 00 8B
00002A90: 7C 24 4C 8D 14 31 8A 04 08 8B 3F 41 3B CB 88 04
00002AA0: 3A 7C E9 8B 7C 24 1C 8B 4C 24 4C 8B 44 24 34 83
00002AB0: C5 04 83 C1 04 48 89 4C 24 4C 89 44 24 34 75 C6
00002AC0: 85 FF 7E 1F 8B 54 24 2C 8D 0C 73 33 C0 85 C9 7E
00002AD0: 0C 8B 2A 40 3B C1 C6 44 28 FF 00 7C F4 83 C2 04
00002AE0: 4F 75 E5 8D 2C 73 33 FF 85 ED 7E 41 8B 44 24 14
00002AF0: 8B 4C 24 5C C7 00 00 00 00 00 85 C9 7E 24 8B 6C
00002B00: 24 10 89 4C 24 4B 8D 00 33 D2 83 C5 04 8A 14
00002B10: 39 8B 08 03 CA 89 08 8B 4C 24 4C 49 89 4C 24 4C
00002B20: 75 E4 47 8D 2C 73 83 C0 04 3B FD 7C C3 8B 44 24
00002B30: 1C 8B FE 8B C8 89 7C 24 24 2B CE 49 3B F1 89 4C
00002B40: 24 44 0F 8D 2C 02 00 00 8B 54 24 10 8D 04 F2 89
00002B50: 44 24 28 8B 44 24 5C 33 C9 33 D2 3B C1 89 54 24
00002B60: 30 89 4C 24 18 89 4C 24 4C 7E 5C 8B 5C 24 10 8B
00002B70: C7 2B C6 8B 6C 24 14 8B 04 83 89 44 24 38 8B 44
00002B80: 24 28 8B 00 89 44 24 34 8B 5C 24 38 33 C0 83 C5
00002B90: 04 8A 04 0B 8B 5C 24 4C 03 D8 33 C0 89 5C 24 4C
00002BA0: 8B 5C 24 34 8A 04 0B 8B 5C 24 18 03 D8 8B 44 24
00002BB0: 5C 89 5C 24 18 8B 5D FC 03 D3 41 3B C8 7C C9 8B
00002BC0: 5C 24 54 89 54 24 30 8D 04 73 8B CE 2B C6 48 3B
00002BD0: 5C 24 54 89 54 24 30 8D 04 73 8B CE 2B C6 48 3B
00002BE0: EF 8D 1C B5 00 00 00 00 2B EE 8D 04 F0 89 5C 24
00002BF0: 20 89 44 24 34 8B 44 24 4C 85 C0 75 6A 8B 44 24
00002C00: 18 85 C0 75 62 8B 44 24 20 2B C3 8B 5C 24 14 83
00002C10: 3C 18 00 75 62 8B 44 24 34 83 38 00 75 49 85 D2
00002C20: 74 45 8D 04 37 3B E8 7D 3E 8B 7C 24 2C 8B D1 2B
00002C30: D6 2B C5 89 54 24 3C 8D 1C 31 8D 3C AF 89 44 24
00002C40: 38 3B D3 7D 10 8B 07 42 3B D3 C6 44 10 FF FF 7C
00002C50: F4 8B 54 24 3C 8B 44 24 38 83 C7 04 48 89 44 24
00002C60: 38 75 DE 8B 7C 24 24 8B 54 24 10 33 DB 8B 14 AA
00002C70: 8B C2 03 D1 2B C6 8A 1C 08 33 C0 8A 44 32 01 8D
00002C80: 14 37 2B C3 8B 5C 24 4C 03 D8 8B 44 24 10 89 5C
00002C90: 24 4C 33 DB 8B 14 90 8D 3C 31 8B C2 03 D1 2B C6
00002CA0: 8A 1C 08 33 C0 8A 44 32 01 8B 54 24 20 2B C3 8B
00002CB0: 5C 24 18 03 D8 8B 44 24 14 89 5C 24 18 8D 1C B5
00002CC0: 00 00 00 00 8B 7C B8 04 2B D3 2B 3C 02 8B 54 24
00002CD0: 20 B8 04 00 00 00 D7 8B 7C 24 20 03 F8 41 89
00002CE0: 7C 24 20 8B 7C 24 34 03 F8 8B 44 24 40 89 7C 24
00002CF0: 34 8B 7C 24 24 3B C8 89 54 24 30 0F 8C F4 FE FF
00002D00: FF 8B 5C 24 54 8D 2C 73 33 D2 85 ED 7E 46 8B 44
00002D10: 24 10 8B CF 8B CE 8D 0C 88 89 4C 24 4C 8B 4C 24
00002D20: 14 8B 44 24 4C 33 DB 83 C1 04 8B 00 8A 1C 10 8B
00002D30: 41 FC 2B C3 33 DB 89 41 FC 8B 44 24 28 8B 40 04
00002D40: 8A 1C 10 8B 41 FC 03 D8 42 89 59 FC 3B D5 7C D1
00002D50: 8B 5C 24 54 8B 4C 24 28 8B 44 24 44 47 83 C1 04
00002D60: 3B F8 89 7C 24 24 28 0F 8C E3 FD FF FF
00002D70: 8B 44 24 1C 85 C0 7E 36 8B 4C 24 10 8B 54 24 2C
00002D80: 2B D1 89 44 24 5C 33 C0 85 ED 7E 14 8B 3C 0A 80
00002D90: 3C 07 FF 75 06 8B 39 C6 04 07 00 40 3B C5 7C EC
00002DA0: 8B 44 24 5C 83 C1 04 48 89 44 24 5C 75 D8 8B 54
00002DB0: 24 58 85 D2 7E 3D 8B 4C 24 10 8B 6C 24 50 89 54
00002DC0: 24 5C 8D 3C B1 33 C9 85 DB 7E 17 8B 17 8B 45 00
00002DD0: 03 D1 41 3B CB 8A 14 32 88 54 08 FF 7C ED 8B 54
00002DE0: 24 58 8B 44 24 5C 83 C7 04 83 C5 04 48 89 44 24
00002DF0: 5C 75 D2 33 C0 85 DB 7E 19 8B 4C 24 50 40 3B C3
00002E00: 8B 74 91 F8 8B 7C 91 FC 8A 4C 30 FF 88 4C 07 FF
00002E10: 7C E7 85 D2 7E 18 8B 74 24 50 8B FA 8B 16 83 C6
00002E20: 04 4F 8A 4C 13 FE 8D 04 13 88 48 FF 75 EE 8B 54
00002E30: 24 14 52 E8 F8 39 00 00 8B 74 24 20 8B 44 24 30
00002E40: 56 50 E8 A9 39 00 00 8B 4C 24 1C 56 51 E9 9E 39
00002E50: 00 00 83 C4 14 5F 5E 5D 5B 83 C4 38 C3 90 90 90
00002E60: 55 56 57 8B 7C 24 14 57 E8 38 00 00 8B 74 24
00002E70: 14 83 C4 04 85 FF DB 06 6B E8 D9 C0 D8 0D C4 94
00002E80: 40 00 D9 5C 24 14 D8 0D C0 94 40 00 D8 44 24 14
00002E90: 7E 51 8B CD 8B C6 2B CE 8B D7 DB 00 83 C0 04 4A
00002EA0: D8 0D BC 94 40 00 DE C1 D9 54 01 FC DB 40 FC D9
00002EB0: 54 24 10 D8 0D B8 94 40 00 D9 C9 D8 0D B4 94 40
```

APPENDIX-continued

```
00002EC0: 00 DE E9 D8 44 24 14 D9 44 24 10 D8 0D BC 94 40
00002ED0: 00 D9 44 01 FC D8 0D B0 94 40 00 DE E9 D9 5C 24
00002EE0: 14 75 B7 DD D8 DB 44 BE FC 8D 4F FF 85 C9 D9 54
00002EF0: 24 14 D8 0D C4 94 40 00 D9 44 24 14 D8 0D C9 94
00002F00: 40 00 D8 C1 D9 5C 24 14 7C 47 8D 44 8D 00 41 D9
00002F10: 00 D9 C0 D8 0D BC 94 40 00 83 E8 04 49 D9 54 24
00002F20: 10 D8 44 24 14 D9 50 04 D9 C9 D8 0D B8 94 40 00
00002F30: D9 C9 D8 0D B4 94 40 00 DE E9 D8 C1 D9 5C 24 14
00002F40: DD D8 D9 40 04 D8 0D B0 94 40 00 D8 6C 24 10 75
00002F50: BE 85 FF DD D8 7E 16 53 8B DD 2B DE D9 04 1E E8
00002F60: 9C 53 00 00 89 06 83 C6 04 4F 75 F0 5B 55 E8 BD
00002F70: 38 00 00 83 C4 04 5F 5E 5D C3 90 90 90 90 90 90
00002F80: A1 34 B0 40 00 83 EC 68 85 C0 53 8B 1D 00 93 40
00002F90: 00 55 8B 2D 04 93 40 00 56 8B 35 C4 92 40 00 57
00002FA0: 8B 3D 10 93 40 00 74 7A 8D 44 24 10 50 FF D6 8D
00002FB0: 4C 24 14 51 FF D7 50 68 C8 B1 40 00 8D 54 24 24
00002FC0: 6A 64 52 FF D3 8D 44 24 2C 50 68 A0 B1 40 00 68
00002FD0: 1C BC 40 00 FF 15 14 93 40 00 68 9C B1 40 00 68
00002FE0: 1C BC 40 00 FF D5 83 C4 2C A3 18 BC 40 00 85 C0
00002FF0: 75 1C 50 68 90 B1 40 00 68 7C B1 40 00 50 FF 15
00003000: 5C 93 40 00 5F 5E 5D 33 C0 5B 83 C4 68 C3 50 FF
00003010: 15 0C 93 40 00 83 C4 04 C7 05 34 B0 40 00 00 00
00003020: 00 00 8D 4C 24 10 51 FF D6 8D 54 24 14 52 FF D7
00003030: 50 68 70 B1 40 00 8D 44 24 24 6A 64 50 FF D3 68
00003040: 6C B1 40 00 68 1C BC 40 00 FF D5 83 C4 20 A3 18
00003050: BC 40 00 85 C0 75 1C 50 68 90 B1 40 00 68 7C B1
00003060: 40 00 50 FF 15 5C 93 40 00 5F 5E 5D 33 C0 5B 83
00003070: C4 68 C3 8B 0D 20 FF D7 00 8D 54 24 14 52 8B 14
00003080: 8D 1C DF D7 00 52 8B 14 8D 1C EF D7 00 52 51 68
00003090: 44 B1 40 00 50 FF 15 EC 92 40 00 A1 18 BC 40 00
000030A0: 50 FF 15 0C 93 40 00 83 C4 1C B8 01 00 00 00 5F
000030B0: 5E 5D 5B 83 C4 68 C3 90 90 90 90 90 90 90 90 90
000030C0: 55 8B EC 83 E4 F8 83 EC 08 A1 10 50 D3 00 53 33
000030D0: DB 55 56 3B C3 57 7E 51 BE F8 BC 40 00 BA 90 00
000030E0: C1 00 8B F8 BD 00 00 F0 3F B9 01 00 00 00 89 5E
000030F0: F0 89 6E F4 89 4C 24 10 89 54 24 14 8B C6 DB 44
00003100: 24 10 41 83 C0 10 83 F9 0A 89 4C 24 10 DC 0A D9
00003110: C0 D9 FE DD 58 E8 D9 FF DD 58 F0 7E E1 83 C2 08
00003120: 81 C6 A8 00 00 00 4F 75 C0 6A 15 6A 01 6A 15 6A
00003130: 01 E8 AA E7 FF FF 6A 15 6A 01 8B E8 E8 4F E7 FF
00003140: FF 83 C4 18 89 44 24 10 BF 08 00 00 00 B9 E8 BC
00003150: 40 00 2B CF 89 4C 24 14 8B 54 9D 04 8B C7 03 C2
00003160: 33 F6 89 30 89 70 04 A1 10 50 D3 00 85 C0 7E 30
00003170: 8D 14 DD E8 BC 40 00 03 CF DD 01 8B 44 9D 04 81
00003180: C1 C8 00 00 00 DC 0A C7 46 81 C2 48 00 00 00 75
00003190: DC 00 DD 18 3B 35 10 50 D3 00 7C DD 8B 4C 24 14
000031A0: 83 C7 08 81 FF B0 00 00 00 7C AD 43 83 FB 15 7C
000031B0: 97 8B 4C 24 10 BF E8 BC 40 00 8D 41 08 33 E6 89
000031C0: 30 89 70 04 39 35 10 50 D3 00 7C 21 BA 10 1B C7
000031D0: 00 8B CF DD 02 DC 09 46 81 C1 A8 00 00 00 83 C2
000031E0: 08 DC 00 DD 18 3B 35 10 50 D3 00 7C E6 83 C7 08
000031F0: 83 C0 08 81 FF 90 BD 40 00 7C C2 8B 74 24 10 6A
00003200: 15 68 E8 FF C0 00 56 55 E8 43 EE FF FF 6A 15 6A
00003210: 01 6A 15 6A 01 55 E8 C5 E7 FF FF 6A 15 6A 01 56
00003220: E8 9B E7 FF FF 83 C4 30 B8 01 00 00 00 5F 5E 5D
00003230: 5B 8B E5 5D C3 90 90 90 90 90 90 90 90 90 90 90
00003240: 83 EC 14 DD 05 D0 94 40 00 DD 05 C8 94 40 00 53
00003250: 55 56 57 E8 AE 50 00 00 E8 A3 50 00 00 8B 5C 24
00003260: 30 8B 7C 24 2C 8B F0 53 57 89 74 24 28 E8 EE 33
00003270: 00 00 53 57 89 44 24 28 E8 E3 33 00 00 53 57 89
00003280: 44 24 44 E8 D8 33 00 00 56 89 44 24 2C E8 4E 34
00003290: 00 00 56 89 44 24 34 E8 44 34 00 00 83 C4 20 8B
000032A0: E8 85 F6 89 6C 24 1C 7E 1F 8B 44 24 14 8B CD 8B
000032B0: D0 2B CA 8B D6 C7 04 01 00 00 00 00 C7 00 00 00
000032C0: 00 00 83 C0 04 4A 75 ED 33 C9 85 DB 7E 4A 8B 74
000032D0: 24 18 8B 6C 24 28 33 C0 85 FF 7E 2C 8B 15 20 50
000032E0: D3 00 8B 1D 28 50 D3 00 03 D1 0F AF 15 AC FC D8
000032F0: 00 03 D3 8B 1E 03 D0 40 3B C7 8A 54 95 01 88 54
00003300: 03 FF 7C D8 8B 5C 24 30 41 83 C6 04 3B CB 7C C6
00003310: 8B 74 24 20 8B 6C 24 1C A1 DC B1 40 00 85 C0 74
00003320: 14 8B 44 24 18 53 57 50 68 D0 B2 40 00 E8 5E 35
00003330: 00 00 83 C4 10 8B 4C 24 2C 8B 54 24 18 68 44 07
00003340: 00 00 6A 3D 6A 3D 53 57 51 52 E8 31 F2 FF FF A1
00003350: DC B1 40 00 83 C4 1C 85 C0 74 14 8B 44 24 2C 53
00003360: 57 50 68 A0 B2 40 00 E8 24 35 00 00 83 C4 10 8B
00003370: 4C 24 10 8B 54 24 18 6A 18 6A 07 6A 07 53 57 51
00003380: 52 E8 FA F1 FF FF A1 DC B1 40 00 83 C4 1C 85 C0
00003390: 74 14 8B 44 24 10 53 57 50 68 70 B2 40 00 E8 ED
000033A0: 34 00 00 83 C4 10 85 DB 7E 56 8B 74 24 2C 8B 6C
000033B0: 24 10 8B C6 89 5C 24 28 2B E8 33 C0 85 FF 7E 2A
000033C0: 8B 14 2E 8B 0E 33 DB 03 C8 8A 1C 02 33 D2 8A 11
000033D0: 2B D3 83 FA 0F 0F 9E C2 4A 81 E2 FF 00 00 00 40
000033E0: 3B C7 88 11 7C DA 8B 5C 24 30 8B 44 24 28 83 C6
000033F0: 04 48 89 44 24 28 75 C2 8B 74 24 20 8B 6C 24 1C
00003400: A1 DC B1 40 00 85 C0 74 14 8B 44 24 2C 53 57 50
00003410: 68 40 B2 40 00 E8 76 34 00 00 83 C4 10 8B 4C 24
00003420: 10 8B 54 24 2C 53 57 51 52 E8 A2 F4 FF FF A1 DC
00003430: B1 40 00 83 C4 10 85 C0 74 14 8B 44 24 10 53 57
00003440: 50 68 10 B2 40 00 E8 45 34 00 00 83 C4 10 8B 4C
00003450: 24 2C 8B 54 24 10 6A 3D 53 57 51 52 E8 4F F5 FF
00003460: FF A1 DC B1 40 00 83 C4 14 85 C0 74 14 8B 44 24
00003470: 2C 53 57 50 68 E0 B1 40 00 E8 12 34 00 00 83 C4
00003480: 10 33 D2 85 DB 7E 55 33 C0 85 FF 7E 4A 8B 4C 24
00003490: 2C 8B 0C 91 80 3C 01 FF 75 38 8B 0D E4 BC 40 00
000034A0: 33 ED 8B 0C 91 66 8B 2C 41 8B 4C 24 14 8D 0C A9
000034B0: 8B 29 45 89 29 8B 0D E0 BC 40 00 33 ED 8B 0C 91
000034C0: 66 8B 2C 41 8B CD 8B 6C 24 1C FF 44 8D 00 8D 4C
000034D0: 8D 00 40 3B C7 7C B6 42 3B D3 7C AB 8B 44 24 14
000034E0: 56 C7 45 00 00 00 00 00 50 C7 00 00 00 00 E8
000034F0: 6C F9 FF FF 56 55 E8 65 F9 FF FF 8B 15 10 BC 40
00003500: 00 83 C4 10 52 FF 15 68 93 40 00 6A 10 50 FF 15
00003510: 04 90 40 00 33 D2 33 C0 85 F6 7E 12 8B 4C 24 14
00003520: 39 11 7E 02 8B D0 40 83 C1 04 3B C6 7C F2 33 C0
00003530: 3B F0 89 44 24 30 7E 16 8B CD 8B 54 24 30 39 11
00003540: 7E 04 89 44 24 30 40 83 C1 04 3B C6 7C EC 33 F6
00003550: 3B DE 89 35 10 50 D3 00 89 74 24 28 0F 8E 86 00
00003560: 00 00 8B 8C 24 2C A1 E0 BC 40 00 8B CD 2B C1 89
00003570: 44 24 20 33 C9 85 FF 7E 5B 81 FE 50 C3 00 00 7D
00003580: 4E 8B 44 24 20 8B 14 28 33 C0 66 8B 04 4A 8B 54
00003590: 24 30 2B C2 99 33 C2 2B C2 83 F8 1E 7F 31 8B 45
000035A0: 00 80 3C 08 FF 75 28 8B 15 28 50 D3 00 A1 20 50
000035B0: D3 00 03 11 8B B5 D0 42 D0 00 8B 54 24 28 03
000035C0: C2 89 04 B5 90 35 CD 00 46 89 35 10 50 D3 00 41
000035D0: 3B CF 7C A5 8B 44 24 28 83 C5 04 40 3B C3 89 44
000035E0: 24 28 7C 8F 8B 6C 24 1C 8B 44 24 18 53 50 E8 FD
000035F0: 31 00 00 8B 4C 24 34 53 51 E8 F2 31 00 00 8B 54
00003600: 24 20 53 52 E8 E7 31 00 00 8B 44 24 2C 50 E8 1D
00003610: 32 00 00 55 E8 17 32 00 00 83 C4 20 B8 01 00 00
00003620: 00 5F 5E 5D 5B 83 C4 14 C3 90 90 90 90 90 90 90
00003630: 51 56 57 33 FF BE E8 BC 40 00 8D 87 4C FF FF FF
00003640: B9 01 00 00 00 89 44 24 08 C7 06 00 00 00 00 DB
00003650: 44 24 08 C7 46 04 00 00 00 F0 3F 89 4C 24 08 8D 46
00003660: 10 DC 0D D8 94 40 00 DB 44 24 08 41 83 C0 10 83
00003670: F9 0A 89 4C 24 08 D8 C9 D9 C0 D9 FE DD 58 E8 D9
00003680: FF DD 58 F0 7E E1 DD 05 90 94 40 00 B8 E8 FF C0
00003690: 00 DD 06 DC 08 83 C0 08 83 C6 08 3D 90 00 C1 00
000036A0: DE C1 7C ED D9 C1 D9 FF D8 C9 DA 05 18 50 D3 00
000036B0: DC 05 88 94 40 00 E8 45 4C 00 00 D9 C9 D9 FE 89
000036C0: 04 BD 48 FA C0 00 D8 C9 DA 05 14 50 D3 00 DC 05
000036D0: 88 94 40 00 E8 27 4C 00 00 89 04 BD A8 F4 C0 00
000036E0: 47 81 FE 28 A9 41 00 DD D8 0F 8C 4B FF FF FF 5F
000036F0: B8 01 00 00 00 5E 59 C3 90 90 90 90 90 90 90 90
00003700: 55 8B EC 83 E4 F8 83 EC 0C 8B 0D 20 50 D3 00 8B
00003710: 15 28 50 D3 00 53 8B 1D 24 50 D3 00 56 8B 35 1C
00003720: 50 D3 00 2B F1 57 2B DA 56 53 33 FF E8 AF 2E 00
00003730: 00 56 53 A3 E4 BC 40 00 E8 A3 2E 00 00 8B 0D 1C
00003740: 50 D3 00 8B 15 20 50 D3 00 51 8B 0D 24 50 D3 00
00003750: 52 8B 15 28 50 D3 00 51 8B 4D 10 52 8B 55 0C A3
00003760: E0 BC 40 00 50 A1 E4 BC 40 00 50 8B 45 08 51 52
00003770: 50 E8 4A EB FF FF 8B 4D 08 56 53 51 E8 BF FA FF
00003780: FF 8B 15 E4 BC 40 00 83 C4 40 56 52 E8 5F 30 00
00003790: 00 A1 E0 BC 40 00 56 50 E8 53 30 00 00 A1 10 50
000037A0: D3 00 83 C4 10 3D 50 C3 00 00 7C 0C B8 0B 00 00
000037B0: 00 5F 5E 5B 8B E5 5D C3 3D F4 01 00 00 7F 0C B8
000037C0: 0C 00 00 00 5F 5E 5B 8B E5 5D C3 6A 00 6A 00 68
000037D0: 14 50 D3 00 68 18 50 D3 00 68 90 35 CD 00 68 D0
000037E0: 42 D0 00 50 E8 E7 E8 FF FF 8B 15 10 50 D3 00 83
000037F0: C4 1C 85 D2 7E 60 33 C0 85 D2 7E 5A 8B 35 14 50
00003800: D3 00 8B 0D 18 50 D3 00 42 D0 00 8B 1D 18 50 D3 00 2B
00003810: CB 89 4C 24 10 8B 0C 85 90 35 CD 00 2B CE 8B D9
00003820: 89 4C 24 14 0F AF D9 DB 44 24 10 89 5C 24 10 40
00003830: DB 44 24 10 D9 C1 D8 CA 3B C2 DE C1 D9 FA DD 1C
00003840: C5 08 1B C7 00 DB 44 24 14 D9 C9 D9 F3 DD 1C C5
00003850: 88 00 C1 00 7C AC E8 65 F8 FF FF 85 C0 75 07 5F
00003860: 5E 5B 8B E5 5D C3 A1 10 50 D3 00 33 F6 85 C0 0F
00003870: 8E 8B 00 00 00 DB 04 B5 90 35 CD 00 6A 3C 83 EC
00003880: 08 DD 1C 24 DB 04 B5 D0 42 D0 00 83 EC 08 DD 1C
00003890: 24 E8 6A E6 FF FF 83 C4 14 85 C0 74 55 8B 04 B5
```

APPENDIX-continued

```
000038A0: 90 35 CD 00 8B 14 B5 D0 42 D0 00 8B 0C F5 10 1B
000038B0: C7 00 89 04 BD 90 35 CD 00 8B 04 F5 90 00 C1 00
000038C0: 89 14 BD D0 42 D0 00 89 0C FD 10 1B C7 00 8B 14
000038D0: F5 14 1B C7 00 89 04 FD 90 00 C1 00 8B 0C F5 94
000038E0: 00 C1 00 89 14 FD 14 1B C7 00 89 0C FD 94 00 C1
000038F0: 00 47 A1 10 50 D3 00 46 3B F0 0F 8C 75 FF FF FF
00003900: 89 3D 10 50 D3 00 E8 B5 F7 FF FF 48 5F F7 D8 1B
00003910: C0 5E 40 5B 8B E5 5D C3 90 90 90 90 90 90 90 90
00003920: 55 8B EC 83 E4 F8 83 EC 50 53 55 56 57 8B 3D 54
00003930: 99 D7 00 33 ED 33 C0 33 C9 3B FD 89 4C 24 10 7E
00003940: 20 8D 54 24 20 BE B0 99 D7 00 83 3E 01 75 06 89
00003950: 02 41 83 C2 04 40 83 C6 5C 3B C7 7C ED 89 4C 24
00003960: 10 3B CD 0F 8E 1A 01 00 00 8D 7C 24 20 89 4C 24
00003970: 14 BB 00 00 F0 3F 8B 0F 83 C7 04 8B C1 8D 34 49
00003980: C1 E6 03 2B F1 C1 E6 02 C1 E0 07 DB 86 58 99 D7
00003990: 00 C1 E1 04 DD 90 10 52 D3 00 DB 86 5C 99 D7 00
000039A0: 89 A9 10 51 D3 00 89 99 14 51 D3 00 89 A9 18 51
000039B0: D3 00 89 99 1C 51 D3 00 DD 5C 24 18 8B 54 24 18
000039C0: 8B 74 24 1C 89 90 18 52 D3 00 89 B0 1C 52 D3 00
000039D0: 89 A8 20 52 D3 00 89 98 24 52 D3 00 89 A8 38 52
000039E0: D3 00 89 A8 3C 52 D3 00 89 A8 30 52 D3 00 89 A8
000039F0: 34 52 D3 00 89 A8 28 52 D3 00 89 A8 2C 52 D3 00
00003A00: 89 A8 60 52 D3 00 89 A8 64 52 D3 00 89 A8 58 52
00003A10: D3 00 89 A8 5C 52 D3 00 89 A8 50 52 D3 00 89 A8
00003A20: 54 52 D3 00 DD 90 68 52 D3 00 D9 C0 D8 C9 89 90
00003A30: 70 52 D3 00 89 B0 74 52 D3 00 89 A8 78 52 D3 00
00003A40: 89 98 7C 52 D3 00 D9 E0 DD 98 40 52 D3 00 DC 4C
00003A50: 24 18 D9 E0 DD 90 48 52 D3 00 DD 80 52 D3 00
00003A60: DD 44 24 18 DC 4C 24 18 D9 E0 DD 98 88 52 D3 00
00003A70: 8B 44 24 14 48 89 44 24 14 0F 85 F7 FE FF FF 8B
00003A80: 4C 24 10 33 F6 89 6C 24 14 BB 08 00 00 00 A1 9C
00003A90: FB D8 00 3B C8 8B 54 B0 04 89 2C 1A 89 6C 1A 04
00003AA0: 7E 10 8D 6C 24 20 89 4C 24 18 8B 45 00 8B 4C 24
00003AB0: 14 C1 E0 04 8B 3D 9C FB D8 00 03 C8 8D 14 30 83
00003AC0: C5 04 C1 E2 03 8B 7C B7 04 DD 82 10 52 D3 00 C1
00003AD0: E1 03 03 FB DC 89 10 52 D3 00 DC 88 10 51 D3 00
00003AE0: DC 07 DD 1F DD 82 50 52 D3 00 8B 3D 9C FB D8 00
00003AF0: DC 89 50 52 D3 00 8B 7C B7 04 03 FB DC 88 18 51
00003B00: D3 00 8B 44 24 18 48 DC 07 89 44 24 18 DD 1F 75
00003B10: 99 8B 4C 24 10 33 ED 8B 7C 24 14 83 C3 08 47 83
00003B20: FB 48 89 7C 24 14 0F 8C 62 FF FF FF 46 83 FE 08
00003B30: 0F 8C 4F FF FF FF 33 DB BF 08 00 00 00 8B 15 98
00003B40: FB D8 00 3B CD 89 2C 17 A1 98 FB D8 00 89 6C 07
00003B50: 04 7E 71 8D 6C 24 20 89 4C 24 18 8B 55 00 83 C5
00003B60: 04 8B CA 8D 04 52 C1 E0 02 C1 E1 03 D9 80 78
00003B70: 98 FB D8 00 8D 34 19 C1 E0 02 C1 E6 03 D9 80 78
00003B80: 99 D7 00 DC 8E 10 52 D3 00 DC 89 10 51 D3 00 DC
00003B90: 04 17 DD 1C 17 D9 80 7C 99 D7 00 DC 8E 50 52 D3
00003BA0: 00 8B 15 98 FB D8 00 8B 44 24 18 48 DC 89 18 51
00003BB0: D3 00 89 44 24 18 DC 04 17 DD 1C 17 75 9D 8B 4C
00003BC0: 24 10 33 ED 83 C7 08 43 83 FF 48 0F 8C 6C FF FF
00003BD0: FF 8B 0D 98 FB D8 00 8B 15 9C FB D8 00 6A 08 68
00003BE0: 18 5A D3 00 51 52 E8 65 E4 FF FF DD 05 38 5A D3
00003BF0: 00 DC 0D 18 5A D3 00 DD 05 50 5A D3 00 DC 0D 40
00003C00: 5A D3 00 83 C4 10 B8 01 00 00 00 DC 0D 18 5A D3
00003C10: 00 5F 5E DE E9 DD 05 20 5A D3 00 DC 0D 30 5A D3
00003C20: 00 DE E9 DD 05 28 5A D3 00 DC 0D 30 5A D3 00 DC
00003C30: 0D 50 5A D3 00 DE C1 DD 05 48 5A D3 00 DC 0D 20
00003C40: 5A D3 00 DC 0D 40 5A D3 00 DE C1 DD 05 48 5A D3
00003C50: 00 DC 0D 28 5A D3 00 DC 0D 38 5A D3 00 DE E9 DD
00003C60: 1D 10 5A D3 00 5D 5B 8B E5 5D C3 90 90 90 90 90
00003C70: 8B 44 24 04 8B 54 24 08 8D 0C 40 C1 E1 03 C8
00003C80: D9 44 8A 08 DC 1D 90 94 40 00 8D 0C 8A DF E0 F6
00003C90: C4 40 75 3D D9 41 0C DC 1D 90 94 40 00 DF E0 F6
00003CA0: C4 40 75 2D D9 41 28 D8 61 08 D9 E1 DC 1D E0 94
00003CB0: 40 00 DF E0 F6 C4 41 74 15 D9 41 2C D8 61 0C D9
00003CC0: E1 DC 1D E0 94 40 00 DF E0 F6 C4 41 75 03 33 C0
00003CD0: C3 B8 01 00 00 00 C3 90 90 90 90 90 90 90 90 90
00003CE0: 8B 44 24 14 53 55 56 8D 48 64 57 83 C0 9C 51 50
00003CF0: 8B 44 24 28 8B 0D 54 5A D7 00 33 FF 8D C7 75 03
00003D00: C0 9C 52 8B 54 24 28 50 A1 60 5A D7 00 50 8B 44
00003D10: 24 2C 51 8B 4C 24 2C 52 50 51 33 DB E8 9F E5 FF
00003D20: FF A1 60 5A D7 00 8B 0D 64 5A D7 00 83 C4 24 2B
00003D30: DC C8 8D B0 84 01 00 00 89 44 24 20 C7 44 24 24 07
00003D40: 00 00 00 EB 0A 8B 4C 24 20 8B 42 8 16 8B 0C 31 2B CA
00003D50: 8D 82 C2 00 00 00 BA 07 00 00 00 33 ED 66 8B 2C
00003D60: 01 83 C0 02 03 FD 33 ED 66 8B 68 FE 03 DD 4A 75
00003D70: EA 8B 44 24 24 83 C6 04 48 89 44 24 24 75 C6 8B
00003D80: 44 24 28 89 7C 24 24 DB 44 24 28 8D 14 40 89 5C
```

APPENDIX-continued

```
00003D90: 24 20 C1 E2 03 DC 0D E8 94 40 00 2B D0 8B 44 24
00003DA0: 2C 8D 34 90 E8 57 45 00 00 DB 44 24 20 89 46 30
00003DB0: DC 0D E8 94 40 00 E8 45 45 00 00 89 46 34 8B 4E
00003DC0: 30 89 4E 38 8B 56 34 89 56 3C 5F DB 46 30 B8 01
00003DD0: 00 00 00 D9 5E 40 DB 46 34 D9 5E 44 5E 5D 5B C3
00003DE0: 83 EC 10 A1 64 5A D7 00 53 8B 5C 24 2C 55 56 8B
00003DF0: 35 60 5A D7 00 57 33 FF 2B C6 89 7C 24 18 89 7C
00003E00: 24 14 89 7C 24 10 89 44 24 1C 33 C9 81 FF D0 07
00003E10: 00 00 0F 8D 90 00 00 00 8B 54 24 3C 8D 04 5B C1
00003E20: E0 03 2B C3 8D 2C 82 8B 44 24 1C 8B 14 30 33 C0
00003E30: 66 8B 04 4A 8B 55 30 2B C2 99 33 C2 2B C2 83 F8
00003E40: 0F 7F 65 8B 06 33 D2 66 8B 14 48 8B C2 8B 55 34
00003E50: 2B C2 99 33 C2 2B C2 83 F8 0F 7F 4C 8B 44 24 30
00003E60: 8B 6C 24 14 47 8D 54 01 9C 8B 44 24 10 89 14 BD
00003E70: A4 79 D7 00 8B 54 24 34 8D 44 02 9C 8B 54 24 1C
00003E80: 89 04 BD 64 5A D7 00 8B 04 32 33 D2 66 8B 14 48
00003E90: 8B 06 03 EA 33 D2 66 8B 14 48 8B 44 24 18 03 C2
00003EA0: 89 6C 24 14 89 44 24 18 41 81 F9 C8 00 00 00 0F
00003EB0: 8C 57 FF FF FF 8B 44 24 10 83 C6 04 40 3D C8 00
00003EC0: 00 00 0F 8C 3E FF FF FF 85 FF 0F 84
00003ED0: 9D 00 00 00 8B 4C 24 3C 8D 04 5B C1 E0 03 2B C3
00003EE0: 8D 34 81 8B 44 24 14 99 F7 FF 89 46 48 8B 44 24
00003EF0: 18 99 F7 FF 8B C8 89 4E 4C 8B 46 48 8B 56 38 89
00003F00: 44 24 38 2B C2 99 33 C2 2B C2 83 F8 0F 7F 62 8B
00003F10: 56 3C 8B C1 2B C2 99 33 C2 2B C2 83 F8 0F 7F 51
00003F20: DB 44 24 38 D8 0D F4 94 40 00 D9 46 40 D8 0D F0
00003F30: 94 40 00 DE C1 D9 5E 40 DB 46 4C D8 0D F4 94 40
00003F40: 00 D9 46 44 D8 0D F0 94 40 00 DE C1 D9 5E 44 D9
00003F50: 46 40 DC 05 88 94 40 00 E8 A3 43 00 00 89 46 38
00003F60: D9 46 44 DC 05 88 94 40 00 E8 92 43 00 00 89 46
00003F70: 3C 8B 44 24 3C 8D 14 5B C1 E2 03 2B D3 81 FF D0
00003F80: 07 00 00 89 7C 90 50 7C 0D 5F 5E 5D B8 0D 00 00
00003F90: 00 5B 83 C4 10 C3 33 C0 83 FF 50 0F 9F C0 48 5F
00003FA0: 83 E0 0D 5E 5D 40 5B 83 C4 10 C3 90 90 90 90 90
00003FB0: 8B 44 24 14 8B 4C 24 10 8B 54 24 0C 53 8B 5C 24
00003FC0: 0C 55 8B 6C 24 24 57 8B 7C 24 24 55 57 50 8B 44
00003FD0: 24 1C 51 52 53 50 E8 05 FE FF FF 83 C4 1C 83 F8
00003FE0: 01 74 16 8D 0C 7F C1 E1 03 2B CF 5F 33 C0 C7 44
00003FF0: 8D 58 00 00 00 5D 5B C3 8D 14 7F 56 C1 E2 03
00004000: 2B D7 8D 44 24 20 8D 4C 24 24 50 8D 74 95 00 8D
00004010: 54 24 2C 51 8D 44 24 34 8B 4E 50 52 50 68 68 5A
00004020: D7 00 68 A8 79 D7 00 51 E8 A3 E0 FF FF 83 C4 1C
00004030: 83 F8 01 0F 85 9F 00 00 00 8B 4C 24 2C 83 F9 0F
00004040: 0F 8E 92 00 00 00 83 C3 F1 3B CB 0F 8D 87 00 00
00004050: 00 8B 5C 24 28 83 FB 0F 7E 7E 8B 54 24 1C 83 C2
00004060: F1 3B DA 7D 73 8B 46 10 2B C1 99 33 C2 2B C2 8B
00004070: 15 FC B2 40 00 3B C2 7C 0D C7 05 30 FF D7 00 01
00004080: 00 00 00 89 4E 10 8B 46 14 8B 0D FC B2 40 00 2B
00004090: C3 99 33 C2 2B C2 3B C1 7C 0D C7 05 30 FF D7 00
000040A0: 01 00 00 00 89 5E 14 DB 46 10 8B 44 24 24 8B 4C
000040B0: 24 20 55 57 D9 5E 20 DB 46 14 D9 5E 24 89 46 28
000040C0: 89 4E 2C E8 A8 FB FF FF 83 C4 08 83 F8 01 75 08
000040D0: 89 46 58 5E 5F 5D 5B C3 C7 46 58 00 00 00 00 5E
000040E0: 5F 5D B8 01 00 00 00 5B C3 90 90 90 90 90 90 90
000040F0: A1 54 99 D7 00 8B 4C 24 08 53 8B 5C 24 14 8B 54
00004100: 24 08 55 8B 6C 24 14 56 57 8B 7C 24 24 68 58 99
00004110: D7 00 50 57 53 55 51 52 E8 C3 FB FF FF 8B F0 83
00004120: C4 1C 83 FE 01 75 22 A1 54 99 D7 00 8B 4C 24 18
00004130: 8B 54 24 14 68 58 99 D7 00 50 57 53 55 51 52 E8
00004140: 6C FE FF FF 83 C4 1C 8B F0 85 F6 75 19 56 68 14
00004150: B3 40 00 68 00 B3 40 00 56 FF 15 5C 93 40 00 8B
00004160: C6 5F 5E 5D 5B C3 8B 0D 54 99 D7 00 5F 8D 04 49
00004170: C1 E0 03 28 C1 C1 E0 02 8B 88 68 99 D7 00 89 88
00004180: 58 99 D7 00 8B 90 6C 99 D7 00 89 90 5C 99 D7 00
00004190: DB 80 58 99 D7 00 D9 98 78 99 D7 00 DB 80 5C 99
000041A0: D7 00 D9 98 7C 99 D7 00 8B 88 80 99 D7 00 89 88
000041B0: 60 99 D7 00 8B 90 84 99 D7 00 89 90 64 99 D7 00
000041C0: C7 80 80 99 D7 00 01 00 00 00 8B C6 5E 5D 5B C3
000041D0: 51 53 55 8B 2D F8 92 40 00 56 57 68 00 FC D8 00
000041E0: FF D5 A1 18 9F D7 00 33 FF 83 C4 04 3B C7 75 0A
000041F0: 68 00 51 D3 00 FF D5 83 C4 04 A1 50 B3 40 00 89
00004200: 7C 24 10 3B C7 74 10 C7 05 30 FF D7 00 01 00 00
00004210: 00 89 3D 50 B3 40 00 A1 54 99 D7 00 3B C7 7E 75
00004220: 8B 5C 24 28 8B 6C 24 1C BE 68 99 D7 00 8B 46 04
00004230: 8B 0E 8D 50 64 83 C0 9C 52 8B 15 64 5A D7 00 50
00004240: 8D 41 64 83 C1 9C 50 8B 44 24 24 51 8B 0D 60 5A
00004250: D7 00 51 52 53 55 50 E8 64 E0 FF FF 8B 4E 04 8B
00004260: 16 8B 44 24 3C 68 58 99 D7 00 57 51 52 53 55 50
00004270: E8 3B FD FF FF 8B 4C 24 50 83 C4 40 03 C8 A1 54
```

APPENDIX-continued

```
00004280: 99 D7 00 47 83 C6 5C 3B F8 89 4C 24 10 7C 9E 8B
00004290: 2D F8 92 40 00 33 D2 85 C0 0F 8E 25 01 00 00 B9
000042A0: B0 99 D7 00 83 39 01 75 01 42 83 C1 5C 48 75 F4
000042B0: 83 FA 04 0F 8C 0B 01 00 00 83 7C 24 10 04 0F 8C
000042C0: 00 01 00 00 E8 57 F6 FF FF 8B D8 A1 54 99 D7 00
000042D0: 33 FF 85 C0 7E 30 BE 5C 99 D7 00 8B 46 54 85 C0
000042E0: 75 17 8B 0E 8B 56 FC 51 8D 46 10 52 8D 4E 0C 50
000042F0: 51 E8 6A DB FF FF 83 C4 10 A1 54 99 D7 00 47 83
00004300: C6 5C 3B F8 7C D5 A1 18 9F D7 00 40 83 F8 14 A3
00004310: 18 9F D7 00 0F 85 83 00 00 00 68 F0 50 D3 00 FF
00004320: D5 A1 F0 50 D3 00 8B 2D 00 51 D3 00 8B 15 28 FF
00004330: D7 00 2B C5 8B 0D 04 51 D3 00 83 C4 04 8D 04 80
00004340: 81 E1 FF FF 00 00 52 8B 15 F4 50 D3 00 8D 04 80
00004350: 81 E2 FF FF 00 00 83 EC 08 8D 04 80 C1 E0 03 2B
00004360: C1 03 C2 89 44 24 24 DB 44 24 24 D8 0D FC 94 40
00004370: 00 DA 35 18 9F D7 00 D8 3D F8 94 40 00 DD 1C 24
00004380: 68 2C B3 40 00 68 A0 50 D3 00 FF 15 14 93 40 00
00004390: 83 C4 14 C7 05 18 9F D7 00 00 00 00 00 A1 48 FC
000043A0: D8 00 68 A0 50 D3 00 6A 20 6A 20 50 68 00 00 00
000043B0: 10 E8 E0 3B 00 00 33 C0 5F 83 FB 01 5E 5D 5B 0F
000043C0: 94 C0 59 C3 8B 0D 10 BC 40 00 6A 00 6A 00 68 02
000043D0: 04 00 00 51 C7 05 44 99 D7 00 01 00 00 00 FF 15
000043E0: 78 93 40 00 5F 5E 5D 33 C0 5B 59 C3 90 90 90 90
000043F0: A1 8C 50 D3 00 85 C0 74 7B DD 44 24 0C DC 1D E0
00004400: 94 40 00 DF E0 F6 C4 01 75 6A 8B 44 24 18 83 C0
00004410: FD 89 44 24 18 DB 44 24 18 DC 5C 24 0C DF E0 F6
00004420: C4 41 75 50 DD 44 24 04 DC 1D E0 94 40 00 DF E0
00004430: F6 C4 01 75 3F 8B 4C 24 14 83 C1 FD 89 4C 24 18
00004440: DB 44 24 18 DC 5C 24 04 DF E0 F6 C4 41 75 25 8B
00004450: 54 24 10 8B 44 24 0C 8B 4C 24 08 6A 00 52 8B 54
00004460: 24 0C 50 51 52 E8 96 DA FF FF 83 C4 14 F7 D8 1B
00004470: C0 F7 D8 C3 33 C0 C3 90 90 90 90 90 90 90 90 90
00004480: 55 8B EC 83 E4 F8 83 EC 44 DD 04 08 45 08 DC 08 88 94
00004490: 40 00 8B 45 20 53 56 83 F8 01 57 C7 05 28 FF D7
000044A0: 00 00 00 00 00 DD 5C 24 28 DD 45 08 DC 0D 00 95
000044B0: 40 00 DD 5C 24 30 0F 85 D2 03 00 00 DB 45 10 8B
000044C0: 75 1C 8B 7D 18 56 57 DD 5C 24 20 DB 45 14 8B 54
000044D0: 24 24 DD 5C 24 28 8B 44 24 2C 8B 4C 24 28 50 8B
000044E0: 44 24 24 51 52 50 E8 05 FF FF FF 83 C4 18 85 C0
000044F0: 74 39 DD 44 24 18 DC 05 88 94 40 00 8B 1D 28 FF
00004500: D7 00 E8 F9 3D 00 00 DD 44 24 20 DC 05 88 94 40
00004510: 00 89 04 9D 1C EF D7 00 E8 E3 3D 00 00 89 04 9D
00004520: 1C DF D7 00 43 89 1D 28 FF D7 00 33 C0 89 44 24
00004530: 10 DD 44 24 18 DC 45 08 85 C0 DD 5C 24 18 0F 8C
00004540: 30 03 00 00 40 89 44 24 10 DD 5C 24 18 DC 64 24
00004550: 28 56 57 DD 5C 24 20 DD 44 24 28 DC 64 24 38 8B
00004560: 54 24 24 8B 44 24 20 DD 5C 24 28 8B 5C 24 2C 8B
00004570: 4C 24 28 53 51 52 50 E8 74 FE FF FF 83 C4 18 85
00004580: C0 74 3F DD 44 24 18 DC 05 88 94 40 00 8B 1E 6D 3D
00004590: 00 00 DD 44 24 20 8B 0D 28 FF D7 00 DC 05 88 94
000045A0: 40 00 89 04 8D 1C EF D7 00 E8 52 3D 00 00 8B 0D
000045B0: 28 FF D7 00 89 04 8D 1C DF D7 00 41 89 0D 28 FF
000045C0: D7 00 8B 44 24 14 48 89 44 24 14 0F 85 78 FF FF
000045D0: FF 8B 54 24 10 8D 42 01 89 44 24 10 DD 44 24 18
000045E0: DC 65 08 8B 44 24 20 56 57 53 50 DD 5C 24 28 8B
000045F0: 4C 24 2C 8B 54 24 28 51 52 E8 F2 FD FF FF 83 C4
00004600: 18 85 C0 74 3F DD 44 24 18 DC 05 88 94 40 00 E8
00004610: EC 3C 00 00 DD 44 24 20 8B 0D 28 FF D7 00 DC 05
00004620: 88 94 40 00 89 04 8D 1C EF D7 00 E8 D0 3C 00 00
00004630: 8B 0D 28 FF D7 00 89 04 8D 1C DF D7 00 41 89 0D
00004640: 28 FF D7 00 8B 44 24 14 48 89 44 24 14 75 8D 8B
00004650: 54 24 10 8D 42 01 89 44 24 10 DD 44 24 18 DC 64
00004660: 24 28 56 57 DD 5C 24 20 DD 44 24 28 DC 44 24 38
00004670: 8B 54 24 24 DD 5C 24 28 8B 44 24 2C 8B 4C 24 28
00004680: 50 8B 44 24 24 51 52 50 E8 63 FD FF FF 83 C4 18
00004690: 85 C0 74 39 DD 44 24 18 DC 05 88 94 40 00 8B 1D
000046A0: 28 FF D7 00 E8 57 3C 00 00 DD 44 24 20 DC 05 88
000046B0: 94 40 00 89 04 9D 1C EF D7 00 E8 41 3C 00 00 89
000046C0: 04 9D 1C DF D7 00 43 89 1D 28 FF D7 00 8B 44 24
000046D0: 14 48 89 44 24 14 75 82 8B 4C 24 10 8D 41 01 89
000046E0: 44 24 14 DD 44 24 18 DC 44 24 28 56 57 DD 5C 24
000046F0: 20 DD 44 24 28 DC 44 24 38 8B 44 24 24 8B 4C 24
00004700: 20 DD 5C 24 28 8B 5C 24 2C 8B 54 24 28 53 52 50
00004710: 51 E8 DA FC FF FF 83 C4 18 85 C0 74 3F DD 44 24
00004720: 18 DC 05 88 94 40 00 E8 D4 3B 00 00 DD 44 24 20
00004730: 8B 15 28 FF D7 00 DC 05 88 94 40 00 89 04 95 1C
00004740: EF D7 00 E8 B8 3B 00 00 8B 0D 28 FF D7 00 89 04
00004750: 8D 1C DF D7 00 41 89 0D 28 FF D7 00 8B 44 24 14
00004760: 48 89 44 24 14 0F 85 78 FF FF FF 8B 44 24 10 40
00004770: 89 44 24 14 DD 44 24 18 DC 45 08 8B 4C 24 20 56
00004780: 57 53 51 DD 5C 24 28 8B 54 24 2C 8B 44 24 28 52
00004790: 50 E8 5A FC FF FF 83 C4 18 85 C0 74 3F DD 44 24
000047A0: 18 DC 05 88 94 40 00 E8 54 3B 00 00 DD 44 24 20
000047B0: 8B 0D 28 FF D7 00 DC 05 88 94 40 00 89 04 8D 1C
000047C0: EF D7 00 E8 38 3B 00 00 8B 0D 28 FF D7 00 89 04
000047D0: 8D 1C DF D7 00 41 89 0D 28 FF D7 00 8B 44 24 14
000047E0: 48 89 44 24 14 75 8D 8B 54 24 10 8D 42 01 89 44
000047F0: 24 14 DD 44 24 18 DC 44 24 28 56 57 DD 5C 24 20
00004800: DD 44 24 28 DC 64 24 38 8B 54 24 24 DD 5C 24 28
00004810: 8B 44 24 2C 8B 4C 24 28 50 8B 44 24 24 51 52 50
00004820: E8 CB FB FF FF 83 C4 18 85 C0 74 39 DD 44 24 18
00004830: DC 05 88 94 40 00 8B 1D 28 FF D7 00 E8 BF 3A 00
00004840: 00 DD 44 24 20 DC 05 88 94 40 00 89 04 9D 1C EF
00004850: D7 00 E8 A9 3A 00 00 89 04 9D 1C DF D7 00 43 89
00004860: 1D 28 FF D7 00 8B 44 24 14 48 89 44 24 14 75 82
00004870: 8B 44 24 10 40 83 F8 0F 89 44 24 10 0F 8C AF FC
00004880: FF FF B8 01 00 00 00 5F 5E 5B 8B E5 5D C3 DB 45
00004890: 10 B8 F2 FF FF FF 89 44 24 10 DD 5C 24 48 DB 45
000048A0: 14 DD 5C 24 38 99 33 C2 BF F2 FF FF FF 2B C2 89
000048B0: 7C 24 14 25 01 00 00 80 79 05 48 83 C8 FE 40 89
000048C0: 44 24 18 DB 44 24 18 DC 4C 24 28 DD 5C 24 40 DB
000048D0: 44 24 10 DC 4C 24 30 DC 44 24 38 DD 5C 24 20 8B
000048E0: 5C 24 24 DB 44 24 14 8B 4D 1C 8B 55 18 8B 44 24
000048F0: 20 51 DC 4D 08 52 53 50 DC 44 24 50 DC 44 24 58
00004900: DD 5C 24 28 8B 4C 24 2C 8B 54 24 28 51 52 E8 DD
00004910: FA FF FF 83 C4 18 85 C0 74 39 DD 44 24 18 DC 05
00004920: 88 94 40 00 8B 35 28 FF D7 00 E8 D1 39 00 00 DD
00004930: 44 24 20 DC 05 88 94 40 00 89 04 B5 1C EF D7 00
00004940: E8 BB 39 00 00 89 04 B5 1C DF D7 00 46 89 35 28
00004950: FF D7 00 47 83 FF 0E 89 7C 24 14 7E 86 8B 44 24
00004960: 10 40 83 F8 0E 89 44 24 10 0F 8E 36 FF FF FF 5F
00004970: 5E B8 01 00 00 00 5B 8B E5 5D C3 90 90 90 90 90
00004980: A1 20 FF D7 00 8B 0D 28 FF D7 00 3B C1 7D 06 40
00004990: A3 20 FF D7 00 C3 90 90 90 90 90 90 90 90 90 90
000049A0: 8B 44 24 04 56 50 8B F1 68 83 00 00 00 E8 94 37
000049B0: 00 00 33 C0 C7 06 00 96 40 00 89 46 60 89 46 64
000049C0: 89 46 68 89 46 6C 89 46 70 89 46 74 89 46 78 89
000049D0: 46 7C 8B C6 5E C2 04 00 90 90 90 90 90 90 90 90
000049E0: 56 8B F1 E8 38 C6 FF FF F6 44 24 08 01 74 09 56
000049F0: E8 57 37 00 00 C3 44 04 8B C6 5E C2 04 00 90 90
00004A00: 53 56 8B 74 24 0C 57 8B F9 8D 5F 60 53 68 F8 03
00004A10: 00 00 56 E8 64 37 00 00 68 00 00 96 40 6A 00 68
00004A20: 00 00 F0 3F 6A 00 53 56 E8 49 37 00 00 8D 47 68
00004A30: 50 68 FB 03 00 00 56 E8 34 37 00 00 8D 5F 6C 53
00004A40: 68 FC 03 00 00 56 E8 1F 37 00 00 8B 0B 6A 0A 6A
00004A50: 00 51 56 E8 0C 37 00 00 8D 57 70 52 68 FD 03 00
00004A60: 00 56 E8 09 37 00 00 8D 47 74 50 68 FE 03 00 00
00004A70: 56 E8 FA 36 00 00 8D 5F 78 53 68 FF 03 00 00 56
00004A80: E8 E5 36 00 00 8B 0B 6A 0A 6A 00 51 56 E8 D2 36
00004A90: 00 00 83 C7 7C 57 68 01 04 00 00 56 E8 BD 36 00
00004AA0: 00 68 00 00 48 42 68 00 00 A0 40 57 56 E8 A6 36
00004AB0: 00 00 5F 5E 5B C2 04 00 90 90 90 90 90 90 90 90
00004AC0: B8 08 95 40 00 C3 90 90 90 90 90 90 90 90 90 90
00004AD0: 53 56 57 8B F1 E8 70 35 00 00 68 F6 03 00 00 8B
00004AE0: CE E8 A2 36 00 00 68 F5 03 00 00 8B CE 8B F8 E8
00004AF0: 94 36 00 00 8B D8 A1 24 FF D7 00 85 C0 6A 00 75
00004B00: 22 8B 47 20 8B 3D 54 93 40 00 6A 01 68 F1 00 00
00004B10: 00 50 FF D7 8B 4B 20 6A 00 6A 00 68 F1 00 00 00
00004B20: 51 EB 20 8B 57 20 8B 3D 54 93 40 00 6A 00 68 F1
00004B30: 00 00 00 52 FF D7 8B 43 20 6A 00 6A 01 68 F1 00
00004B40: 00 00 50 FF D7 8B 0D 58 B3 40 00 8B 15 5C B3 40
00004B50: 00 89 4E 60 89 56 64 A1 FC B2 40 00 6A 00 89 46
00004B60: 6C 8B 0D DC B1 40 00 89 4E 68 8B 15 2C FF D7 00
00004B70: 89 56 70 A1 94 FB D8 00 89 46 74 8B 0D D4 B4 40
00004B80: 00 89 4E 78 8B 15 D8 B4 40 00 8B CE 89 56 7C E8
00004B90: EE 35 00 00 5F 5E B8 01 00 00 00 5B C3 90 90 90
00004BA0: 56 8B F1 6A 01 E8 D8 35 00 00 8B 46 60 8B 4E 64
00004BB0: A3 58 B3 40 00 89 0D 5C B3 40 00 5E C3 90 90 90
00004BC0: B4 40 00 C3 90 90 90 90 90 90 90 90 90 90 90 90
00004BD0: 56 8B F1 6A 01 E8 98 35 00 00 8B 46 7C 5E A3 D8
00004BE0: 56 8B F1 6A 01 E8 98 35 00 00 8B 46 7C 5E A3 D8
00004BF0: B4 40 00 C3 90 90 90 90 90 90 90 90 90 90 90 90
00004C00: 56 8B F1 6A 01 E8 78 35 00 00 8B 46 6C 5E A3 FC
00004C10: B2 40 00 C3 90 90 90 90 90 90 90 90 90 90 90 90
00004C20: C7 05 24 FF D7 00 01 00 00 00 C3 90 90 90 90 90
00004C30: C7 05 24 FF D7 00 00 00 00 00 C3 90 90 90 90 90
00004C40: 56 8B F1 6A 01 E8 38 35 00 00 8B 46 68 5E A3 DC
00004C50: B1 40 00 C3 90 90 90 90 90 90 90 90 90 90 90 90
```

APPENDIX-continued

```
00004C60: 56 8B F1 6A 01 E8 18 35 00 00 8B 46 70 5E A3 2C
00004C70: FF D7 00 C3 90 90 90 90 90 90 90 90 90 90 90 90
00004C80: 81 EC CC 00 00 00 56 8B F1 6A 01 E8 F2 34 00 00
00004C90: 8B 0D 60 B3 40 00 8B 46 74 85 C9 A3 94 FB D8 00
00004CA0: 0F 84 8C 00 00 00 85 C0 0F 84 84 00 00 00 8D 44
00004CB0: 24 04 50 FF 15 C4 92 40 00 8D 4C 24 08 51 FF 15
00004CC0: 10 93 40 00 50 68 C8 B1 40 00 8D 54 24 18 6A 64
00004CD0: 52 FF 15 00 93 40 00 8D 44 24 20 8D 8C 24 84 00
00004CE0: 00 00 50 68 7C B3 40 00 51 FF 15 14 93 40 00 8D
00004CF0: 94 24 90 00 00 00 68 9C B1 40 00 52 FF 15 04 93
00004D00: 40 00 83 C4 2C A3 10 FC D8 00 85 C0 75 1A 50 68
00004D10: 90 B1 40 00 68 64 B3 40 00 8B CE E8 6E 34 00 00
00004D20: 5E 81 C4 CC 00 00 00 C3 C7 05 60 B3 40 00 00 00
00004D30: 00 00 5E 81 C4 CC 00 00 00 C3 90 90 90 90 90 90
00004D40: A1 64 91 40 00 C3 90 90 90 90 90 90 90 90 90 90
00004D50: B8 D8 96 40 00 C3 90 90 90 90 90 90 90 90 90 90
00004D60: 56 8B F1 6A 00 E8 AE 34 00 00 C7 06 10 97 40 00
00004D70: 8B C6 5E C3 90 90 90 90 90 90 90 90 90 90 90 90
00004D80: 56 8B F1 E8 18 00 00 00 F6 44 24 08 01 74 09 56
00004D90: E8 B7 33 00 00 83 C4 04 8B C6 5E C2 04 00 90 90
00004DA0: E9 79 34 00 00 90 90 90 90 90 90 90 90 90 90 90
00004DB0: E8 0B 00 00 00 E9 16 00 00 00 90 90 90 90 90 90
00004DC0: B9 38 FF D7 00 E9 96 FF FF FF 90 90 90 90 90 90
00004DD0: 68 E0 4D 40 00 E8 5E 35 00 00 59 C3 90 90 90 90
00004DE0: B9 38 FF D7 00 E9 B6 FF FF FF 90 90 90 90 90 90
00004DF0: 6A FF 68 A3 85 40 00 64 A1 00 00 00 00 50 64 89
00004E00: 25 00 00 00 00 81 EC 68 02 00 00 56 8B F1 6A 00
00004E10: E8 1B 34 00 00 83 C4 04 8B CE E8 B8 34 00 00 6A
00004E20: 00 8D 4C 24 08 E8 F6 01 00 00 8D 44 24 04 8D 4C
00004E30: 24 04 C7 84 24 74 02 00 00 00 00 00 89 46 20
00004E40: E8 0B 32 00 00 8D 8C 24 24 02 00 00 C7 84 24 74
00004E50: 02 00 00 08 00 00 00 E8 C8 33 00 00 8D 8C 24 E4
00004E60: 01 00 00 C6 84 24 74 02 00 00 07 E8 B4 33 00 00
00004E70: 8D 8C 24 A4 01 00 00 C6 84 24 74 02 00 00 06 E8
00004E80: A0 33 00 00 8D 8C 24 64 01 00 00 C6 84 24 74 02
00004E90: 00 00 05 E8 8C 33 00 00 8D 8C 24 24 01 00 00 C6
00004EA0: 84 24 74 02 00 00 04 E8 78 33 00 00 8D 8C 24 E4
00004EB0: 00 00 00 C6 84 24 74 02 00 00 03 E8 64 33 00 00
00004EC0: 8D 8C 24 A4 00 00 00 C6 84 24 74 02 00 00 02 E8
00004ED0: 50 33 00 00 8D 4C 24 64 C6 84 24 74 02 00 00 01
00004EE0: E8 3F 33 00 00 8D 4C 24 04 C7 84 24 74 02 00 00
00004EF0: FF FF FF FF E8 59 32 00 00 8B 8C 24 6C 02 00 00
00004F00: 33 C0 5E 64 89 0D 00 00 00 00 81 C4 74 02 00 00
00004F10: C3 90 90 90 90 90 90 90 90 90 90 90 90 90 90 90
00004F20: 6A FF 68 17 86 40 00 64 A1 00 00 00 00 83 C4 6C
00004F30: 25 00 00 00 00 51 56 8B F1 89 74 24 04 8D 8E 20
00004F40: 02 00 00 C7 44 24 10 07 00 00 00 E8 D4 32 00 00
00004F50: 8D 8E E0 01 00 00 C6 44 24 10 06 E8 C4 32 00 00
00004F60: 8D 8E A0 01 00 00 C6 44 24 10 05 E8 B4 32 00 00
00004F70: 8D 8E 60 01 00 00 C6 44 24 10 04 E8 A4 32 00 00
00004F80: 8D 8E 20 01 00 00 C6 44 24 10 03 E8 94 32 00 00
00004F90: 8D 8E E0 00 00 00 C6 44 24 10 02 E8 84 32 00 00
00004FA0: 8D 8E A0 00 00 00 C6 44 24 10 01 E8 74 32 00 00
00004FB0: 8D 4E 60 C6 44 24 10 00 E8 67 32 00 00 8B CE C7
00004FC0: 44 24 10 FF FF FF FF E8 86 31 00 00 8B 4C 24 08
00004FD0: 5E 64 89 0D 00 00 00 00 83 C4 10 C3 90 90 90 90
00004FE0: 56 6A 00 8B F1 6A 64 E8 5A 31 00 00 C7 06 D8 99
00004FF0: 40 00 8B C6 5E C3 90 90 90 90 90 90 90 90 90 90
00005000: C2 04 00 90 90 90 90 90 90 90 90 90 90 90 90 90
00005010: B8 B8 97 40 00 C3 90 90 90 90 90 90 90 90 90 90
00005020: 6A FF 68 A5 86 40 00 64 A1 00 00 00 00 50 64 89
00005030: 25 00 00 00 00 51 8B 44 24 14 56 57 8B F1 50 6A
00005040: 66 89 74 24 10 E8 FC 30 00 00 8D 7E 60 C7 44 24
00005050: 14 00 00 00 00 8B CF E8 10 32 00 00 C7 07 88 9B
00005060: 40 00 8D BE A0 00 00 00 C6 44 24 14 01 8B CF E8
00005070: F8 31 00 00 C7 07 88 9B 40 00 8D BE E0 00 00 00
00005080: C6 44 24 14 02 8B CF E8 E0 31 00 00 C7 07 88 9B
00005090: 40 00 8D BE 20 01 00 00 C6 44 24 14 03 8B CF E8
000050A0: C8 31 00 00 C7 07 88 9B 40 00 8D BE 60 01 00 00
000050B0: C6 44 24 14 04 8B CF E8 B0 31 00 00 C7 07 88 9B
000050C0: 40 00 8D BE A0 01 00 00 C6 44 24 14 05 8B CF E8
000050D0: 98 31 00 00 C7 07 88 9B 40 00 8D BE E0 01 00 00
000050E0: C6 44 24 14 06 8B CF E8 80 31 00 00 C7 07 88 9B
000050F0: 40 00 8D BE 20 02 00 00 C6 44 24 14 07 8B CF E8
00005100: 68 31 00 00 C7 07 88 9B 40 00 C6 44 24 14 08 C7
00005110: 06 B0 9A 40 00 C7 86 60 02 00 00 00 00 00 E8
00005120: 42 31 00 00 68 80 00 00 00 6A 0E 68 80 00 00 00
00005130: E8 2B 31 00 00 50 FF 15 58 93 40 00 8B 4C 24 0C
00005140: 89 86 64 02 00 00 8B C6 5F 5E 64 89 0D 00 00 00
00005150: 00 83 C4 10 C2 04 00 90 90 90 90 90 90 90 90 90
00005160: 56 8B F1 E8 B8 FD FF FF F6 44 24 08 01 74 09 56
00005170: E8 D7 2F 00 00 83 C4 04 8B C6 5E C2 04 00 90 90
00005180: 56 8B F1 57 8B 7C 24 0C 8D 46 60 50 68 EE 03 00
00005190: 00 57 E8 DB 30 00 00 8D 8E A0 00 00 00 51 68 FD
000051A0: 03 00 00 57 E8 C9 30 00 00 8D 96 E0 00 00 00 52
000051B0: 68 ED 03 00 00 57 E8 B7 30 00 00 8D 86 20 01 00
000051C0: 00 50 68 EB 03 00 00 57 E8 A5 30 00 00 8D 8E 60
000051D0: 01 00 00 51 68 EC 03 00 00 57 E8 93 30 00 00 8D
000051E0: 96 A0 01 00 00 00 52 68 EA 03 00 00 57 E8 81 30 00
000051F0: 00 8D 86 E0 01 00 00 50 68 E9 03 00 00 57 E8 6F
00005200: 30 00 00 8D 8E 20 02 00 00 51 68 E8 03 00 00 57
00005210: E8 5D 30 00 00 81 C6 60 02 00 00 56 68 00 04 00
00005220: 00 57 E8 49 2F 00 00 5F 5E C2 04 00 90 90 90 90
00005230: B8 D8 97 40 00 C3 90 90 90 90 90 90 90 90 90 90
00005240: 6A FF 68 B8 86 40 00 64 A1 00 00 00 00 50 64 89
00005250: 25 00 00 00 00 51 53 56 57 8B F1 E8 EA 2D 00 00
00005260: 8B 46 20 33 FF 57 50 FF 15 3C 93 40 00 50 E8 23
00005270: 30 00 00 8B D8 3B DF 74 55 8D 4C 24 0C E8 0E 30
00005280: 00 00 6A 65 8D 4C 24 10 89 7C 24 1C E8 F9 2F 00
00005290: 00 8B 4C 24 0C 39 79 F8 74 23 8B 53 04 55 8B 2D
000052A0: 38 93 40 00 57 57 68 00 08 00 00 52 FF D5 8B 44
000052B0: 24 10 8B 4B 04 50 6A 10 57 51 FF D5 5D 8D 4C 24
000052C0: 0C C7 44 24 18 FF FF FF FF E8 B6 2F 00 00 8B 96
000052D0: 64 02 00 00 8B 46 20 8B 1D 54 93 40 00 52 6A 01
000052E0: 68 80 00 00 00 50 FF D3 8B 8E 64 02 00 00 8B 56
000052F0: 20 51 57 68 80 00 00 00 52 FF D3 8B 46 20 6A 01
00005300: A3 10 BC 40 00 B8 1C 00 00 00 A3 68 00 D8 00 A3
00005310: 88 00 D8 00 B8 17 00 00 00 68 88 00 D8 00 A3 6C
00005320: 00 D8 00 A3 8C 00 D8 00 B8 64 00 00 00 6A 01 A3
00005330: 74 00 D8 00 A3 94 00 D8 00 B8 32 00 00 00 8B CE
00005340: 89 3D 70 00 D8 00 89 3D 90 00 D8 00 A3 78 00 D8
00005350: 00 A3 98 00 D8 00 89 3D 7C 00 D8 00 89 3D 9C 00
00005360: D8 00 E8 17 2F 00 00 6A 01 68 68 00 D8 00 57 8B
00005370: CE E8 08 2F 00 00 8B 4E 20 57 6A 03 51 FF 15 40
00005380: 93 40 00 E8 68 18 00 00 85 C0 74 1C E8 FF 13 00
00005390: 00 6A 01 8D 8E 20 02 00 00 C7 05 94 FC D8 00 01
000053A0: 00 00 00 E8 D0 2E 00 00 8B 4C 24 10 5F 5E B8 01
000053B0: 00 00 00 5B 64 89 0D 00 00 00 00 83 C4 10 C3 90
000053C0: 64 A1 00 00 00 00 6A FF 68 D8 86 40 00 50 8B 44
000053D0: 24 10 64 89 25 00 00 00 00 25 F0 FF 00 00 83 EC
000053E0: 60 83 F8 10 75 3C 8D 4C 24 00 E8 F1 FB FF FF 8D
000053F0: 4C 24 00 C7 44 24 68 00 00 00 00 E8 50 2C 00 00
00005400: 8D 4C 24 00 C7 44 24 68 FF FF FF FF E8 41 2D 00
00005410: 00 8B 4C 24 64 89 0D 00 00 00 00 83 C4 6C C2
00005420: 08 00 E8 75 2E 00 00 8B 4C 24 60 64 89 0D 00 00
00005430: 00 00 83 C4 6C C2 08 00 90 90 90 90 90 90 90 90
00005440: 83 EC 64 56 8B F1 8B 46 20 50 FF 15 50 93 40 00
00005450: 85 C0 0F 84 92 00 00 00 53 57 56 8D 4C 24 20 E8
00005460: 44 2E 00 00 8B 7C 24 20 8D 44 24 1C 8B 4E 20 6A
00005470: 00 F7 D8 1B C0 23 C7 50 6A 27 51 FF 15 54 93 40
00005480: 00 8B 3D 4C 93 40 00 6A 0B FF D7 6A 0C 8B D8 FF
00005490: D7 8B F8 8B 46 20 8D 54 24 0C 52 50 FF 15 48 93
000054A0: 40 00 8B 8E 64 02 00 00 8B 44 24 18 51 8B 4C 24
000054B0: 14 2B C1 2B C7 40 99 2B C2 8B 54 24 10 D1 F8 50
000054C0: 8B 44 24 1C 2B C2 2B C3 40 99 2B C2 8B 54 24 28
000054D0: D1 F8 50 52 FF 15 44 93 40 00 8D 4C 24 1C E8 BF
000054E0: 2D 00 00 5F 5B 5E 83 C4 64 C3 8B CE E8 AB 2D 00
000054F0: 00 C7 05 0C BC 40 00 01 00 00 00 5E 83 C4 64 C3
00005500: 8B 81 64 02 00 00 C3 90 90 90 90 90 90 90 90 90
00005510: 6A 01 81 C1 A0 00 00 00 E8 5B 2D 00 00 C7 05 9C
00005520: 50 D3 00 01 00 00 00 C3 90 90 90 90 90 90 90 90
00005530: 56 8B F1 E8 E8 1C 00 00 6A 00 8D 8E 20 02 00 00
00005540: C7 05 98 FC D8 00 01 00 00 00 E8 29 2D 00 00 6A
00005550: 01 8D 8E E0 01 00 00 E8 1C 2D 00 00 6A 01 8D 8E
00005560: A0 01 00 00 E8 0F 2D 00 00 5E C3 90 90 90 90 90
00005570: A1 94 FB D8 00 56 85 C0 8B F1 74 0F A1 10 FC D8
00005580: 00 50 FF 15 0C 93 40 00 83 C4 04 8B 0D B4 FC D8
00005590: 00 51 FF 15 4C 90 40 00 68 C8 00 00 00 FF 15 24
000055A0: 90 40 00 E8 38 25 00 00 E8 93 12 00 00 6A 00 8D
000055B0: 8E 20 02 00 00 C7 05 94 FC D8 00 00 00 00 00 E8
000055C0: B4 2C 00 00 6A 00 8D 8E E0 01 00 00 E8 A7 2C 00
000055D0: 00 6A 00 8D 8E A0 01 00 00 E8 9A 2C 00 00 6A 00
000055E0: 8D 8E 20 01 00 00 E8 8D 2C 00 00 6A 00 8D 8E 4E 60
000055F0: E8 83 2C 00 00 6A 00 8D 8E 60 01 00 00 E8 76 2C
00005600: 00 00 6A 00 8D 8E E0 00 00 00 E8 69 2C 00 00 6A
00005610: 00 8D 8E A0 00 00 00 E8 5C 2C 00 00 5E C3 90 90
00005620: 83 EC 68 E8 18 1C 00 00 85 C0 74 77 E8 5F BA FF
00005630: FF A1 2C FF D7 00 C7 05 8C 50 D3 00 01 00 00 00
```

APPENDIX-continued

```
00005640: 85 C0 74 5F 8D 44 24 00 50 FF 15 C4 92 40 00 8D
00005650: 4C 24 04 51 FF 15 10 93 40 00 50 68 C8 B1 40 00
00005660: 8D 54 24 14 6A 64 52 FF 15 00 93 40 00 8D 44 24
00005670: 1C 50 68 AC B3 40 00 68 00 00 D8 00 FF 15 14 93
00005680: 40 00 8B 0D B0 FC D8 00 8B 15 AC FC D8 00 A1 2C
00005690: FC D8 00 51 52 50 68 00 00 D8 00 E8 70 13 00 00
000056A0: 83 C4 34 83 C4 68 C3 90 90 90 90 90 90 90 90 90
000056B0: E8 DB B9 FF FF C7 05 48 99 D7 00 01 00 00 00 C3
000056C0: E8 CB B9 FF FF C7 05 88 FB D8 00 01 00 00 00 C3
000056D0: 6A FF 68 F8 86 40 00 64 A1 00 00 00 00 50 64 89
000056E0: 25 00 00 00 00 83 EC 48 53 55 8B D9 56 57 8D 4C
000056F0: 24 10 C7 44 24 10 50 9C 40 00 E8 D9 2B 00 00 8B
00005700: 4C 24 6C 8B 15 AC FC D8 00 8B C1 33 FF C1 F9 10
00005710: 25 FF FF 00 00 81 E1 FF FF 00 00 3B C2 89 7C 24
00005720: 60 A3 5C 5A D3 00 89 0D 58 5A D3 00 0F 8D F5 02
00005730: 00 00 8B 35 B0 FC D8 00 3B CE 0F 8D E7 02 00 00
00005740: BD 01 00 00 00 39 2D 48 99 D7 00 75 79 51 50 A1
00005750: 2C FC D8 00 56 52 50 E8 94 E9 FF FF 83 C4 14 3B
00005760: C5 75 11 A1 54 99 D7 00 89 2D 50 99 D7 00 40 A3
00005770: 54 99 D7 00 83 3D 54 99 D7 00 10 75 33 E8 3E B9
00005780: FF FF 57 8D 8B 20 01 00 00 89 3D 48 99 D7 00 89
00005790: 2D 4C 99 D7 00 E8 DE 2A 00 00 55 8D 8B 60 01 00
000057A0: 00 E8 D2 2A 00 00 E8 55 BA FF FF E8 D0 1A 00 00
000057B0: 39 3D 50 99 D7 00 0F 84 6B 02 00 00 E8 CF BD FF
000057C0: FF E9 61 02 00 00 39 2D 8C 50 D3 00 0F 85 A1 01
000057D0: 00 00 55 51 50 53 8D 4C 24 20 E8 F3 2A 00 00 8B
000057E0: 44 24 20 8B 3D AC FC D8 00 3B C7 0F 8D 36 02 00
000057F0: 00 8B 54 24 24 8B 0D B0 FC D8 00 3B D1 0F 8D 24
00005800: 02 00 00 8B 4C 24 18 8B F0 2B F1 8B 74 24 1C 75
00005810: 0F 8B EA 2B EE 0F 84 0C 02 00 00 BD 01 00 00 00
00005820: 3B C1 7E 0D A3 24 50 D3 00 89 0D 28 50 D3 00 EB
00005830: 0B 89 0D 24 50 D3 00 A3 28 50 D3 00 3B D6 7E 0E
00005840: 89 15 1C 50 D3 00 89 35 20 50 D3 00 0C 89 35
00005850: 1C 50 D3 00 89 15 20 50 D3 00 8B 0D B0 FC D8 00
00005860: 8B 15 2C FC D8 00 51 57 52 E8 92 DE FF FF 83 C4
00005870: 0C 3B C5 0F 85 AE 01 00 00 E8 B2 DD EF FF A1 B0
00005880: FC D8 00 8B 0D AC FC D8 00 50 51 E8 80 BD FF FF
00005890: 83 C4 08 8B CB 6A 03 68 20 B4 40 00 68 D4 B3 40
000058A0: 00 E8 E8 28 00 00 83 F8 06 0F 85 B1 00 00 00 8B
000058B0: 15 B0 FC D8 00 A1 AC FC D8 00 52 50 E8 4F BD FF
000058C0: FF A1 24 FF D7 00 83 C4 08 3B C5 75 03 55 EB 02
000058D0: 6A 00 8B 0D B0 FC D8 00 8B 15 AC FC D8 00 A1 14
000058E0: 50 D3 00 51 8B 0D 18 50 D3 00 52 8B 15 5C B3 40
000058F0: 00 50 A1 58 B3 40 00 51 52 50 E8 81 EB FF FF A1
00005900: 28 FF D7 00 83 C4 1C 85 C0 7E 25 C1 E0 02 8B C8
00005910: BE 1C DF D7 00 C1 E9 02 BF 1C 9F D7 00 F3 A5 8B
00005920: C8 BE 1C EF D7 00 C1 E9 02 BF 1C AF D7 00 F3 A5
00005930: 6A 00 8D 8B A0 01 00 00 89 2D 90 50 D3 00 E8 35
00005940: 29 00 00 55 8D 4B 60 E8 2C 29 00 00 C7 05 8C 50
00005950: D3 00 00 00 00 00 E8 65 B7 FF FF E9 C7 00 00 00
00005960: 83 F8 07 0F 85 BE 00 00 00 E8 92 B8 FF FF E9 B4
00005970: 00 00 00 39 2D 88 FB D8 00 0F 85 A8 00 00 00 51
00005980: 8B 0D 2C FC D8 00 50 56 52 51 E8 F1 0A 00 00 83
00005990: C4 14 3B C5 75 39 57 8D 4B 60 89 2D 90 FB D8 00
000059A0: 89 2D 8C FB D8 00 E8 CD 28 00 00 55 8D 8B 20 01
000059B0: 00 00 E8 C1 28 00 00 89 3D 88 FB D8 00 E8 FE B6
000059C0: FF FF 39 3D 90 FB D8 00 74 05 E8 11 BC FF FF D9
000059D0: 05 F4 FA D8 00 D8 05 F0 FA D8 00 DC D8 00 DD 35 D8
000059E0: B4 40 00 D9 1D DC B4 40 00 D9 05 F8 94 40 00 D8
000059F0: 35 DC B4 40 00 D9 1D C0 00 D8 00 DD 05 58 B3 40
00005A00: 00 D8 0D C0 00 D8 00 DD 05 E0 94 40 00 D9 FA DA
00005A10: 0D 28 FF D7 00 D8 C9 D8 C9 D8 0D 4C 9C 40 00 D9
00005A20: 1D 98 50 D3 00 DD D8 8D 4C 24 10 C7 44 24 60 FF
00005A30: FF FF FF E8 94 28 00 00 8B 4C 24 58 5F 5E 5D 5B
00005A40: 64 89 0D 00 00 00 00 83 C4 54 C2 08 00 90 90 90
00005A50: 8B 44 24 08 8B 15 AC FC D8 00 56 8B F1 8B C8 C1
00005A60: F8 10 81 E1 FF FF 00 00 25 FF FF 00 00 3B CA 89
00005A70: 0D 5C 5A D3 00 A3 58 5A D3 00 0F 8D F3 00 00 00
00005A80: 3B 05 B0 FC D8 00 0F 8D E7 00 00 00 E8 2F B6 FF
00005A90: FF 83 3D 48 99 D7 00 01 75 7E A1 54 99 D7 00 C7
00005AA0: 05 48 99 D7 00 00 00 00 00 83 F8 04 7C 49 6A 00
00005AB0: 8D 8E 20 01 00 00 C7 05 44 99 D7 00 00 00 00 00
00005AC0: C7 05 4C 99 D7 00 01 00 00 00 E8 A9 27 00 00 6A
00005AD0: 01 8D 8E 60 01 00 00 E8 9C 27 00 00 6A 01 8D 8E
00005AE0: E0 00 00 00 E8 8F 27 00 00 E8 12 B7 FF FF E8 8D
00005AF0: 17 00 00 5E C2 08 00 6A 00 68 58 B4 40 00 68 38
00005B00: B4 40 00 8B CE C7 05 54 99 D7 00 00 00 00 00 E8
00005B10: 7A 26 00 00 5E C2 08 00 83 3D 88 FB D8 00 01 75
00005B20: 52 6A 00 8D 4E 60 E8 4D 27 00 00 6A 01 8D 8E 20
00005B30: 01 00 00 E8 40 27 00 00 C7 05 88 FB D8 00 00 00
00005B40: 00 00 E8 79 B5 FF FF DD 05 58 B3 40 00 D8 0D C0
00005B50: 00 D8 00 DD 05 E0 94 40 00 D9 FA DA 0D 28 FF D7
00005B60: 00 D8 C9 D8 C9 D8 0D 4C 9C 40 00 D9 1D 98 50 D3
00005B70: 00 DD D8 5E C2 08 00 90 90 90 90 90 90 90 90 90
00005B80: A1 2C FF D7 00 C7 05 30 FF D7 00 01 00 00 00 85
00005B90: C0 74 05 E8 E8 D3 FF FF E8 E3 ED FF FF C7 05 0C
00005BA0: BC 40 00 01 00 00 00 C7 05 50 B3 40 00 01 00 00
00005BB0: 00 C3 90 90 90 90 90 90 90 90 90 90 90 90 90 90
00005BC0: 83 EC 68 8D 44 24 00 56 8B F1 50 E8 0E 27 00 00
00005BD0: 8B 00 51 8B 0D 28 FC D8 00 A3 1C FC D8 00 A3 24
00005BE0: FC D8 00 8B C4 8D 54 24 08 89 08 52 B9 24 FC D8
00005BF0: 00 E8 FA 03 00 00 8B 00 51 8B 0D 20 FC D8 00 A3
00005C00: 18 FC D8 00 8B C4 8D 54 24 08 52 89 08 B9 1C FC
00005C10: D8 00 E8 D9 03 00 00 DB 05 C4 FC D8 00 8B 00 83
00005C20: EC 08 A3 14 FC D8 00 8B 0D C4 FC D8 00 DA 35 14
00005C30: FC D8 00 8B 15 C0 FC D8 00 8D 44 24 10 DD 1C 24
00005C40: DB 05 C0 FC D8 00 51 83 EC 08 DA 35 18 FC D8 00
00005C50: DD 1C 24 52 68 80 B4 40 00 50 FF 15 14 93 40 00
00005C60: 83 C4 20 8D 4C 24 08 6A 00 68 6C B4 40 00 51 8B
00005C70: CE E8 18 25 00 00 5E 83 C4 68 C3 90 90 90 90 90
00005C80: 6A FF 68 18 87 40 00 64 A1 00 00 00 00 50 64 89
00005C90: 25 00 00 00 00 83 EC 60 6A 00 8D 4C 24 04 E8 5D
00005CA0: B3 FF FF 8D 4C 24 00 C7 44 24 68 00 00 00 00 E8
00005CB0: 9C 23 00 00 8D 4C 24 00 C7 44 24 68 FF FF FF FF
00005CC0: E8 8D 24 00 00 8B 4C 24 60 64 89 0D 00 00 00 00
00005CD0: 83 C4 6C C3 90 90 90 90 90 90 90 90 90 90 90 90
00005CE0: 6A FF 68 3B 87 40 00 64 A1 00 00 00 00 50 64 89
00005CF0: 25 00 00 00 00 81 EC 80 00 00 00 6A 00 8D 4C 24
00005D00: 04 E8 9A EC FF FF 8D 4C 24 00 C7 84 24 88 00 00
00005D10: 00 00 00 00 00 00 E8 36 23 00 00 8D 4C 24 00 C7 84
00005D20: 24 88 00 00 00 00 FF FF FF FF E8 24 24 00 00 8B 8C
00005D30: 24 80 00 00 00 64 89 0D 00 00 00 00 81 C4 8C 00
00005D40: 00 00 C3 90 90 90 90 90 90 90 90 90 90 90 90 90
00005D50: C7 05 A4 00 D8 00 01 00 00 00 C3 90 90 90 90 90
00005D60: 6A 00 81 C1 A0 00 00 00 C7 05 44 99 D7 00 00 00
00005D70: 00 00 E8 01 25 00 00 C7 05 C8 FC D8 00 00 00 00
00005D80: 00 E8 7A B4 FF FF C7 05 A8 00 D8 00 01 00 00 00
00005D90: C3 90 90 90 90 90 90 90 90 90 90 90 90 90 90 90
00005DA0: 56 57 BF 01 00 00 00 8B F1 57 E8 D3 23 00 00 8B
00005DB0: 86 60 02 00 00 85 C0 74 13 C7 05 30 B0 40 00 02
00005DC0: 00 00 00 8B 46 20 57 6A 03 50 EB 0E 89 3D 30 B0
00005DD0: 40 00 8B 4E 20 6A 00 6A 03 51 FF 15 40 93 40 00
00005DE0: 89 3D AC 00 D8 00 89 3D 30 FF D7 00 5F 5E C3 90
00005DF0: 53 55 56 6A 17 68 68 00 D8 00 8B F1 6A 00 E8 E7
00005E00: 24 00 00 8B 5C 24 10 A1 7C 00 D8 00 8B 6C 24 14
00005E10: 83 FB 07 77 79 FF 24 9D D0 5E 40 00 8B 0D 70 00
00005E20: D8 00 3B C1 7F 08 89 0D 7C 00 D8 00 EB 60 48 A3
00005E30: 7C 00 D8 00 EB 58 8B 0D 74 00 D8 00 3B C1 7C 08
00005E40: 89 0D 7C 00 D8 00 EB 46 40 A3 7C 00 D8 00 EB 3E
00005E50: 8B 0D 70 00 D8 00 3B C1 7F 08 89 0D 7C 00 D8 00
00005E60: EB 2C 83 C0 F6 A3 7C 00 D8 00 EB 22 8B 0D 74 00
00005E70: D8 00 3B C1 7C 08 89 0D 7C 00 D8 00 EB 10 83 C0
00005E80: 0A A3 7C 00 D8 00 EB 06 89 2D 7C 00 D8 00 6A 01
00005E90: 68 68 00 D8 00 6A 00 8B CE C7 05 6C 00 D8 00 04
00005EA0: 00 00 00 E8 D6 23 00 00 8B 44 24 18 8B CE 50 55
00005EB0: 53 C7 05 B8 00 D8 00 01 00 00 00 C7 05 30 FF D7
00005EC0: 00 01 00 00 00 E8 1A 24 00 00 5E 5D 5B C2 0C 00
00005ED0: 1C 5E 40 00 36 5E 40 00 50 5E 40 00 6C 5E 40 00
00005EE0: 88 5E 40 00 88 5E 40 00 88 5E 40 00 88 5E 40 00
00005EF0: 53 56 57 6A 17 68 88 00 D8 00 8B F1 6A 01 E8 E7
00005F00: 23 00 00 8B 0D 8B 7C 24 10 A1 9C 00 D8 00 8B 5C 24 14
00005F10: 83 FF 07 77 79 FF 24 BD D0 5F 40 00 8B 0D 90 00
00005F20: D8 00 3B C1 7F 08 89 0D 9C 00 D8 00 EB 60 48 A3
00005F30: 9C 00 D8 00 EB 58 8B 0D 94 00 D8 00 3B C1 7C 08
00005F40: 89 0D 9C 00 D8 00 EB 46 40 A3 9C 00 D8 00 EB 3E
00005F50: 8B 0D 90 00 D8 00 3B C1 7F 08 89 0D 9C 00 D8 00
00005F60: EB 2C 83 C0 F6 A3 9C 00 D8 00 EB 22 8B 0D 94 00
00005F70: D8 00 3B C1 7C 08 89 0D 9C 00 D8 00 EB 10 83 C0
00005F80: 0A A3 9C 00 D8 00 EB 06 89 1D 9C 00 D8 00 6A 01
00005F90: 68 88 00 D8 00 6A 01 8B CE C7 05 8C 00 D8 00 04
00005FA0: 00 00 00 E8 D6 22 00 00 8B 44 24 18 8B CE 50 53
00005FB0: 57 C7 05 B8 00 D8 00 01 00 00 00 C7 05 30 FF D7
00005FC0: 00 01 00 00 E8 26 23 00 00 5F 5E 5B C2 0C 00
00005FD0: 1C 5F 40 00 36 5E 40 00 50 5E 40 00 6C 5F 40 00
00005FE0: 88 5F 40 00 88 5F 40 00 88 5F 40 00 88 5F 40 00
00005FF0: 8B 09 8B 44 24 08 2B C8 8B 44 24 04 89 08 C2 08
00006000: 00 90 90 90 90 90 90 90 90 90 90 90 90 90 90 90
00006010: 56 8B F1 E8 0C 22 00 00 F6 44 24 08 01 74 09 56
```

APPENDIX-continued

```
00006020: E8 27 21 00 00 83 C4 04 8B C6 5E C2 04 00 90 90
00006030: 56 8B F1 E8 94 22 00 00 F6 44 24 08 01 74 09 56
00006040: E8 07 21 00 00 83 C4 04 8B C6 5E C2 04 00 90 90
00006050: E9 0B 00 00 00 00 90 90 90 90 90 90 90 90 90 90
00006060: D9 05 F8 94 40 00 D8 35 DC B4 40 00 D9 1D C0 00
00006070: D8 00 C3 90 90 90 90 90 90 90 90 90 90 90 90 90
00006080: 8B 4C 24 04 D9 41 08 DC 1D 90 94 40 00 DF E0 F6
00006090: C4 40 75 3D D9 41 0C DC 1D 90 94 40 00 DF E0 F6
000060A0: C4 40 75 2D D9 41 28 D8 61 08 D9 E1 DC 1D 68 9C
000060B0: 40 00 DF E0 F6 C4 41 74 15 D9 41 2C D8 61 0C D9
000060C0: E1 DC 1D 68 9C 40 00 DF E0 F6 C4 41 75 03 33 C0
000060D0: C3 B8 01 00 00 00 C3 90 90 90 90 90 90 90 90 90
000060E0: 8B 44 24 14 53 55 56 8D 48 64 57 83 C0 9C 51 50
000060F0: 8B 44 24 28 8B 0D 64 5A D7 00 33 FF 8D 50 64 53
00006100: C0 9C 52 8B 54 24 28 50 A1 60 5A D7 00 50 8B 44
00006110: 24 2C 51 8B 4C 24 2C 52 50 51 33 DB E8 9F C1 FF
00006120: FF A1 60 5A D7 00 8B 0D 64 5A D7 00 83 C4 24 2B
00006130: C8 8D B0 7C 01 00 00 89 4C 24 20 C7 44 24 24 0B
00006140: 00 00 00 EB 04 8B 4C 24 20 8B 16 8B 0C 31 2B CA
00006150: 8D 82 BE 00 00 00 BA 0B 00 00 00 33 ED 66 8B 2C
00006160: 01 83 C0 02 03 FD 33 ED 66 8B 68 FE 03 DD 4A 75
00006170: EA 8B 44 24 24 83 C6 04 48 89 44 24 24 75 C6 89
00006180: 7C 24 24 89 5C 24 20 DB 44 24 24 DC 0D 70 9C 40
00006190: 00 E8 6A 21 00 00 DB 44 24 20 8B 74 24 28 8B F8
000061A0: 89 7C 24 24 DC 0D 70 9C 40 00 89 7E 30 E8 4E 21
000061B0: 00 00 DB 44 24 24 89 44 24 20 89 7E 38 89 46 34
000061C0: 89 46 3C D9 5E 40 DB 44 24 20 5F B8 01 00 00 00
000061D0: D9 5E 44 5E 5D 5B C3 90 90 90 90 90 90 90 90 90
000061E0: 83 EC 0C 53 8B 1D 64 5A D7 00 55 8B 6C 24 2C 56
000061F0: 57 8B 3D 60 5A D7 00 33 F6 89 74 24 18 89 74 24
00006200: 14 89 74 24 10 2B DF 33 C9 81 FE 40 1F 00 00 7D
00006210: 7B 8B 04 3B 33 D2 66 8B 14 48 8B C2 8B 55 30 2B
00006220: C2 99 33 C2 2B C2 83 F8 0F 7F 61 8B 07 33 D2 66
00006230: 8B 14 48 8B C2 8B 55 34 2B C2 99 33 C2 2B C2 83
00006240: F8 0F 7F 48 8B 44 24 2C 46 8D 54 01 9C 8B 44 24
00006250: 10 89 14 B5 C0 7D D8 00 8B 54 24 30 8D 44 02 9C
00006260: 89 04 B5 C0 00 D8 00 8B 14 3B 33 C0 66 8B 04 4A
00006270: 8B 54 24 14 03 D0 33 C0 89 54 24 14 8B 17 66 8B
00006280: 04 4A 8B 54 24 18 03 D0 89 54 24 18 41 81 F9 C8
00006290: 00 00 00 0F 8C 70 FF FF FF 8B 44 24 10 83 C7 04
000062A0: 40 3D C8 00 00 00 89 44 24 10 0F 8C 57 FF FF FF
000062B0: 85 F6 0F 84 96 00 00 00 8B 44 24 14 99 F7 FE 8B
000062C0: C8 8B 44 24 18 99 F7 FE 8B 55 38 89 4C 24 34 89
000062D0: 4D 48 8B F8 8B C1 2B C2 89 7C 24 2C 99 33 C2 89
000062E0: 7D 4C 2B C2 83 F8 0F 7F 65 8B 4D 3C 8B C7 2B C1
000062F0: 99 33 C2 2B C2 83 F8 0F 7F 54 DB 44 24 34 D8 0D
00006300: F4 94 40 00 D9 45 40 D8 0D F0 94 40 00 DE C1 D9
00006310: 55 40 DB 44 24 2C D8 0D F4 94 40 00 D9 45 44 D8
00006320: 0D F0 94 40 00 DE C1 D9 54 24 34 D9 55 44 DC 05
00006330: 88 94 40 00 E8 C7 1F 00 00 D9 44 24 34 DC 05 88
00006340: 94 40 00 89 45 38 E8 B5 1F 00 00 89 45 3C 81 FE
00006350: 40 1F 00 00 89 75 50 7C 0D 5F 5E 5D B8 0F 00 00
00006360: 00 5B 83 C4 0C C3 33 C0 83 FE 64 0F 9F C0 48 5F
00006370: 83 E0 0F 5E 5D 40 5B 83 C4 0C C3 90 90 90 90 90
00006380: 8B 44 24 14 8B 4C 24 10 8B 54 24 04 53 8B 5C 24
00006390: 10 56 8B 74 24 20 57 8B 7C 24 14 56 50 51 53 57
000063A0: 52 E8 3A FE FF FF 83 C4 18 83 F8 01 74 0D C7 46
000063B0: 58 00 00 00 00 5F 5E 33 C0 5B C3 8B 44 24 20 83
000063C0: 4C 24 1C 50 8D 54 24 24 51 8B 4E 50 8D 44 24 2C
000063D0: 52 50 68 C4 00 D8 00 68 C4 7D D8 00 51 E8 EE BC
000063E0: FF FF 83 C4 1C 83 F8 01 75 7D 8B 4C 24 24 83 F9
000063F0: 0F 7E 74 83 C7 F1 3B CF 7D 6D 8B 7C 24 20 83 FF
00006400: 0F 7E 64 83 C3 F1 3B FB 7D 5D 8B 46 10 2B C1 99
00006410: 33 C2 2B C2 8B 15 D0 B4 40 00 3B C2 7C 03 89 4E
00006420: 10 8B 46 14 8B 0D D0 B4 40 00 2B C7 99 33 C2 2B
00006430: C2 3B C1 7C 03 89 7E 14 DB 46 10 D8 0D F0 94 40
00006440: 44 24 18 56 89 56 28 D9 5E 20 DB 46 14 89 46 2C
00006450: D9 5E 24 E8 28 FC FF FF 83 C4 04 83 F8 01 75 07
00006460: 89 46 58 5F 5E 5B C3 C7 46 58 00 00 00 00 5F 5E
00006470: 5B C3 90 90 90 90 90 5B C3 90 90 90 90 90 90 90
00006480: 8B 44 24 08 53 8B 5C 24 14 8B 4C 24 08 55 8B 6C
00006490: 24 14 56 57 8B 7C 24 24 68 C8 FA D8 00 57 53 55
000064A0: 50 51 E8 39 FC FF FF 8B F0 83 C4 18 83 FE 01 75
000064B0: 1C 8B 54 24 18 8B 44 24 14 08 C8 FA D8 00 57 53
000064C0: 55 52 50 E8 B8 FE FF FF 83 C4 18 8B F0 85 F6 75
000064D0: 19 56 68 F8 B4 40 00 68 E0 B4 40 00 56 FF 15 5C
000064E0: 93 40 00 8B C6 5F 5E 5D 5B C3 DB 05 D8 FA D8 00
000064F0: A1 F0 FA D8 00 8B 0D D8 FA D8 00 8B 15 DC FA D8
00006500: 00 A3 D0 FA D8 00 D9 1D E8 FA D8 00 DB 05 DC FA
00006510: D8 00 89 0D C8 FA D8 00 8B 0D F4 FA D8 00 8B C6
00006520: 5F D9 1D EC FA D8 00 5E 5D 89 15 CC FA D8 00 89
00006530: 0D D4 FA D8 00 C7 05 20 FB D8 00 01 00 00 00 5B
00006540: C3 90 90 90 90 90 90 90 90 90 90 90 90 90 90 90
00006550: 8B 0D 20 FF D7 00 53 56 57 8B 04 8D 1C DF D7 00
00006560: 8B 0C 8D 1C EF D7 00 8B 74 24 18 8B 7C 24 14 8D
00006570: 50 64 83 C0 9C 52 8B 15 64 5A D7 00 50 8D 41 64
00006580: 8B 5C 24 18 83 C1 9C 50 51 8B 0D 60 5A D7 00 51
00006590: 52 56 57 53 E8 27 BD FF FF A1 20 FF D7 00 68 C8
000065A0: FA D8 00 8B 0C 85 1C DF D7 00 8B 14 85 1C EF D7
000065B0: 00 51 52 56 57 53 E8 C5 FD FF FF 83 C4 3C 83 F8
000065C0: 01 5F 5E 5B 74 0D C7 05 84 FB D8 00 01 00 00 00
000065D0: 33 C0 C3 B8 01 00 00 00 C3 90 90 90 90 90 90 90
000065E0: 55 57 8B 7C 24 10 8D 04 BD 00 00 00 00 50 FF 15
000065F0: 20 93 40 00 8B E8 83 C4 04 85 ED 75 12 50 68 54
00006600: B5 40 00 68 44 B5 40 00 50 FF 15 5C 93 40 00 85
00006610: FF 7E 3A 8B 4C 24 0C 53 56 8B F5 8D 1C 09 53 FF
00006620: 15 20 93 40 00 83 C4 04 89 06 85 C0 75 12 50 68
00006630: 14 B5 40 00 68 44 B5 40 00 50 FF 15 5C 93 40 00
00006640: 83 C6 04 4F 75 D8 5E 5B 8B C5 5F 5D C3 8B C5 5F
00006650: 5D C3 90 90 90 90 90 90 90 90 90 90 90 90 90 90
00006660: 55 8B 2D 20 93 40 00 56 57 8B 7C 24 14 8D 04 BD
00006670: 00 00 00 00 50 FF D5 8B F0 83 C4 04 85 F6 89 74
00006680: 24 14 75 12 50 68 B4 B5 40 00 68 44 B5 40 00 50
00006690: FF 15 5C 93 40 00 85 FF 7E 32 53 8B 5C 24 14 53
000066A0: FF D5 83 C4 04 89 06 85 C0 75 12 50 68 84 B5 40
000066B0: 00 68 44 B5 40 00 50 FF 15 5C 93 40 00 83 C6 04
000066C0: 4F 75 DC 8B 44 24 18 5B 5F 5E 5D C3 8B C6 5F 5E
000066D0: 5D C3 90 90 90 90 90 90 90 90 90 90 90 90 90 90
000066E0: 8B 44 24 04 56 8D 0C 85 00 00 00 00 51 FF 15 20
000066F0: 93 40 00 8B F0 83 C4 04 85 F6 75 12 50 68 E4 B5
00006700: 40 00 68 44 B5 40 00 50 FF 15 5C 93 40 00 8B C6
00006710: 5E C3 90 90 90 90 90 90 90 90 90 90 90 90 90 90
00006720: 8B 44 24 04 56 50 FF 15 20 93 40 00 8B F0 83 C4
00006730: 04 85 F6 75 12 50 68 10 B6 40 00 68 44 B5 40 00
00006740: 50 FF 15 5C 93 40 00 8B C6 5E C3 90 90 90 90 90
00006750: 8B 44 24 04 56 8D 0C 85 00 00 00 00 51 FF 15 20
00006760: 93 40 00 8B F0 83 C4 04 85 F6 75 12 50 68 40 B6
00006770: 40 00 68 44 B5 40 00 50 FF 15 5C 93 40 00 8B C6
00006780: 5E C3 90 90 90 90 90 90 90 90 90 90 90 90 90 90
00006790: 68 C9 00 00 00 68 C9 00 00 00 E8 41 FE FF FF 68
000067A0: C9 00 00 00 68 C9 00 00 00 A3 64 5A D7 00 E8 2D
000067B0: FE FF FF 6A 08 6A 01 6A 08 6A 01 A3 60 5A D7 00
000067C0: E8 1B B1 FF FF 6A 08 6A 01 A3 9C FB D8 00 E8 BD
000067D0: B0 FF FF A3 98 FB D8 00 83 C4 28 B8 01 00 00 00
000067E0: C3 90 90 90 90 90 90 90 90 90 90 90 90 90 90 90
000067F0: 53 8B 1D 1C 93 40 00 55 8B 6C 24 0C 57 8B 7C 24
00006800: 14 85 FF 7E 12 56 8B F5 8B 06 50 FF D3 83 C4 04
00006810: 83 C6 04 4F 75 F2 5E 55 FF D3 83 C4 04 5F 5D 5B
00006820: C3 90 90 90 90 90 90 90 90 90 90 90 90 90 90 90
00006830: 8B 44 24 04 50 FF 15 1C 93 40 00 59 C3 90 90 90
00006840: A1 64 5A D7 00 68 C9 00 00 00 50 E8 A0 FF FF FF
00006850: 8B 0D 60 5A D7 00 68 C9 00 00 00 51 E8 8F FF FF
00006860: FF 8B 15 9C FB D8 00 6A 08 6A 01 6A 08 6A 01 52
00006870: E8 6B B1 FF FF A1 98 FB D8 00 6A 08 6A 01 50 E8
00006880: 3C B1 FF FF 83 C4 30 B8 01 00 00 00 C3 90 90 90
00006890: 83 EC 3C 53 56 57 B9 0D 00 00 00 33 C0 8D 7C 24
000068A0: 11 C6 44 24 10 00 68 84 B6 40 00 F3 AB 8B 4C 24
000068B0: 50 C6 44 24 10 00 AA 33 C0 51 66 89 44 24 15 88
000068C0: 44 24 17 FF 15 04 93 40 00 8B F0 33 DB 83 C4 08
000068D0: 3B F3 75 19 53 68 90 B1 40 00 68 70 B6 40 00 53
000068E0: FF 15 5C 93 40 00 5F 5E 5B 83 C4 3C C3 8B 4C 24
000068F0: 54 55 8B 3D F0 92 40 00 56 8D 41 03 6A 36 99 83
00006900: E2 03 6A 01 03 C2 8B 54 24 68 C1 F8 02 C1 E0 02
00006910: 8B E8 0F AF C2 05 38 04 00 00 89 54 24 36 89 44
00006920: 24 22 8D 54 24 20 B8 00 01 00 00 52 2B E9 C6 44
00006930: 24 24 42 C6 44 24 25 4D C6 44 24 2A 00 C6 44 24
00006940: 2C 00 C7 44 24 2E 36 04 00 00 C6 44 24 32 28 89
00006950: 4C 24 36 C6 44 24 3E 01 C6 44 24 40 08 C6 44 24
00006960: 42 00 89 5C 24 46 C6 44 24 4A 00 C6 44 24 4E 00
00006970: 89 44 24 52 89 44 24 56 FF D7 83 C4 10 56 6A 04
00006980: 8D 44 24 58 6A 01 50 88 5C 24 62 88 5C 24 61 88
00006990: 5C 24 60 C6 44 24 63 00 FF D7 83 C4 10 43 81 FB
000069A0: 00 01 00 00 7C D7 8B 44 24 5C 85 C0 7E 3C 8B 4C
000069B0: 24 54 89 44 24 5C 8D 5C 81 FC 8B 54 24 58 8B 03
000069C0: 56 52 6A 01 50 FF D7 83 C4 10 85 ED 74 0E 56 55
000069D0: 8D 4C 24 18 6A 01 51 FF D7 83 C4 10 8B 44 24 5C
000069E0: 83 EB 04 48 89 44 24 5C 75 D0 56 6A 02 8D 54 24
000069F0: 18 6A 01 52 FF D7 56 FF 15 0C 93 40 00 83 C4 14
```

APPENDIX-continued

```
00006A00: 5D 5F 5E 5B 83 C4 3C C3 90 90 90 90 90 90 90 90
00006A10: 83 EC 40 57 B9 0D 00 00 00 33 C0 8D 7C 24 0D C6
00006A20: 44 24 0C 00 68 84 B6 40 00 F3 AB 8B 4C 24 4C C6
00006A30: 44 24 0C 00 AA 33 C0 51 66 89 44 24 11 88 44 24
00006A40: 13 FF 15 04 93 40 00 83 C4 08 89 44 24 04 85 C0
00006A50: 75 17 50 68 90 B1 40 00 68 70 B6 40 00 50 FF 15
00006A60: 5C 93 40 00 5F 83 C4 40 C3 53 55 8B 6C 24 58 56
00006A70: 8D 44 6D 03 99 83 E2 03 03 C2 8B F0 C1 FE 02 C1
00006A80: E6 02 56 E8 98 FC FF FF 8B 7C 24 64 8B D6 0F AF
00006A90: D7 8B D8 33 C0 89 44 24 3E 88 44 24 42 88 44 24
00006AA0: 46 89 44 24 4A 89 44 24 4E 8B 44 24 14 50 6A 36
00006AB0: 8D 4C 24 24 83 C2 38 6A 01 51 C6 44 24 2C 42 C6
00006AC0: 44 24 2D 4D 89 54 24 2E C6 44 24 32 00 C6 44 24
00006AD0: 34 00 C7 44 24 36 36 00 00 00 C6 44 24 3A 28 89
00006AE0: 6C 24 3E 89 7C 24 42 C6 44 24 46 01 C6 44 24 48
00006AF0: 18 C6 44 24 4A 00 FF 15 F0 92 40 00 83 C4 14 85
00006B00: FF 7E 77 8B C5 8D 14 BD FC FF FF FF F7 D8 C1 E0
00006B10: 02 0F AF D5 89 44 24 60 8B 44 24 58 89 7C 24 5C
00006B20: 8D 4C 02 02 89 4C 24 54 85 ED 7E 23 8B 44 24 54
00006B30: 8D 4B 02 8B FD 8A 50 FE 83 C0 04 88 51 FE 8A 50
00006B40: FB 88 51 FF 8A 50 FC 88 11 83 C1 03 4F 75 E6 8B
00006B50: 44 24 10 50 56 6A 01 53 FF 15 F0 92 40 00 8B 4C
00006B60: 24 70 8B 54 24 64 8B 44 24 6C 83 C4 10 03 D1 48
00006B70: 89 54 24 54 89 44 24 5C 75 AE 8B 74 24 10 8D 54
00006B80: 24 14 56 6A 02 6A 01 52 FF 15 F0 92 40 00 53 E8
00006B90: 9C FC FF FF 56 FF 15 0C 93 40 00 83 C4 18 5E 5D
00006BA0: 5B 5F 83 C4 40 C3 90 90 90 90 90 90 90 90 90 90
00006BB0: E9 0B 00 00 00 90 90 90 90 90 90 90 90 90 90 90
00006BC0: C3 90 90 90 90 90 90 90 90 90 90 90 90 90 90 90
00006BD0: E9 0B 00 00 00 90 90 90 90 90 90 90 90 90 90 90
00006BE0: C3 90 90 90 90 90 90 90 90 90 90 90 90 90 90 90
00006BF0: 68 B4 FC D8 00 6A 00 68 AC B6 40 00 68 A4 B6 40
00006C00: 00 6A 00 E8 E8 0F 00 00 83 C4 14 85 C0 75 01 C3
00006C10: 68 B8 FC D8 00 6A 00 6A 00 68 9C B6 40 00 6A 00
00006C20: E8 CB 0F 00 00 83 C4 14 85 C0 75 01 C3 68 BC FC
00006C30: D8 00 6A 00 68 90 B6 40 00 68 A4 B6 40 00 6A 00
00006C40: E8 A8 0F 00 00 83 C4 14 85 C0 75 01 C3 A1 B4 FC
00006C50: D8 00 50 FF 15 48 90 40 00 8B 0D 10 BC 40 00 51
00006C60: E8 8B 03 00 00 83 C4 04 85 C0 74 13 8B 15 10 BC
00006C70: 40 00 52 E8 88 04 00 00 83 C4 04 85 C0 75 08 E8
00006C80: 5C 0E 00 00 33 C0 C3 E8 44 B5 FF FF E8 5F A4 FF
00006C90: FF B8 01 00 00 00 C3 90 90 90 90 90 90 90 90 90
00006CA0: 53 55 8B 6C 24 10 56 57 33 DB BE B4 B7 40 00 8B
00006CB0: C5 8A 10 8A CA 3A 16 75 1C 84 C9 74 14 8A 50 01
00006CC0: 8A CA 3A 56 01 75 0E 83 C0 02 83 C6 02 84 C9 75
00006CD0: E0 33 C0 EB 05 1B C0 83 D8 FF 85 C0 75 14 8B 7C
00006CE0: 24 1C 57 68 00 00 00 10 E8 CD 12 00 00 E9 59 01
00006CF0: 00 00 BE AC B7 40 00 8B C5 8A 10 8A CA 3A 16 75
00006D00: 1C 84 C9 74 14 8A 50 01 8A CA 3A 56 01 75 0E 83
00006D10: C0 02 83 C6 02 84 C9 75 E0 33 C0 EB 05 1B C0 83
00006D20: D8 FF 85 C0 75 1A 8B 7C 24 1C 57 68 00 00 00 10
00006D30: 50 68 90 7F 40 00 E8 79 12 00 00 E9 0B 01 00 00
00006D40: BE A0 B7 40 00 8B C5 8A 10 8A CA 3A 16 75 1C 84
00006D50: C9 74 14 8A 50 01 8A CA 3A 56 01 75 0E 83 C0 02
00006D60: 83 C6 02 84 C9 75 E0 33 C0 EB 05 1B C0 83 D8 FF
00006D70: 85 C0 75 24 8B 7C 24 1C A1 8C FC D8 00 57 68 00
00006D80: 00 00 10 68 94 B7 40 00 68 00 00 00 10 50 E8 1B
00006D90: 12 00 00 E9 B3 00 00 00 BE 8C B7 40 00 8B C5 8A
00006DA0: 10 8A CA 3A 16 75 1C 84 C9 74 14 8A 50 01 8A CA
00006DB0: 3A 56 01 75 0E 83 C0 02 83 C6 02 84 C9 75 E0 33
00006DC0: C0 EB 05 1B C0 83 D8 FF 85 C0 75 21 8B 7C 24 1C
00006DD0: A1 8C FC D8 00 57 68 00 00 00 10 68 80 B7 40 00
00006DE0: 68 00 00 00 10 50 E8 BD 11 00 00 EB 5E BE 78 B7
00006DF0: 40 00 8B C5 8A 10 8A CA 3A 16 75 1C 84 C9 74 14
00006E00: 8A 50 01 8A CA 3A 56 01 75 0E 83 C0 02 83 C6 02
00006E10: 84 C9 75 E0 33 C0 EB 05 1B C0 83 D8 FF 85 C0 75
00006E20: 32 8B 7C 24 1C 8B 44 24 24 8B 4C 24 20 8B 54 24
00006E30: 30 57 50 8B 44 24 34 51 8B 4C 24 34 52 8B 15 8C
00006E40: FC D8 00 50 51 52 E8 57 11 00 00 85 C0 0F 85 4B
00006E50: 01 00 00 BE B4 B7 40 00 8B C5 8A 10 8A CA 3A 16
00006E60: 75 1C 84 C9 74 14 8A 50 01 8A CA 3A 56 01 75 0E
00006E70: 83 C0 02 83 C6 02 84 C9 75 E0 33 C0 EB 05 1B C0
00006E80: 83 D8 FF 85 C0 75 0A BB 54 B7 40 00 E9 ED 00 00
00006E90: 00 BE AC B7 40 00 8B C5 8A 10 8A CA 3A 16 75 1C
00006EA0: 84 C9 74 14 8A 50 01 8A CA 3A 56 01 75 0E 83 C0
00006EB0: 02 83 C6 02 84 C9 75 E0 33 C0 EB 05 1B C0 83 D8
00006EC0: FF 85 C0 75 0A BB 34 B7 40 00 E9 AF 00 00 00 BE
00006ED0: A0 B7 40 00 8B C5 8A 10 8A CA 3A 16 75 1C 84 C9
00006EE0: 74 14 8A 50 01 8A CA 3A 56 01 75 0E 83 C0 02 83
00006EF0: C6 02 84 C9 75 E0 33 C0 EB 05 1B C0 83 D8 FF 85
00006F00: C0 75 07 BB 10 B7 40 00 EB 74 BE 8C B7 40 00 8B
00006F10: C5 8A 10 8A CA 3A 16 75 1C 84 C9 74 14 8A 50 01
00006F20: 8A CA 3A 56 01 75 0E 83 C0 02 83 C6 02 84 C9 75
00006F30: E0 33 C0 EB 05 1B C0 83 D8 FF 85 C0 75 07 BB F0
00006F40: B6 40 00 EB 39 BE 78 B7 40 00 8B C5 8A 10 8A CA
00006F50: 3A 16 75 1C 84 C9 74 14 8A 50 01 8A CA 3A 56 01
00006F60: 75 0E 83 C0 02 83 C6 02 84 C9 75 E0 33 C0 EB 05
00006F70: 1B C0 83 D8 FF 85 C0 75 05 BB C8 B6 40 00 8B 44
00006F80: 24 14 6A 00 6A 00 68 B4 B6 40 00 53 6A 10 50 E8
00006F90: DC 0E 00 00 83 C4 18 33 C0 5F 5E 5D 5B C3 BE 78
00006FA0: B7 40 00 8B C5 8A 10 8A 1E 8A CA 3A D3 75 1E 84
00006FB0: C9 74 16 8A 50 01 8A 5E 01 8A CA 3A D3 75 0E 83
00006FC0: C0 02 83 C6 02 84 C9 75 DC 33 C0 EB 05 1B C0 83
00006FD0: D8 FF 85 C0 75 0A 50 50 8B 07 50 E8 BC 0F 00 00
00006FE0: 5F 5E 5D B8 01 00 00 00 5B C3 90 90 90 90 90 90
00006FF0: 56 8B 74 24 08 6A 00 6A 00 6A 00 6A 00 6A 00 68
00007000: 90 FC D8 00 68 B4 B7 40 00 56 E8 91 FC FF FF 83
00007010: C4 20 85 C0 75 02 5E C3 6A 00 6A 00 6A 00 6A 00
00007020: 6A 00 68 8C FC D8 00 68 AC B7 40 00 56 E8 6E FC
00007030: FF FF 83 C4 20 85 C0 75 02 5E C3 A1 8C FC D8 00
00007040: 6A 00 68 D4 07 00 00 50 E8 79 0F 00 00 85 C0 6A
00007050: 00 6A 00 7F 19 68 B4 B6 40 00 68 C0 B7 40 00 6A
00007060: 30 56 E8 09 00 00 00 83 C4 18 33 C0 5E C3 6A 00
00007070: 6A 00 6A 00 68 88 FC D8 00 68 A0 B7 40 00 56 E8
00007080: 1C FC FF FF 83 C4 20 85 C0 75 02 5E C3 8B 0D 88
00007090: FC D8 00 6A 00 68 ED 03 00 00 51 E8 20 0F 00 00
000070A0: 8B 15 88 FC D8 00 6A 00 68 EA 03 00 00 52 A3 A8
000070B0: FC D8 00 E8 08 0F 00 00 A3 AC FC D8 00 A1 88 FC
000070C0: D8 00 6A 00 68 EB 03 00 00 50 E8 F1 0E 00 00 6A
000070D0: 00 6A 00 6A 00 6A 00 6A 00 68 84 FC D8 00 68 8C
000070E0: B7 40 00 56 A3 B0 FC D8 00 E8 B2 FB FF FF 83 C4
000070F0: 20 F7 D8 1B C0 5E F7 D8 C3 90 90 90 90 90 90 90
00007100: 56 57 8B 7C 24 0C BE 48 FC D8 00 A1 B0 FC D8 00
00007110: 8B 0D AC FC D8 00 8B 15 A8 FC D8 00 50 51 52 6A
00007120: 3C 6A 08 56 68 78 B7 40 00 57 E8 71 FB FF FF 83
00007130: C4 20 85 C0 0F 84 D7 00 00 00 8B 15 A4 FC D8 00
00007140: 83 C6 04 42 81 FE 50 FC D8 00 89 15 A4 FC D8 00
00007150: 7C B9 33 F6 8B 8E 48 FC D8 00 8D 86 40 FC D8 00
00007160: 50 68 00 10 00 00 51 E8 78 0E 00 00 8B 86 48 FC
00007170: D8 00 8D 96 38 FC D8 00 52 68 00 20 00 00 50 E8
00007180: 60 0E 00 00 8B 96 48 FC D8 00 8D 8E 30 FC D8 00
00007190: 51 68 00 40 00 00 52 E8 48 0E 00 00 83 C6 04 83
000071A0: FE 08 7C B0 A1 84 FC D8 00 85 C0 74 5C 68 F1 D8
000071B0: FF FF 68 EE 0B 00 00 50 E8 21 0E 00 00 A1 84 FC
000071C0: D8 00 68 F3 D8 FF FF 68 C8 0B 00 00 50 E8 0C 0E
000071D0: 00 00 8B 0D 84 FC D8 00 6A 00 6A 00 6A 03 6A 01
000071E0: 51 E8 F2 0D 00 00 8B 15 48 FC D8 00 A1 84 FC D8
000071F0: 00 57 52 50 E8 D9 0D 00 00 8B 0D 84 FC D8 00 6A
00007200: 01 6A 01 51 E8 C3 0D 00 00 5F B8 01 00 00 00 5E
00007210: C3 5F 33 C0 5E C3 90 90 90 90 90 90 90 90 90 90
00007220: A1 48 FC D8 00 8B 0D 88 FC D8 00 50 51 E8 B8 0D
00007230: 00 00 C3 90 90 90 90 90 90 90 90 90 90 90 90 90
00007240: A1 88 FC D8 00 50 E8 B1 0D 00 00 8B 0D 48 FC D8
00007250: 00 8B 15 88 FC D8 00 51 52 E8 98 0D 00 00 A1 40
00007260: FC D8 00 6A 00 68 00 00 00 80 50 E8 80 0D 00 00
00007270: A3 2C FC D8 00 B8 01 00 00 00 C3 90 90 90 90 90
00007280: 56 8B 35 E4 92 40 00 6A 00 6A 00 68 40 77 40 00
00007290: FF D6 83 C4 0C 85 C0 75 10 A1 B4 FC D8 00 50 FF
000072A0: 15 4C 90 40 00 33 C0 5E C3 6A 00 6A 00 68 E0 72
000072B0: 40 00 FF D6 83 C4 0C 85 C0 75 11 8B 0D B4 FC D8
000072C0: 00 51 FF 15 4C 90 40 00 33 C0 5E C3 B8 01 00 00
000072D0: 00 5E C3 90 90 90 90 90 90 90 90 90 90 90 90 90
000072E0: 51 53 55 8B 2D F8 92 40 00 56 57 A1 9C FC D8 00
000072F0: 33 DB 3B C3 74 0C 89 1D 9C FC D8 00 FF 15 E0 92
00007300: 40 00 E8 79 03 00 00 85 C0 0F 84 06 03 00 00 A1
00007310: 8C B6 40 00 53 68 C5 13 00 00 8B 0C 85 48 FC D8
00007320: 00 51 E8 C9 0C 00 00 85 C0 75 1D 8B 15 8C B6 40
00007330: 00 53 68 C5 13 00 00 8B 04 95 48 FC D8 00 50 E8
00007340: AC 0C 00 00 85 C0 74 E3 39 1D 94 FB D8 00 74 45
00007350: 68 00 FC D8 00 FF D5 8B 0D 04 FC D8 00 8B 15 C4
00007360: FC D8 00 A1 C0 FC D8 00 81 E1 FF FF 00 00 51 8B
00007370: 0D 88 B6 40 00 52 8B 15 8C B6 40 00 50 A1 10 FC
00007380: D8 00 51 52 6A 09 68 40 B8 40 00 50 FF 15 EC 92
00007390: 40 00 83 C4 24 A1 C8 FC D8 00 BE 01 00 00 00 3B
000073A0: C6 0F 8E EA 01 00 00 8B 0D 8C B6 40 00 53 68 00
000073B0: 00 00 80 8B 14 8D 40 FC D8 00 52 E8 30 0C 00 00
000073C0: 8B 0D 44 99 D7 00 A3 2C FC D8 00 3B CB 74 57 8B
000073D0: 15 54 99 D7 00 3B D3 7E 1C B8 70 99 D7 00 8B 48
```

APPENDIX-continued

```
000073E0: E8 89 08 89 48 F8 8B 48 EC 89 48 04 89 48 FC 83
000073F0: C0 5C 4A 75 E9 39 35 9C 50 D3 00 0F 85 8A 01 00
00007400: 00 E8 FA 9D FF FF FF A1 B0 FC D8 00 8B 0D AC FC D8
00007410: 00 50 51 E8 F8 A1 FF FF 83 C4 08 89 1D 9C 50 D3
00007420: 00 E9 65 01 00 00 39 1D 4C 99 D7 00 0F 84 59 01
00007430: 00 00 8B 15 54 99 D7 00 3B D3 7E 16 B9 70 99 D7
00007440: 00 8B 79 F8 89 39 8B 79 FC 89 79 04 83 C1 5C 4A
00007450: 75 EF 8B 15 D8 FA D8 00 8B 0D DC FA D8 00 89 15
00007460: E0 FA D8 00 8B 15 B0 FC D8 00 89 0D E4 FA D8 00
00007470: 8B 0D AC FC D8 00 52 51 50 E8 52 CD FF FF 83 C4
00007480: 0C 3B C6 75 33 A1 28 FF D7 00 3B C3 7E 25 C1 E0
00007490: 02 8B C8 BE 1C DF D7 00 C1 E9 02 BF 1C BF D7 00
000074A0: F3 A5 8B C8 BE 1C EF D7 00 C1 E9 02 BF 1C CF D7
000074B0: 00 F3 A5 E8 E8 A8 FF FF 8B 15 B0 FC D8 00 A1 AC
000074C0: FC D8 00 8B 0D 2C FC D8 00 52 50 51 E8 7F F0 FF
000074D0: FF 83 C4 0C 83 F8 01 0F 85 8B 00 00 00 A1 30 B0
000074E0: 40 00 B9 14 00 00 00 83 F8 02 8B F1 75 11 8B 15
000074F0: B0 00 D8 00 A1 B4 00 D8 00 8D 4A 0A 8D 70 0A 8B
00007500: 3D 20 FF D7 00 A1 28 FF D7 00 3B F8 7D 4D 8B 04
00007510: BD 1C EF D7 00 8B 15 D8 FA D8 00 8B 1D D4 B4 40
00007520: 00 2B C2 99 33 C2 2B C2 3B C3 7D 2D 8B 04 BD 1C
00007530: DF D7 00 8B 15 DC FA D8 00 2B C2 99 33 C2 2B C2
00007540: 3B C3 7D 15 68 00 FF 00 40 6A 14 56 51 E8 9E A1
00007550: FF FF 83 C4 10 33 DB EB 0F 33 DB 53 6A 14 56 51
00007560: E8 8B A1 FF FF 83 C4 10 E8 E3 9F FF FF E8 1E A0
00007570: FF FF 83 3D 30 FF D7 00 01 75 10 E8 10 9F FF FF
00007580: E8 6B 9F FF FF 89 1D 30 FF D7 00 89 1D A8 00 D8
00007590: 00 39 1D 94 FB D8 00 74 45 68 00 FC D8 00 FF D5
000075A0: 8B 0D 04 FC D8 00 8B 15 C8 FC D8 00 A1 C0 FC D8
000075B0: 00 81 E1 FF FF 00 00 51 8B 0D 88 B6 40 00 52 8B
000075C0: 15 8C B6 40 00 50 A1 10 FC D8 00 51 52 6A 09 68
000075D0: F4 B7 40 00 50 FF 15 EC 92 40 00 83 C4 24 39 1D
000075E0: C0 FC D8 00 75 12 8D 4C 24 10 51 E8 EE 0C 00 00
000075F0: 8B 10 89 15 28 FC D8 00 8B 0D C0 FC D8 00 A1 C8
00007600: FC D8 00 41 40 89 0D C0 FC D8 00 A3 C8 FC D8 00
00007610: E9 D6 FC FF FF 5F 5E 5D 5B 59 C3 90 90 90 90 90
00007620: 8B 44 24 08 3D 02 01 00 00 77 30 74 2B 85 C0 74
00007630: 27 3D 80 00 00 00 75 42 8B 44 24 04 6A 00 6A 00
00007640: 50 68 B8 B8 40 00 6A 10 6A 00 E8 21 08 00 00 83
00007650: C4 18 B8 01 00 00 00 C3 33 C0 C3 83 F8 FF 75 1A
00007660: 8B 4C 24 04 6A 00 6A 00 51 68 8C B8 40 00 6A 10
00007670: 6A 00 E8 F9 07 00 00 83 C4 18 B8 01 00 00 00 C3
00007680: 53 8B 1D 3C 90 40 00 55 8B 2D 40 90 40 00 56 57
00007690: 8B 3D 44 90 40 00 A1 BC FC D8 00 68 DC 05 00 00
000076A0: 50 FF D7 8B F0 83 FE FF 75 02 FF D3 56 68 B4 B6
000076B0: 40 00 E8 69 FF FF FF 83 C4 08 85 C0 75 66 8B 0D
000076C0: B8 FC D8 00 68 DC 05 00 00 51 FF D7 8B F0 83 FE
000076D0: FF 75 02 FF D3 56 68 B4 B6 40 00 E8 40 FF FF FF
000076E0: 83 C4 08 85 C0 75 3D A1 B8 FC D8 00 15 88 B6
000076F0: 40 00 50 89 15 8C B6 40 00 FF D5 85 C0 74 0B 83
00007700: 3D 8C B6 40 00 02 7C 23 EB 8C 6A 00 6A 00 68 B4
00007710: B6 40 00 68 D0 B9 40 00 6A 10 6A 00 E8 4F 07 00
00007720: 00 83 C4 18 5F 5E 5D 33 C0 5B C3 5F 5E 5D B8 01
00007730: 00 00 00 5B C3 90 90 90 90 90 90 90 90 90 90 90
00007740: 83 EC 18 A1 88 FC D8 00 53 55 56 57 33 ED 68 00
00007750: 00 00 40 55 68 B0 0F 00 00 50 89 6C 24 20 E8 AB
00007760: 08 00 00 8B 0D 88 FC D8 00 68 00 00 28 40 55 68
00007770: EA 0F 00 00 51 E8 94 08 00 00 A1 88 FC D8 00 68
00007780: 0C FC D8 00 68 20 7A 40 00 8D 54 24 18 6A 05 50
00007790: 89 15 0C FC D8 00 E8 6D 08 00 00 8B 3D F8 92 40
000077A0: 00 8B 1D EC 92 40 00 89 6C 24 10 8B 0D B4 FC D8
000077B0: 00 55 51 FF 15 44 90 40 00 85 C0 75 7C 6A 64 C7
000077C0: 05 9C FC D8 00 01 00 00 00 FF 15 24 90 40 00 39
000077D0: 2D 94 FB D8 00 74 41 68 00 FC D8 00 FF D7 8B 15
000077E0: 04 FC D8 00 A1 C4 FC D8 00 8B 0D C0 FC D8 00 81
000077F0: E2 FF FF 00 00 52 8B 15 88 B6 40 00 50 A1 8C B6
00007800: 40 00 51 8B 0D 10 FC D8 00 52 50 6A 09 68 8C BA
00007810: 40 00 51 FF D3 83 C4 24 8B 15 88 FC D8 00 68 0C
00007820: FC D8 00 68 20 7A 40 00 68 05 00 00 04 52 E8 D5
00007830: 07 00 00 FF 15 E8 92 40 00 8B 44 24 10 8B 0D 8C
00007840: B6 40 00 3B C1 0F 84 BA 01 00 00 39 2D 94 FB D8
00007850: 00 74 45 68 00 FC D8 00 FF D7 8B 0D 04 FC D8 00
00007860: 8B 15 C4 FC D8 00 A1 C0 FC D8 00 81 E1 FF FF 00
00007870: 00 51 8B 0D 88 B6 40 00 52 8B 15 8C B6 40 00 50
00007880: 8B 44 24 20 51 8B 0D 10 FC D8 00 52 50 68 40 BA
00007890: 40 00 51 FF D3 83 C4 24 39 2D AC 00 D8 00 74 3F
000078A0: A1 30 B0 40 00 8B 15 84 FC D8 00 50 50 52 E8 19
000078B0: 07 00 00 83 3D 30 B0 40 00 01 75 04 55 55 EB 0E
000078C0: 8B 0D B4 00 D8 00 8B 15 B0 00 D8 00 51 52 A1 84
000078D0: FC D8 00 50 E8 29 07 00 00 89 2D AC 00 D8 00 83
000078E0: 3D 30 B0 40 00 02 0F 85 90 00 00 00 39 2D B8 00
000078F0: D8 00 0F 84 84 00 00 00 DB 05 7C 00 D8 00 8B 0D
00007900: 74 00 D8 00 8B 35 78 00 D8 00 2B CE 89 6C 24 1C
00007910: DA 0D AC FC D8 00 41 89 4C 24 18 D8 0D 78 9C 40
00007920: 00 DA 74 24 18 E8 D6 09 00 00 DB 05 9C 00 D8 00
00007930: 8B 15 94 00 D8 00 8B 0D 98 00 D8 00 2B D1 89 6C
00007940: 24 24 DA 0D B0 FC D8 00 42 8B F0 89 54 24 20 89
00007950: 35 B0 00 D8 00 D8 0D 78 9C 40 00 DA 74 24 20 E8
00007960: 9C 09 00 00 A3 B4 00 D8 00 50 A1 84 FC D8 00 56
00007970: 50 E8 8C 06 00 00 89 2D B8 00 D8 00 8B 4C 24 10
00007980: A1 88 FC D8 00 8B 14 8D 48 FC D8 00 52 50 E8 63
00007990: 06 00 00 39 2D C4 FC D8 00 75 12 8D 4C 24 14 51
000079A0: E8 39 09 00 00 8B 10 89 15 20 FC D8 00 8B 0D C4
000079B0: FC D8 00 A1 94 FB D8 00 41 3B C5 89 0D C4 FC D8
000079C0: 00 74 42 68 00 FC D8 00 FF D7 A1 04 FC D8 00 8B
000079D0: 0D C4 FC D8 00 8B 15 C0 FC D8 00 25 FF FF 00 00
000079E0: 50 A1 88 B6 40 00 51 8B 0D 8C B6 40 00 52 8B 54
000079F0: 24 20 50 A1 10 FC D8 00 51 52 68 F4 B9 40 00 50
00007A00: FF D3 83 C4 24 88 44 24 10 40 83 F8 02 89 44 24
00007A10: 10 0F 8C 94 FD FF FF E9 8B FD FF FF 90 90 90 90
00007A20: A1 B8 FC D8 00 68 DC 05 00 00 50 FF 15 44 90 40
00007A30: 00 85 C0 74 06 83 C8 FF C2 0C 00 8B 4C 24 0C 8B
00007A40: 15 B8 02 A3 88 B6 40 00 A1 94 FB D8 00 85 C0 74
00007A50: 49 68 40 00 FC D8 00 FF 15 F8 92 40 00 8B 0D 04 FC
00007A60: D8 00 8B 15 C4 FC D8 00 A1 C0 FC D8 00 81 E1 FF
00007A70: FF 00 00 51 8B 0D 88 B6 40 00 52 8B 15 8C B6 40
00007A80: 00 50 A1 10 FC D8 00 51 52 6A 09 68 D8 BA 40 00
00007A90: 50 FF 15 EC 92 40 00 83 C4 24 8B 0D B8 FC D8 00
00007AA0: 51 FF 15 40 90 40 00 85 C0 75 1D 50 50 68 B4 B6
00007AB0: 40 00 68 D0 B9 40 00 6A 10 50 E8 B1 03 00 00 83
00007AC0: C4 18 83 C8 FF C2 0C 00 8B 15 BC FC D8 00 52 FF
00007AD0: 15 4C 90 40 00 33 C0 C2 0C 00 90 90 90 90 90 90
00007AE0: A1 B4 FC D8 00 56 50 FF 15 48 90 40 00 33 F6 8B
00007AF0: 86 40 FC D8 00 85 C0 74 06 50 E8 2D 05 00 00 8B
00007B00: 86 38 FC D8 00 85 C0 74 06 50 E8 1D 05 00 00 8B
00007B10: 86 30 FC D8 00 85 C0 74 06 50 E8 0D 05 00 00 83
00007B20: C6 04 83 FE 08 7C C8 8B 0D A4 FC D8 00 8D 41 FF
00007B30: 85 C0 7C 1E 57 8D 34 85 48 FC D8 00 8D 78 01 8B
00007B40: 06 85 C0 74 06 50 E8 E1 04 00 00 83 EE 04 4F 75
00007B50: EE 5F 8B 15 10 BC 40 00 68 BC FC D8 00 68 A4 B6
00007B60: 40 00 52 E8 28 02 00 00 A1 10 BC 40 00 68 B8 FC
00007B70: D8 00 68 9C B6 40 00 50 E8 13 02 00 00 A1 84 FC
00007B80: D8 00 83 C4 18 85 C0 5E 74 06 50 E8 96 04 00 00
00007B90: A1 88 FC D8 00 85 C0 74 06 50 E8 81 04 00 00 A1
00007BA0: 8C FC D8 00 85 C0 74 06 50 E8 6C 04 00 00 68 F4
00007BB0: 01 00 00 FF 15 24 90 40 00 A1 90 FC D8 00 85 C0
00007BC0: 74 06 50 E8 4C 04 00 00 8B 0D 10 BC 40 00 68 B4
00007BD0: FC D8 00 68 A4 B6 40 00 51 E8 B2 01 00 00 83 C4
00007BE0: 0C E8 DA 95 FF FF B8 01 00 00 00 C3 90 90 90 90
00007BF0: 51 53 8B 5C 24 10 56 57 33 FF BE A4 B6 40 00 89
00007C00: 7C 24 0C 8B C3 8A 10 8A CA 3A 16 75 1C 84 C9 74
00007C10: 14 8A 50 01 8A CA 3A 56 01 75 0E 83 C0 02 83 C6
00007C20: 02 84 C9 75 E0 33 C0 EB 05 1B C0 83 D8 FF 55 8B
00007C30: 6C 24 28 85 C0 75 4D 8B 44 24 20 BE AC B6 40 00
00007C40: 8A 10 8A CA 3A 16 75 1C 84 C9 74 14 8A 50 01 8A
00007C50: CA 3A 56 01 75 0E 83 C0 02 83 C6 02 84 C9 75 E0
00007C60: 33 C0 EB 05 1B C0 83 D8 FF 85 C0 75 05 BF 01 00
00007C70: 00 00 8B 44 24 24 6A 00 50 57 6A 00 FF 15 34 90
00007C80: 40 00 EB 42 BE 9C B6 40 00 8B C3 8A 10 8A CA 3A
00007C90: 16 75 1C 84 C9 74 14 8A 50 01 8A CA 3A 56 01 75
00007CA0: 0E 83 C0 02 83 C6 02 84 C9 75 E0 33 C0 EB 05 1B
00007CB0: C0 83 D8 FF 85 C0 75 11 50 8B 44 24 28 50 6A 00
00007CC0: FF 15 38 90 40 00 89 45 00 8B 45 00 5D 85 C0 0F
00007CD0: 85 A2 00 00 00 BE A4 B6 40 00 8B C3 8A 10 8A CA
00007CE0: 3A 16 75 1C 84 C9 74 14 8A 50 01 8A CA 3A 56 01
00007CF0: 75 0E 83 C0 02 83 C6 02 84 C9 75 E0 33 C0 EB 05
00007D00: 1B C0 83 D8 FF 85 C0 75 0A C7 44 24 0C 3C BB 40
00007D10: 00 EB 40 BE 9C B6 40 00 8B C3 8A 10 8A 1E 8A CA
00007D20: 3A D3 75 1E 84 C9 74 16 8A 50 01 8A 5E 01 8A CA
00007D30: 3A D3 75 0E 83 C0 02 83 C6 02 84 C9 75 DC 33 C0
00007D40: EB 05 1B C0 83 D8 FF 85 C0 75 08 C7 44 24 0C 24
00007D50: BB 40 00 8B 44 24 0C 8B 4C 24 14 6A 00 6A 00 68
00007D60: B4 B6 40 00 50 6A 10 51 E8 03 01 00 00 83 C4 18
00007D70: 33 C0 5F 5E 5B 59 C3 5F 5E B8 01 00 00 00 5B 59
00007D80: C3 90 90 90 90 90 90 90 90 90 90 90 90 90 90 90
00007D90: 8B 44 24 0C 53 56 57 8B 00 85 C0 0F 84 BD 00 00
00007DA0: 00 50 FF 15 30 90 40 00 85 C0 0F 85 AE 00 00 00
00007DB0: 8B 7C 24 14 BE A4 B6 40 00 8B C7 8A 10 8A 1E 8A
```

APPENDIX-continued

```
00007DC0: CA 3A D3 75 1E 84 C9 74 16 8A 50 01 8A 5E 01 8A
00007DD0: CA 3A D3 75 0E 83 C0 02 83 C6 02 84 C9 75 DC 33
00007DE0: C0 EB 05 1B C0 83 D8 FF 85 C0 75 1F 50 50 8B 44
00007DF0: 24 18 68 B4 B6 40 00 68 80 BB 40 00 6A 10 50 E8
00007E00: 6C 00 00 00 83 C4 18 5F 5E 5B C3 BE 9C B6 40 00
00007E10: 8B C7 8A 10 8A 1E 8A CA 3A D3 75 1E 84 C9 74 16
00007E20: 8A 50 01 8A 5E 01 8A CA 3A D3 75 0E 83 C0 02 83
00007E30: C6 02 84 C9 75 DC 33 C0 EB 05 1B C0 83 D8 FF 85
00007E40: C0 75 1B 50 50 8B 44 24 18 68 B4 B6 40 00 68 54
00007E50: BB 40 00 6A 10 50 E8 15 00 00 00 83 C4 18 5F 5E
00007E60: 5B C3 90 90 90 90 90 90 90 90 90 90 90 90 90 90
00007E70: 81 EC 64 01 00 00 A0 CC FC D8 00 53 56 57 88 44
00007E80: 24 0C B9 58 00 00 00 33 C0 8D 7C 24 0D F3 AB 66
00007E90: AB 8B BC 24 84 01 00 00 85 FF 75 1B 8B 8C 24 7C
00007EA0: 01 00 00 8D 54 24 0C 51 52 FF 15 14 93 40 00 83
00007EB0: C4 08 E9 A7 00 00 00 BE B4 BB 40 00 8B C7 8A 10
00007EC0: 8A 1E 8A CA 3A D3 75 1E 84 C9 74 16 8A 50 01 8A
00007ED0: 5E 01 8A CA 3A D3 75 0E 83 C0 02 83 C6 02 84 C9
00007EE0: 75 DC 33 C0 EB 05 1B C0 83 DB FF 85 C0 75 19 8B
00007EF0: 84 24 88 01 00 00 8B 94 24 7C 01 00 00 8B 08 8D
00007F00: 44 24 0C 51 52 50 EB 4D BE AC BB 40 00 8B C7 8A
00007F10: 10 8A 1E 8A CA 3A D3 75 1E 84 C9 74 16 8A 50 01
00007F20: 8A 5E 01 8A CA 3A D3 75 0E 83 C0 02 83 C6 02 84
00007F30: C9 75 DC 33 C0 EB 05 1B C0 83 D8 FF 85 C0 75 1E
00007F40: 8B 84 24 88 01 00 00 8B 8C 24 7C 01 00 00 50 8D
00007F50: 54 24 10 51 52 FF 15 14 93 40 00 83 C4 0C 8B 84
00007F60: 24 78 01 00 00 8B 8C 24 80 01 00 00 25 FF FF 00
00007F70: 00 8D 54 24 0C 50 8B 84 24 78 01 00 00 51 52 50
00007F80: FF 15 5C 93 40 00 5F 5E 5B 81 C4 64 01 00 00 C3
00007F90: FF 25 A8 92 40 00 FF 25 74 92 40 00 FF 25 8C 92
00007FA0: 40 00 FF 25 6C 92 40 00 FF 25 68 92 40 00 FF 25
00007FB0: 70 92 40 00 FF 25 60 92 40 00 FF 25 5C 92 40 00
00007FC0: FF 25 64 92 40 00 FF 25 7C 92 40 00 FF 25 80 92
00007FD0: 40 00 FF 25 84 92 40 00 FF 25 88 92 40 00 FF 25
00007FE0: 78 92 40 00 FF 25 90 92 40 00 FF 25 58 92 40 00
00007FF0: FF 25 54 92 40 00 FF 25 94 92 40 00 FF 25 98 92
00008000: 40 00 FF 25 9C 92 40 00 FF 25 A0 92 40 00 FF 25
00008010: 40 92 40 00 FF 25 50 92 40 00 FF 25 3C 92 40 00
00008020: FF 25 4C 92 40 00 FF 25 48 92 40 00 FF 25 44 92
00008030: 40 00 FF 25 70 90 40 00 FF 25 74 90 40 00 FF 25
00008040: 78 90 40 00 FF 25 7C 90 40 00 FF 25 80 90 40 00
00008050: FF 25 84 90 40 00 FF 25 88 90 40 00 FF 25 8C 90
00008060: 40 00 FF 25 90 90 40 00 FF 25 94 90 40 00 FF 25
00008070: 98 90 40 00 FF 25 9C 90 40 00 FF 25 A0 90 40 00
00008080: FF 25 A4 90 40 00 FF 25 A8 90 40 00 FF 25 AC 90
00008090: 40 00 FF 25 B0 90 40 00 FF 25 B4 90 40 00 FF 25
000080A0: B8 90 40 00 FF 25 BC 90 40 00 FF 25 C0 90 40 00
000080B0: FF 25 C4 90 40 00 FF 25 C8 90 40 00 FF 25 CC 90
000080C0: 40 00 FF 25 D0 90 40 00 FF 25 D4 90 40 00 FF 25
000080D0: D8 90 40 00 FF 25 DC 90 40 00 FF 25 E0 90 40 00
000080E0: FF 25 E4 90 40 00 FF 25 E8 90 40 00 FF 25 EC 90
000080F0: 40 00 FF 25 F0 90 40 00 FF 25 F4 90 40 00 FF 25
00008100: F8 90 40 00 FF 25 FC 90 40 00 FF 25 00 91 40 00
00008110: FF 25 04 91 40 00 FF 25 08 91 40 00 FF 25 0C 91
00008120: 40 00 FF 25 10 91 40 00 FF 25 14 91 40 00 FF 25
00008130: 18 91 40 00 FF 25 1C 91 40 00 FF 25 20 91 40 00
00008140: FF 25 24 91 40 00 FF 25 28 91 40 00 FF 25 2C 91
00008150: 40 00 FF 25 30 91 40 00 FF 25 38 91 40 00 FF 25
00008160: 3C 91 40 00 FF 25 40 91 40 00 FF 25 44 91 40 00
00008170: FF 25 48 91 40 00 FF 25 4C 91 40 00 FF 25 50 91
00008180: 40 00 FF 25 60 90 40 00 FF 25 64 90 40 00 FF 25
00008190: 5C 91 40 00 FF 25 68 90 40 00 FF 25 6C 90 40 00
000081A0: FF 25 6C 91 40 00 FF 25 70 91 40 00 FF 25 74 91
000081B0: 40 00 FF 25 78 91 40 00 FF 25 7C 91 40 00 FF 25
000081C0: 80 91 40 00 FF 25 84 91 40 00 FF 25 88 91 40 00
000081D0: FF 25 8C 91 40 00 FF 25 90 91 40 00 FF 25 94 91
000081E0: 40 00 FF 25 98 91 40 00 FF 25 9C 91 40 00 FF 25
000081F0: A0 91 40 00 FF 25 A4 91 40 00 FF 25 A8 91 40 00
00008200: FF 25 AC 91 40 00 FF 25 B0 91 40 00 FF 25 B4 91
00008210: 40 00 FF 25 B8 91 40 00 FF 25 54 90 40 00 FF 25
00008220: C0 91 40 00 FF 25 C4 91 40 00 FF 25 C8 91 40 00
00008230: FF 25 CC 91 40 00 FF 25 D0 91 40 00 FF 25 D4 91
00008240: 40 00 FF 25 D8 91 40 00 FF 25 DC 91 40 00 FF 25
00008250: E0 91 40 00 FF 25 E4 91 40 00 FF 25 58 90 40 00
00008260: FF 25 5C 90 40 00 FF 25 F0 91 40 00 FF 25 F4 91
00008270: 40 00 FF 25 F8 91 40 00 FF 25 FC 91 40 00 FF 25
00008280: 00 92 40 00 FF 25 04 92 40 00 FF 25 08 92 40 00
00008290: FF 25 0C 92 40 00 FF 25 EC 91 40 00 FF 25 E8 91
000082A0: 40 00 FF 25 18 92 40 00 FF 25 1C 92 40 00 FF 25
000082B0: 20 92 40 00 FF 25 24 92 40 00 FF 25 28 92 40 00
000082C0: FF 25 2C 92 40 00 FF 25 30 92 40 00 FF 25 34 92
000082D0: 40 00 FF 25 10 92 40 00 FF 25 14 92 40 00 FF 25
000082E0: 54 91 40 00 FF 25 58 91 40 00 FF 25 6C 90 40 00
000082F0: FF 25 68 90 40 00 CC CC CC CC CC CC CC CC CC CC
00008300: FF 25 E8 92 40 00 FF 25 FC 92 40 00 83 3D F4 FC
00008310: D8 00 FF 75 0C FF 74 24 04 FF 15 08 93 40 00 59
00008320: C3 68 F0 FC D8 00 68 F4 FC D8 00 FF 74 24 0C E8
00008330: 7A 01 00 00 83 C4 0C C3 FF 74 24 04 E8 CB FF FF
00008340: FF F7 D8 1B C0 59 F7 D8 48 C3 FF 25 F4 92 40 00
00008350: 55 8B EC 6A FF 68 80 9C 40 00 68 D6 84 40 00 64
00008360: A1 00 00 00 00 50 64 89 25 00 00 00 00 83 EC 68
00008370: 53 56 57 89 65 E8 33 DB 89 5D FC 6A 02 FF 15 CC
00008380: 92 40 00 59 83 0D F0 FC D8 00 FF 83 0D F4 FC D8
00008390: 00 FF FF 15 28 93 40 00 8B 0D E4 FC D8 00 89 08
000083A0: FF 15 24 93 40 00 8B 0D E0 FC D8 00 89 08 A1 BC
000083B0: 92 40 00 8B 00 A3 EC FC D8 00 E8 16 01 00 00 39
000083C0: 1D C0 BB 40 00 75 0C 68 D2 84 40 00 FF 15 B8 92
000083D0: 40 00 59 E8 E8 00 00 00 68 20 B0 40 00 68 1C B0
000083E0: 40 00 E8 D3 00 00 00 A1 DC FC D8 00 89 45 94 8D
000083F0: 45 94 50 FF 35 D8 FC D8 00 8D 45 9C 50 8D 45 90
00008400: 50 8D 45 A0 50 FF 15 B0 92 40 00 68 18 B0 40 00
00008410: 68 00 B0 40 00 E8 A0 00 00 00 83 C4 24 A1 C0 92
00008420: 40 00 8B 30 89 75 8C 80 3E 22 75 3A 46 89 75 8C
00008430: 8A 06 3A C3 74 04 3C 22 75 F2 80 3E 22 75 04 46
00008440: 89 75 8C 8A 06 3A C3 74 04 3C 20 76 F2 89 5D D0
00008450: 8D 45 A4 50 FF 15 28 90 40 00 F6 45 D0 01 74 11
00008460: 0F B7 45 D4 EB 0E 80 3E 20 76 D8 46 89 75 8C EB
00008470: F5 6A 0A 58 50 56 53 53 FF 15 2C 90 40 00 50 E8
00008480: 5E 00 00 00 89 45 98 50 FF 15 2C 93 40 00 8B 45
00008490: EC 8B 08 8B 09 89 4D 88 50 51 E8 15 00 00 00 59
000084A0: 59 C3 8B 65 E8 FF 75 88 FF 15 C8 92 40 00 FF 25
000084B0: DC 92 40 00 FF 25 D8 92 40 00 FF 25 B4 92 40 00
000084C0: 68 00 00 03 00 68 00 00 01 00 E8 0D 00 00 00 59
000084D0: 59 C3 33 C0 C3 C3 FF 25 D0 92 40 00 FF 25 D4 92
000084E0: 40 00 FF 74 24 10 FF 74 24 10 FF 74 24 10 FF 74
000084F0: 24 10 E8 43 00 00 00 C2 10 00 E8 67 FD FF FF 8B
00008500: 4C 24 04 8B 54 24 08 85 C9 88 48 14 89 90 40 10
00008510: 00 00 75 09 6A FD FF 15 30 93 40 00 59 6A 01 58
00008520: C2 08 00 E9 00 00 00 00 68 00 06 00 00 6A 00 E8
00008530: C6 FF FF FF A2 E8 FC D8 00 C3 FF 25 BC 91 40 00
00008540: 8D 8D 8C FD FF FF E9 D5 C9 FF FF 8D 8D 8C FD FF
00008550: FF E9 FC FB FF FF 8D 8D EC FD FF FF E9 C3 FC FF
00008560: FF 8D 8D 2C FE FF FF E9 B8 FC FF FF 8D 8D 6C FE
00008570: FF FF E9 AD FC FF FF 8D 8D AC FE FF FF E9 A2 FC
00008580: FF FF 8D 8D EC FE FF FF E9 97 FC FF FF 8D 8D 2C
00008590: FF FF FF E9 8C FC FF FF 8D 8D 6C FF FF FF E9 81
000085A0: FC FF FF B8 90 9C 40 00 E9 9D FD FF FF CC CC CC
000085B0: 8B 4D F0 E9 9A FB FF FF 8B 4D F0 83 C1 60 E9 61
000085C0: FC FF FF 8B 4D F0 81 C1 A0 00 00 00 E9 53 FC FF
000085D0: FF 8B 4D F0 81 C1 E0 00 00 00 E9 45 FC FF FF 8B
000085E0: 4D F0 81 C1 20 01 00 00 E9 37 FC FF FF 8B 4D F0
000085F0: 81 C1 60 01 00 00 E9 29 FC FF FF 8B 4D F0 81 C1
00008600: A0 01 00 00 E9 1B FC FF FF 8B 4D F0 81 C1 E0 01
00008610: 00 00 E9 0D FC FF FF B8 F8 9C 40 00 E9 29 FD FF
00008620: FF CC CC CC CC CC CC CC CC CC CC CC CC CC CC CC
00008630: 8B 4D F0 E9 1A FB FF FF 8B 4D F0 83 C1 60 E9 E1
00008640: FB FF FF 8B 4D F0 81 C1 A0 00 00 00 E9 D3 FB FF
00008650: FF 8B 4D F0 81 C1 E0 00 00 00 E9 C5 FB FF FF 8B
00008660: 4D F0 81 C1 20 01 00 00 E9 B7 FB FF FF 8B 4D F0
00008670: 81 C1 60 01 00 00 E9 A9 FB FF FF 8B 4D F0 81 C1
00008680: A0 01 00 00 E9 9B FB FF FF 8B 4D F0 81 C1 E0 01
00008690: 00 00 E9 8D FB FF FF 8B 4D F0 81 C1 20 02 00 00
000086A0: E9 7F FB FF FF B8 58 9D 40 00 E9 9B FC FF FF CC
000086B0: 8D 4D F0 E9 CC FB FF FF B8 C0 9D 40 00 E9 88 FC
000086C0: FF FF CC CC CC CC CC CC CC CC CC CC CC CC CC CC
000086D0: 8D 4D 94 E9 48 89 FF FF B8 E8 9D 40 00 E9 68 FC
000086E0: FF FF CC CC CC CC CC CC CC CC CC CC CC CC CC CC
000086F0: 8D 4D AC E9 D4 FB FF FF B8 10 9E 40 00 E9 48 FC
00008700: FF FF CC CC CC CC CC CC CC CC CC CC CC CC CC CC
00008710: 8D 4D 94 E9 08 89 FF FF B8 38 9E 40 00 E9 28 FC
00008720: FF FF CC CC CC CC CC CC CC CC CC CC CC CC CC CC
00008730: 8D 8D 74 FF FF FF E9 E5 88 FF FF B8 60 9E 40 00
00008740: E9 05 FC FF FF 00 00 00 00 00 00 00 00 00 00 00
00008750: 00 00 00 00 00 00 00 00 00 00 00 00 00 00 00 00
00008760: 00 00 00 00 00 00 00 00 00 00 00 00 00 00 00 00
00008770: 00 00 00 00 00 00 00 00 00 00 00 00 00 00 00 00
00008780: 00 00 00 00 00 00 00 00 00 00 00 00 00 00 00 00
00008790: 00 00 00 00 00 00 00 00 00 00 00 00 00 00 00 00
```

APPENDIX-continued

```
000087A0: 00 00 00 00 00 00 00 00 00 00 00 00 00 00 00 00
000087B0: 00 00 00 00 00 00 00 00 00 00 00 00 00 00 00 00
000087C0: 00 00 00 00 00 00 00 00 00 00 00 00 00 00 00 00
000087D0: 00 00 00 00 00 00 00 00 00 00 00 00 00 00 00 00
000087E0: 00 00 00 00 00 00 00 00 00 00 00 00 00 00 00 00
000087F0: 00 00 00 00 00 00 00 00 00 00 00 00 00 00 00 00
00008800: 00 00 00 00 00 00 00 00 00 00 00 00 00 00 00 00
00008810: 00 00 00 00 00 00 00 00 00 00 00 00 00 00 00 00
00008820: 00 00 00 00 00 00 00 00 00 00 00 00 00 00 00 00
00008830: 00 00 00 00 00 00 00 00 00 00 00 00 00 00 00 00
00008840: 00 00 00 00 00 00 00 00 00 00 00 00 00 00 00 00
00008850: 00 00 00 00 00 00 00 00 00 00 00 00 00 00 00 00
00008860: 00 00 00 00 00 00 00 00 00 00 00 00 00 00 00 00
00008870: 00 00 00 00 00 00 00 00 00 00 00 00 00 00 00 00
00008880: 00 00 00 00 00 00 00 00 00 00 00 00 00 00 00 00
00008890: 00 00 00 00 00 00 00 00 00 00 00 00 00 00 00 00
000088A0: 00 00 00 00 00 00 00 00 00 00 00 00 00 00 00 00
000088B0: 00 00 00 00 00 00 00 00 00 00 00 00 00 00 00 00
000088C0: 00 00 00 00 00 00 00 00 00 00 00 00 00 00 00 00
000088D0: 00 00 00 00 00 00 00 00 00 00 00 00 00 00 00 00
000088E0: 00 00 00 00 00 00 00 00 00 00 00 00 00 00 00 00
000088F0: 00 00 00 00 00 00 00 00 00 00 00 00 00 00 00 00
00008900: 00 00 00 00 00 00 00 00 00 00 00 00 00 00 00 00
00008910: 00 00 00 00 00 00 00 00 00 00 00 00 00 00 00 00
00008920: 00 00 00 00 00 00 00 00 00 00 00 00 00 00 00 00
00008930: 00 00 00 00 00 00 00 00 00 00 00 00 00 00 00 00
00008940: 00 00 00 00 00 00 00 00 00 00 00 00 00 00 00 00
00008950: 00 00 00 00 00 00 00 00 00 00 00 00 00 00 00 00
00008960: 00 00 00 00 00 00 00 00 00 00 00 00 00 00 00 00
00008970: 00 00 00 00 00 00 00 00 00 00 00 00 00 00 00 00
00008980: 00 00 00 00 00 00 00 00 00 00 00 00 00 00 00 00
00008990: 00 00 00 00 00 00 00 00 00 00 00 00 00 00 00 00
000089A0: 00 00 00 00 00 00 00 00 00 00 00 00 00 00 00 00
000089B0: 00 00 00 00 00 00 00 00 00 00 00 00 00 00 00 00
000089C0: 00 00 00 00 00 00 00 00 00 00 00 00 00 00 00 00
000089D0: 00 00 00 00 00 00 00 00 00 00 00 00 00 00 00 00
000089E0: 00 00 00 00 00 00 00 00 00 00 00 00 00 00 00 00
000089F0: 00 00 00 00 00 00 00 00 00 00 00 00 00 00 00 00
00008A00: 00 00 00 00 00 00 00 00 00 00 00 00 00 00 00 00
00008A10: 00 00 00 00 00 00 00 00 00 00 00 00 00 00 00 00
00008A20: 00 00 00 00 00 00 00 00 00 00 00 00 00 00 00 00
00008A30: 00 00 00 00 00 00 00 00 00 00 00 00 00 00 00 00
00008A40: 00 00 00 00 00 00 00 00 00 00 00 00 00 00 00 00
00008A50: 00 00 00 00 00 00 00 00 00 00 00 00 00 00 00 00
00008A60: 00 00 00 00 00 00 00 00 00 00 00 00 00 00 00 00
00008A70: 00 00 00 00 00 00 00 00 00 00 00 00 00 00 00 00
00008A80: 00 00 00 00 00 00 00 00 00 00 00 00 00 00 00 00
00008A90: 00 00 00 00 00 00 00 00 00 00 00 00 00 00 00 00
00008AA0: 00 00 00 00 00 00 00 00 00 00 00 00 00 00 00 00
00008AB0: 00 00 00 00 00 00 00 00 00 00 00 00 00 00 00 00
00008AC0: 00 00 00 00 00 00 00 00 00 00 00 00 00 00 00 00
00008AD0: 00 00 00 00 00 00 00 00 00 00 00 00 00 00 00 00
00008AE0: 00 00 00 00 00 00 00 00 00 00 00 00 00 00 00 00
00008AF0: 00 00 00 00 00 00 00 00 00 00 00 00 00 00 00 00
00008B00: 00 00 00 00 00 00 00 00 00 00 00 00 00 00 00 00
00008B10: 00 00 00 00 00 00 00 00 00 00 00 00 00 00 00 00
00008B20: 00 00 00 00 00 00 00 00 00 00 00 00 00 00 00 00
00008B30: 00 00 00 00 00 00 00 00 00 00 00 00 00 00 00 00
00008B40: 00 00 00 00 00 00 00 00 00 00 00 00 00 00 00 00
00008B50: 00 00 00 00 00 00 00 00 00 00 00 00 00 00 00 00
00008B60: 00 00 00 00 00 00 00 00 00 00 00 00 00 00 00 00
00008B70: 00 00 00 00 00 00 00 00 00 00 00 00 00 00 00 00
00008B80: 00 00 00 00 00 00 00 00 00 00 00 00 00 00 00 00
00008B90: 00 00 00 00 00 00 00 00 00 00 00 00 00 00 00 00
00008BA0: 00 00 00 00 00 00 00 00 00 00 00 00 00 00 00 00
00008BB0: 00 00 00 00 00 00 00 00 00 00 00 00 00 00 00 00
00008BC0: 00 00 00 00 00 00 00 00 00 00 00 00 00 00 00 00
00008BD0: 00 00 00 00 00 00 00 00 00 00 00 00 00 00 00 00
00008BE0: 00 00 00 00 00 00 00 00 00 00 00 00 00 00 00 00
00008BF0: 00 00 00 00 00 00 00 00 00 00 00 00 00 00 00 00
00008C00: 00 00 00 00 00 00 00 00 00 00 00 00 00 00 00 00
00008C10: 00 00 00 00 00 00 00 00 00 00 00 00 00 00 00 00
00008C20: 00 00 00 00 00 00 00 00 00 00 00 00 00 00 00 00
00008C30: 00 00 00 00 00 00 00 00 00 00 00 00 00 00 00 00
00008C40: 00 00 00 00 00 00 00 00 00 00 00 00 00 00 00 00
00008C50: 00 00 00 00 00 00 00 00 00 00 00 00 00 00 00 00
00008C60: 00 00 00 00 00 00 00 00 00 00 00 00 00 00 00 00
00008C70: 00 00 00 00 00 00 00 00 00 00 00 00 00 00 00 00
00008C80: 00 00 00 00 00 00 00 00 00 00 00 00 00 00 00 00
00008C90: 00 00 00 00 00 00 00 00 00 00 00 00 00 00 00 00
00008CA0: 00 00 00 00 00 00 00 00 00 00 00 00 00 00 00 00
00008CB0: 00 00 00 00 00 00 00 00 00 00 00 00 00 00 00 00
00008CC0: 00 00 00 00 00 00 00 00 00 00 00 00 00 00 00 00
00008CD0: 00 00 00 00 00 00 00 00 00 00 00 00 00 00 00 00
00008CE0: 00 00 00 00 00 00 00 00 00 00 00 00 00 00 00 00
00008CF0: 00 00 00 00 00 00 00 00 00 00 00 00 00 00 00 00
00008D00: 00 00 00 00 00 00 00 00 00 00 00 00 00 00 00 00
00008D10: 00 00 00 00 00 00 00 00 00 00 00 00 00 00 00 00
00008D20: 00 00 00 00 00 00 00 00 00 00 00 00 00 00 00 00
00008D30: 00 00 00 00 00 00 00 00 00 00 00 00 00 00 00 00
00008D40: 00 00 00 00 00 00 00 00 00 00 00 00 00 00 00 00
00008D50: 00 00 00 00 00 00 00 00 00 00 00 00 00 00 00 00
00008D60: 00 00 00 00 00 00 00 00 00 00 00 00 00 00 00 00
00008D70: 00 00 00 00 00 00 00 00 00 00 00 00 00 00 00 00
00008D80: 00 00 00 00 00 00 00 00 00 00 00 00 00 00 00 00
00008D90: 00 00 00 00 00 00 00 00 00 00 00 00 00 00 00 00
00008DA0: 00 00 00 00 00 00 00 00 00 00 00 00 00 00 00 00
00008DB0: 00 00 00 00 00 00 00 00 00 00 00 00 00 00 00 00
00008DC0: 00 00 00 00 00 00 00 00 00 00 00 00 00 00 00 00
00008DD0: 00 00 00 00 00 00 00 00 00 00 00 00 00 00 00 00
00008DE0: 00 00 00 00 00 00 00 00 00 00 00 00 00 00 00 00
00008DF0: 00 00 00 00 00 00 00 00 00 00 00 00 00 00 00 00
00008E00: 00 00 00 00 00 00 00 00 00 00 00 00 00 00 00 00
00008E10: 00 00 00 00 00 00 00 00 00 00 00 00 00 00 00 00
00008E20: 00 00 00 00 00 00 00 00 00 00 00 00 00 00 00 00
00008E30: 00 00 00 00 00 00 00 00 00 00 00 00 00 00 00 00
00008E40: 00 00 00 00 00 00 00 00 00 00 00 00 00 00 00 00
00008E50: 00 00 00 00 00 00 00 00 00 00 00 00 00 00 00 00
00008E60: 00 00 00 00 00 00 00 00 00 00 00 00 00 00 00 00
00008E70: 00 00 00 00 00 00 00 00 00 00 00 00 00 00 00 00
00008E80: 00 00 00 00 00 00 00 00 00 00 00 00 00 00 00 00
00008E90: 00 00 00 00 00 00 00 00 00 00 00 00 00 00 00 00
00008EA0: 00 00 00 00 00 00 00 00 00 00 00 00 00 00 00 00
00008EB0: 00 00 00 00 00 00 00 00 00 00 00 00 00 00 00 00
00008EC0: 00 00 00 00 00 00 00 00 00 00 00 00 00 00 00 00
00008ED0: 00 00 00 00 00 00 00 00 00 00 00 00 00 00 00 00
00008EE0: 00 00 00 00 00 00 00 00 00 00 00 00 00 00 00 00
00008EF0: 00 00 00 00 00 00 00 00 00 00 00 00 00 00 00 00
00008F00: 00 00 00 00 00 00 00 00 00 00 00 00 00 00 00 00
00008F10: 00 00 00 00 00 00 00 00 00 00 00 00 00 00 00 00
00008F20: 00 00 00 00 00 00 00 00 00 00 00 00 00 00 00 00
00008F30: 00 00 00 00 00 00 00 00 00 00 00 00 00 00 00 00
00008F40: 00 00 00 00 00 00 00 00 00 00 00 00 00 00 00 00
00008F50: 00 00 00 00 00 00 00 00 00 00 00 00 00 00 00 00
00008F60: 00 00 00 00 00 00 00 00 00 00 00 00 00 00 00 00
00008F70: 00 00 00 00 00 00 00 00 00 00 00 00 00 00 00 00
00008F80: 00 00 00 00 00 00 00 00 00 00 00 00 00 00 00 00
00008F90: 00 00 00 00 00 00 00 00 00 00 00 00 00 00 00 00
00008FA0: 00 00 00 00 00 00 00 00 00 00 00 00 00 00 00 00
00008FB0: 00 00 00 00 00 00 00 00 00 00 00 00 00 00 00 00
00008FC0: 00 00 00 00 00 00 00 00 00 00 00 00 00 00 00 00
00008FD0: 00 00 00 00 00 00 00 00 00 00 00 00 00 00 00 00
00008FE0: 00 00 00 00 00 00 00 00 00 00 00 00 00 00 00 00
00008FF0: 00 00 00 00 00 00 00 00 00 00 00 00 00 00 00 00
00009000: 74 A6 00 00 92 A6 00 00 84 A6 00 00 26 A6 00 00
00009010: 6A A6 00 00 5A A6 00 00 46 A6 00 00 32 A6 00 00
00009020: 00 00 00 00 62 A4 00 00 FC A4 00 00 E8 A4 00 00
00009030: DA A4 00 00 CA A4 00 00 BA A4 00 00 AA A4 00 00
00009040: 9A A4 00 00 84 A4 00 00 76 A4 00 00 6A A4 00 00
00009050: 00 00 00 00 31 02 00 80 F6 0D 00 80 7A 04 00 80
00009060: BE 18 00 80 14 0C 00 80 1C 14 00 80 A8 0E 00 80
00009070: 91 14 00 80 18 11 00 80 F5 12 00 80 86 13 00 80
00009080: 66 12 00 80 D2 09 00 80 A4 17 00 80 EE 0F 00 80
00009090: EF 06 00 80 37 11 00 80 79 14 00 80 51 09 00 80
000090A0: 2B 14 00 80 E6 18 00 80 01 11 00 80 A0 14 00 80
000090B0: D6 0E 00 80 E5 12 00 80 59 11 00 80 58 0A 00 80
000090C0: 07 08 00 80 E8 18 00 80 A5 0E 00 80 C9 13 00 80
000090D0: BF 06 00 80 8D 14 00 80 8E 09 00 80 4C 08 00 80
000090E0: 9D 14 00 80 A6 0B 00 80 4B 0C 00 80 BB 0C 00 80
000090F0: 71 11 00 80 40 0C 00 80 BE 0C 00 80 A9 0B 00 80
00009100: 09 0C 00 80 A0 0B 00 80 F6 0E 00 80 F7 0E 00 80
00009110: F1 0E 00 80 07 0C 00 80 F0 0F 00 80 13 12 00 80
00009120: 49 11 00 80 0D 0E 00 80 44 01 00 80 39 03 00 80
00009130: 81 02 00 80 8A 10 00 80 F5 08 00 80 3E 09 00 80
00009140: F6 08 00 80 3A 09 00 80 FD 08 00 80 F3 08 00 80
00009150: 3F 09 00 80 E3 0E 00 80 56 12 00 80 80 10 00 80
00009160: 41 12 00 80 B2 10 00 80 E7 18 00 80 86 11 00 80
00009170: FA 09 00 80 D0 09 00 80 63 16 00 80 52 0F 00 80
```

APPENDIX-continued

```
00009180: 41 04 00 80 4F 14 00 80 5C 09 00 80 12 0D 00 80
00009190: B4 14 00 80 B6 14 00 80 A5 0A 00 80 EF 0F 00 80
000091A0: 5A 12 00 80 BB 14 00 80 A9 14 00 80 52 16 00 80
000091B0: 0E 12 00 80 48 11 00 80 9A 0E 00 80 28 06 00 80
000091C0: 2F 03 00 80 61 02 00 83 3D 0A 00 80 6E 04 00 80
000091D0: 0F 0A 00 80 A7 17 00 80 F0 06 00 80 2C 11 00 80
000091E0: AA 14 00 80 4A 0D 00 80 4B 09 00 80 2F 0B 00 80
000091F0: 90 04 00 80 37 02 00 80 FE 08 00 80 52 0A 00 80
00009200: F0 17 00 80 20 03 00 80 40 10 00 80 1C 02 00 80
00009210: 80 18 00 80 FA 07 00 80 F3 02 00 80 D6 01 00 80
00009220: 97 0C 00 80 95 0C 00 80 22 11 00 80 45 04 00 80
00009230: 21 0A 00 80 09 03 00 80 00 00 00 00 13 01 00 80
00009240: 8D 00 00 80 7B 00 00 80 98 00 00 80 8E 00 00 80
00009250: 66 00 00 80 81 00 00 80 90 00 00 80 64 00 00 80
00009260: 11 01 00 80 93 00 00 80 96 00 00 80 6E 00 00 80
00009270: 8A 00 00 80 D7 00 00 80 22 03 00 80 14 01 00 80
00009280: 9E 00 00 80 90 03 00 80 9B 00 00 80 72 00 00 80
00009290: 71 00 00 80 8F 00 00 80 92 00 00 80 9C 00 00 80
000092A0: 21 03 00 80 00 00 00 00 64 00 00 80 00 00 00 00
000092B0: D0 A3 00 00 E0 A3 00 00 EC A3 00 00 A4 00 00
000092C0: C6 A3 00 00 20 A3 00 00 B0 A3 00 00 2E A4 00 00
000092D0: 40 A4 00 00 54 A4 00 00 B8 A3 00 00 98 A3 00 00
000092E0: 7E A3 00 00 6E A3 00 00 CC A2 00 00 DC A2 00 00
000092F0: 64 A3 00 00 50 A3 00 00 46 A3 00 00 3C A3 00 00
00009300: 30 A3 00 00 28 A3 00 00 A6 A3 00 00 00 A3 00 00
00009310: 14 A3 00 00 0A A3 00 00 E6 A2 00 00 F8 A2 00 00
00009320: EE A2 00 00 10 A4 00 00 20 A4 00 00 D4 A2 00 00
00009330: A6 A6 00 00 00 00 00 00 C0 A5 00 00 CE A5 00 00
00009340: B0 A5 00 00 DE A5 00 00 EA A5 00 00 FA A5 00 00
00009350: 0E A6 00 00 94 A5 00 00 A4 A5 00 00 76 A5 00 00
00009360: 6A A5 00 00 5E A5 00 00 56 A5 00 00 48 A5 00 00
00009370: 38 A5 00 00 2C A5 00 00 84 A5 00 00 1C A5 00 00
00009380: 00 00 00 00 00 00 00 00 30 10 40 00 90 93 40 00
00009390: 00 00 00 00 00 00 00 00 00 00 00 00 00 00 00 00
000093A0: 00 00 00 00 00 00 00 00 40 81 40 00 E0 49 40 00
000093B0: 60 10 40 00 50 10 40 00 60 10 40 00 3A 81 40 00
000093C0: 34 81 40 00 2E 81 40 00 28 81 40 00 22 81 40 00
000093D0: 1C 81 40 00 16 81 40 00 40 10 40 00 10 81 40 00
000093E0: 0A 81 40 00 04 81 40 00 FE 80 40 00 F8 80 40 00
000093F0: F2 80 40 00 EC 80 40 00 E6 80 40 00 E0 80 40 00
00009400: DA 80 40 00 D4 80 40 00 CE 80 40 00 C8 80 40 00
00009410: C2 80 40 00 BC 80 40 00 B6 80 40 00 B0 80 40 00
00009420: AA 80 40 00 A4 80 40 00 9E 80 40 00 98 80 40 00
00009430: 92 80 40 00 00 50 40 00 70 10 40 00 80 10 40 00
00009440: 8C 80 40 00 86 80 40 00 80 80 40 00 7A 80 40 00
00009450: 74 80 40 00 6E 80 40 00 68 80 40 00 62 80 40 00
00009460: 5C 80 40 00 56 80 40 00 50 80 40 00 4A 80 40 00
00009470: 44 80 40 00 3E 80 40 00 38 80 40 00 32 80 40 00
00009480: 00 00 00 00 00 00 F0 3F 00 00 00 00 00 00 E0 3F
00009490: 00 00 00 00 00 00 00 00 00 00 00 00 00 00 00 00
000094A0: 00 00 00 00 E0 FF EF 40 00 00 00 00 00 00 50 40
000094B0: BB 5A D3 3E 2F 4D 92 BF FE 25 0A 3E FE 25 8A 3D
000094C0: EF 91 A3 3F 3C D1 B0 BE 00 00 00 00 00 00 30 40
000094D0: 00 00 00 00 00 00 40 39 9D 52 A2 46 DF 91 3F
000094E0: 00 00 00 00 00 00 08 40 39 05 2F A7 E0 E5 94 3F
000094F0: 33 33 33 3F 9A 99 99 3E 00 00 80 3F 6F 12 83 3A
00009500: AA 4C 58 E8 7A B6 EB 3F 30 10 40 00 10 95 40 00
00009510: 11 01 00 00 03 00 00 00 F8 03 00 00 F8 03 00 00
00009520: 0C 00 00 00 A0 4B 40 00 11 01 00 00 00 00 00 00
00009530: F5 03 00 00 F5 03 00 00 0C 00 00 00 20 4C 40 00
00009540: 11 01 00 00 00 00 00 00 F6 03 00 00 F6 03 00 00
00009550: 0C 00 00 00 30 4C 40 00 11 01 00 00 00 00 00 00
00009560: FB 03 00 00 FB 03 00 00 0C 00 00 00 40 4C 40 00
00009570: 11 01 00 00 00 03 00 00 FC 03 00 00 FC 03 00 00
00009580: 0C 00 00 00 4C 40 00 11 01 00 00 00 00 00 00
00009590: FD 03 00 00 FD 03 00 00 0C 00 00 00 60 4C 40 00
000095A0: 11 01 00 00 00 00 00 00 FE 03 00 00 FE 03 00 00
000095B0: 0C 00 00 00 80 4C 40 00 11 01 00 00 00 03 00 00
000095C0: FF 03 00 00 FF 03 00 00 0C 00 00 00 C0 4B 40 00
000095D0: 11 01 00 00 00 03 00 00 01 04 00 00 01 04 00 00
000095E0: 0C 00 00 00 E0 4B 40 00 00 00 00 00 00 00 00 00
000095F0: 00 00 00 00 00 00 00 00 00 00 00 00 00 00 00 00
00009600: 40 81 40 00 E0 49 40 00 60 10 40 00 50 10 40 00
00009610: 60 10 40 00 3A 81 40 00 34 81 40 00 2E 81 40 00
00009620: 28 81 40 00 22 81 40 00 1C 81 40 00 16 81 40 00
00009630: C0 4A 40 00 10 81 40 00 0A 81 40 00 04 81 40 00
00009640: FE 80 40 00 F8 80 40 00 F2 80 40 00 EC 80 40 00
00009650: E6 80 40 00 E0 80 40 00 DA 80 40 00 D4 80 40 00
00009660: CE 80 40 00 C8 80 40 00 C2 80 40 00 BC 80 40 00
00009670: B6 80 40 00 B0 80 40 00 AA 80 40 00 A4 80 40 00
00009680: 9E 80 40 00 98 80 40 00 92 80 40 00 00 4A 40 00
00009690: 70 10 40 00 80 10 40 00 8C 80 40 00 86 80 40 00
000096A0: 80 80 40 00 7A 80 40 00 74 80 40 00 6E 80 40 00
000096B0: 68 80 40 00 62 80 40 00 5C 80 40 00 56 80 40 00
000096C0: 50 80 40 00 D0 4A 40 00 44 80 40 00 3E 80 40 00
000096D0: 38 80 40 00 32 80 40 00 40 4D 40 00 E0 96 40 00
000096E0: 11 01 00 00 00 00 00 00 46 E1 00 00 46 E1 00 00
000096F0: 0C 00 00 00 94 81 40 00 00 00 00 00 00 00 00 00
00009700: 00 00 00 00 00 00 00 00 00 00 00 00 00 00 00 00
00009710: 12 82 40 00 80 4D 40 00 60 10 40 00 50 10 40 00
00009720: 60 10 40 00 0C 82 40 00 06 82 40 00 2E 81 40 00
00009730: 28 81 40 00 22 81 40 00 1C 81 40 00 16 81 40 00
00009740: 50 4D 40 00 10 81 40 00 0A 81 40 00 04 81 40 00
00009750: FE 80 40 00 F8 80 40 00 F2 80 40 00 EC 80 40 00
00009760: E6 80 40 00 E0 80 40 00 F0 4D 40 00 00 82 40 00
00009770: FA 81 40 00 F4 81 40 00 EE 81 40 00 E8 81 40 00
00009780: E2 81 40 00 DC 81 40 00 D6 81 40 00 D0 81 40 00
00009790: CA 81 40 00 C4 81 40 00 BE 81 40 00 B8 81 40 00
000097A0: B2 81 40 00 AC 81 40 00 A6 81 40 00 A0 81 40 00
000097B0: 9A 81 40 00 00 00 00 00 30 10 40 00 C0 97 40 00
000097C0: 00 00 00 00 00 00 00 00 00 00 00 00 00 00 00 00
000097D0: 00 00 00 00 00 00 00 00 30 10 40 00 E0 97 40 00
000097E0: 12 01 00 00 00 00 00 00 00 00 00 00 00 00 00 00
000097F0: 12 00 00 00 C0 53 40 00 0F 00 00 00 00 00 00 00
00009800: 00 00 00 00 00 00 00 0C 00 00 00 40 54 40 00
00009810: 37 00 00 00 00 00 00 00 00 00 00 00 00 00 00 00
00009820: 23 00 00 00 55 40 00 11 01 00 00 00 00 00 00
00009830: E8 03 00 00 E8 03 00 00 0C 00 00 00 30 55 40 00
00009840: 11 01 00 00 00 00 00 00 E9 03 00 00 E9 03 00 00
00009850: 0C 00 00 00 70 55 40 00 11 01 00 00 00 00 00 00
00009860: EA 03 00 00 EA 03 00 00 0C 00 00 00 20 56 40 00
00009870: 11 01 00 00 00 00 00 00 EB 03 00 00 EB 03 00 00
00009880: 0C 00 00 00 B0 56 40 00 11 01 00 00 00 00 00 00
00009890: EC 03 00 00 EC 03 00 00 0C 00 00 00 80 5B 40 00
000098A0: 11 01 00 00 00 00 00 00 ED 03 00 00 ED 03 00 00
000098B0: 0C 00 00 00 C0 5B 40 00 11 01 00 00 00 00 00 00
000098C0: F2 03 00 00 F2 03 00 00 0C 00 00 00 80 5C 40 00
000098D0: 11 01 00 00 00 00 00 00 FA 03 00 00 FA 03 00 00
000098E0: 0C 00 00 00 E0 5C 40 00 11 01 00 00 00 00 00 00
000098F0: FC 03 00 00 FC 03 00 00 0C 00 00 00 50 5D 40 00
00009900: 11 01 00 00 00 00 00 00 FD 03 00 00 FD 03 00 00
00009910: 0C 00 00 00 60 5D 40 00 11 01 00 00 00 00 00 00
00009920: EE 03 00 00 EE 03 00 00 0C 00 00 00 C0 56 40 00
00009930: 11 01 00 00 00 00 00 00 04 00 00 00 04 00 00 00
00009940: 0C 00 00 00 A0 5D 40 00 14 01 00 00 00 00 00 00
00009950: 00 00 00 00 00 00 00 00 1D 00 00 00 F0 5D 40 00
00009960: 15 01 00 00 00 00 00 00 00 00 00 00 00 00 00 00
00009970: 1D 00 00 00 F0 5E 40 00 01 02 00 00 00 00 00 00
00009980: 00 00 00 00 00 00 00 00 0A 00 00 00 D0 56 40 00
00009990: 04 02 00 00 00 00 00 00 00 00 00 00 00 00 00 00
000099A0: 0A 00 00 00 50 5A 40 00 02 04 00 00 00 00 00 00
000099B0: 00 00 00 00 00 00 00 00 0A 00 00 00 10 55 40 00
000099C0: 00 00 00 00 00 00 00 00 00 00 00 00 00 00 00 00
000099D0: 00 00 00 00 00 00 00 00 40 81 40 00 E0 49 40 00
000099E0: 60 10 40 00 50 10 40 00 60 10 40 00 3A 81 40 00
000099F0: 34 81 40 00 2E 81 40 00 28 81 40 00 22 81 40 00
00009A00: 1C 81 40 00 16 81 40 00 10 50 40 00 10 81 40 00
00009A10: 0A 81 40 00 04 81 40 00 FE 80 40 00 F8 80 40 00
00009A20: F2 80 40 00 EC 80 40 00 E6 80 40 00 E0 80 40 00
00009A30: DA 80 40 00 D4 80 40 00 CE 80 40 00 C8 80 40 00
00009A40: C2 80 40 00 BC 80 40 00 B6 80 40 00 B0 80 40 00
00009A50: AA 80 40 00 A4 80 40 00 9E 80 40 00 98 80 40 00
00009A60: 92 80 40 00 00 50 40 00 70 10 40 00 80 10 40 00
00009A70: 8C 80 40 00 86 80 40 00 80 80 40 00 7A 80 40 00
00009A80: 74 80 40 00 6E 80 40 00 68 80 40 00 62 80 40 00
00009A90: 5C 80 40 00 56 80 40 00 50 80 40 00 4A 80 40 00
00009AA0: 44 80 40 00 3E 80 40 00 38 80 40 00 32 80 40 00
00009AB0: 40 81 40 00 60 51 40 00 60 10 40 00 50 10 40 00
00009AC0: 60 10 40 00 3A 81 40 00 34 81 40 00 2E 81 40 00
00009AD0: 28 81 40 00 22 81 40 00 1C 81 40 00 16 81 40 00
00009AE0: 30 52 40 00 10 81 40 00 0A 81 40 00 04 81 40 00
00009AF0: FE 80 40 00 F8 80 40 00 F2 80 40 00 EC 80 40 00
00009B00: E6 80 40 00 E0 80 40 00 DA 80 40 00 D4 80 40 00
00009B10: CE 80 40 00 C8 80 40 00 C2 80 40 00 BC 80 40 00
00009B20: B6 80 40 00 B0 80 40 00 AA 80 40 00 A4 80 40 00
00009B30: 9E 80 40 00 98 80 40 00 92 80 40 00 80 51 40 00
00009B40: 70 10 40 00 80 10 40 00 8C 80 40 00 86 80 40 00
00009B50: 80 80 40 00 7A 80 40 00 74 80 40 00 6E 80 40 00
```

APPENDIX-continued

```
00009B60: 68 80 40 00 62 80 40 00 5C 80 40 00 56 80 40 00
00009B70: 50 80 40 00 40 52 40 00 44 80 40 00 3E 80 40 00
00009B80: 38 80 40 00 32 80 40 00 5A 82 40 00 10 60 40 00
00009B90: 60 10 40 00 50 10 40 00 60 10 40 00 0C 82 40 00
00009BA0: 34 81 40 00 2E 81 40 00 28 81 40 00 22 81 40 00
00009BB0: 1C 81 40 00 16 81 40 00 54 82 40 00 10 81 40 00
00009BC0: 0A 81 40 00 04 81 40 00 FE 80 40 00 F8 80 40 00
00009BD0: F2 80 40 00 EC 80 40 00 E6 80 40 00 E0 80 40 00
00009BE0: DA 80 40 00 D4 80 40 00 CE 80 40 00 C8 80 40 00
00009BF0: C2 80 40 00 BC 80 40 00 B6 80 40 00 B0 80 40 00
00009C00: AA 80 40 00 A4 80 40 00 9E 80 40 00 98 80 40 00
00009C10: 92 80 40 00 60 10 40 00 70 10 40 00 80 10 40 00
00009C20: 4E 82 40 00 86 80 40 00 80 80 40 00 7A 80 40 00
00009C30: 74 80 40 00 6E 80 40 00 48 82 40 00 42 82 40 00
00009C40: 5C 80 40 00 3C 82 40 00 36 82 40 00 00 00 40 3F
00009C50: C6 82 40 00 C0 82 40 00 BA 82 40 00 B4 82 40 00
00009C60: 30 60 40 00 AE 82 40 00 00 00 00 00 00 14 40
00009C70: 90 9C E6 6B F5 EC 80 3F 00 00 00 3F 00 00 00 00
00009C80: FF FF FF FF 8E 84 40 00 A2 84 40 00 00 00 00 00
00009C90: 20 05 93 19 09 00 00 00 B0 9C 40 00 00 00 00 00
00009CA0: 00 00 00 00 00 00 00 00 00 00 00 00 00 00 00 00
00009CB0: FF FF FF FF 40 85 40 00 FF FF FF FF 4B 85 40 00
00009CC0: 01 00 00 00 56 85 40 00 02 00 00 00 61 85 40 00
00009CD0: 03 00 00 00 6C 85 40 00 04 00 00 00 77 85 40 00
00009CE0: 05 00 00 00 82 85 40 00 06 00 00 00 8D 85 40 00
00009CF0: 07 00 00 00 98 85 40 00 20 05 93 19 08 00 00 00
00009D00: 18 9D 40 00 00 00 00 00 00 00 00 00 00 00 00 00
00009D10: 00 00 00 00 00 00 00 00 FF FF FF FF B0 85 40 00
00009D20: 00 00 00 00 B8 85 40 00 01 00 00 00 C3 85 40 00
00009D30: 02 00 00 00 D1 85 40 00 03 00 00 00 DF 85 40 00
00009D40: 04 00 00 00 ED 85 40 00 05 00 00 00 FB 85 40 00
00009D50: 06 00 00 00 09 86 40 00 20 05 93 19 09 00 00 00
00009D60: 78 9D 40 00 00 00 00 00 00 00 00 00 00 00 00 00
00009D70: 00 00 00 00 00 00 00 00 FF FF FF FF 30 86 40 00
00009D80: 00 00 00 00 38 86 40 00 01 00 00 00 43 86 40 00
00009D90: 02 00 00 00 51 86 40 00 03 00 00 00 5F 86 40 00
00009DA0: 04 00 00 00 6D 86 40 00 05 00 00 00 7B 86 40 00
00009DB0: 06 00 00 00 89 86 40 00 07 00 00 00 97 86 40 00
00009DC0: 20 05 93 19 01 00 00 00 E0 9D 40 00 00 00 00 00
00009DD0: 00 00 00 00 00 00 00 00 00 00 00 00 00 00 00 00
00009DE0: FF FF FF FF B0 86 40 00 20 05 93 19 01 00 00 00
00009DF0: 08 9E 40 00 00 00 00 00 00 00 00 00 00 00 00 00
00009E00: 00 00 00 00 00 00 00 00 FF FF FF FF D0 86 40 00
00009E10: 20 05 93 19 01 00 00 00 30 9E 40 00 00 00 00 00
00009E20: 00 00 00 00 00 00 00 00 00 00 00 00 00 00 00 00
00009E30: FF FF FF FF F0 86 40 00 20 05 93 19 01 00 00 00
00009E40: 58 9E 40 00 00 00 00 00 00 00 00 00 00 00 00 00
00009E50: 00 00 00 00 00 00 00 00 FF FF FF FF 10 87 40 00
00009E60: 20 05 93 19 01 00 00 00 80 9E 40 00 00 00 00 00
00009E70: 00 00 00 00 00 00 00 00 00 00 00 00 00 00 00 00
00009E80: FF FF FF FF 30 87 40 00 D0 A1 00 00 00 00 00 00
00009E90: 00 00 00 00 AC A2 00 00 A8 92 00 00 64 A1 00 00
00009EA0: 00 00 00 00 00 00 00 00 BA A2 00 00 3C 92 00 00
00009EB0: 7C 9F 00 00 00 00 00 00 00 00 00 00 C2 A2 00 00
00009EC0: 54 90 00 00 D8 A1 00 00 00 00 00 00 00 00 00 00
00009ED0: 8C A3 00 00 B0 92 00 00 4C 9F 00 00 00 00 00 00
00009EE0: 00 00 00 00 0E A5 00 00 24 90 00 00 60 A2 00 00
00009EF0: 00 00 00 00 00 00 00 00 1A A6 00 00 38 93 00 00
00009F00: 28 9F 00 00 00 00 00 00 00 00 00 00 9C A6 00 00
00009F10: 00 90 00 00 00 00 00 00 00 00 00 00 00 00 00 00
00009F20: 00 00 00 00 00 00 00 00 74 A6 00 00 92 A6 00 00
00009F30: 84 A6 00 00 26 A6 00 00 6A A6 00 00 5A A6 00 00
00009F40: 46 A6 00 00 32 A6 00 00 00 00 00 00 62 A4 00 00
00009F50: FC A4 00 00 E8 A4 00 00 DA A4 00 00 CA A4 00 00
00009F60: BA A4 00 00 AA A4 00 00 9A A4 00 00 84 A4 00 00
00009F70: 76 A4 00 00 6A A4 00 00 00 00 00 00 31 02 00 80
00009F80: F6 0D 00 80 7A 04 00 80 BE 18 00 80 14 0C 00 80
00009F90: 1C 14 00 80 A8 0E 00 80 91 14 00 80 18 11 00 80
00009FA0: F5 12 00 80 86 13 00 80 66 12 00 80 D2 09 00 80
00009FB0: A4 17 00 80 EE 0F 00 80 EF 00 00 80 37 11 00 80
00009FC0: 79 14 00 80 51 09 00 80 2B 14 00 80 E6 18 00 80
00009FD0: 01 11 00 80 A0 14 00 80 D6 0E 00 80 E5 12 00 80
00009FE0: 59 11 00 80 58 0A 00 80 07 08 00 80 E8 18 00 80
00009FF0: A5 0E 00 80 C9 13 00 80 BF 06 00 80 8D 14 00 80
0000A000: 8E 09 00 80 4C 08 00 80 9D 14 00 80 A6 0B 00 80
0000A010: 4B 0C 00 80 BB 0C 00 80 71 11 00 80 40 0C 00 80
0000A020: BE 0C 00 80 A9 0B 00 80 09 0C 00 80 A0 0B 00 80
0000A030: F6 0E 00 80 F7 0E 00 80 F1 0E 00 80 07 0C 00 80
0000A040: F0 0F 00 80 13 12 00 80 49 11 00 80 0D 0E 00 80
0000A050: 44 01 00 80 39 03 00 80 81 02 00 80 8A 10 00 80
0000A060: F5 08 00 80 3E 09 00 80 F6 08 00 80 3A 09 00 80
0000A070: FD 08 00 80 F3 08 00 80 3F 09 00 80 E3 0E 00 80
0000A080: 56 12 00 80 80 10 00 80 41 12 00 80 B2 10 00 80
0000A090: E7 18 00 80 86 11 00 80 FA 09 00 80 D0 09 00 80
0000A0A0: 63 16 00 80 52 0F 00 80 41 04 00 80 4F 14 00 80
0000A0B0: 5C 09 00 80 12 0D 00 80 B4 14 00 80 B6 14 00 80
0000A0C0: A5 0A 00 80 EF 0F 00 80 5A 12 00 80 BB 14 00 80
0000A0D0: A9 14 00 80 52 16 00 80 0E 12 00 80 48 11 00 80
0000A0E0: 9A 0E 00 80 28 06 00 80 2F 03 00 80 61 02 00 80
0000A0F0: 3D 0A 00 80 6E 04 00 80 0F 0A 00 80 A7 17 00 80
0000A100: F0 06 00 80 2C 11 00 80 AA 14 00 80 4A 0D 00 80
0000A110: 4B 09 00 80 2F 0B 00 80 90 04 00 80 37 02 00 80
0000A120: FE 08 00 80 52 0A 00 80 F0 17 00 80 20 03 00 80
0000A130: 40 10 00 80 1C 02 00 80 80 18 00 80 FA 07 00 80
0000A140: F3 02 00 80 D6 01 00 80 97 0C 00 80 95 0C 00 80
0000A150: 22 11 00 80 45 04 00 80 21 0A 00 80 09 03 00 80
0000A160: 00 00 00 00 13 01 00 80 8D 00 00 80 7B 00 00 80
0000A170: 98 00 00 80 8E 00 00 80 66 00 00 80 81 00 00 80
0000A180: 90 00 00 80 64 00 00 80 11 01 00 80 93 00 00 80
0000A190: 96 00 00 80 6E 00 00 80 8A 00 00 80 D7 00 00 80
0000A1A0: 22 03 00 80 14 01 00 80 9E 00 00 80 90 03 00 80
0000A1B0: 9B 00 00 80 72 00 00 80 71 00 00 80 8F 00 00 80
0000A1C0: 92 00 00 80 9C 00 00 80 21 03 00 80 00 00 00 00
0000A1D0: 64 00 00 80 00 00 00 00 D0 A3 00 00 E0 A3 00 00
0000A1E0: EC A3 00 00 00 A4 00 00 C6 A3 00 00 20 A3 00 00
0000A1F0: B0 A3 00 00 2E A4 00 00 40 A4 00 00 54 A4 00 00
0000A200: B8 A3 00 00 98 A3 00 00 7E A3 00 00 6E A3 00 00
0000A210: CC A2 00 00 DC A2 00 00 64 A3 00 00 50 A3 00 00
0000A220: 46 A3 00 00 3C A3 00 00 30 A3 00 00 28 A3 00 00
0000A230: A6 A3 00 00 0A A3 00 00 14 A3 00 00 0A A3 00 00
0000A240: E6 A2 00 00 F8 A2 00 00 EE A2 00 00 10 A4 00 00
0000A250: 20 A4 00 00 D4 A2 00 00 A6 A6 00 00 00 00 00 00
0000A260: C0 A5 00 00 CE A5 00 00 B0 A5 00 00 DE A5 00 00
0000A270: EA A5 00 00 FA A5 00 00 0E A6 00 00 94 A5 00 00
0000A280: A4 A5 00 00 76 A5 00 00 6A A5 00 00 5E A5 00 00
0000A290: 56 A5 00 00 48 A5 00 00 38 A5 00 00 2C A5 00 00
0000A2A0: 84 A5 00 00 1C A5 00 00 00 00 00 00 4D 49 4C 4F
0000A2B0: 52 49 4F 4E 2E 64 6C 6C 00 00 4D 49 4C 2E 64 6C
0000A2C0: 6C 00 4D 46 43 34 32 2E 44 4C 4C 00 F1 00 5F 66
0000A2D0: 74 6F 6C 00 49 02 65 78 69 74 00 00 58 02 66 70
0000A2E0: 72 69 6E 74 66 00 13 01 5F 69 6F 62 00 00 91 02
0000A2F0: 6D 61 6C 6C 6F 63 00 00 5E 02 66 72 65 65 00 00
0000A300: 4C 02 66 63 6C 6F 73 65 00 00 B2 02 73 70 72 69
0000A310: 6E 74 66 00 8D 02 6C 6F 6F 67 63 61 6C 74 69 6D 65 00
0000A320: D0 02 74 69 6D 65 00 00 57 02 66 6F 70 65 6E 00
0000A330: BD 02 73 74 72 66 74 69 6D 65 00 00 3B 00 5F 43
0000A340: 49 70 6F 77 00 00 F0 00 5F 66 74 69 6D 65 00 00
0000A350: 49 00 5F 5F 43 78 78 46 72 61 6D 65 48 61 6E 64
0000A360: 6C 65 72 00 66 02 66 77 72 69 74 65 00 00 A5 00
0000A370: 5F 62 65 67 69 6E 74 68 72 65 61 64 00 00 C4 00
0000A380: 5F 65 6E 64 74 68 72 65 61 64 00 00 4D 53 56 43
0000A390: 52 54 2E 64 6C 6C 00 00 55 00 5F 5F 5F 64 6C 6C
0000A3A0: 6E 65 65 78 69 74 00 86 01 5F 6F 6E 65 78 69 74
0000A3B0: D3 00 5F 65 78 69 74 00 48 00 5F 58 63 70 74 46
0000A3C0: 69 6C 74 65 72 00 8F 00 5F 61 63 6D 64 6C 6E 00
0000A3D0: 58 00 5F 5F 67 65 74 6D 61 69 6E 61 72 67 73 00
0000A3E0: 0F 01 5F 69 6F 6E 69 74 74 65 72 6D 00 83 00 5F 5F
0000A3F0: 73 65 74 75 73 65 72 6D 61 74 68 65 72 72 6F 00
0000A400: 9D 00 5F 61 64 6A 75 73 74 5F 66 64 69 76 00 00
0000A410: 6A 00 5F 5F 70 5F 5F 63 6F 6D 6D 6F 64 65 00 00
0000A420: 6F 00 5F 5F 70 5F 5F 66 6D 6F 64 65 00 00 81 00
0000A430: 5F 5F 73 74 5F 5F 61 70 70 5F 74 79 70 65 00 00
0000A440: CA 00 5F 65 78 63 65 70 74 5F 68 61 6E 64 6C 65
0000A450: 72 33 00 00 B7 00 5F 63 6F 6E 74 72 6F 6C 66 70
0000A460: 00 00 96 02 53 6C 65 65 70 00 65 02 53 65 74 45
0000A470: 76 65 6E 74 00 00 2B 02 52 65 73 65 74 45 76 65
0000A480: 6E 74 00 00 CE 02 57 61 69 74 46 6F 72 53 69 6E
0000A490: 67 6C 65 4F 62 6A 65 63 74 00 25 02 52 65 6C 65
0000A4A0: 61 73 65 4D 75 74 65 78 00 00 1A 01 47 65 74 4C
0000A4B0: 61 73 74 45 72 72 6F 72 00 00 3F 00 43 72 65 61
0000A4C0: 74 65 4D 75 74 65 78 41 00 00 31 00 43 72 65 61
0000A4D0: 74 65 45 76 65 6E 74 41 00 00 1B 00 43 6C 6F 73
0000A4E0: 65 48 61 6E 64 6C 65 00 20 01 47 65 74 4D 6F 64
0000A4F0: 75 6C 65 48 61 6E 64 6C 65 41 00 00 50 01 47 65
0000A500: 74 53 74 61 72 74 75 70 49 6E 66 6F 41 00 4B 45
0000A510: 52 4E 45 4C 33 32 2E 64 6C 6C 00 00 B7 00 45 6E
0000A520: 61 62 6C 65 57 69 6E 64 6F 77 00 00 26 02 53 65
0000A530: 74 43 75 72 73 6F 72 00 20 02 53 65 74 43 6C 61
```

APPENDIX-continued

```
0000A540: 73 73 4C 6F 6E 67 41 00 9A 01 4C 6F 61 64 43 75
0000A550: 72 73 6F 72 41 00 FD 00 47 65 74 44 43 00 03 02
0000A560: 52 65 6C 65 61 73 65 44 43 00 D4 00 46 69 6C 6C
0000A570: 52 65 63 74 00 00 BE 01 4D 65 73 73 61 67 65 42
0000A580: 6F 78 41 00 DE 01 50 6F 73 74 4D 65 73 73 61 67
0000A590: 65 41 00 00 14 02 53 65 6E 64 4D 65 73 73 61 67
0000A5A0: 65 41 00 00 9E 01 4C 6F 61 64 49 63 6F 6E 41 00
0000A5B0: 68 02 53 68 6F 77 53 63 72 6F 6C 6C 42 61 72 00
0000A5C0: 07 00 41 70 70 65 6E 64 4D 65 6E 75 41 00 45 01
0000A5D0: 47 65 74 53 79 73 74 65 6D 4D 65 6E 75 00 A9 00
0000A5E0: 44 72 61 77 49 63 6F 6E 00 00 F0 00 47 65 74 43
0000A5F0: 6C 69 65 6E 74 52 65 63 74 00 46 01 47 65 74 53
0000A600: 79 73 74 65 6D 4D 65 74 72 69 63 73 00 00 8C 01
0000A610: 49 73 49 63 6F 6E 69 63 00 00 55 53 45 52 33 32
0000A620: 2E 64 6C 6C 00 00 44 00 43 72 65 61 74 65 50 65
0000A630: 6E 00 3D 00 43 72 65 61 74 65 48 61 74 63 68 42
0000A640: 72 75 73 68 00 00 4D 00 43 72 65 61 74 65 53 6F
0000A650: 6C 69 64 42 72 75 73 68 00 00 53 00 44 65 6C 65
0000A660: 74 65 4F 62 6A 65 63 74 00 00 58 00 45 6C 6C 69
0000A670: 70 73 65 00 C7 01 53 65 6C 65 63 74 4F 62 6A 65
0000A680: 63 74 00 00 CD 01 53 65 74 42 6B 43 6F 6C 6F 72
0000A690: 00 00 EC 01 53 65 74 52 4F 50 32 00 47 44 49 33
0000A6A0: 32 2E 64 6C 6C 00 AA 01 5F 73 65 74 6D 62 63 70
0000A6B0: 00 00 00 00 00 00 00 00 00 00 00 00 00 00 00 00
0000A6C0: 00 00 00 00 00 00 00 00 00 00 00 00 00 00 00 00
0000A6D0: 00 00 00 00 00 00 00 00 00 00 00 00 00 00 00 00
0000A6E0: 00 00 00 00 00 00 00 00 00 00 00 00 00 00 00 00
0000A6F0: 00 00 00 00 00 00 00 00 00 00 00 00 00 00 00 00
0000A700: 00 00 00 00 00 00 00 00 00 00 00 00 00 00 00 00
0000A710: 00 00 00 00 00 00 00 00 00 00 00 00 00 00 00 00
0000A720: 00 00 00 00 00 00 00 00 00 00 00 00 00 00 00 00
0000A730: 00 00 00 00 00 00 00 00 00 00 00 00 00 00 00 00
0000A740: 00 00 00 00 00 00 00 00 00 00 00 00 00 00 00 00
0000A750: 00 00 00 00 00 00 00 00 00 00 00 00 00 00 00 00
0000A760: 00 00 00 00 00 00 00 00 00 00 00 00 00 00 00 00
0000A770: 00 00 00 00 00 00 00 00 00 00 00 00 00 00 00 00
0000A780: 00 00 00 00 00 00 00 00 00 00 00 00 00 00 00 00
0000A790: 00 00 00 00 00 00 00 00 00 00 00 00 00 00 00 00
0000A7A0: 00 00 00 00 00 00 00 00 00 00 00 00 00 00 00 00
0000A7B0: 00 00 00 00 00 00 00 00 00 00 00 00 00 00 00 00
0000A7C0: 00 00 00 00 00 00 00 00 00 00 00 00 00 00 00 00
0000A7D0: 00 00 00 00 00 00 00 00 00 00 00 00 00 00 00 00
0000A7E0: 00 00 00 00 00 00 00 00 00 00 00 00 00 00 00 00
0000A7F0: 00 00 00 00 00 00 00 00 00 00 00 00 00 00 00 00
0000A800: 00 00 00 00 00 00 00 00 00 00 00 00 00 00 00 00
0000A810: 00 00 00 00 00 00 00 00 00 00 00 00 00 00 00 00
0000A820: 00 00 00 00 00 00 00 00 00 00 00 00 00 00 00 00
0000A830: 00 00 00 00 00 00 00 00 00 00 00 00 00 00 00 00
0000A840: 00 00 00 00 00 00 00 00 00 00 00 00 00 00 00 00
0000A850: 00 00 00 00 00 00 00 00 00 00 00 00 00 00 00 00
0000A860: 00 00 00 00 00 00 00 00 00 00 00 00 00 00 00 00
0000A870: 00 00 00 00 00 00 00 00 00 00 00 00 00 00 00 00
0000A880: 00 00 00 00 00 00 00 00 00 00 00 00 00 00 00 00
0000A890: 00 00 00 00 00 00 00 00 00 00 00 00 00 00 00 00
0000A8A0: 00 00 00 00 00 00 00 00 00 00 00 00 00 00 00 00
0000A8B0: 00 00 00 00 00 00 00 00 00 00 00 00 00 00 00 00
0000A8C0: 00 00 00 00 00 00 00 00 00 00 00 00 00 00 00 00
0000A8D0: 00 00 00 00 00 00 00 00 00 00 00 00 00 00 00 00
0000A8E0: 00 00 00 00 00 00 00 00 00 00 00 00 00 00 00 00
0000A8F0: 00 00 00 00 00 00 00 00 00 00 00 00 00 00 00 00
0000A900: 00 00 00 00 00 00 00 00 00 00 00 00 00 00 00 00
0000A910: 00 00 00 00 00 00 00 00 00 00 00 00 00 00 00 00
0000A920: 00 00 00 00 00 00 00 00 00 00 00 00 00 00 00 00
0000A930: 00 00 00 00 00 00 00 00 00 00 00 00 00 00 00 00
0000A940: 00 00 00 00 00 00 00 00 00 00 00 00 00 00 00 00
0000A950: 00 00 00 00 00 00 00 00 00 00 00 00 00 00 00 00
0000A960: 00 00 00 00 00 00 00 00 00 00 00 00 00 00 00 00
0000A970: 00 00 00 00 00 00 00 00 00 00 00 00 00 00 00 00
0000A980: 00 00 00 00 00 00 00 00 00 00 00 00 00 00 00 00
0000A990: 00 00 00 00 00 00 00 00 00 00 00 00 00 00 00 00
0000A9A0: 00 00 00 00 00 00 00 00 00 00 00 00 00 00 00 00
0000A9B0: 00 00 00 00 00 00 00 00 00 00 00 00 00 00 00 00
0000A9C0: 00 00 00 00 00 00 00 00 00 00 00 00 00 00 00 00
0000A9D0: 00 00 00 00 00 00 00 00 00 00 00 00 00 00 00 00
0000A9E0: 00 00 00 00 00 00 00 00 00 00 00 00 00 00 00 00
0000A9F0: 00 00 00 00 00 00 00 00 00 00 00 00 00 00 00 00
0000AA00: 00 00 00 00 00 00 00 00 00 00 00 00 00 00 00 00
0000AA10: 00 00 00 00 00 00 00 00 00 00 00 00 00 00 00 00
0000AA20: 00 00 00 00 00 00 00 00 00 00 00 00 00 00 00 00
0000AA30: 00 00 00 00 00 00 00 00 00 00 00 00 00 00 00 00
0000AA40: 00 00 00 00 00 00 00 00 00 00 00 00 00 00 00 00
0000AA50: 00 00 00 00 00 00 00 00 00 00 00 00 00 00 00 00
0000AA60: 00 00 00 00 00 00 00 00 00 00 00 00 00 00 00 00
0000AA70: 00 00 00 00 00 00 00 00 00 00 00 00 00 00 00 00
0000AA80: 00 00 00 00 00 00 00 00 00 00 00 00 00 00 00 00
0000AA90: 00 00 00 00 00 00 00 00 00 00 00 00 00 00 00 00
0000AAA0: 00 00 00 00 00 00 00 00 00 00 00 00 00 00 00 00
0000AAB0: 00 00 00 00 00 00 00 00 00 00 00 00 00 00 00 00
0000AAC0: 00 00 00 00 00 00 00 00 00 00 00 00 00 00 00 00
0000AAD0: 00 00 00 00 00 00 00 00 00 00 00 00 00 00 00 00
0000AAE0: 00 00 00 00 00 00 00 00 00 00 00 00 00 00 00 00
0000AAF0: 00 00 00 00 00 00 00 00 00 00 00 00 00 00 00 00
0000AB00: 00 00 00 00 00 00 00 00 00 00 00 00 00 00 00 00
0000AB10: 00 00 00 00 00 00 00 00 00 00 00 00 00 00 00 00
0000AB20: 00 00 00 00 00 00 00 00 00 00 00 00 00 00 00 00
0000AB30: 00 00 00 00 00 00 00 00 00 00 00 00 00 00 00 00
0000AB40: 00 00 00 00 00 00 00 00 00 00 00 00 00 00 00 00
0000AB50: 00 00 00 00 00 00 00 00 00 00 00 00 00 00 00 00
0000AB60: 00 00 00 00 00 00 00 00 00 00 00 00 00 00 00 00
0000AB70: 00 00 00 00 00 00 00 00 00 00 00 00 00 00 00 00
0000AB80: 00 00 00 00 00 00 00 00 00 00 00 00 00 00 00 00
0000AB90: 00 00 00 00 00 00 00 00 00 00 00 00 00 00 00 00
0000ABA0: 00 00 00 00 00 00 00 00 00 00 00 00 00 00 00 00
0000ABB0: 00 00 00 00 00 00 00 00 00 00 00 00 00 00 00 00
0000ABC0: 00 00 00 00 00 00 00 00 00 00 00 00 00 00 00 00
0000ABD0: 00 00 00 00 00 00 00 00 00 00 00 00 00 00 00 00
0000ABE0: 00 00 00 00 00 00 00 00 00 00 00 00 00 00 00 00
0000ABF0: 00 00 00 00 00 00 00 00 00 00 00 00 00 00 00 00
0000AC00: 00 00 00 00 00 00 00 00 00 00 00 00 00 00 00 00
0000AC10: 00 00 00 00 00 00 00 00 00 00 00 00 00 00 00 00
0000AC20: 00 00 00 00 00 00 00 00 00 00 00 00 00 00 00 00
0000AC30: 00 00 00 00 00 00 00 00 00 00 00 00 00 00 00 00
0000AC40: 00 00 00 00 00 00 00 00 00 00 00 00 00 00 00 00
0000AC50: 00 00 00 00 00 00 00 00 00 00 00 00 00 00 00 00
0000AC60: 00 00 00 00 00 00 00 00 00 00 00 00 00 00 00 00
0000AC70: 00 00 00 00 00 00 00 00 00 00 00 00 00 00 00 00
0000AC80: 00 00 00 00 00 00 00 00 00 00 00 00 00 00 00 00
0000AC90: 00 00 00 00 00 00 00 00 00 00 00 00 00 00 00 00
0000ACA0: 00 00 00 00 00 00 00 00 00 00 00 00 00 00 00 00
0000ACB0: 00 00 00 00 00 00 00 00 00 00 00 00 00 00 00 00
0000ACC0: 00 00 00 00 00 00 00 00 00 00 00 00 00 00 00 00
0000ACD0: 00 00 00 00 00 00 00 00 00 00 00 00 00 00 00 00
0000ACE0: 00 00 00 00 00 00 00 00 00 00 00 00 00 00 00 00
0000ACF0: 00 00 00 00 00 00 00 00 00 00 00 00 00 00 00 00
0000AD00: 00 00 00 00 00 00 00 00 00 00 00 00 00 00 00 00
0000AD10: 00 00 00 00 00 00 00 00 00 00 00 00 00 00 00 00
0000AD20: 00 00 00 00 00 00 00 00 00 00 00 00 00 00 00 00
0000AD30: 00 00 00 00 00 00 00 00 00 00 00 00 00 00 00 00
0000AD40: 00 00 00 00 00 00 00 00 00 00 00 00 00 00 00 00
0000AD50: 00 00 00 00 00 00 00 00 00 00 00 00 00 00 00 00
0000AD60: 00 00 00 00 00 00 00 00 00 00 00 00 00 00 00 00
0000AD70: 00 00 00 00 00 00 00 00 00 00 00 00 00 00 00 00
0000AD80: 00 00 00 00 00 00 00 00 00 00 00 00 00 00 00 00
0000AD90: 00 00 00 00 00 00 00 00 00 00 00 00 00 00 00 00
0000ADA0: 00 00 00 00 00 00 00 00 00 00 00 00 00 00 00 00
0000ADB0: 00 00 00 00 00 00 00 00 00 00 00 00 00 00 00 00
0000ADC0: 00 00 00 00 00 00 00 00 00 00 00 00 00 00 00 00
0000ADD0: 00 00 00 00 00 00 00 00 00 00 00 00 00 00 00 00
0000ADE0: 00 00 00 00 00 00 00 00 00 00 00 00 00 00 00 00
0000ADF0: 00 00 00 00 00 00 00 00 00 00 00 00 00 00 00 00
0000AE00: 00 00 00 00 00 00 00 00 00 00 00 00 00 00 00 00
0000AE10: 00 00 00 00 00 00 00 00 00 00 00 00 00 00 00 00
0000AE20: 00 00 00 00 00 00 00 00 00 00 00 00 00 00 00 00
0000AE30: 00 00 00 00 00 00 00 00 00 00 00 00 00 00 00 00
0000AE40: 00 00 00 00 00 00 00 00 00 00 00 00 00 00 00 00
0000AE50: 00 00 00 00 00 00 00 00 00 00 00 00 00 00 00 00
0000AE60: 00 00 00 00 00 00 00 00 00 00 00 00 00 00 00 00
0000AE70: 00 00 00 00 00 00 00 00 00 00 00 00 00 00 00 00
0000AE80: 00 00 00 00 00 00 00 00 00 00 00 00 00 00 00 00
0000AE90: 00 00 00 00 00 00 00 00 00 00 00 00 00 00 00 00
0000AEA0: 00 00 00 00 00 00 00 00 00 00 00 00 00 00 00 00
0000AEB0: 00 00 00 00 00 00 00 00 00 00 00 00 00 00 00 00
0000AEC0: 00 00 00 00 00 00 00 00 00 00 00 00 00 00 00 00
0000AED0: 00 00 00 00 00 00 00 00 00 00 00 00 00 00 00 00
0000AEE0: 00 00 00 00 00 00 00 00 00 00 00 00 00 00 00 00
0000AEF0: 00 00 00 00 00 00 00 00 00 00 00 00 00 00 00 00
0000AF00: 00 00 00 00 00 00 00 00 00 00 00 00 00 00 00 00
0000AF10: 00 00 00 00 00 00 00 00 00 00 00 00 00 00 00 00
```

APPENDIX-continued

```
0000AF20: 00 00 00 00 00 00 00 00 00 00 00 00 00 00 00 00
0000AF30: 00 00 00 00 00 00 00 00 00 00 00 00 00 00 00 00
0000AF40: 00 00 00 00 00 00 00 00 00 00 00 00 00 00 00 00
0000AF50: 00 00 00 00 00 00 00 00 00 00 00 00 00 00 00 00
0000AF60: 00 00 00 00 00 00 00 00 00 00 00 00 00 00 00 00
0000AF70: 00 00 00 00 00 00 00 00 00 00 00 00 00 00 00 00
0000AF80: 00 00 00 00 00 00 00 00 00 00 00 00 00 00 00 00
0000AF90: 00 00 00 00 00 00 00 00 00 00 00 00 00 00 00 00
0000AFA0: 00 00 00 00 00 00 00 00 00 00 00 00 00 00 00 00
0000AFB0: 00 00 00 00 00 00 00 00 00 00 00 00 00 00 00 00
0000AFC0: 00 00 00 00 00 00 00 00 00 00 00 00 00 00 00 00
0000AFD0: 00 00 00 00 00 00 00 00 00 00 00 00 00 00 00 00
0000AFE0: 00 00 00 00 00 00 00 00 00 00 00 00 00 00 00 00
0000AFF0: 00 00 00 00 00 00 00 00 00 00 00 00 00 00 00 00
0000B000: 00 00 00 00 23 85 40 00 B0 4D 40 00 50 60 40 00
0000B010: B0 6B 40 00 D0 6B 40 00 00 00 00 00 00 00 00 00
0000B020: 00 00 00 00 00 00 00 00 00 00 00 00 00 00 00 00
0000B030: 01 00 00 00 01 00 00 00 2E 2E 2E 6E 6F 77 20 65
0000B040: 78 69 74 69 6E 67 20 74 6F 20 73 79 73 74 65 6D
0000B050: 2E 2E 2E 0A 00 00 00 00 25 73 0A 00 00 4E 75 6D
0000B060: 72 69 63 61 6C 20 52 65 63 69 70 65 73 20 72 75
0000B070: 6E 2D 74 69 6D 65 20 65 72 72 6F 72 2E 2E 2E 0A
0000B080: 00 00 00 00 61 6C 6C 6F 63 61 74 69 6F 6E 20 66
0000B090: 61 69 6C 75 72 65 20 69 6E 20 69 76 65 63 74 6F
0000B0A0: 72 28 29 00 61 6C 6C 6F 63 61 74 69 6F 6E 20 66
0000B0B0: 61 69 6C 75 72 65 20 69 6E 20 64 76 65 63 74 6F
0000B0C0: 72 28 29 00 61 6C 6C 6F 63 61 74 69 6F 6E 20 66
0000B0D0: 61 69 6C 75 72 65 20 32 20 69 6E 20 6D 61 74 72
0000B0E0: 69 78 28 29 00 00 00 00 61 6C 6C 6F 63 61 74 69
0000B3F0: 20 3D 20 53 74 61 72 74 20 6C 6F 6F 6B 69 6E 67
0000B400: 20 61 67 61 69 6E 20 0A 43 61 6E 63 65 6C 20 3D
0000B410: 20 4D 61 6E 75 61 6C 20 66 69 6E 64 00 00 00 00
0000B420: 49 6E 74 65 72 69 6F 72 72 20 52 65 65 6F 6E 20
0000B430: 46 6F 75 6E 64 00 00 00 53 74 61 72 74 20 47 65
0000B440: 74 74 69 6E 67 20 4D 61 72 6B 65 72 73 20 41 67
0000B450: 61 69 6E 21 00 00 00 00 4E 6F 74 20 45 6E 6F 75
0000B460: 67 68 20 4D 61 72 6B 65 72 73 00 00 00 56 69 64 65
0000B470: 6F 20 53 74 61 74 69 73 74 69 63 73 00 00 00 00
0000B480: 50 72 6F 63 65 73 73 65 64 3A 20 46 72 61 6D 65
0000B490: 73 20 3D 20 25 6C 64 2C 20 52 61 74 65 20 3D 20
0000B4A0: 25 33 2E 31 66 20 0A 47 72 61 62 62 65 64 3A 20
0000B4B0: 20 20 46 72 61 6D 65 73 20 3D 20 25 6C 64 2C 20
0000B4C0: 52 61 74 65 20 3D 20 25 33 2E 31 66 00 00 00 00
0000B4D0: 02 00 00 00 05 00 00 00 00 00 98 41 00 00 40 40
0000B4E0: 44 65 73 69 67 6E 61 74 65 20 74 68 69 73 20 64
0000B4F0: 75 63 6B 65 72 00 00 00 00 44 69 64 6E 27 74 20 66
0000B500: 69 6E 64 20 61 20 54 72 61 69 6E 65 64 75 63 65 72
0000B510: 21 00 00 00 41 6C 6C 6F 63 61 74 69 6F 6E 20 66
0000B520: 61 69 6C 75 72 65 20 32 20 69 6E 20 41 6C 6C 6F
0000B530: 63 61 74 65 55 53 68 6F 72 74 41 72 72 61 79 28
0000B540: 20 29 00 00 00 4D 65 6D 6F 72 79 20 65 72 72 6F
0000B550: 72 00 00 00 41 6C 6C 6F 63 61 74 69 6F 6E 20 66
0000B560: 61 69 6C 75 72 65 20 31 20 69 6E 20 41 6C 6C 6F
0000B570: 63 61 74 65 55 53 68 6F 72 74 41 72 72 61 79 28
0000B580: 20 29 00 00 41 6C 6C 6F 63 61 74 69 6F 6E 20 66
0000B590: 61 69 6C 75 72 65 20 32 20 69 6E 20 41 6C 6C 6F
0000B5A0: 63 61 74 65 55 43 68 61 72 41 72 72 61 79 28 20
0000B5B0: 29 00 00 00 41 6C 6C 6F 63 61 74 69 6F 6E 20 66
0000B5C0: 61 69 6C 75 72 65 20 31 20 69 6E 20 41 6C 6C 6F
0000B5D0: 63 61 74 65 55 43 68 61 72 41 72 72 61 79 28 20
0000B5E0: 29 00 00 00 41 6C 6C 6F 63 61 74 69 6F 6E 20 66
0000B5F0: 61 69 6C 75 72 65 20 69 6E 20 41 6C 6C 6F 63 61
0000B600: 74 65 4C 6F 6E 67 56 65 63 74 6F 72 28 20 29 00
0000B610: 41 6C 6C 6F 63 61 74 69 6F 6E 20 66 61 69 6C 75
0000B620: 72 65 20 69 6E 20 41 6C 6C 6F 63 61 74 65 55 43
0000B630: 68 61 72 56 65 63 74 6F 72 28 20 29 00 00 00 00
0000B640: 41 6C 6C 6F 63 61 74 69 6F 6E 20 66 61 69 6C 75
0000B650: 72 65 20 69 6E 20 41 6C 6C 6F 63 61 74 65 46 6C
0000B660: 6F 61 74 56 65 63 74 6F 72 28 20 29 00 00 00 00
0000B670: 43 61 6E 27 74 20 6F 70 65 6E 20 42 42 4D 50 20 66
0000B680: 69 6C 65 00 77 62 00 00 03 00 00 00 03 00 00 00
0000B690: 41 75 74 6F 6D 61 74 69 63 00 00 00 4D 75 74 65
0000B6A0: 78 00 00 00 45 76 65 6E 74 00 00 00 4D 61 6E 75
0000B6B0: 61 6C 00 00 54 72 61 69 6E 65 64 20 41 70 70 6C 69 63
0000B6C0: 61 74 69 6F 6E 00 00 00 43 6F 75 6C 64 20 6E 6F
0000B6D0: 74 20 61 6C 6C 6F 63 61 74 65 20 4D 49 4C 20 49
0000B6E0: 6D 61 67 65 20 62 75 66 66 65 72 2E 00 00 00 00
0000B0F0: 6F 6E 20 66 61 69 6C 75 72 65 20 31 20 69 6E 20
0000B100: 6D 61 74 72 69 78 28 29 00 00 00 00 67 61 75 73
0000B110: 73 6A 3A 20 53 69 6E 67 75 6C 61 72 20 4D 61 74
0000B120: 72 69 78 2D 32 00 00 00 67 61 75 73 73 6A 3A 20
0000B130: 53 69 6E 67 75 6C 61 72 20 4D 61 74 72 69 78 2D
0000B140: 31 00 00 00 4E 75 6D 6D 20 3D 20 25 64 2C 20 58 20
0000B150: 3D 20 25 64 2C 20 59 20 3D 20 25 64 2C 20 54 69
0000B160: 6D 65 20 3D 20 25 73 0A 00 00 00 00 61 74 00 00
0000B170: 25 48 3A 25 4D 3A 25 53 00 00 00 00 43 61 6E 27
0000B180: 74 20 6F 70 65 6E 20 4C 6F 67 67 20 66 69 6C 65 00
0000B190: 46 69 6C 65 20 45 72 72 6F 72 00 00 77 74 00 00
0000B1A0: 63 3A 5C 49 6C 69 61 5C 55 6C 74 72 61 73 68 61
0000B1B0: 70 65 5C 54 72 61 63 6B 5C 4C 6F 67 5C 4C 6F 67
0000B1C0: 25 73 2E 64 61 74 00 00 5F 25 64 5F 25 62 5F 25
0000B1D0: 59 5F 25 48 5F 25 4D 00 68 01 00 00 01 00 00 00
0000B1E0: 63 3A 5C 49 6C 69 61 5C 55 6C 74 72 61 73 68 61
0000B1F0: 70 65 5C 54 72 61 63 6B 5C 49 6D 61 67 65 73 5C
0000B200: 49 6D 61 67 65 5F 45 5F 66 62 72 73 2E 62 6D 70 00
0000B210: 63 3A 5C 49 6C 69 61 5C 55 6C 74 72 61 73 68 61
0000B220: 70 65 5C 54 72 61 63 6B 5C 49 6D 61 67 65 73 5C
0000B230: 49 6D 61 67 65 5F 45 72 6F 64 65 2E 62 6D 70 00
0000B240: 63 3A 5C 49 6C 69 61 5C 55 6C 74 72 61 73 68 61
0000B250: 70 65 5C 54 72 61 63 6B 5C 49 6D 61 67 65 73 5C
0000B260: 49 6D 61 67 65 5F 49 64 78 2E 62 6D 70 00 00 00
0000B270: 63 3A 5C 49 6C 69 61 5C 55 6C 74 72 61 73 68 61
0000B280: 70 65 5C 54 72 61 63 6B 5C 49 6D 61 67 65 73 5C
0000B290: 49 6D 61 67 65 5F 4D 65 64 37 2E 62 6D 70 00 00
0000B2A0: 63 3A 5C 49 6C 69 61 5C 55 6C 74 72 61 73 68 61
0000B2B0: 70 65 5C 54 72 61 63 6B 5C 49 6D 61 67 65 73 5C
0000B2C0: 49 6D 61 67 65 5F 4D 65 64 36 31 2E 62 6D 70 00
0000B2D0: 63 3A 5C 49 6C 69 61 5C 55 6C 74 72 61 73 68 61
0000B2E0: 70 65 5C 54 72 61 63 6B 5C 49 6D 61 67 65 73 5C
0000B2F0: 49 6D 61 67 65 5F 59 2E 62 6D 70 00 02 00 00 00
0000B300: 44 65 73 69 67 6E 61 74 65 20 4D 61 72 6B 65 72
0000B310: 73 00 00 00 44 69 64 6E 27 74 20 66 6F 66 6E 64 20
0000B320: 61 20 4D 61 72 6B 65 72 21 00 00 00 52 61 74 65
0000B330: 20 3D 20 25 2E 31 66 2C 20 4E 75 6D 4F 66 4E 6F
0000B340: 64 65 73 20 3D 20 25 64 00 00 00 00 00 00 00 00
0000B350: 01 00 00 00 00 00 00 00 00 00 00 00 00 00 3E 40
0000B360: 01 00 00 00 43 61 6E 27 74 20 6F 70 65 6E 20 54
0000B370: 69 6D 69 6E 67 20 66 69 6C 65 00 00 63 3A 5C 49
0000B380: 6C 69 61 5C 55 6C 74 72 61 73 68 61 70 65 5C 54
0000B390: 72 61 63 6B 5C 54 69 6D 69 6E 67 5C 54 69 6D 69
0000B3A0: 6E 67 25 73 2E 64 61 74 00 00 00 00 63 3A 5C 49
0000B3B0: 6C 69 61 5C 55 6C 74 72 61 73 68 61 70 65 5C 54
0000B3C0: 72 61 63 6B 5C 4C 6F 67 5C 4C 6F 67 25 73 2E 62
0000B3D0: 6D 70 00 00 00 59 65 73 20 3D 20 54 68 68 65 20 72 65 65
0000B3E0: 73 75 6C 74 20 69 73 20 67 6F 6F 64 20 0A 4E 6F
0000B6F0: 43 6F 75 6C 64 20 6E 6F 74 20 61 6C 6C 6F 63 61
0000B700: 74 65 20 4D 49 4C 20 44 69 73 70 6C 61 79 2E 00
0000B710: 43 6F 75 6C 64 20 6E 6F 74 20 61 6C 6C 6F 63 61
0000B720: 74 65 20 4D 49 4C 20 44 69 67 69 74 69 7A 65 72
0000B730: 2E 00 00 00 43 6F 75 6C 64 20 6E 6F 74 20 61 6C
0000B740: 6C 6F 63 61 74 65 20 4D 49 4C 20 53 79 73 74 65
0000B750: 6D 2E 00 00 43 6F 75 6C 64 20 6E 6F 74 20 61 6C
0000B760: 6C 6F 63 61 74 65 20 4D 49 4C 20 41 70 70 6C 69 63
0000B770: 63 61 74 69 6F 6E 2E 00 42 75 66 66 65 72 00 00
0000B780: 4D 5F 44 45 46 41 55 4C 54 00 00 00 44 69 73 70
0000B790: 6C 61 79 00 50 61 6C 79 63 2E 64 63 66 00 00 00
0000B7A0: 44 69 67 67 74 69 67 7A 65 72 00 00 00 53 79 73 74 74
0000B7B0: 65 6D 00 00 41 70 70 6C 69 63 61 74 69 6F 6E 00
0000B7C0: 54 68 65 72 65 20 69 73 20 6E 6F 20 64 69 67 69
0000B7D0: 74 69 7A 65 72 20 69 6E 20 74 68 65 20 73 70 65
0000B7E0: 63 69 66 65 64 20 4D 49 4C 20 73 79 73 74 65
0000B7F0: 6D 2E 00 00 49 6E 50 72 6F 63 32 5F 5F 5F 3A 20
0000B800: 20 6A 3D 20 25 64 2C 20 53 61 66 65 3D 20 25 64
0000B810: 2C 20 47 72 61 62 3D 20 25 64 2C 20 46 72 61 6D
0000B820: 65 31 3D 20 25 64 2C 20 46 72 61 6D 65 32 3D 20
0000B830: 25 64 2C 20 53 65 63 73 3D 20 25 75 20 0A 0A 00
0000B840: 49 6E 50 72 6F 63 31 5F 5F 5F 3A 20 20 6A 3D 20
0000B850: 25 64 2C 20 53 61 66 65 3D 20 25 64 2C 20 47 72
0000B860: 61 62 3D 20 25 64 2C 20 46 72 61 6D 65 31 3D 20
0000B870: 25 64 2C 20 46 72 61 6D 65 32 3D 20 25 64 2C 20
0000B880: 53 65 63 73 3D 20 25 75 20 0A 0A 00 57 61 69 74
0000B890: 46 6F 72 53 69 6E 67 6C 65 4F 62 6A 65 63 74 28
0000B8A0: 29 20 66 6F 72 20 74 68 69 73 20 66 72 61 6D 65
0000B8B0: 65 64 20 21 00 00 00 00 57 61 69 74 46 6F 72 53
0000B8C0: 69 6E 67 6C 65 4F 62 6A 65 63 74 28 29 20 61 62
0000B8D0: 61 6E 64 6F 6E 65 64 20 65 72 72 6F 72 3A 20 54
0000B8E0: 68 65 20 73 70 65 63 69 66 69 65 64 20 6F 62 6A
0000B8F0: 65 63 74 20 69 73 20 61 6D 75 74 65 78 20 6F
```

APPENDIX-continued

```
0000B900: 62 6A 65 63 74 20 74 68 61 74 20 77 61 73 20 6E
0000B910: 6F 74 20 72 65 6C 65 61 73 65 64 20 62 79 20 74
0000B920: 68 65 20 74 68 72 65 61 64 20 74 68 61 74 20 6F
0000B930: 77 6E 65 64 20 74 68 65 20 6D 75 74 65 78 20 6F
0000B940: 62 6A 65 63 74 20 62 65 66 6F 72 65 20 74 68 65
0000B950: 20 6F 77 6E 69 6E 67 20 74 68 72 65 61 64 20 74
0000B960: 65 72 6D 69 6E 61 74 65 64 2E 20 4F 77 6E 65 72
0000B970: 73 68 69 70 20 6F 66 20 74 68 65 20 6D 75 74 65
0000B980: 78 20 6F 62 6A 65 63 74 20 69 73 20 67 72 61 6E
0000B990: 74 65 64 20 74 6F 20 74 68 65 20 63 61 6C 6C 69
0000B9A0: 6E 67 20 74 68 72 65 61 64 2C 20 61 6E 64 20 74
0000B9B0: 68 65 20 6D 75 74 65 78 20 69 73 20 73 20 73 65 74 20
0000B9C0: 74 6F 20 6E 6F 6E 73 69 67 6E 61 6C 65 64 2E 00
0000B9D0: 43 6F 75 6C 64 20 6E 6F 74 20 72 65 6C 65 61 73
0000B9E0: 65 20 65 78 69 73 74 65 64 20 6D 75 74 65 78 2E
0000B9F0: 00 00 00 00 41 66 74 65 72 47 72 61 62 5F 3A 20
0000BA00: 20 6A 3D 20 25 64 2C 20 53 61 66 65 3D 20 25 64
0000BA10: 2C 20 47 72 61 62 3D 20 25 64 2C 20 46 72 61 6D
0000BA20: 65 31 3D 20 25 64 2C 20 46 72 61 6D 65 32 3D 20
0000BA30: 25 64 2C 20 53 65 63 73 3D 20 25 75 20 0A 00 00
0000BA40: 42 65 66 6F 72 65 47 72 61 62 3A 20 20 6A 3D 20
0000BA50: 25 64 2C 20 53 61 66 65 3D 20 25 64 2C 20 47 72
0000BA60: 61 62 3D 20 25 64 2C 20 46 72 61 6D 65 31 3D 20
0000BA70: 25 64 2C 20 46 72 61 6D 65 32 3D 20 25 64 2C 20
0000BA80: 53 65 63 73 3D 20 25 75 20 0A 00 00 55 6E 68 6F
0000BA90: 6F 6B 5F 5F 5F 5F 3A 20 20 6A 3D 20 25 64 2C 20
0000BAA0: 53 61 66 65 3D 20 25 64 2C 20 47 72 61 62 3D 20
0000BAB0: 25 64 2C 20 46 72 61 6D 65 31 3D 20 25 64 2C 20
0000BAC0: 46 72 61 6D 65 32 3D 20 25 64 2C 20 53 65 63 73
0000BAD0: 3D 20 25 75 20 0A 00 00 00 49 6E 48 6F 6F 6B 5F 5F
0000BAE0: 5F 5F 3A 20 20 6A 3D 20 25 64 2C 20 53 61 66 65
0000BAF0: 3D 20 25 64 2C 20 47 72 61 62 3D 20 25 64 2C 20
0000BB00: 46 72 61 6D 65 31 3D 20 25 64 2C 20 46 72 61 6D
0000BB10: 65 32 3D 20 25 64 2C 20 53 65 63 73 3D 20 25 75
0000BB20: 20 0A 00 00 4D 75 74 65 78 20 63 72 65 61 74 69
0000BB30: 6F 6E 20 66 61 69 6C 65 64 20 21 00 45 76 65 6E
0000BB40: 74 20 63 72 65 61 74 69 6F 6E 20 66 61 69 6C 65
0000BB50: 64 20 21 00 43 6F 75 6C 64 20 6E 6F 74 20 63 6C
0000BB60: 6F 73 65 20 68 61 6E 64 6C 65 20 74 6F 20 65 78
0000BB70: 69 73 74 65 64 20 6D 75 74 65 78 2E 00 00 00 00
0000BB80: 43 6F 75 6C 64 20 6E 6F 74 20 63 6C 6F 73 65 20
0000BB90: 68 61 6E 64 6C 65 20 74 6F 20 65 78 69 73 74 65
0000BBA0: 64 20 65 76 65 6E 74 2E 00 00 00 00 53 74 72 69
0000BBB0: 6E 67 00 00 4E 75 6D 62 65 72 00 00 00 00 00 00
0000BBC0: 01 00 00 00 00 00 00 00 00 00 00 00 00 00 00 00
0000BBD0: 00 00 00 00 00 00 00 00 00 00 00 00 00 00 00 00
0000BBE0: 00 00 00 00 00 00 00 00 00 00 00 00 00 00 00 00
0000BBF0: 00 00 00 00 00 00 00 00 00 00 00 00 00 00 00 00
0000BC00: 00 00 00 00 00 00 00 00 00 00 00 00 00 00 00 00
0000BC10: 00 00 00 00 00 00 00 00 00 00 00 00 00 00 00 00
0000BC20: 00 00 00 00 00 00 00 00 00 00 00 00 00 00 00 00
0000BC30: 00 00 00 00 00 00 00 00 00 00 00 00 00 00 00 00
0000BC40: 00 00 00 00 00 00 00 00 00 00 00 00 00 00 00 00
0000BC50: 00 00 00 00 00 00 00 00 00 00 00 00 00 00 00 00
0000BC60: 00 00 00 00 00 00 00 00 00 00 00 00 00 00 00 00
0000BC70: 00 00 00 00 00 00 00 00 00 00 00 00 00 00 00 00
0000BC80: 00 00 00 00 00 00 00 00 00 00 00 00 00 00 00 00
0000BC90: 00 00 00 00 00 00 00 00 00 00 00 00 00 00 00 00
0000BCA0: 00 00 00 00 00 00 00 00 00 00 00 00 00 00 00 00
0000BCB0: 00 00 00 00 00 00 00 00 00 00 00 00 00 00 00 00
0000BCC0: 00 00 00 00 00 00 00 00 00 00 00 00 00 00 00 00
0000BCD0: 00 00 00 00 00 00 00 00 00 00 00 00 00 00 00 00
0000BCE0: 00 00 00 00 00 00 00 00 00 00 00 00 00 00 00 00
0000BCF0: 00 00 00 00 00 00 00 00 00 00 00 00 00 00 00 00
0000BD00: 00 00 00 00 00 00 00 00 00 00 00 00 00 00 00 00
0000BD10: 00 00 00 00 00 00 00 00 00 00 00 00 00 00 00 00
0000BD20: 00 00 00 00 00 00 00 00 00 00 00 00 00 00 00 00
0000BD30: 00 00 00 00 00 00 00 00 00 00 00 00 00 00 00 00
0000BD40: 00 00 00 00 00 00 00 00 00 00 00 00 00 00 00 00
0000BD50: 00 00 00 00 00 00 00 00 00 00 00 00 00 00 00 00
0000BD60: 00 00 00 00 00 00 00 00 00 00 00 00 00 00 00 00
0000BD70: 00 00 00 00 00 00 00 00 00 00 00 00 00 00 00 00
0000BD80: 00 00 00 00 00 00 00 00 00 00 00 00 00 00 00 00
0000BD90: 00 00 00 00 00 00 00 00 00 00 00 00 00 00 00 00
0000BDA0: 00 00 00 00 00 00 00 00 00 00 00 00 00 00 00 00
0000BDB0: 00 00 00 00 00 00 00 00 00 00 00 00 00 00 00 00
0000BDC0: 00 00 00 00 00 00 00 00 00 00 00 00 00 00 00 00
0000BDD0: 00 00 00 00 00 00 00 00 00 00 00 00 00 00 00 00
0000BDE0: 00 00 00 00 00 00 00 00 00 00 00 00 00 00 00 00
0000BDF0: 00 00 00 00 00 00 00 00 00 00 00 00 00 00 00 00
0000BE00: 00 00 00 00 00 00 00 00 00 00 00 00 00 00 00 00
0000BE10: 00 00 00 00 00 00 00 00 00 00 00 00 00 00 00 00
0000BE20: 00 00 00 00 00 00 00 00 00 00 00 00 00 00 00 00
0000BE30: 00 00 00 00 00 00 00 00 00 00 00 00 00 00 00 00
0000BE40: 00 00 00 00 00 00 00 00 00 00 00 00 00 00 00 00
0000BE50: 00 00 00 00 00 00 00 00 00 00 00 00 00 00 00 00
0000BE60: 00 00 00 00 00 00 00 00 00 00 00 00 00 00 00 00
0000BE70: 00 00 00 00 00 00 00 00 00 00 00 00 00 00 00 00
0000BE80: 00 00 00 00 00 00 00 00 00 00 00 00 00 00 00 00
0000BE90: 00 00 00 00 00 00 00 00 00 00 00 00 00 00 00 00
0000BEA0: 00 00 00 00 00 00 00 00 00 00 00 00 00 00 00 00
0000BEB0: 00 00 00 00 00 00 00 00 00 00 00 00 00 00 00 00
0000BEC0: 00 00 00 00 00 00 00 00 00 00 00 00 00 00 00 00
0000BED0: 00 00 00 00 00 00 00 00 00 00 00 00 00 00 00 00
0000BEE0: 00 00 00 00 00 00 00 00 00 00 00 00 00 00 00 00
0000BEF0: 00 00 00 00 00 00 00 00 00 00 00 00 00 00 00 00
0000BF00: 00 00 00 00 00 00 00 00 00 00 00 00 00 00 00 00
0000BF10: 00 00 00 00 00 00 00 00 00 00 00 00 00 00 00 00
0000BF20: 00 00 00 00 00 00 00 00 00 00 00 00 00 00 00 00
0000BF30: 00 00 00 00 00 00 00 00 00 00 00 00 00 00 00 00
0000BF40: 00 00 00 00 00 00 00 00 00 00 00 00 00 00 00 00
0000BF50: 00 00 00 00 00 00 00 00 00 00 00 00 00 00 00 00
0000BF60: 00 00 00 00 00 00 00 00 00 00 00 00 00 00 00 00
0000BF70: 00 00 00 00 00 00 00 00 00 00 00 00 00 00 00 00
0000BF80: 00 00 00 00 00 00 00 00 00 00 00 00 00 00 00 00
0000BF90: 00 00 00 00 00 00 00 00 00 00 00 00 00 00 00 00
0000BFA0: 00 00 00 00 00 00 00 00 00 00 00 00 00 00 00 00
0000BFB0: 00 00 00 00 00 00 00 00 00 00 00 00 00 00 00 00
0000BFC0: 00 00 00 00 00 00 00 00 00 00 00 00 00 00 00 00
0000BFD0: 00 00 00 00 00 00 00 00 00 00 00 00 00 00 00 00
0000BFE0: 00 00 00 00 00 00 00 00 00 00 00 00 00 00 00 00
0000BFF0: 00 00 00 00 00 00 00 00 00 00 00 00 00 00 00 00
0000C000: 00 00 00 00 00 00 00 00 00 00 00 00 00 00 04 00
0000C010: 05 00 00 00 30 00 00 80 06 00 00 00 60 00 00 80
0000C020: 10 00 00 00 78 00 00 80 F0 00 00 00 90 00 00 80
0000C030: 00 00 00 00 00 00 00 00 00 00 00 00 00 00 04 00
0000C040: 64 00 00 00 A8 00 00 80 66 00 00 00 C0 00 00 80
0000C050: 81 00 00 00 D8 00 00 80 83 00 00 00 F0 00 00 80
0000C060: 00 00 00 00 00 00 00 00 00 00 00 00 00 00 01 00
0000C070: 07 00 00 00 08 01 00 80 00 00 00 00 00 00 00 00
0000C080: 00 00 00 00 00 00 01 00 01 00 00 00 20 01 00 80
0000C090: 00 00 00 00 00 00 00 00 00 00 00 00 00 00 01 00
0000C0A0: 81 00 00 00 38 01 00 80 00 00 00 00 00 00 00 00
0000C0B0: 00 00 00 00 00 00 01 00 09 04 00 00 50 01 00 00
0000C0C0: 00 00 00 00 00 00 00 00 00 00 00 00 00 00 01 00
0000C0D0: 09 04 00 00 60 01 00 00 00 00 00 00 00 00 00 00
0000C0E0: 00 00 00 00 00 00 01 00 0D 04 00 00 70 01 00 00
0000C0F0: 00 00 00 00 00 00 00 00 00 00 00 00 00 00 01 00
0000C100: 0D 04 00 00 80 01 00 00 00 00 00 00 00 00 00 00
0000C110: 00 00 00 00 00 00 01 00 09 04 00 00 90 01 00 00
0000C120: 00 00 00 00 00 00 00 00 00 00 00 00 00 00 01 00
0000C130: 09 04 00 00 A0 01 00 00 00 00 00 00 00 00 00 00
0000C140: 00 00 00 00 00 00 01 00 0D 04 00 00 B0 01 00 00
0000C150: C0 01 99 00 02 01 00 00 00 00 00 00 00 00 00 00
0000C160: C8 02 99 00 1A 03 00 00 00 00 00 00 00 00 00 00
0000C170: D0 08 99 00 D4 00 00 00 00 00 00 00 00 00 00 00
0000C180: A8 09 99 00 64 03 00 00 00 00 00 00 00 00 00 00
0000C190: 30 0D 99 00 3E 00 00 00 00 00 00 00 00 00 00 00
0000C1A0: E8 05 99 00 E4 02 00 00 00 00 00 00 00 00 00 00
0000C1B0: 10 0D 99 00 1E 00 00 00 00 00 00 00 00 00 00 00
0000C1C0: C0 00 C8 80 00 00 00 00 00 00 00 00 00 00 EB 00
0000C1D0: 37 00 00 00 00 00 41 00 62 00 6F 00 75 00 74 00
0000C1E0: 20 00 54 00 72 00 61 00 63 00 6B 00 00 00 08 00
0000C1F0: 4D 00 53 00 20 00 53 00 61 00 6E 00 73 00 20 00
0000C200: 53 00 65 00 72 00 69 00 66 00 00 00 03 00 00 50
0000C210: 00 00 00 00 0B 00 11 00 14 00 14 00 FF FF FF FF
0000C220: 82 00 FF FF 80 00 00 00 80 00 02 50 00 00 00 00
0000C230: 28 00 0A 00 77 00 08 00 FF FF FF FF 82 00 54 00
0000C240: 72 00 61 00 63 00 6B 00 20 00 56 00 65 00 72 00
0000C250: 73 00 69 00 6F 00 6E 00 20 00 31 00 2E 00 30 00
0000C260: 00 00 00 00 00 00 02 50 00 00 00 00 28 00 19 00
0000C270: 77 00 08 00 FF FF FF FF 82 00 43 00 6F 00 70 00
0000C280: 79 00 72 00 69 00 67 00 68 00 74 00 20 00 28 00
0000C290: 43 00 29 00 20 00 32 00 30 00 30 00 30 00 31 00
0000C2A0: 00 00 00 00 01 00 03 50 00 00 00 00 B2 00 07 00
0000C2B0: 32 00 0E 00 01 00 FF FF 80 00 4F 00 4B 00 00 00
0000C2C0: 00 00 00 00 00 00 00 00 01 00 FF FF 00 00 00 00
0000C2D0: 00 00 04 00 C0 00 F8 90 0D 00 00 00 00 00 FD 01
```

APPENDIX-continued

```
0000C2E0: 66 01 00 00 00 00 54 00 72 00 61 00 63 00 6B 00
0000C2F0: 00 00 08 00 00 00 00 01 4D 00 53 00 20 00 53 00
0000C300: 61 00 6E 00 73 00 20 00 53 00 65 00 72 00 69 00
0000C310: 66 00 00 00 00 00 00 00 00 00 00 00 01 00 01 50
0000C320: AD 01 06 00 32 00 0E 00 01 00 00 00 FF FF 80 00
0000C330: 45 00 26 00 78 00 69 00 74 00 00 00 00 00 00 00
0000C340: 00 00 00 00 00 00 00 00 00 00 01 58 AD 01 27 00
0000C350: 32 00 0E 00 E8 03 00 00 FF FF 80 00 26 00 53 00
0000C360: 74 00 61 00 72 00 74 00 20 00 56 00 69 00 64 00
0000C370: 65 00 6F 00 00 00 00 00 00 00 00 00 00 00 00 00
0000C380: 00 00 01 58 AD 01 3A 00 32 00 0E 00 E9 03 00 00
0000C390: FF FF 80 00 53 00 26 00 74 00 6F 00 70 00 20 00
0000C3A0: 56 00 69 00 64 00 65 00 6F 00 00 00 00 00 00 00
0000C3B0: 00 00 00 00 00 00 00 00 00 01 58 AD 01 5D 00
0000C3C0: 32 00 0E 00 EA 03 00 00 FF FF 80 00 47 00 65 00
0000C3D0: 74 00 20 00 26 00 52 00 65 00 67 00 69 00 6F 00
0000C3E0: 6E 00 00 00 00 00 00 00 00 00 00 00 00 00 00 00
0000C3F0: 00 00 01 58 AD 01 87 00 32 00 0E 00 EB 03 00 00
0000C400: FF FF 80 00 47 00 65 00 74 00 20 00 26 00 4D 00
0000C410: 61 00 72 00 6B 00 65 00 72 00 73 00 00 00 00 00
0000C420: 00 00 00 00 00 00 00 00 00 00 01 58 AD 01 9D 00
0000C430: 32 00 0E 00 EC 03 00 00 FF FF 80 00 26 00 4E 00
0000C440: 65 00 78 00 74 00 20 00 4E 00 6F 00 64 00 65 00
0000C450: 00 00 00 00 00 00 00 00 00 00 00 00 00 00 01 58
0000C460: AD 01 D5 00 32 00 0E 00 ED 03 00 00 FF FF 80 00
0000C470: 26 00 56 00 69 00 64 00 65 00 6F 00 20 00 53 00
0000C480: 74 00 61 00 74 00 69 00 73 00 74 00 69 00 63 00
0000C490: 73 00 00 00 00 00 00 00 00 00 00 00 00 00 00 00
0000C4A0: 00 00 01 50 AD 01 EA 00 32 00 0E 00 F2 03 00 00
0000C4B0: FF FF 80 00 26 00 43 00 61 00 6D 00 65 00 72 00
0000C4C0: 61 00 20 00 43 00 6F 00 6E 00 74 00 72 00 6F 00
0000C4D0: 6C 00 00 00 00 00 00 00 00 00 00 00 00 00 00 00
0000C4E0: 00 00 01 5A AD 01 FF 00 32 00 0E 00 FA 03 00 00
0000C4F0: FF FF 80 00 26 00 50 00 61 00 72 00 61 00 6D 00
0000C500: 65 00 74 00 65 00 72 00 73 00 00 00 00 00 00 00
0000C510: 00 00 00 00 00 00 00 00 00 00 01 50 AD 01 22 01
0000C520: 32 00 0E 00 FC 03 00 00 FF FF 80 00 26 00 42 00
0000C530: 72 00 65 00 61 00 6B 00 00 00 00 00 00 00 00 00
0000C540: 00 00 00 00 00 01 58 AD 01 B3 00 32 00 0E 00
0000C550: FD 03 00 00 FF FF 80 00 26 00 52 00 65 00 73 00
0000C560: 79 00 6E 00 63 00 68 00 72 00 6F 00 6E 00 69 00
0000C570: 7A 00 65 00 00 00 00 00 00 00 00 00 00 00 00 00
0000C580: 00 00 01 58 AD 01 71 00 32 00 0E 00 EE 03 00 00
0000C590: FF FF 80 00 47 00 65 00 74 00 20 00 26 00 54 00
0000C5A0: 72 00 61 00 6E 00 73 00 64 00 75 00 63 00 65 00
0000C5B0: 72 00 00 00 00 00 00 00 00 00 00 00 00 00 00 00
0000C5C0: 03 00 01 50 B8 01 46 01 22 00 0A 00 00 04 00 00
0000C5D0: FF FF 80 00 26 00 5A 00 6F 00 6F 00 6D 00 00 00
0000C5E0: 00 00 00 00 00 00 00 00 E4 02 34 00 00 00 56 00
0000C5F0: 53 00 5F 00 56 00 45 00 52 00 53 00 49 00 4F 00
0000C600: 4E 00 5F 00 49 00 4E 00 46 00 4F 00 00 00 00 00
0000C610: BD 04 EF FE 00 00 01 00 00 00 01 00 01 00 00 00
0000C620: 00 00 01 00 01 00 00 00 00 3F 00 00 00 00 00 00
0000C630: 04 00 00 00 01 00 00 00 00 00 00 00 00 00 00 00
0000C640: 00 00 00 00 42 02 00 00 01 00 53 00 74 00 72 00
0000C650: 69 00 6E 00 67 00 46 00 69 00 6C 00 65 00 49 00
0000C660: 6E 00 66 00 6F 00 00 00 1E 02 00 00 01 00 30 00
0000C670: 34 00 30 00 39 00 30 00 34 00 42 00 30 00 00 00
0000C680: 20 00 00 00 01 00 43 00 6F 00 6D 00 70 00 61 00
0000C690: 6E 00 79 00 4E 00 61 00 6D 00 65 00 00 00 00 00
0000C6A0: 54 00 16 00 01 00 46 00 69 00 6C 00 65 00 44 00
0000C6B0: 65 00 73 00 63 00 72 00 69 00 70 00 74 00 69 00
0000C6C0: 6F 00 6E 00 00 00 00 00 54 00 72 00 61 00 63 00
0000C6D0: 6B 00 20 00 4D 00 46 00 43 00 20 00 41 00 70 00
0000C6E0: 70 00 6C 00 69 00 63 00 61 00 74 00 69 00 6F 00
0000C6F0: 6E 00 00 00 36 00 0B 00 01 00 46 00 69 00 6C 00
0000C700: 65 00 56 00 65 00 72 00 73 00 69 00 6F 00 6E 00
0000C710: 00 00 00 00 31 00 2C 00 20 00 30 00 2C 00 20 00
0000C720: 30 00 2C 00 20 00 31 00 00 00 00 00 2C 00 06 00
0000C730: 01 00 49 00 6E 00 74 00 65 00 72 00 6E 00 61 00
0000C740: 6C 00 4E 00 61 00 6D 00 65 00 00 00 54 00 72 00
0000C750: 61 00 63 00 6B 00 00 00 4A 00 13 00 01 00 4C 00
0000C760: 65 00 67 00 61 00 6C 00 43 00 6F 00 70 00 79 00
0000C770: 72 00 69 00 67 00 68 00 74 00 00 00 43 00 6F 00
0000C780: 70 00 79 00 72 00 69 00 67 00 68 00 74 00 20 00
0000C790: 28 00 43 00 29 00 20 00 32 00 30 00 30 00 31 00
0000C7A0: 00 00 00 00 28 00 00 00 01 00 4C 00 65 00 67 00
0000C7B0: 61 00 6C 00 54 00 72 00 61 00 64 00 65 00 6D 00
0000C7C0: 61 00 72 00 6B 00 73 00 00 00 00 00 3C 00 0A 00
0000C7D0: 01 00 4F 00 72 00 69 00 67 00 69 00 6E 00 61 00
0000C7E0: 6C 00 46 00 69 00 6C 00 65 00 4E 00 61 00 6D 00
0000C7F0: 65 00 00 00 54 00 72 00 61 00 63 00 6B 00 2E 00
0000C800: 45 00 58 00 45 00 00 00 00 00 44 00 12 00 01 00 50 00
0000C810: 72 00 6F 00 64 00 75 00 63 00 74 00 4E 00 61 00
0000C820: 6D 00 65 00 00 00 00 00 00 00 54 00 72 00 61 00 63 00
0000C830: 6B 00 20 00 41 00 70 00 70 00 6C 00 69 00 63 00
0000C840: 61 00 74 00 69 00 6F 00 6E 00 00 00 3A 00 0B 00
0000C850: 01 00 50 00 72 00 6F 00 64 00 75 00 63 00 74 00
0000C860: 56 00 65 00 72 00 73 00 69 00 6F 00 6E 00 00 00
0000C870: 31 00 2C 00 20 00 30 00 2C 00 20 00 30 00 2C 00
0000C880: 20 00 31 00 00 00 00 00 44 00 00 00 01 00 56 00
0000C890: 61 00 72 00 46 00 69 00 6C 00 65 00 49 00 6E 00
0000C8A0: 66 00 6F 00 00 00 00 00 24 00 04 00 00 00 54 00
0000C8B0: 72 00 61 00 6E 00 73 00 6C 00 61 00 74 00 69 00
0000C8C0: 6F 00 6E 00 00 00 00 00 00 00 09 04 B0 04 00 00 00 00
0000C8D0: C0 00 C8 80 00 00 00 02 00 00 00 00 BB 00
0000C8E0: 73 00 00 00 00 00 00 00 43 00 61 00 6D 00 65 00 72 00
0000C8F0: 61 00 20 00 44 00 69 00 61 00 6C 00 6F 00 67 00
0000C900: 00 00 08 00 4D 00 53 00 20 00 53 00 61 00 6E 00
0000C910: 73 00 20 00 53 00 65 00 72 00 69 00 66 00 00 00
0000C920: 01 00 01 50 00 00 00 00 82 00 07 00 32 00 0E 00
0000C930: 01 00 FF FF 80 00 4F 00 4B 00 00 00 00 00 00 00
0000C940: 00 00 01 50 00 00 00 00 07 00 1A 00 AD 00 29 00
0000C950: F1 03 7B 00 34 00 43 00 42 00 31 00 36 00 46 00
0000C960: 33 00 37 00 2D 00 43 00 31 00 43 00 36 00 2D 00
0000C970: 31 00 31 00 44 00 33 00 2D 00 38 00 34 00 46 00
0000C980: 42 00 2D 00 30 00 30 00 30 00 30 00 38 00 33 00
0000C990: 41 00 32 00 33 00 31 00 44 00 43 00 33 00 7D 00 00 00
0000C9A0: 00 00 00 00 00 00 00 00 C0 00 C8 80 00 00 00 00
0000C9B0: 0F 00 00 00 00 00 BB 00 A0 00 00 00 00 00 50 00
0000C9C0: 61 00 72 00 61 00 6D 00 65 00 74 00 65 00 72 00
0000C9D0: 73 00 00 00 08 00 4D 00 53 00 20 00 53 00 61 00
0000C9E0: 6E 00 73 00 20 00 53 00 65 00 72 00 69 00 66 00
0000C9F0: 00 00 00 00 01 00 01 50 00 00 00 00 82 00 07 00
0000CA00: 32 00 0E 00 01 00 FF FF 80 00 4F 00 4B 00 00 00
0000CA10: 00 00 00 00 00 09 00 02 50 00 00 00 00 54 00 2C 00
0000CA20: 33 00 0A 00 F5 03 FF FF 80 00 26 00 53 00 70 00
0000CA30: 69 00 72 00 61 00 6C 00 20 00 53 00 63 00 61 00
0000CA40: 6E 00 00 00 00 00 00 00 00 00 09 00 00 50 00 00 00 00
0000CA50: 54 00 37 00 46 00 0A 00 F6 03 FF FF 80 00 26 00
0000CA60: 52 00 65 00 63 00 74 00 61 00 6E 00 67 00 75 00
0000CA70: 6C 00 61 00 72 00 20 00 53 00 63 00 61 00 6E 00
0000CA80: 00 00 00 00 07 00 00 50 00 00 00 00 4D 00 22 00
0000CA90: 55 00 28 00 F7 03 FF FF 80 00 4E 00 6F 00 64 00
0000CAA0: 65 00 73 00 20 00 53 00 63 00 61 00 6E 00 20 00
0000CAB0: 50 00 61 00 74 00 74 00 65 00 72 00 6E 00 00 00
0000CAC0: 00 00 00 00 80 00 81 50 00 00 00 00 07 00 3A 00
0000CAD0: 28 00 0E 00 F8 03 FF FF 81 00 00 00 00 00 00 00
0000CAE0: 00 00 02 50 00 00 00 00 07 00 2E 00 34 00 08 00
0000CAF0: F9 03 FF FF 82 00 4E 00 6F 00 64 00 65 00 73 00
0000CB00: 20 00 44 00 69 00 73 00 74 00 61 00 6E 00 63 00
0000CB10: 65 00 00 00 00 00 00 00 03 00 01 50 00 00 00 00
0000CB20: 0D 00 8F 00 76 00 0A 00 FB 03 FF FF 80 00 53 00
0000CB30: 61 00 76 00 65 00 20 00 26 00 42 00 4D 00 50 00
0000CB40: 20 00 66 00 69 00 6C 00 65 00 73 00 20 00 66 00
0000CB50: 6F 00 72 00 20 00 69 00 6E 00 74 00 65 00 72 00
0000CB60: 69 00 6F 00 72 00 20 00 72 00 65 00 67 00 69 00
0000CB70: 6F 00 6E 00 00 00 00 00 00 02 50 00 00 00 00
0000CB80: 07 00 11 00 3C 00 08 00 FA 03 FF FF 82 00 4D 00
0000CB90: 61 00 72 00 6B 00 65 00 72 00 73 00 20 00 48 00
0000CBA0: 79 00 73 00 74 00 65 00 72 00 65 00 73 00 69 00
0000CBB0: 73 00 00 00 00 00 00 00 80 00 81 50 00 00 00 00
0000CBC0: 07 00 1C 00 28 00 0E 00 FC 03 FF FF 81 00 00 00
0000CBD0: 00 00 00 00 00 03 00 01 50 00 00 00 00 0D 00 7C 00
0000CBE0: 39 00 0A 00 FD 03 FF FF 80 00 53 00 61 00 76 00
0000CBF0: 65 00 20 00 26 00 4C 00 6F 00 67 00 20 00 66 00
0000CC00: 69 00 6C 00 65 00 00 00 00 00 00 03 00 01 50
0000CC10: 00 00 00 00 0D 00 69 00 42 00 0A 00 FE 03 FF FF
0000CC20: 80 00 53 00 61 00 76 00 65 00 20 00 26 00 54 00
0000CC30: 69 00 6D 00 69 00 6E 00 67 00 20 00 66 00 69 00
0000CC40: 6C 00 65 00 00 00 00 00 80 00 81 50 00 00 00 00
0000CC50: 07 00 57 00 28 00 0E 00 FF 03 FF FF 81 00 00 00
0000CC60: 00 00 00 00 00 02 50 00 00 00 00 07 00 4C 00
0000CC70: 46 00 08 00 00 04 FF FF 82 00 54 00 72 00 61 00
0000CC80: 6E 00 73 00 64 00 75 00 63 00 65 00 72 00 20 00
0000CC90: 41 00 6C 00 69 00 67 00 6E 00 6D 00 65 00 6E 00
0000CCA0: 74 00 00 00 00 00 00 00 80 00 81 50 00 00 00 00
0000CCB0: 58 00 56 00 28 00 0E 00 01 04 FF FF 81 00 00 00
```

APPENDIX-continued

```
0000CCC0: 00 00 00 00 00 00 02 50 00 00 00 00 57 00 4C 00
0000CCD0: 4C 00 08 00 02 04 FF FF 82 00 54 00 72 00 61 00
0000CCE0: 6E 00 73 00 64 00 75 00 63 00 65 00 72 00 20 00
0000CCF0: 53 00 69 00 7A 00 65 00 20 00 28 00 69 00 6E 00
0000CD00: 20 00 6D 00 6D 00 29 00 00 00 00 00 00 00 00 00
0000CD10: F1 03 76 03 14 00 00 00 00 00 00 00 00 00 01 00
0000CD20: 9C 1C 00 00 C8 06 00 00 00 00 00 00 00 00 00 00
0000CD30: 00 00 00 00 00 00 00 00 00 00 0F 00 26 00 41 00
0000CD40: 62 00 6F 00 75 00 74 00 20 00 54 00 72 00 61 00
0000CD50: 63 00 6B 00 2E 00 2E 00 2E 00 00 00 00 00 00 00
0000CD60: 00 00 00 00 00 00 00 00 00 00 00 00 00 00 00 00
0000CD70: 00 00 00 00 00 00 00 00 00 00 00 00 00 00 00 00
0000CD80: 00 00 00 00 00 00 00 00 00 00 00 00 00 00 00 00
0000CD90: 00 00 00 00 00 00 00 00 00 00 00 00 00 00 00 00
0000CDA0: 00 00 00 00 00 00 00 00 00 00 00 00 00 00 00 00
0000CDB0: 00 00 00 00 00 00 00 00 00 00 00 00 00 00 00 00
0000CDC0: 00 00 00 00 00 00 00 00 00 00 00 00 00 00 00 00
0000CDD0: 00 00 00 00 00 00 00 00 00 00 00 00 00 00 00 00
0000CDE0: 00 00 00 00 00 00 00 00 00 00 00 00 00 00 00 00
0000CDF0: 00 00 00 00 00 00 00 00 00 00 00 00 00 00 00 00
0000CE00: 00 00 00 00 00 00 00 00 00 00 00 00 00 00 00 00
0000CE10: 00 00 00 00 00 00 00 00 00 00 00 00 00 00 00 00
0000CE20: 00 00 00 00 00 00 00 00 00 00 00 00 00 00 00 00
0000CE30: 00 00 00 00 00 00 00 00 00 00 00 00 00 00 00 00
0000CE40: 00 00 00 00 00 00 00 00 00 00 00 00 00 00 00 00
0000CE50: 00 00 00 00 00 00 00 00 00 00 00 00 00 00 00 00
0000CE60: 00 00 00 00 00 00 00 00 00 00 00 00 00 00 00 00
0000CE70: 00 00 00 00 00 00 00 00 00 00 00 00 00 00 00 00
0000CE80: 00 00 00 00 00 00 00 00 00 00 00 00 00 00 00 00
0000CE90: 00 00 00 00 00 00 00 00 00 00 00 00 00 00 00 00
0000CEA0: 00 00 00 00 00 00 00 00 00 00 00 00 00 00 00 00
0000CEB0: 00 00 00 00 00 00 00 00 00 00 00 00 00 00 00 00
0000CEC0: 00 00 00 00 00 00 00 00 00 00 00 00 00 00 00 00
0000CED0: 00 00 00 00 00 00 00 00 00 00 00 00 00 00 00 00
0000CEE0: 00 00 00 00 00 00 00 00 00 00 00 00 00 00 00 00
0000CEF0: 00 00 00 00 00 00 00 00 00 00 00 00 00 00 00 00
0000CF00: 00 00 00 00 00 00 00 00 00 00 00 00 00 00 00 00
0000CF10: 00 00 00 00 00 00 00 00 00 00 00 00 00 00 00 00
0000CF20: 00 00 00 00 00 00 00 00 00 00 00 00 00 00 00 00
0000CF30: 00 00 00 00 00 00 00 00 00 00 00 00 00 00 00 00
0000CF40: 00 00 00 00 00 00 00 00 00 00 00 00 00 00 00 00
0000CF50: 00 00 00 00 00 00 00 00 00 00 00 00 00 00 00 00
0000CF60: 00 00 00 00 00 00 00 00 00 00 00 00 00 00 00 00
0000CF70: 00 00 00 00 00 00 00 00 00 00 00 00 00 00 00 00
0000CF80: 00 00 00 00 00 00 00 00 00 00 00 00 00 00 00 00
0000CF90: 00 00 00 00 00 00 00 00 00 00 00 00 00 00 00 00
0000CFA0: 00 00 00 00 00 00 00 00 00 00 00 00 00 00 00 00
0000CFB0: 00 00 00 00 00 00 00 00 00 00 00 00 00 00 00 00
0000CFC0: 00 00 00 00 00 00 00 00 00 00 00 00 00 00 00 00
0000CFD0: 00 00 00 00 00 00 00 00 00 00 00 00 00 00 00 00
0000CFE0: 00 00 00 00 00 00 00 00 00 00 00 00 00 00 00 00
0000CFF0: 00 00 00 00 00 00 00 00 00 00 00 00 00 00 00 00
```

The invention claimed is:

1. A method for lysing cellulite comprising the steps of:
   directing focused ultrasonic energy at a target volume in a region of a body containing both cellulite and non-cellulite tissue; and
   modulating said focused ultrasonic energy so as to selectively lyse said cellulite in said target volume and generally not lyse non-cellulite tissue in said target volume which receives said ultrasonic energy.

2. A method for lysing cellulite according to claim 1 and wherein said directing focused ultrasonic energy generally prevents lysis of tissue outside of said target volume.

3. A method for lysing cellulite according to claim 1 and also comprising:
   ultrasonic imaging of said region at least partially concurrently with said directing focused ultrasonic energy at said target volume.

4. A method for lysing cellulite according to claim 1 and wherein said directing comprises positioning at least one ultrasonic transducer relative to said body in order to direct said focused ultrasonic energy at said target volume.

5. A method for lysing cellulite according to claim 1 and wherein said directing comprises varying the focus of at least one ultrasonic transducer in order to direct said focused ultrasonic energy at said target volume.

6. A method for lysing cellulite according to claim 5 and wherein said varying the focus comprises changing the volume of said target volume.

7. A method for lysing cellulite according to claim 5 and wherein said varying the focus comprises changing the distance of said target volume from said at least one ultrasonic transducer.

8. A method for lysing cellulite according to claim 1 and also comprising sensing ultrasonic energy coupled to an external surface of said body adjacent said target volume.

9. A method for lysing cellulite according to claim 1 and also comprising sensing of cavitation at said target volume.

10. A method according to claim 1 and wherein said directing takes place from an ultrasonic transducer located outside of the body.

11. A method according to claim 1 and wherein said directing takes place to a target volume bounded by dermis and fascia.

12. A method according to claim 1 and wherein said ultrasonic energy has a frequency in a range of 50 KHz-1000 KHz.

13. A method according to claim 1 and wherein said ultrasonic energy has a frequency in a range of 100 KHz-500 KHz.

14. A method according to claim 1 and wherein said ultrasonic energy has a frequency in a range of 150 KHz-300 KHz.

15. A method according to claim 1 and wherein said modulating provides a duty cycle between 1:2 and 1:50.

16. A method according to claim 1 and wherein said modulating provides a duty cycle between 1:5 and 1:30.

17. A method according to claim 1 and wherein said modulating provides a duty cycle between 1:10 and 1:20.

18. A method for lysing cellulite comprising the steps of:
   generating, at a source outside a body, ultrasonic energy which selectively generally lyses cellulite and generally does not lyse non-cellulite tissue; and
   directing said ultrasonic energy, from said source outside said body, at a target volume in a region of said body containing both cellulite and non-cellulite tissue.

19. A method for lysing cellulite according to claim 18 and wherein said directing said ultrasonic energy generally prevents lysis of tissue outside of said target volume.

20. A method for lysing cellulite comprising the steps of
   defining a region in a body at least partially by detecting spatial indications on said body;
   directing ultrasonic energy at a multiplicity of target volumes containing both cellulite and non-cellulite tissue within said region, thereby to selectively lyse said cellulite in said target volumes and generally not lyse non-cellulite tissue in said target volumes which receives said ultrasonic energy.

* * * * *